United States Patent
Guo et al.

(10) Patent No.: US 11,401,295 B2
(45) Date of Patent: Aug. 2, 2022

(54) CYCLIC DINUCLEOTIDE COMPOUND AND USES THEREOF

(71) Applicants: SHANGHAI JEMINCARE PHARMACEUTICALS CO., LTD., Shanghai (CN); JIANGXI JEMINCARE GROUP CO., LTD., Nanchang (CN)

(72) Inventors: Shuchun Guo, Shanghai (CN); Jianbiao Peng, Shanghai (CN); Yang Liu, Shanghai (CN); Haibing Guo, Shanghai (CN)

(73) Assignees: SHANGHAI JEMINCARE PHARMACEUTICALS CO., LTD., Shanghai (CN); JIANGXI JEMINCARE GROUP CO., LTD., Nanchang (CN)

( * ) Notice: Subject to any disclaimer, the term of this patent is extended or adjusted under 35 U.S.C. 154(b) by 0 days.

(21) Appl. No.: 17/284,154

(22) PCT Filed: Oct. 12, 2019

(86) PCT No.: PCT/CN2019/110800
§ 371 (c)(1),
(2) Date: Apr. 9, 2021

(87) PCT Pub. No.: WO2020/074004
PCT Pub. Date: Apr. 16, 2020

(65) Prior Publication Data
US 2021/0340169 A1    Nov. 4, 2021

(30) Foreign Application Priority Data

Oct. 12, 2018   (CN) .......................... 201811188184.3
Nov. 2, 2018    (CN) .......................... 201811301854.8
Nov. 16, 2018   (CN) .......................... 201811367721.0
Feb. 21, 2019   (CN) .......................... 201910129734.2
May 30, 2019    (CN) .......................... 201910463705.X

(51) Int. Cl.
C07H 19/213   (2006.01)
C07H 21/00    (2006.01)
C07H 21/02    (2006.01)
C07H 21/04    (2006.01)
A61P 35/00    (2006.01)

(52) U.S. Cl.
CPC ............ *C07H 19/213* (2013.01); *A61P 35/00* (2018.01); *C07H 21/00* (2013.01); *C07H 21/02* (2013.01); *C07H 21/04* (2013.01)

(58) Field of Classification Search
None
See application file for complete search history.

(56) References Cited

FOREIGN PATENT DOCUMENTS

| | | |
|---|---|---|
| CN | 102199183 A | 9/2011 |
| WO | 2017123657 A1 | 7/2017 |
| WO | 2017161349 A1 | 9/2017 |
| WO | 2018065360 A1 | 4/2018 |
| WO | WO-2018065360 A1 * | 4/2018 ............. C12P 19/40 |
| WO | 2019043634 A2 | 3/2019 |

OTHER PUBLICATIONS

Jan. 6, 2020 International Search Report issued in International Patent Application No. PCT/CN2019/110800.
Jan. 6, 2020 Written Opinion of the International Searching Authority issued in International Patent Application No. PCT/CN2019/110800.
Chinese Patent Application No. 201811188184.3 (not published).
Chinese Patent Application No. 201811301854.8 (not published).
Chinese Patent Application No. 201811367721.0 (not published).
Chinese Patent Application No. 201910129734.2 (not published).
Chinese Patent Application No. 201910463705.X (not published).

* cited by examiner

*Primary Examiner* — Traviss C McIntosh, III
(74) *Attorney, Agent, or Firm* — SZDC Law P.C.

(57) ABSTRACT

Provided are a compound of formula (I), an optical isomer thereof, a pharmaceutically acceptable salt thereof, uses of said compound acting as a STING agonist.

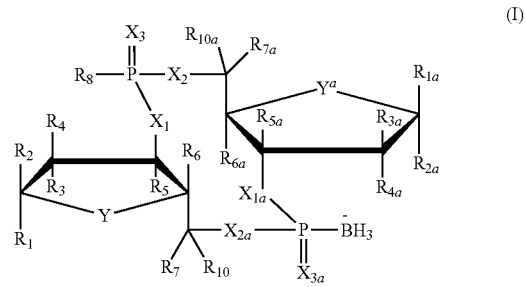

20 Claims, 2 Drawing Sheets

CYCLIC DINUCLEOTIDE COMPOUND AND USES THEREOF

This application is the National Stage Application of PCT/CN2019/110800, filed on Oct. 12, 2019, which claims the priorities of the following applications: CN201811188184.3, filed on Oct. 12, 2018; CN201811301854.8, filed on Nov. 2, 2018; CN201811367721.0, filed on Nov. 16, 2018; CN201910129734.2, filed on Feb. 21, 2019; CN201910463705.X, filed on May 30, 2019, all of which are incorporated by reference for all purposes as if fully set forth herein.

TECHNICAL FIELD

The present disclosure relates to a compound represented by formula (I), an optical isomer thereof and a pharmaceutically acceptable salt thereof, and a use of the compound as a STING agonist.

BACKGROUND ART

For a long time, researchers have been trying to activate patients' immune system so that their own immune system can effectively fight against tumors and completely remove tumor cells. However, the probability of spontaneous tumor response is extremely low, so the vast majority of patients cannot benefit from it. In the 1960s and 1970s, treatment methods such as BCG injection and non-specific intensive immune system function emerged. In the 1980s, interferon and IL-2, which can activate T cells and NK cells, were also tried to be applied to the treatment of cancer, but these methods still have many limitations, such as the short half-life of exogenous cytokines in blood, which must be compensated by frequent administration and high dose. Non-specific activation of the immune system leads to inflammatory reactions in normal tissues, cytokine storms, and so on, so the toxic and side effects of many therapies are very strong. As immunomodulatory agents that trigger the production of specifically therapeutically beneficial cytokines in the body, STING-targeted therapies have brought dawn to solve this dilemma.

It is currently known that human STING is activated in three ways: 1) Activated by binding to exogenous (3', 3') cyclic di-nucleotides (c-diGMP, c-diAMP, and c-GAMP) released by invade bacteria or archaea, which shows that STING has an innate immune activation in anti-infection; 2) Activated by binding to (2' 3') cyclic guanosine monophosphate-adenosine monophosphate (2',3' c-GAMP), which is an endogenous cyclic di-nucleotide induced by cyclic GMP-AMP di-nucleotide synthetase (cGAS) in the presence of exogenous double-stranded DNA (e.g., released by invading bacteria, viruses, or protozoa) or self-DNA in mammals, showing that STING has an effect of innate immunity induced by endogenous or exogenous DNA; 3) Activation by binding to synthetic ligands.

As a receptor for DNA in the cytoplasm, STING activation can lead to the activation of two downstream IRF3 and NF-κB pathways to activate the immune system. The activation of NF-κB pathway leads to the activation of a series of downstream inflammatory cytokines, while the activation of IRF3 pathway leads to the activation of type I interferon (IFN-α/β), dendritic cells, cytotoxic cells, NK cells, and so on, thus playing an anti-tumor role.

DNA in the human body generally does not activate the STING protein, as it normally exists only within the nucleus (except for mitochondrial DNA). However, if DNA leaks into the cytoplasm, it will activate STING and trigger an immune response. Recently, it has been found that radiotherapy as well as chemotherapy can also activate STING, which may also be caused by DNA leakage in dead tumor cells.

CONTENT OF THE DISCLOSURE

The present disclosure provides a compound represented by formula (I), an optical isomer thereof and a pharmaceutically acceptable salt thereof,

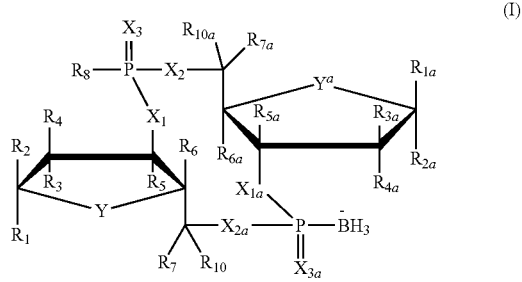

wherein,
each of $R_1$ and $R_{1a}$ is independently selected from

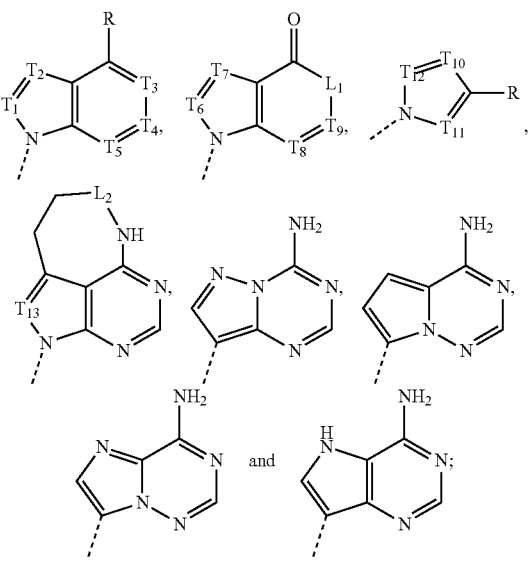

each of $T_1$, $T_2$, $T_3$, $T_4$, $T_5$, $T_6$, $T_7$, $T_8$, $T_9$, $T_{10}$, $T_{11}$, $T_{12}$ and $T_{13}$ is independently selected from —C(R)— and —N—;
each of $L_1$ and $L_2$ is independently selected from —O—, —N(R)—, —C(RR)— and —C(=O)—;
each of R is independently selected from H, halogen, OH, $NH_2$, CN,

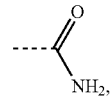

$C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R';

R' is selected from F, Cl, Br, I, OH, $NH_2$ and $CH_3$;

each of $R_2$ and $R_{2a}$ is independently selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_3$ and $R_{3a}$ is independently selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_4$ and $R_{4a}$ is independently selected from H, halogen, OH, $NH_2$, CN, $N_3$, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_5$ and $R_{5a}$ is independently selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_6$ and $R_{6a}$ is independently selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol and $C_{1-6}$ alkylamino are optionally substituted by one, two or three of R;

each of $R_7$ and $R_{7a}$ is independently selected from H, halogen, OH, $NH_2$, CN, $C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R;

each of $R_{10}$ and $R_{10a}$ is independently selected from H, halogen, OH, $NH_2$, CN, $C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R;

alternatively, $R_7$ and $R_{10}$ are attached together to form a $C_{3-6}$ cycloalkyl, $C_{3-6}$ cycloalkenyl or $C_{3-6}$ cycloalkynyl, wherein the $C_{3-6}$ cycloalkyl, $C_{3-6}$ cycloalkenyl or $C_{3-6}$ cycloalkynyl is optionally substituted by one, two or three of R;

$R_{7a}$ and $R_{10a}$ are attached together to form a $C_{3-6}$ cycloalkyl, $C_{3-6}$ cycloalkenyl or $C_{3-6}$ cycloalkynyl, wherein the $C_{3-6}$ cycloalkyl, $C_{3-6}$ cycloalkenyl or $C_{3-6}$ cycloalkynyl is optionally substituted by one, two or three of R;

$R_8$ is selected from $BH_3^-$ and $-S(R_9)$;

$R_9$ is selected from H, $CH_2OC(=O)R_{11}$, $CH_2OC(=O)OR_{11}$, $CH_2CH_2SC(=O)R_{11}$ and $CH_2CH_2SSCH_2R_{11}$;

$R_{11}$ is selected from $C_{6-10}$ aryl, 5-10 membered heteroaryl, $C_{1-6}$ heterocycloalkyl and $C_{1-20}$ alkyl, wherein the $C_{1-20}$ alkyl is optionally substituted by one, two, three, four or five of $C_{6-10}$ aryl, $C_{3-6}$ cycloalkyl, OH and F;

alternatively, $R_4$ and $R_6$, or $R_{4a}$ and $R_{6a}$ are attached together to form a 5-6 membered heterocycloalkyl;

each of $X_1$ and $X_{1a}$ is independently selected from $-NH-$, $-O-$, $-S-$ and $-CH_2-$;

each of $X_2$ and $X_{2a}$ is independently selected from $-NH-$, $-O-$, $-S-$ and $-CH_2-$;

each of $X_3$ and $X_{3a}$ is independently selected from $-O-$ and $-S-$;

each of Y and $Y_a$ is independently selected from $-O-$, $-S-$, $-CH_2-$ and $-C(=CH_2)-$;

the 5-6 membered heterocycloalkyl, 5-10 membered heteroaryl or $C_{1-6}$ heterocycloalkyl contains one, two or three of heteroatom or heteroatomic group independently selected from $-O-$, $-NH-$, $-S-$, $-C(=O)-$, $-C(=O)O-$, $-S(=O)-$, $-S(=O)_2-$ and N;

and, when $R_1$ or $R_{1a}$ is selected from

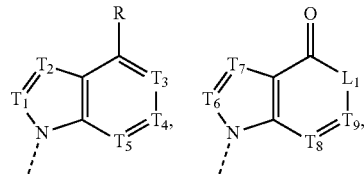

then the compound represented by formula (I) is not selected from

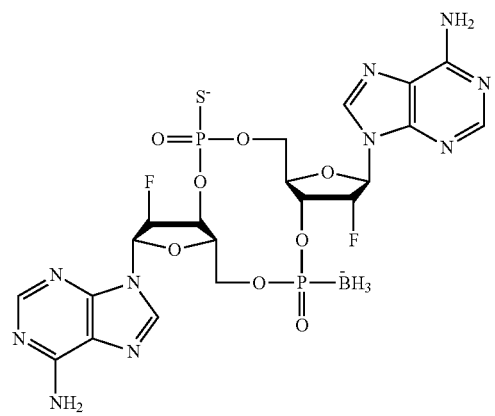

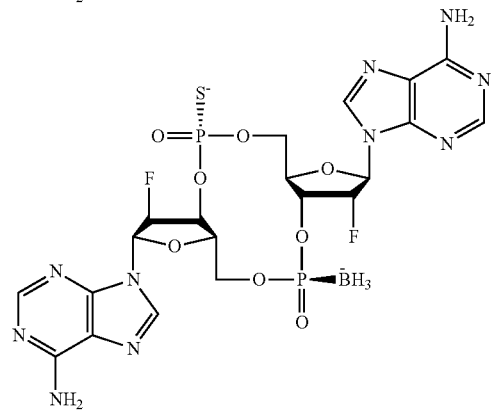

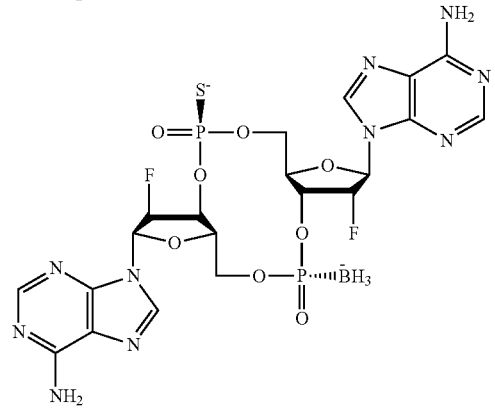

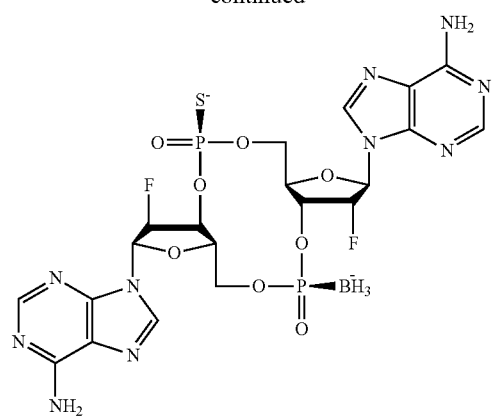
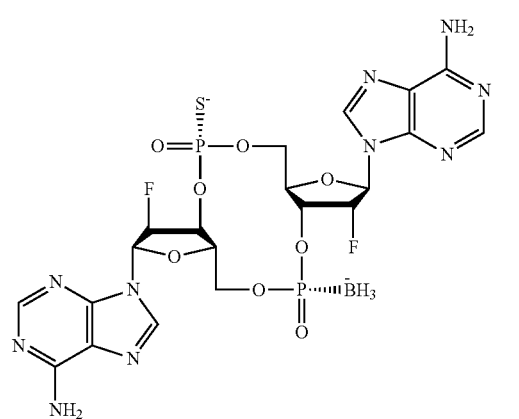
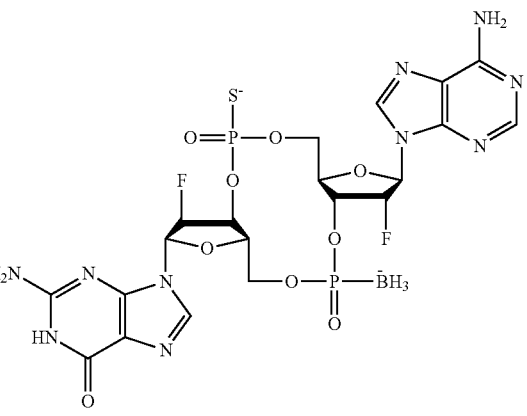
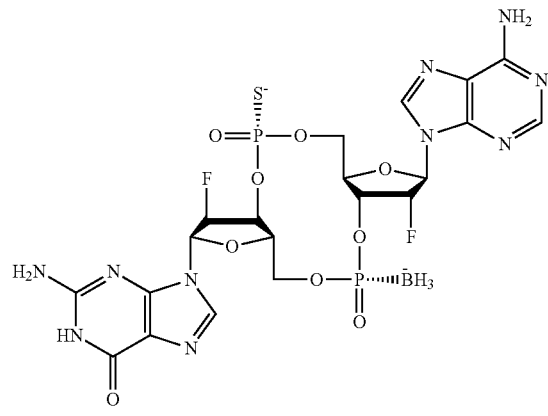
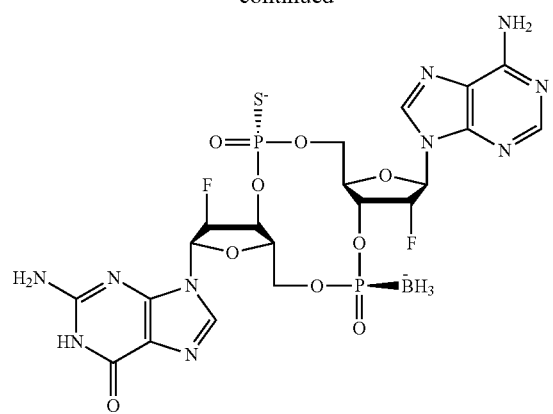
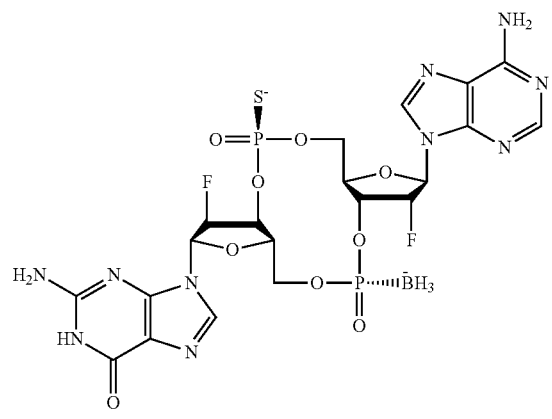
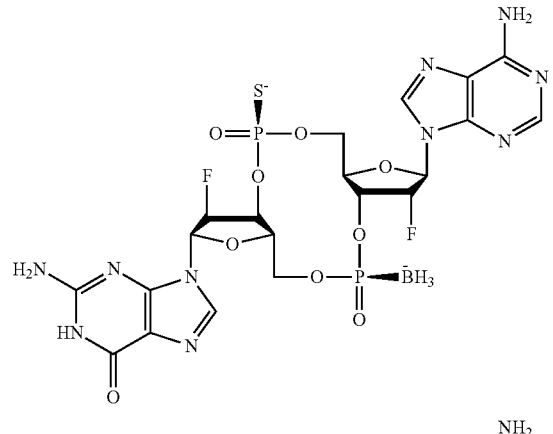
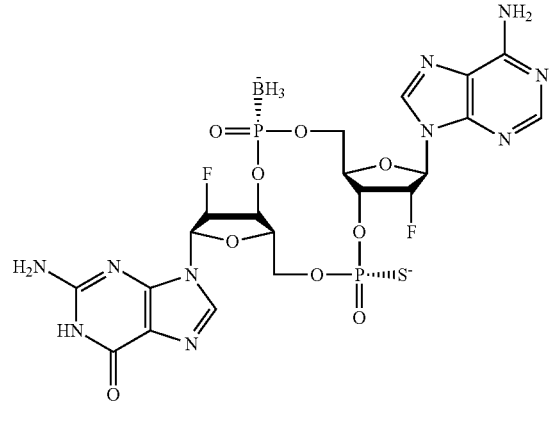

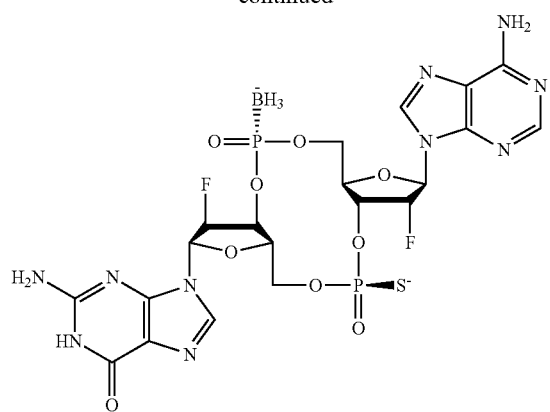
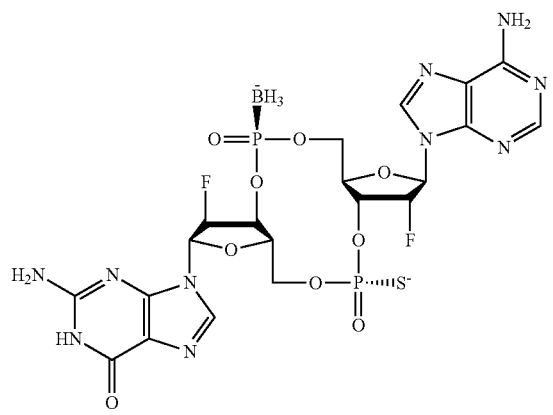
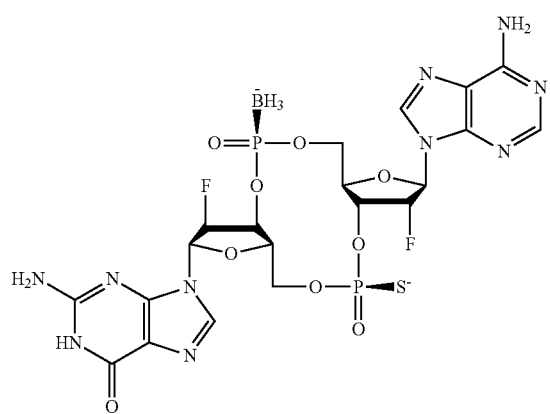
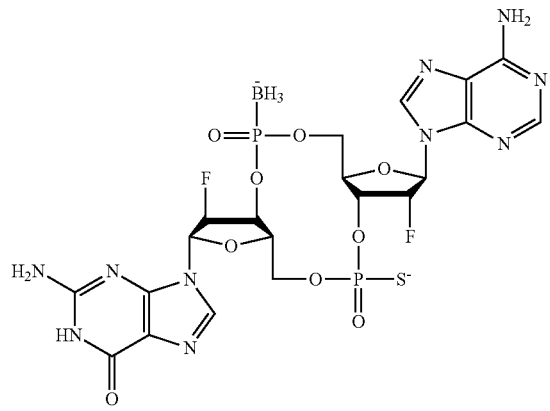
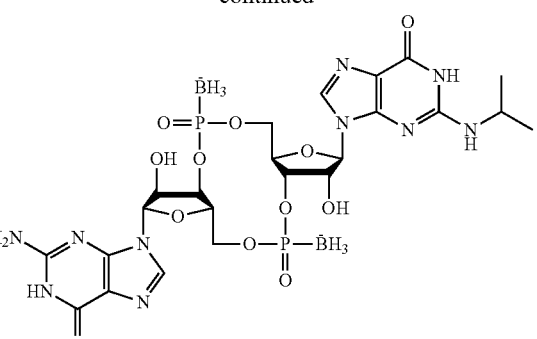
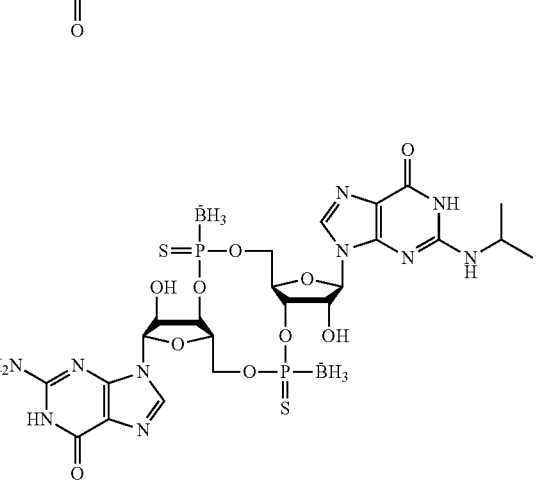
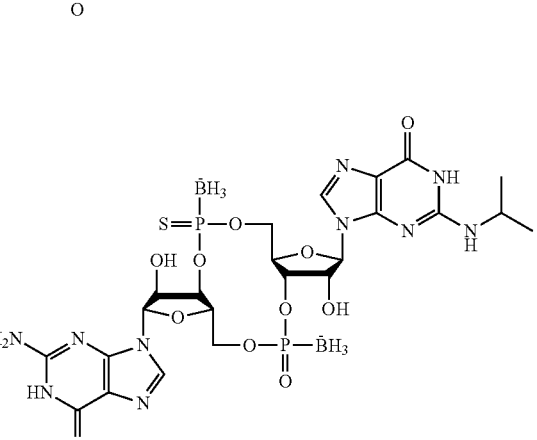
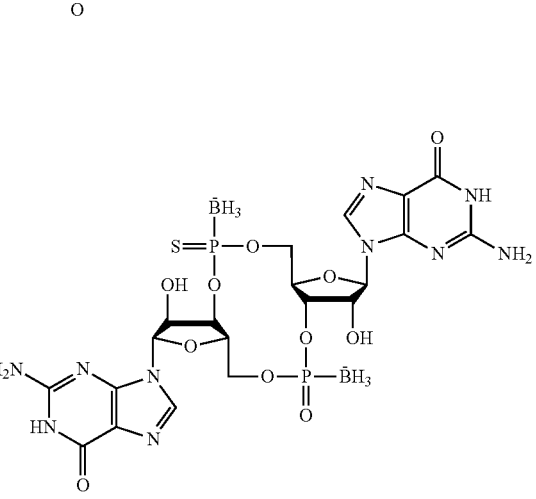

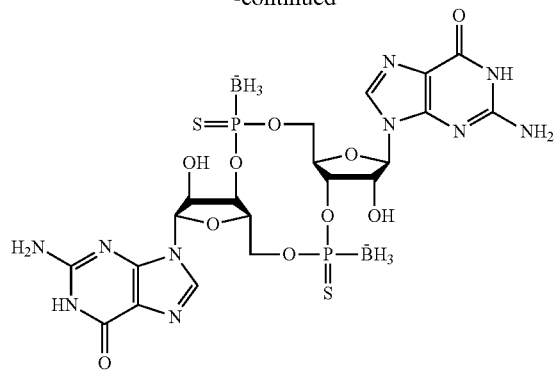

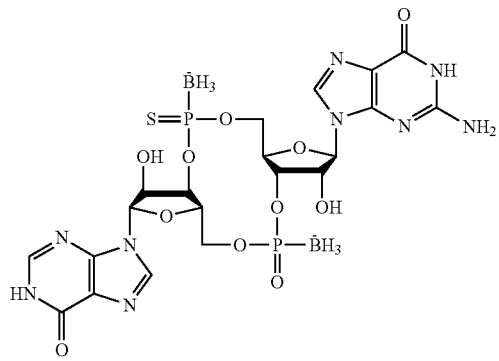

and

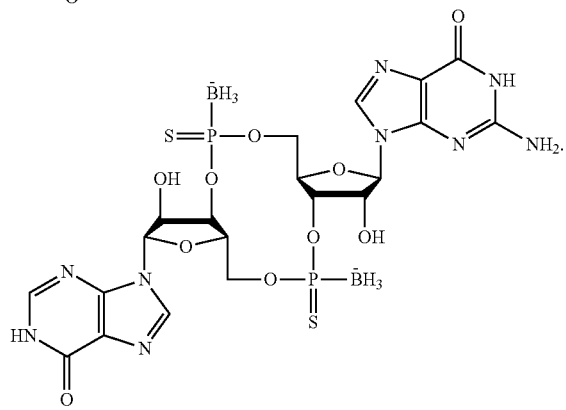

In some embodiments of the present disclosure, when $R_8$ is $BH_3^-$, then one of $R_4$ and $R_{4a}$ is selected from F, Cl and Br, the other one is selected from F, Cl, Br, OH, $OCH_3$ and $N_3$, and other variables are as defined in the present disclosure.

In some embodiments of the present disclosure, each of R is independently selected from H, halogen, OH, $NH_2$, CN,

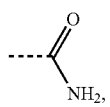

$C_{1-3}$ alkyl, $C_{1-3}$ alkoxy, $C_{1-3}$ alkylthiol and $C_{1-3}$ alkylamino, wherein the $C_{1-3}$ alkyl, $C_{1-3}$ alkoxy, $C_{1-3}$ alkylthiol and $C_{1-3}$ alkylamino are optionally substituted by one, two or three of R', and other variables are as defined in the present disclosure.

In some embodiments of the present disclosure, each of R is independently selected from H, F, Cl, Br, I, OH, $NH_2$, CN, Me,

wherein the Me,

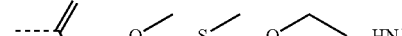

are optionally substituted by one, two or three of R', and other variables are as defined in the present disclosure.

In some embodiments of the present disclosure, each of R is independently selected from H, F, Cl, Br, I, OH, $NH_2$, CN, Me, and other variables are as defined in the present disclosure.

In some embodiments of the present disclosure, each of $R_1$ and $R_{1a}$ is independently selected from

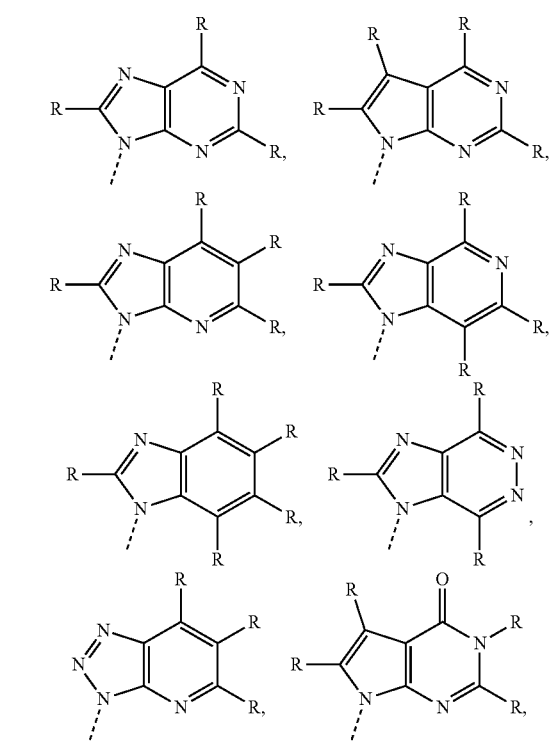

-continued
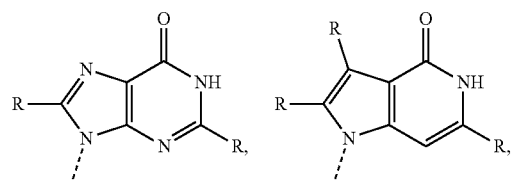
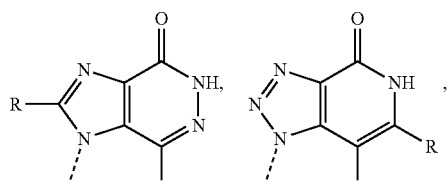
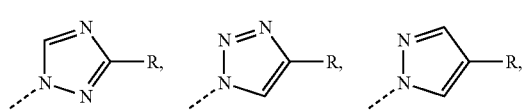
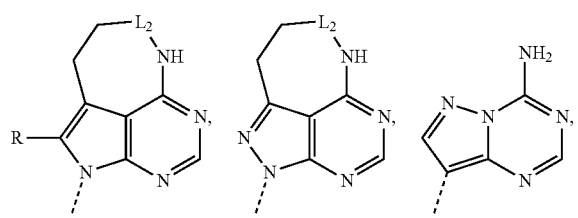
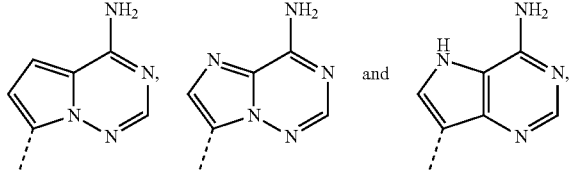
and other variables are as defined in the present disclosure.
In some embodiments of the present disclosure, each of $R_1$ and $R_{1a}$ is independently selected from
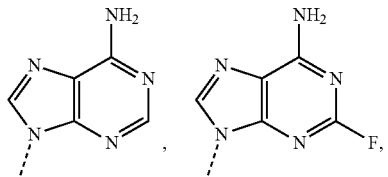
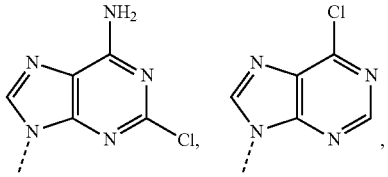
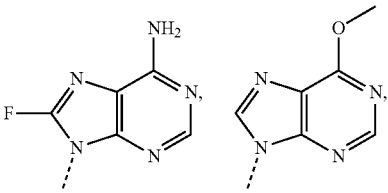
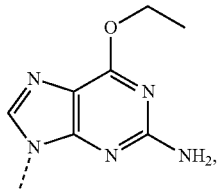
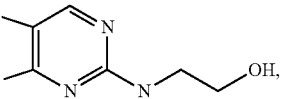
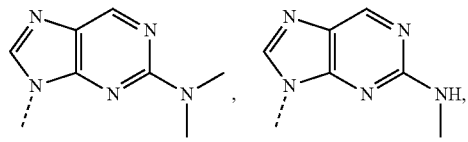
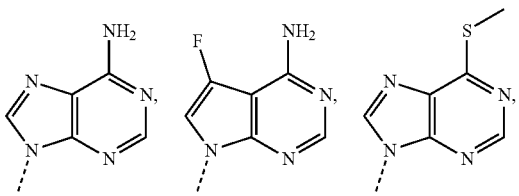
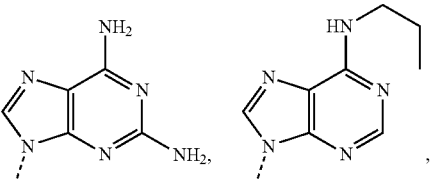
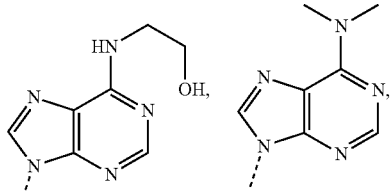
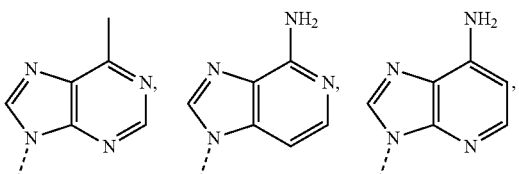
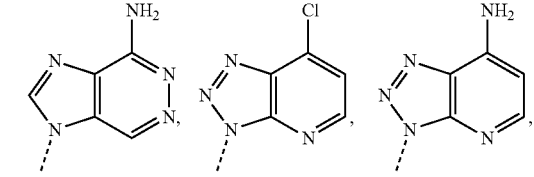
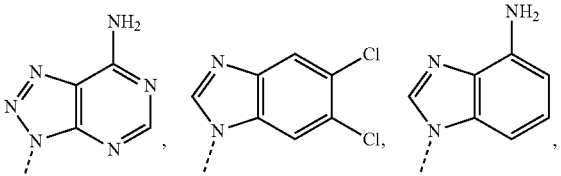
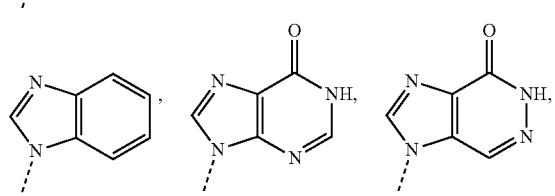

-continued

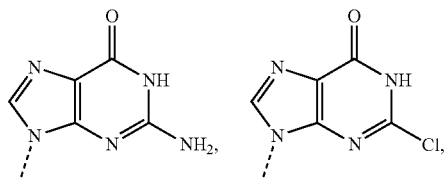

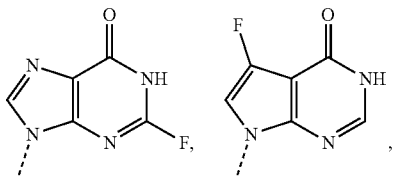

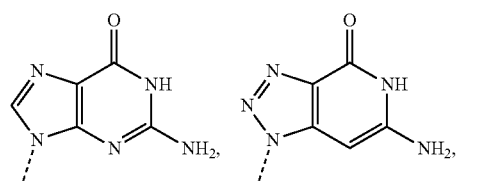

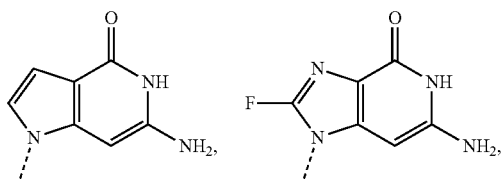

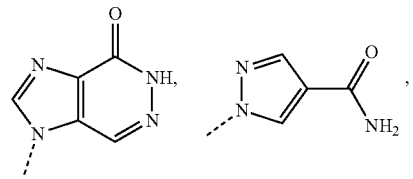

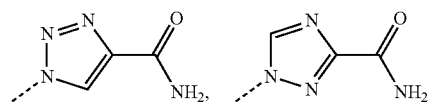

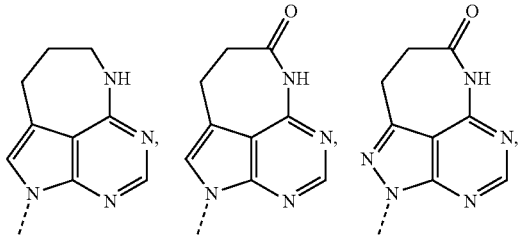

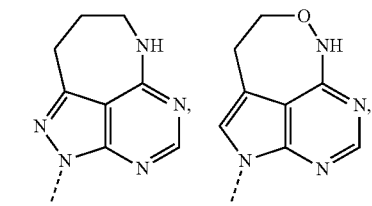

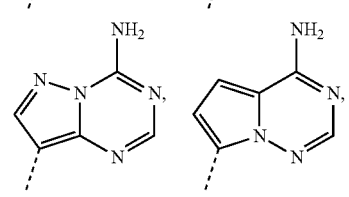

-continued

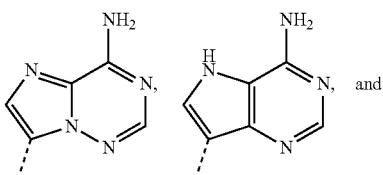

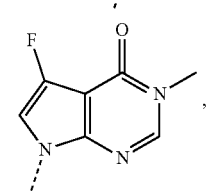

and other variables are as defined in the present disclosure.

In some embodiments of the present disclosure, each of $R_2$, $R_{2a}$, $R_3$, $R_{3a}$, $R_5$, $R_{5a}$, $R_6$ and $R_{6a}$ is independently H, and other variables are as defined in the present disclosure.

In some embodiments of the present disclosure, each of $R_6$ and $R_{6a}$ is independently selected from H and methyl, and other variables are as defined in the present disclosure.

In some embodiments of the present disclosure, each of $R_4$ and $R_{4a}$ is independently selected from F, OH, $NH_2$, $N_3$ and

and other variables are as defined in the present disclosure.

In some embodiments of the present disclosure, each of $R_7$ and $R_{7a}$ is independently selected from H and $CH_3$, and other variables are as defined in the present disclosure.

In some embodiments of the present disclosure, $R_4$ and $R_6$ are attached together, the structure moiety

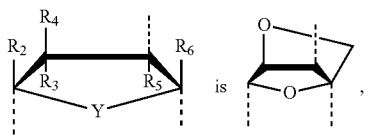

and other variables are as defined in the present disclosure.

In some embodiments of the present disclosure, $R_{4a}$ and $R_{6a}$ are attached together, the structure moiety

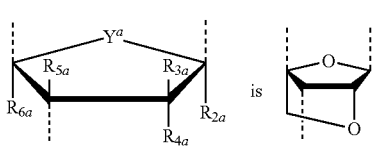

and other variables are as defined in the present disclosure.

In some embodiments of the present disclosure, the compound, the optical isomer and the pharmaceutically acceptable salt thereof, wherein the compound is selected from

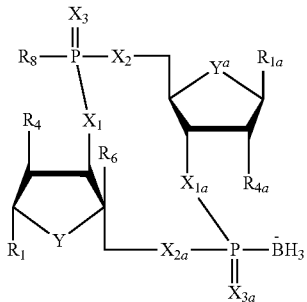

(I-A)

wherein,
each of $R_1$ and $R_{1a}$ is independently selected from

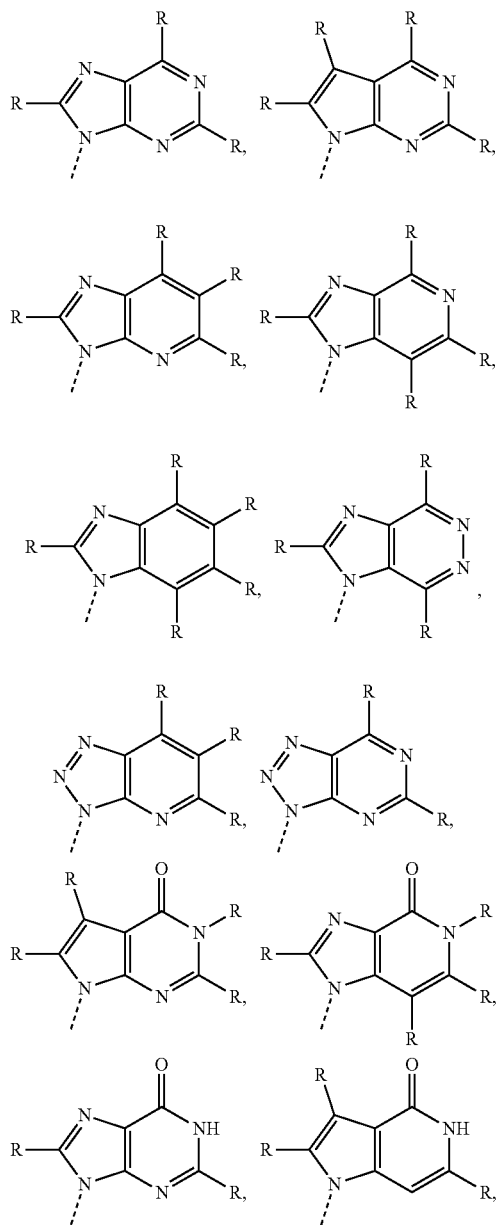

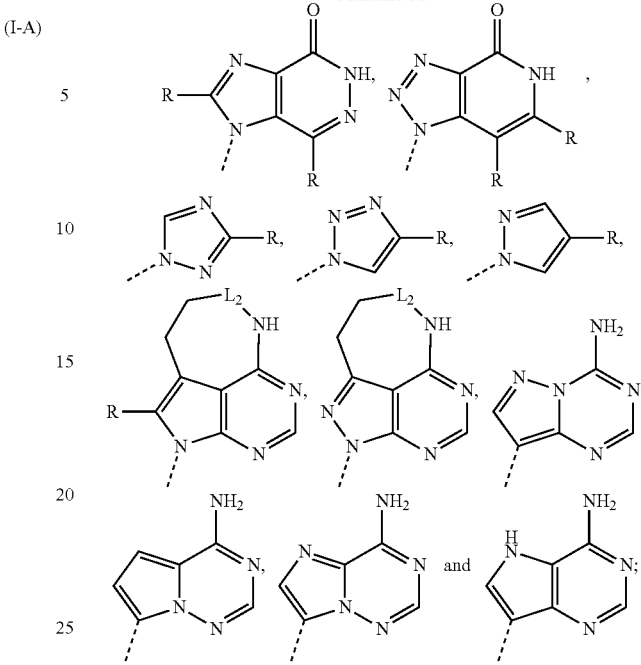

each of $R_4$ and $R_{4a}$ is independently selected from H, halogen, OH, $NH_2$, CN, $N_3$, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

$R_6$ is selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol and $C_{1-6}$ alkylamino are optionally substituted by one, two or three of R;

alternatively, $R_4$ and $R_6$ are attached together to form a 5-6 membered heterocycloalkyl; $R_8$ is selected from $BH_3^-$ and $—S(R_9)$;

$R_9$ is selected from H, $CH_2OC(=O)R_{11}$, $CH_2OC(=O)OR_{11}$, $CH_2CH_2SC(=O)R_{11}$ and $CH_2CH_2SSCH_2R_{11}$;

$R_{11}$ is selected from $C_{6-10}$ aryl, 5-10 membered heteroaryl, $C_{1-6}$ heterocycloalkyl and $C_{1-20}$ alkyl, wherein the $C_{1-20}$ alkyl is optionally substituted by one, two, three, four or five of $C_{6-10}$ aryl, $C_{3-6}$ cycloalkyl, OH and F;

each of $X_1$ and $X_{1a}$ is independently selected from —NH—, —O—, —S— and —$CH_2$—;

each of $X_2$ and $X_{2a}$ is independently selected from —NH—, —O—, —S— and —$CH_2$—;

each of $X_3$ and $X_{3a}$ is independently selected from —O— and —S—;

each of Y and $Y_a$ is independently selected from —O—, —S—, —$CH_2$— and —$C(=CH_2)$—;

when $R_8$ is selected from $BH_3^-$, then one of $R_4$ and $R_{4a}$ is selected from F, Cl and Br, the other one is selected from F, Cl, Br, OH, $OCH_3$ or $N_3$;

when $R_8$ is selected from —$S(R_9)$, then one of $R_4$ and $R_{4a}$ is selected from F, Cl and Br, the other one is selected from OH, $OCH_3$ and $N_3$;

alternatively, when $R_8$ is —$S(R_9)$, and one of $R_4$ and $R_{4a}$ is selected from F, Cl and Br, the other one is not selected from OH, $OCH_3$ and $N_3$, then $R_4$ and $R_{4a}$ are not selected from

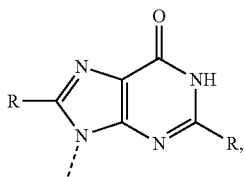

and $R_4$ and $R_{4a}$ are not

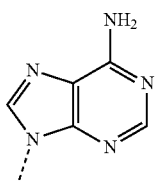

at the same time.

In some embodiments of the present disclosure, the compound, the optical isomer and the pharmaceutically acceptable salt thereof, wherein the compound is selected from

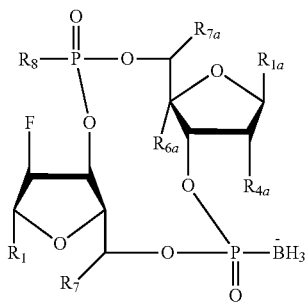

(I-1)

wherein, $R_1$, $R_{1a}$, $R_{4a}$, $R_7$, $R_{7a}$, $R_8$, $R_{6a}$ are as defined in the present disclosure.

In some embodiments of the present disclosure, the compound, the optical isomer and the pharmaceutically acceptable salt thereof, wherein the compound is selected from

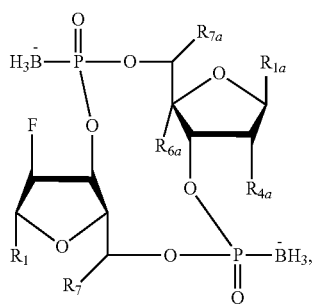

(I-2)

wherein, each variable is as defined in the present disclosure.

In some embodiments of the present disclosure, the compound, the optical isomer and the pharmaceutically acceptable salt thereof, wherein the compound is selected from

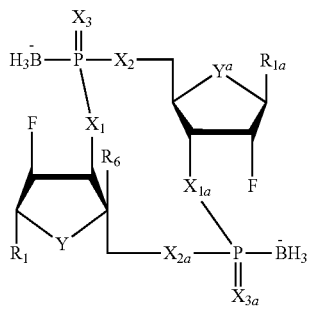

(I-A1)

and

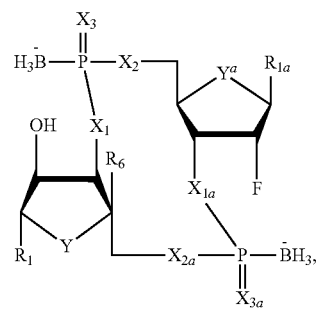

(I-A2)

wherein, each of $R_1$ and $R_{1a}$ is independently selected from

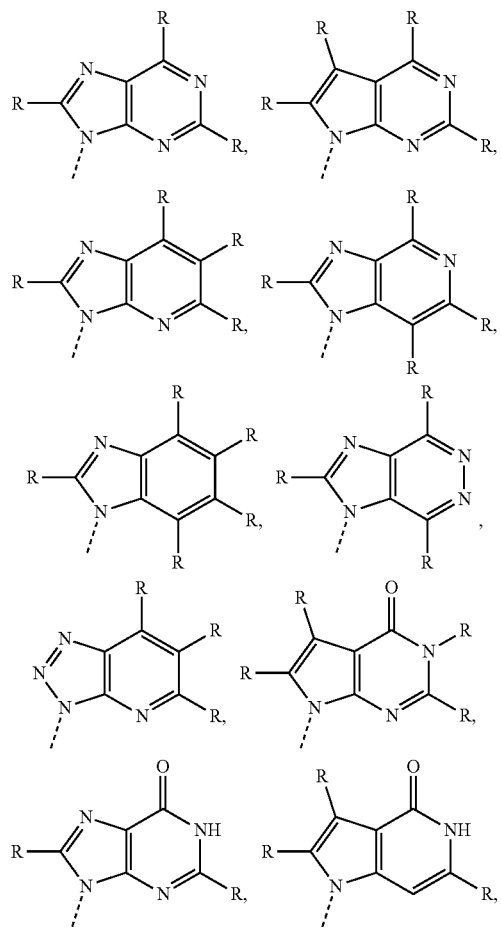

-continued

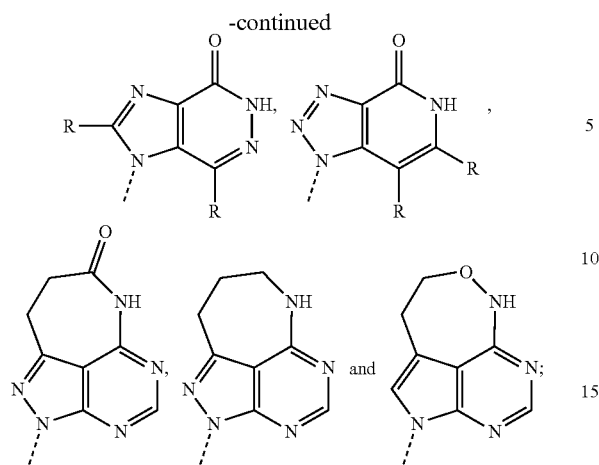

each of $X_1$ and $X_{1a}$ is independently selected from —NH—, —O—, —S— and —CH$_2$—;

each of $X_2$ and $X_{2a}$ is independently selected from —NH—, —O—, —S— and —CH$_2$—;

each of $X_3$ and $X_{3a}$ is independently selected from —O— and —S—;

each of Y and $Y_a$ is independently selected from —O—, —S—, —CH$_2$— and —C(=CH$_2$)—.

In some embodiments of the present disclosure, the compound, the optical isomer and the pharmaceutically acceptable salt thereof, wherein the compound is selected from (I-A1a)

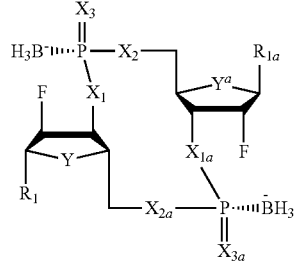

(I-A1b)

(I-A1c)

-continued (I-A1d)

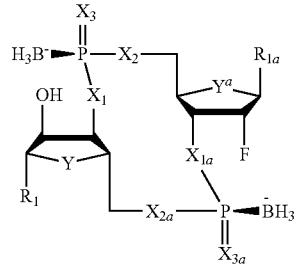

(I-A2a)

(I-A2b)

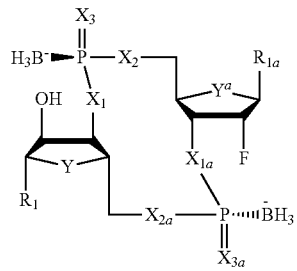

(I-A2c)

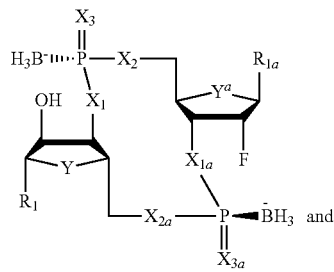

and (I-A2d)

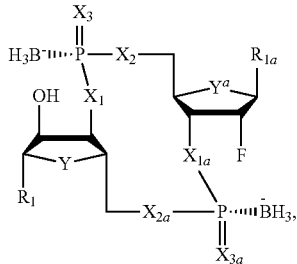

and other variables are as defined in the present disclosure.

In some embodiments of the present disclosure, each of $R_1$ and $R_{1a}$ is independently selected from
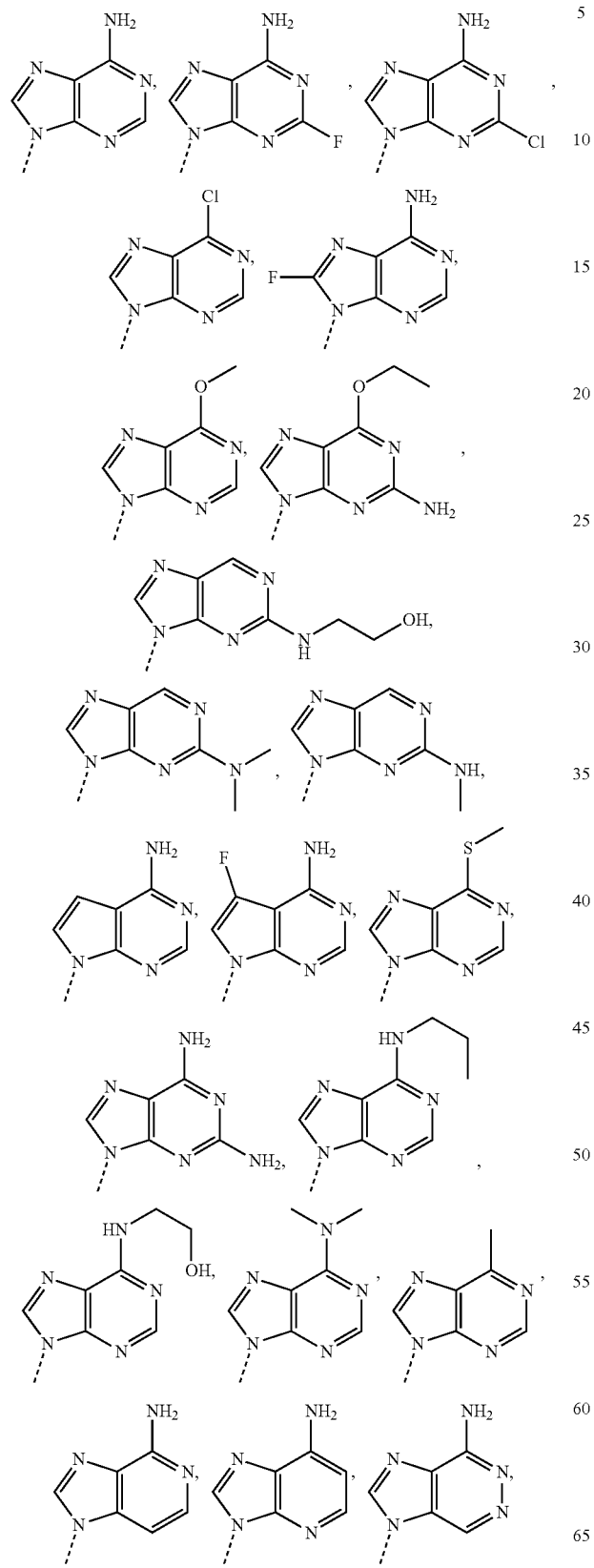
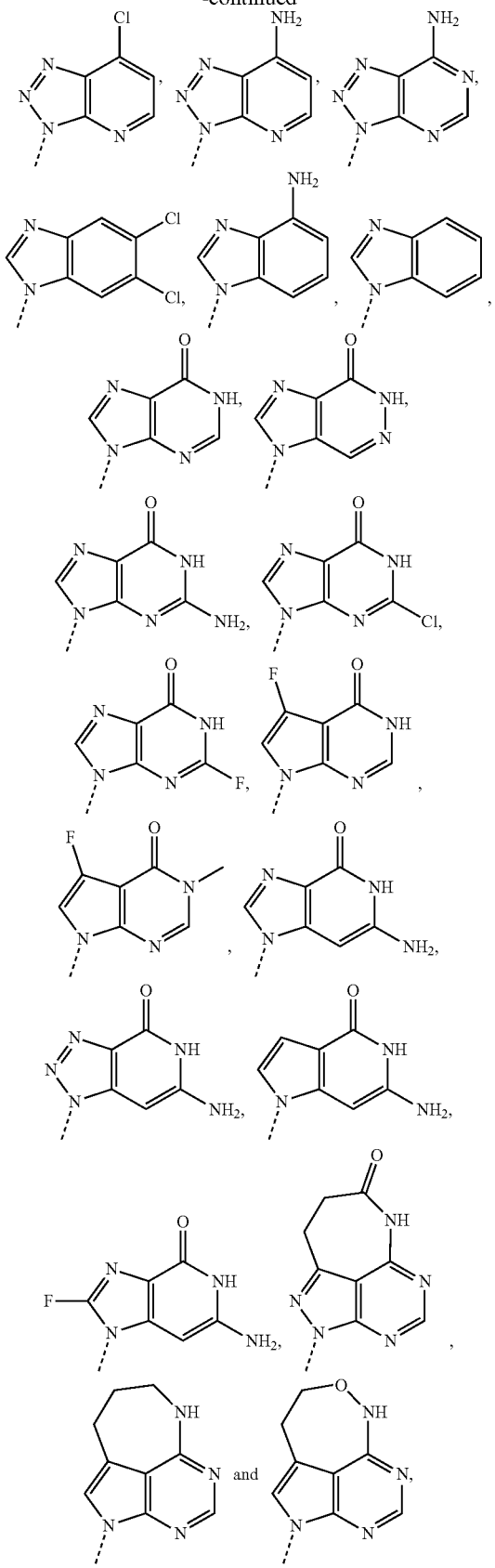
and other variables are as defined in the present disclosure.

The present disclosure provides a compound represented by formula (I), an optical isomer thereof and a pharmaceutically acceptable salt thereof,

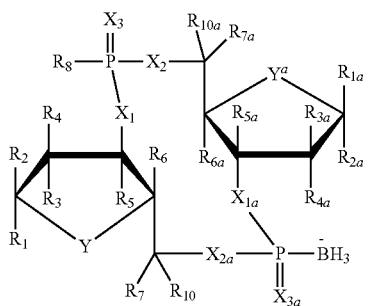

(I)

wherein, each of $R_1$ and $R_{1a}$ is independently selected from

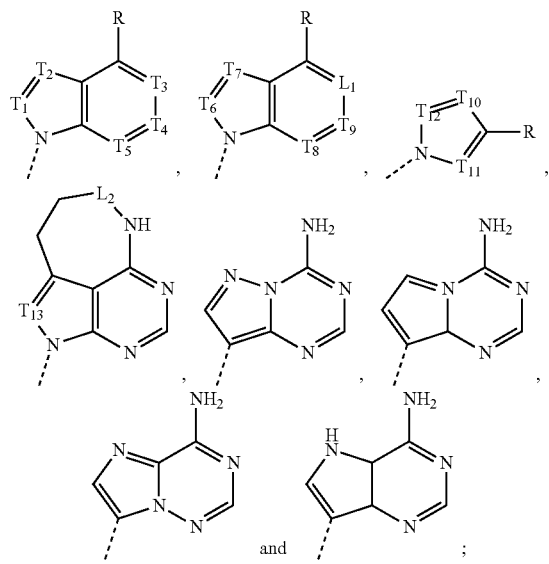

and ;

each of $T_1$, $T_2$, $T_3$, $T_4$, $T_5$, $T_6$, $T_7$, $T_8$, $T_9$, $T_{10}$, $T_{11}$, $T_{12}$ and $T_{13}$ is independently selected from —C(R)— and —N—;
each of $L_1$ and $L_2$ is independently selected from —O—, —N(R)—, —C(RR)— and —C(=O)—; each of R is independently selected from H, halogen, OH, $NH_2$, CN,

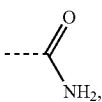

$C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R';
R' is selected from F, Cl, Br, I, OH, $NH_2$ and $CH_3$;
each of $R_2$ and $R_{2a}$ is independently selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_3$ and $R_{3a}$ is independently selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_4$ and $R_{4a}$ is independently selected from H, halogen, OH, $NH_2$, CN, $N_3$, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_5$ and $R_{5a}$ is independently selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_6$ and $R_{6a}$ is independently selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol and $C_{1-6}$ alkylamino are optionally substituted by one, two or three of R;

each of $R_7$ and $R_{7a}$ is independently selected from H, halogen, OH, $NH_2$, CN, $C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R;

each of $R_{10}$ and $R_{10a}$ is independently selected from H, halogen, OH, $NH_2$, CN, $C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R;

alternatively, $R_7$ and $R_{10}$ are attached together to form a $C_{3-6}$ cycloalkyl, $C_{3-6}$ cycloalkenyl or $C_{3-6}$ cycloalkynyl, wherein the $C_{3-6}$ cycloalkyl, $C_{3-6}$ cycloalkenyl or $C_{3-6}$ cycloalkynyl is optionally substituted by one, two or three of R;

$R_{7a}$ and $R_{10a}$ are attached together to form a $C_{3-6}$ cycloalkyl, $C_{3-6}$ cycloalkenyl or $C_{3-6}$ cycloalkynyl, wherein the $C_{3-6}$ cycloalkyl, $C_{3-6}$ cycloalkenyl or $C_{3-6}$ cycloalkynyl is optionally substituted by one, two or three of R;

$R_8$ is selected from $BH_3^-$ and —S($R_9$);
$R_9$ is selected from H, $CH_2OC(=O)R_{11}$, $CH_2OC(=O)OR_{11}$, $CH_2CH_2SC(=O)R_{11}$ and $CH_2CH_2SSCH_2R_{11}$;
$R_{11}$ is selected from $C_{6-10}$ aryl, 5-10 membered heteroaryl, $C_{1-6}$ heterocycloalkyl and $C_{1-20}$ alkyl, wherein the $C_{1-20}$ alkyl is optionally substituted by one, two, three, four or five of $C_{6-10}$ aryl, $C_{3-6}$ cycloalkyl, OH and F;

alternatively, $R_4$ and $R_6$, or $R_{4a}$ and $R_{6a}$ are attached together to form a 5-6 membered heterocycloalkyl;
each of $X_1$ and $X_{1a}$ is independently selected from —NH—, —O—, —S— and —$CH_2$—;
each of $X_2$ and $X_{2a}$ is independently selected from —NH—, —O—, —S— and —$CH_2$—;
each of $X_3$ and $X_{3a}$ is independently selected from —O— and —S—;
each of Y and $Y_a$ is independently selected from —O—, —S—, —$CH_2$— and —C(=$CH_2$)—;
the 5-6 membered heterocycloalkyl, 5-10 membered heteroaryl or $C_{1-6}$ heterocycloalkyl contains one, two or three of heteroatom or heteroatomic group independently selected from —O—, —NH—, —S—, —C(=O)—, —C(=O)O—, —S(=O)—, —S(=O)$_2$— and N.

In some embodiments of the present disclosure, each of R is independently selected from H, halogen, OH, $NH_2$, CN,

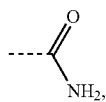

$C_{1-3}$ alkyl, $C_{1-3}$ alkoxy, $C_{1-3}$ alkylthiol and $C_{1-3}$ alkylamino, wherein the $C_{1-3}$ alkyl, $C_{1-3}$ alkoxy, $C_{1-3}$ alkylthiol and $C_{1-3}$ alkylamino are optionally substituted by one, two or three of R'.

In some embodiments of the present disclosure, each of R is independently selected from H, F, Cl, Br, I, OH, $NH_2$, CN, Me,

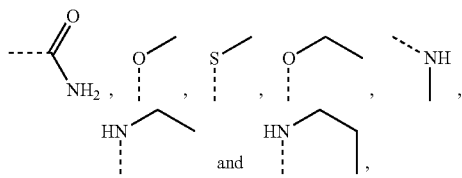

wherein the Me,

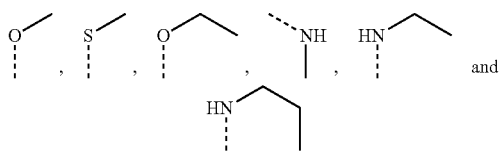

are optionally substituted by one, two or three of R'.

In some embodiments of the present disclosure, each of R is independently selected from H, F, Cl, Br, I, OH, $NH_2$, CN, Me,

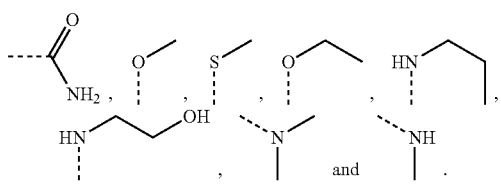

In some embodiments of the present disclosure, each of $R_1$ and $R_{1a}$ is independently selected from

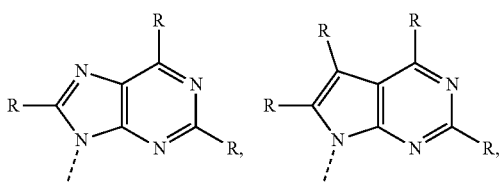

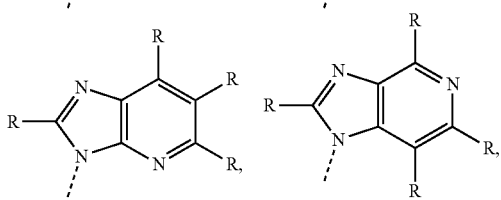

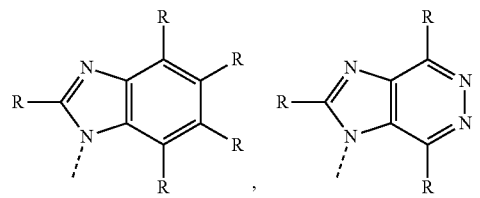

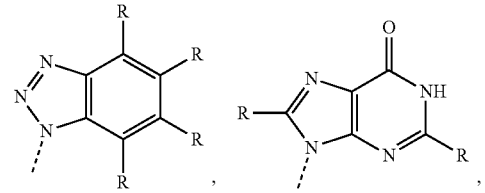

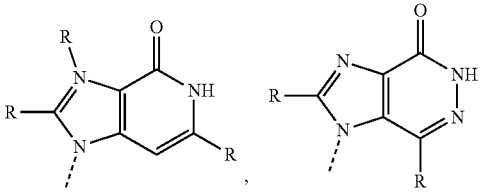

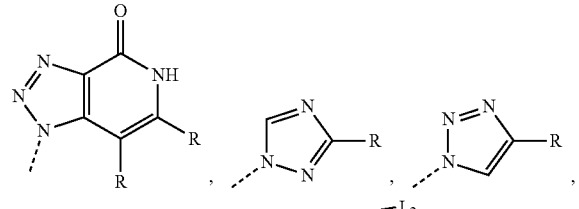

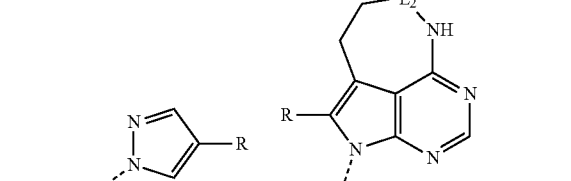

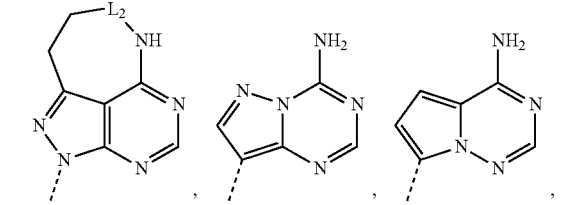

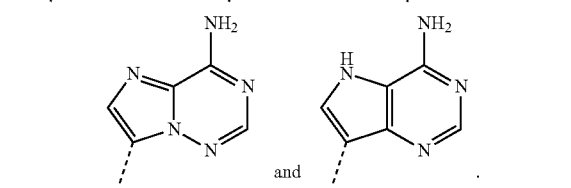

In some embodiments of the present disclosure, each of $R_1$ and $R_{1a}$ is independently selected from

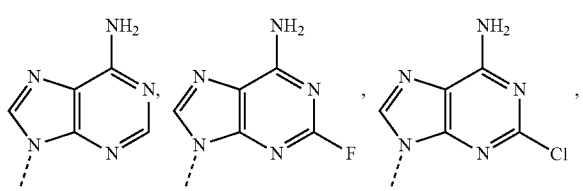

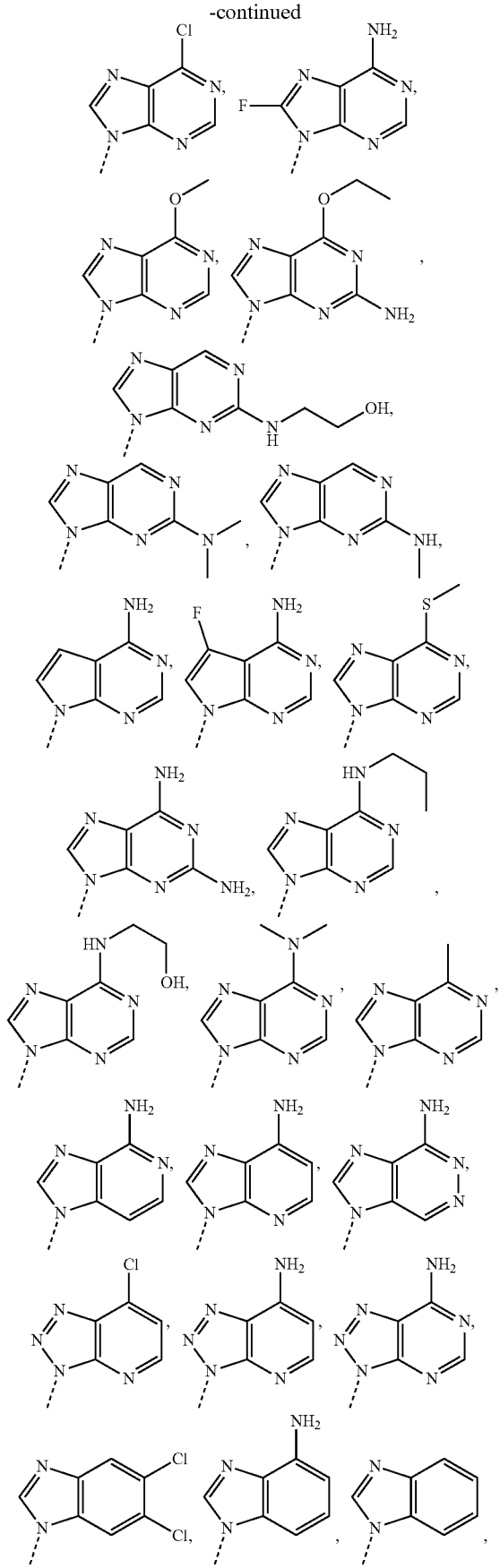
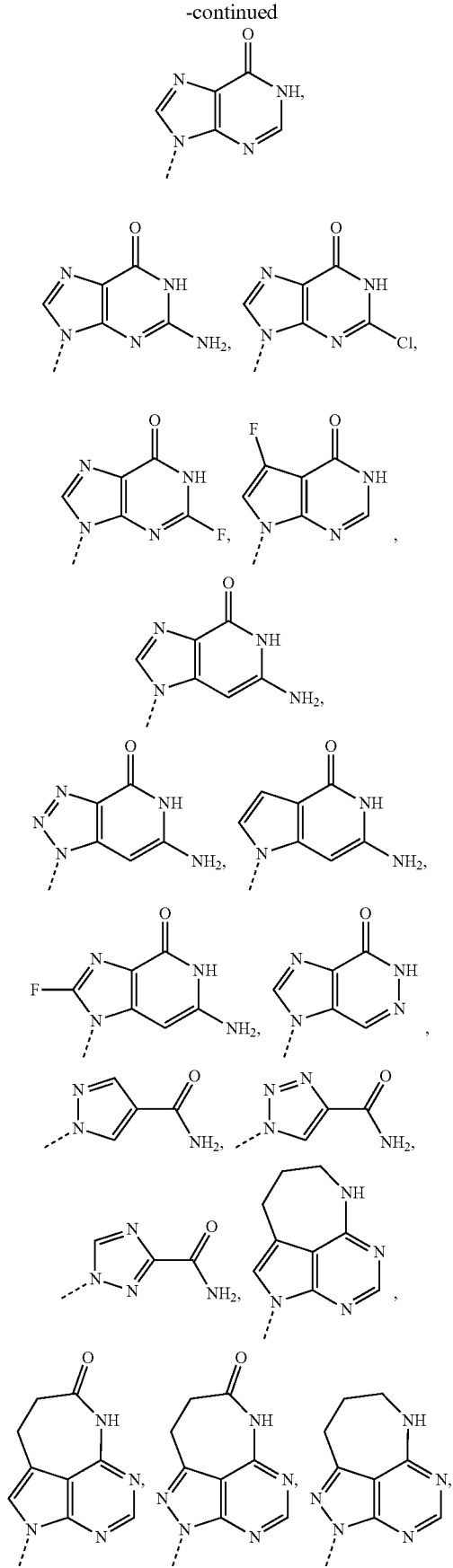

-continued

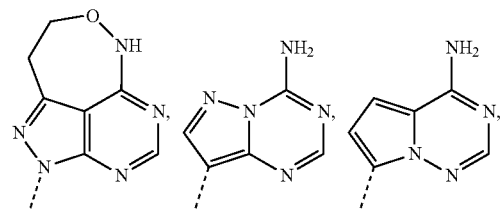

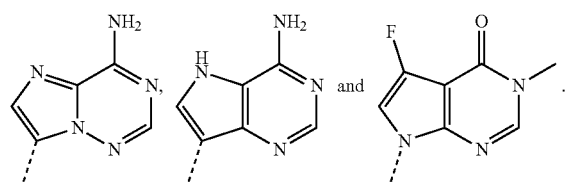

In some embodiments of the present disclosure, each of $R_2$, $R_{2a}$, $R_3$, $R_{3a}$, $R_5$, $R_{5a}$, $R_6$ and $R_{6a}$ is independently H.

In some embodiments of the present disclosure, each of $R_4$ and $R_{4a}$ is independently selected from F, OH, $NH_2$, $N_3$ and

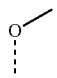

In some embodiments of the present disclosure, each of $R_7$ and $R_{7a}$ is independently selected from H and $CH_3$.

In some embodiments of the present disclosure, $R_4$ and $R_6$ are attached together, and the structure moiety

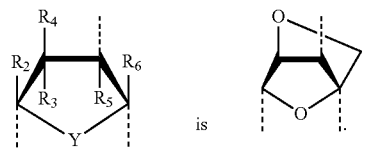

is

In some embodiments of the present disclosure, $R_{4a}$ and $R_{6a}$ are attached together, and the structure moiety

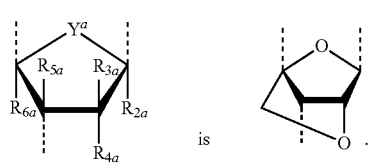

is

In some embodiments of the present disclosure, the compound, the optical isomer and the pharmaceutically acceptable salt thereof, wherein the compound is selected from (I-1)

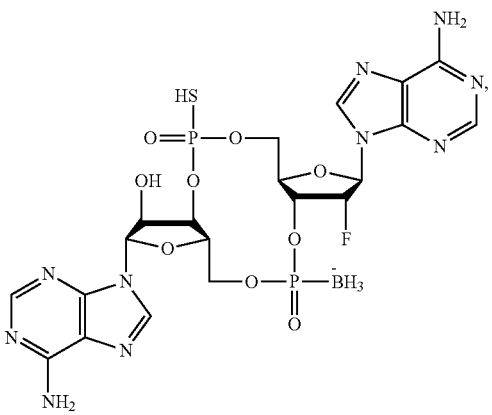

wherein, $R_1$, $R_{1a}$, $R_{4a}$, $R_7$, $R_{7a}$, $R_8$ and $R_{6a}$ are as defined in the present disclosure.

The present disclosure also provides a compound, an optical isomer and a pharmaceutically acceptable salt thereof, wherein the compound is selected from

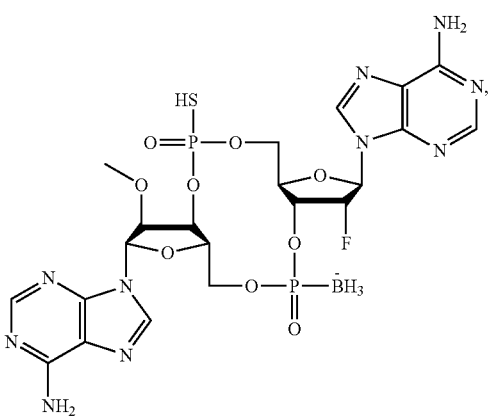

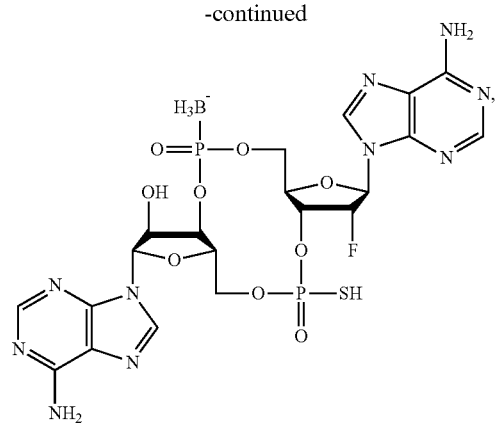
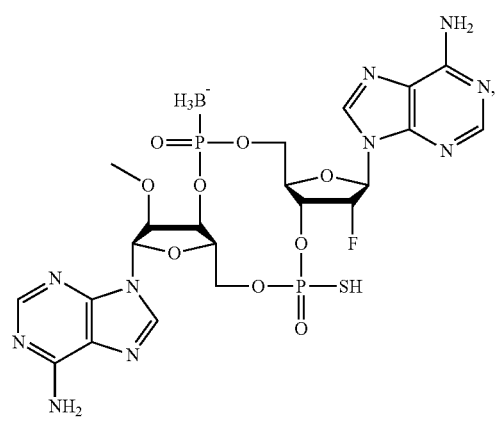
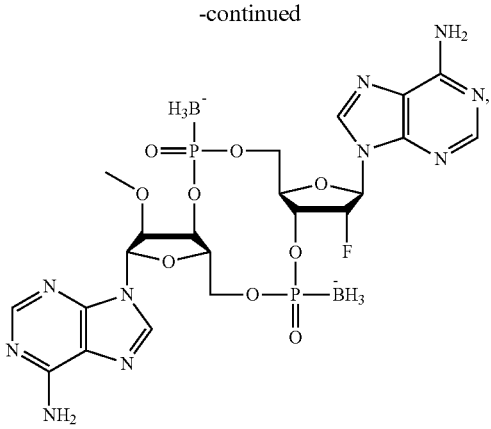
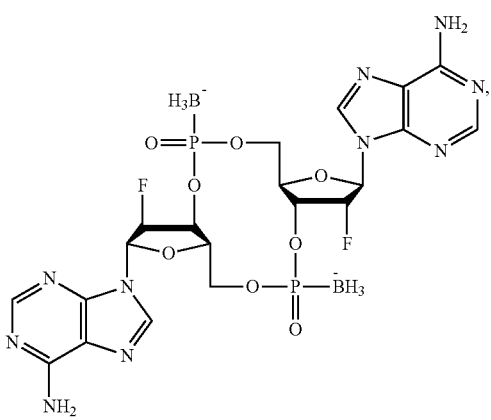
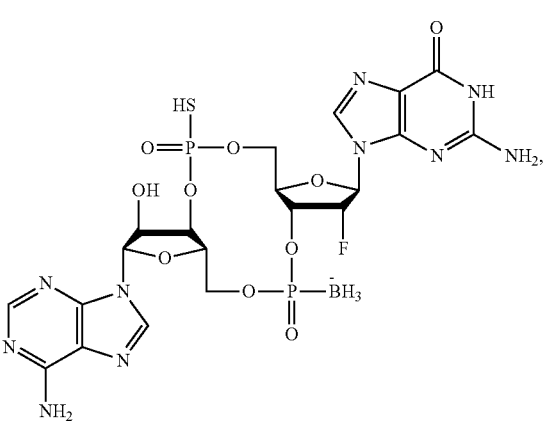
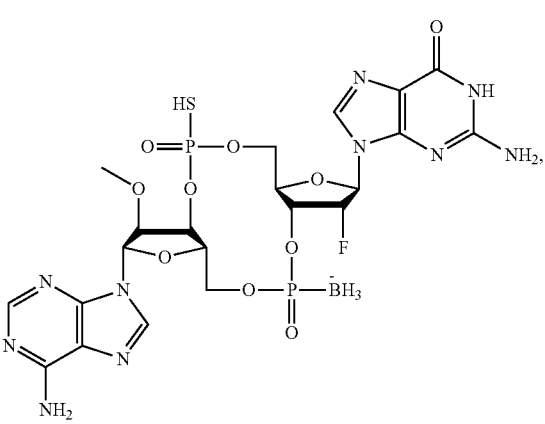

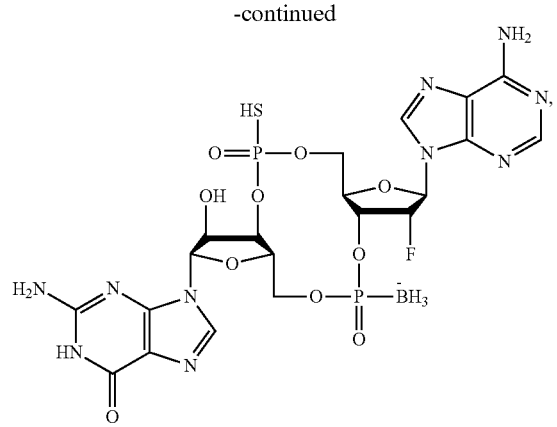
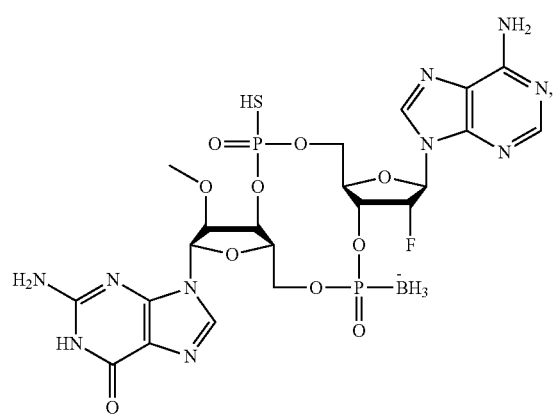
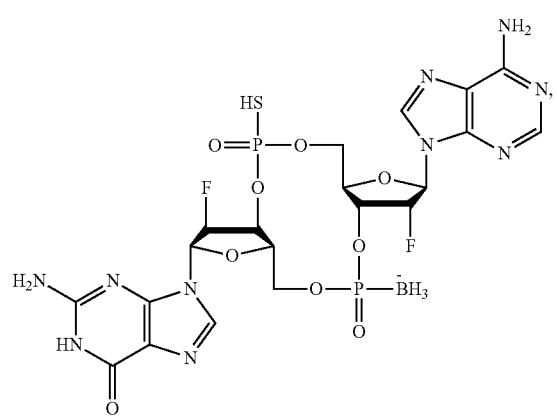
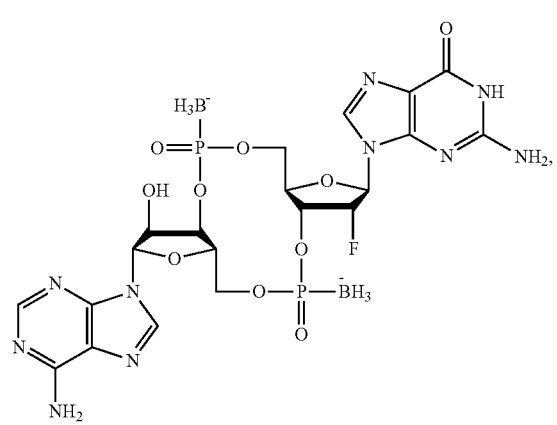
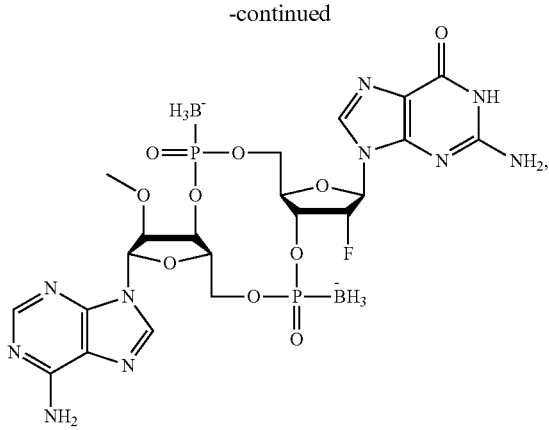
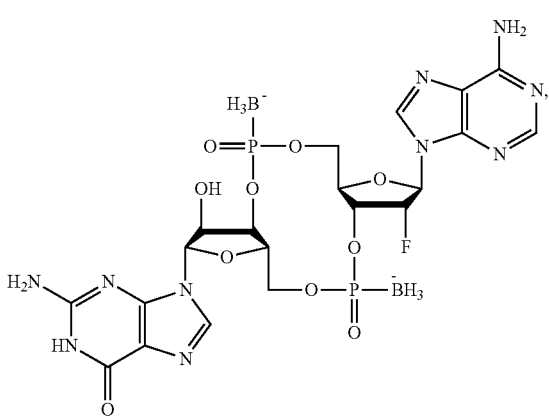
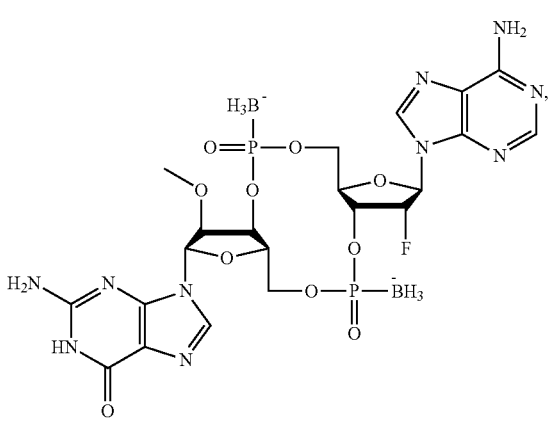
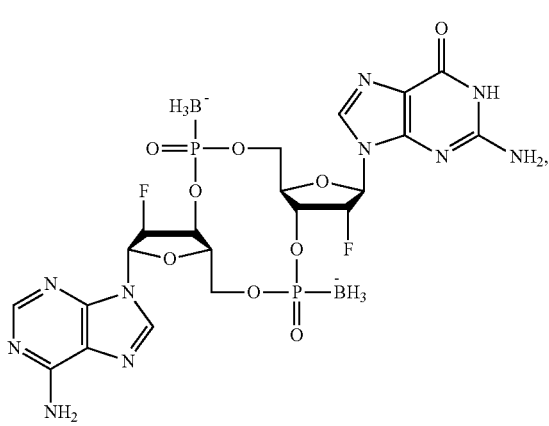

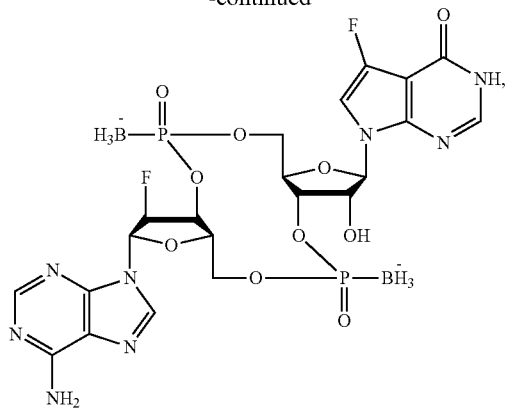
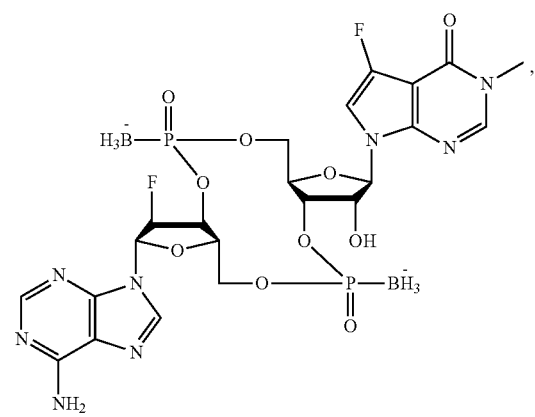
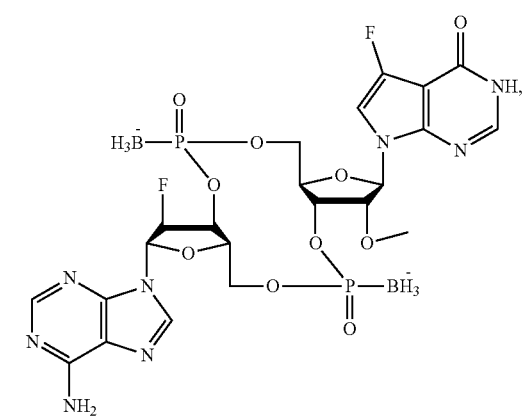
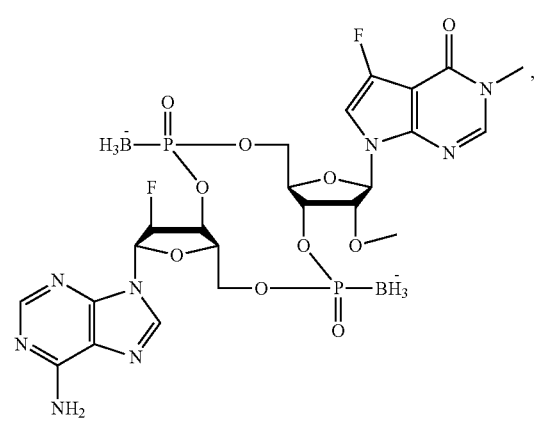
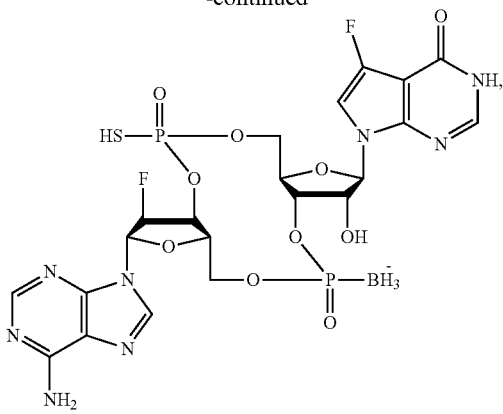
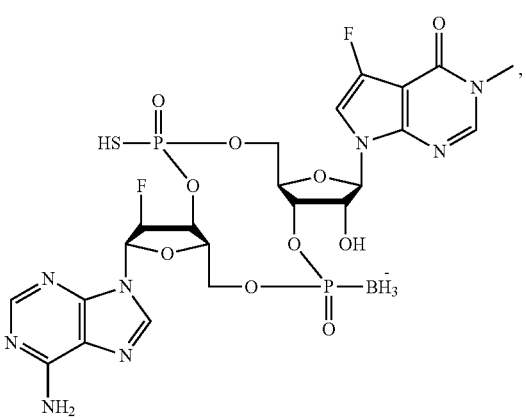
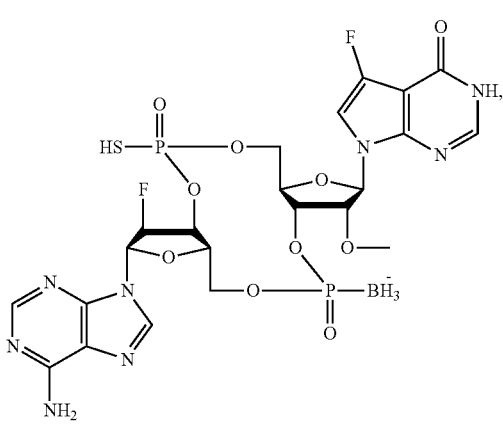
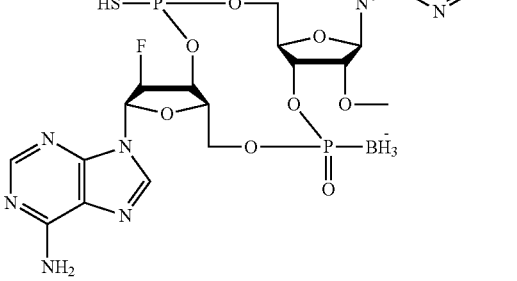

37
-continued
38
-continued
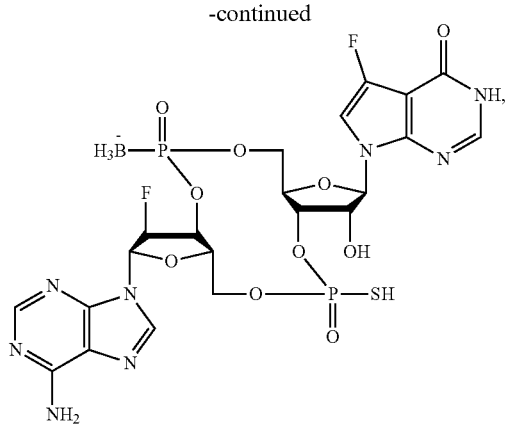
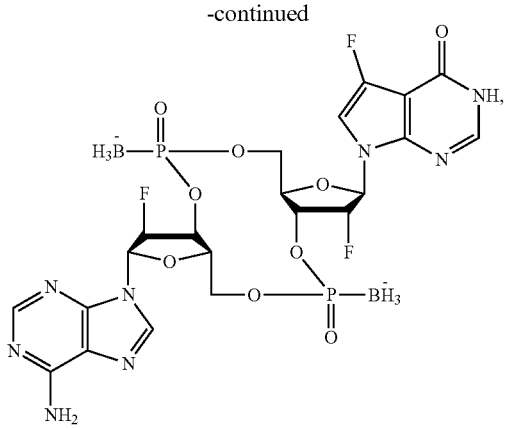

39
-continued
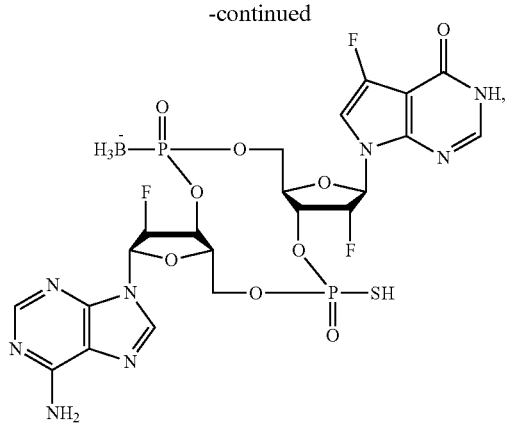
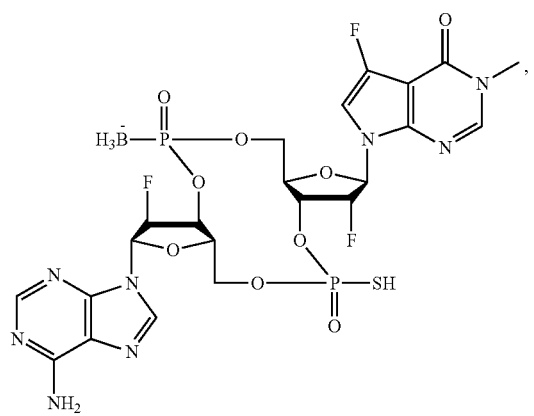
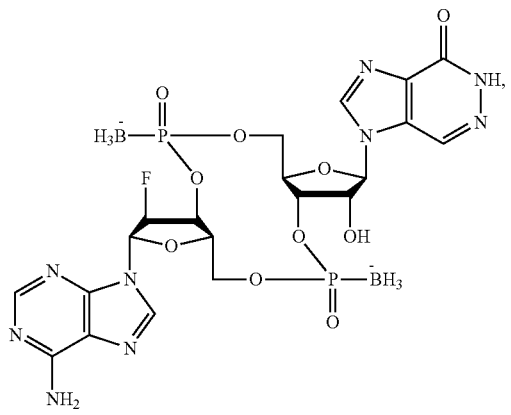
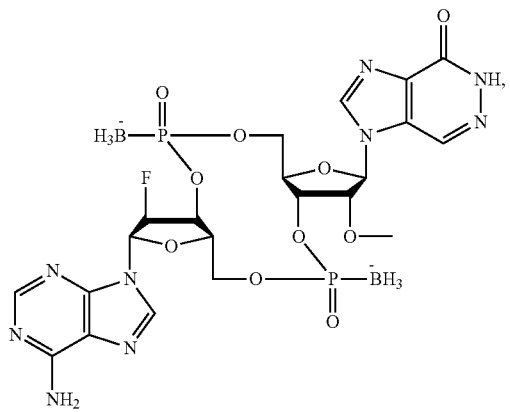
40
-continued
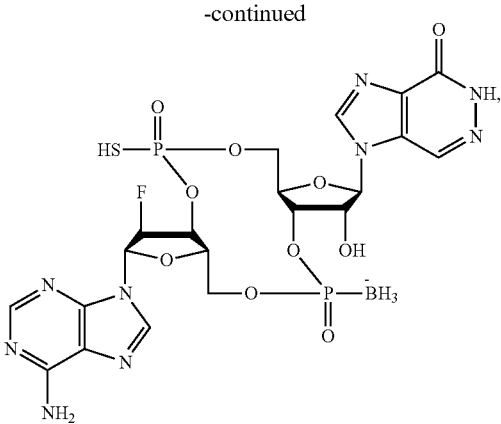
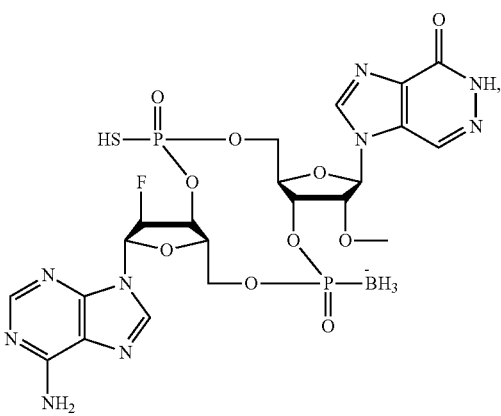
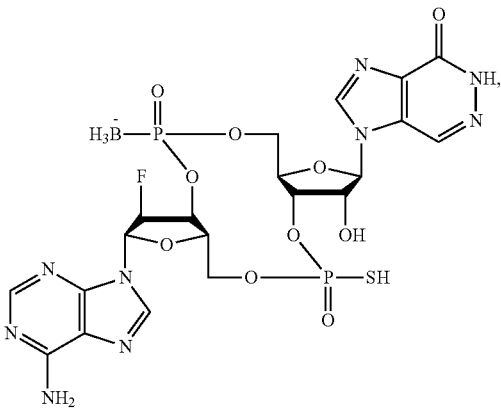
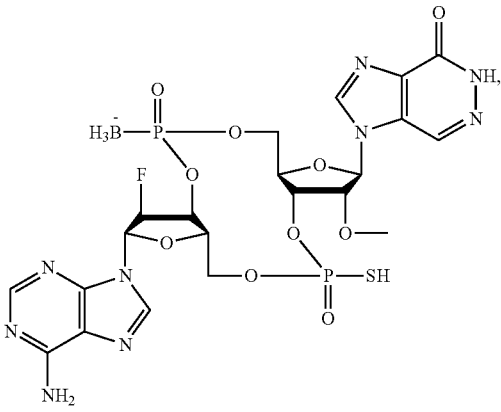

41
-continued
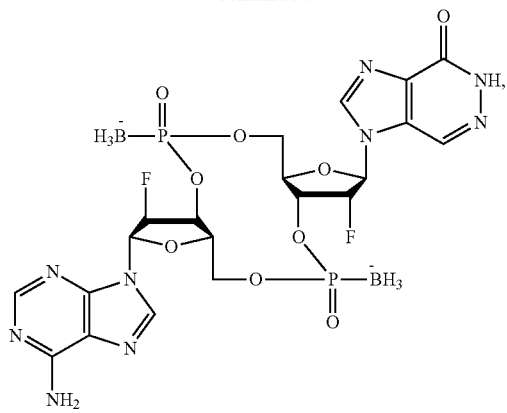
42
-continued
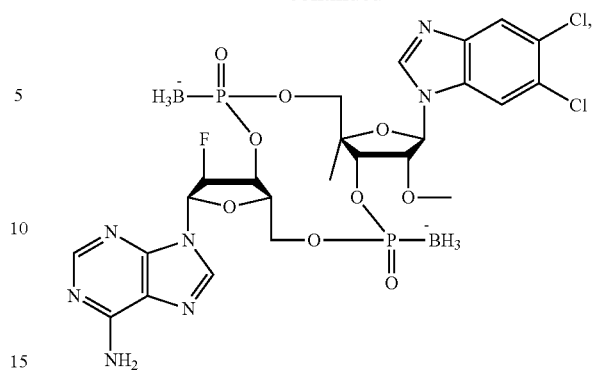
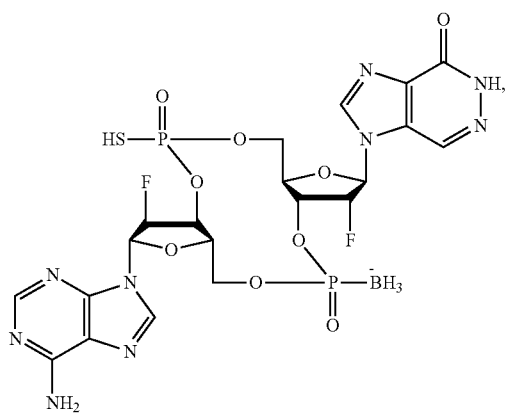
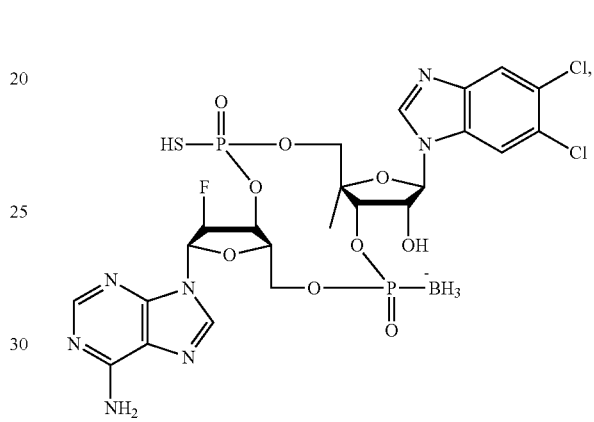
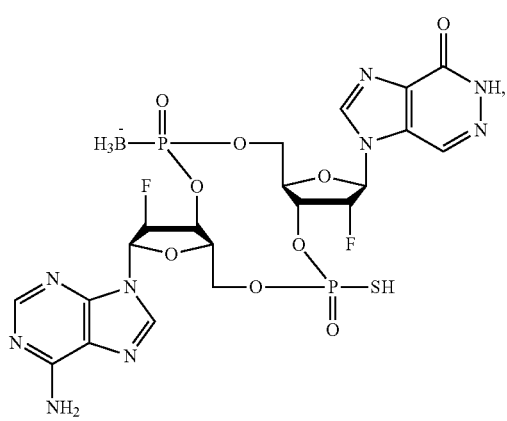
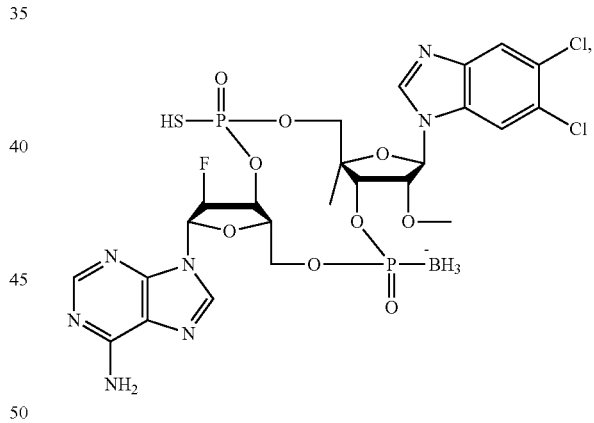
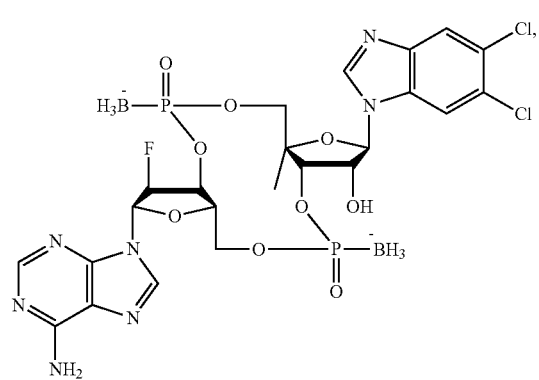

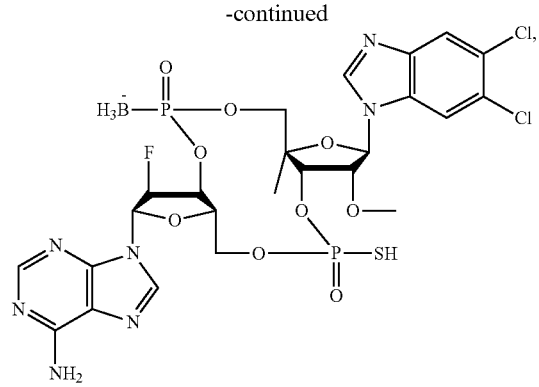
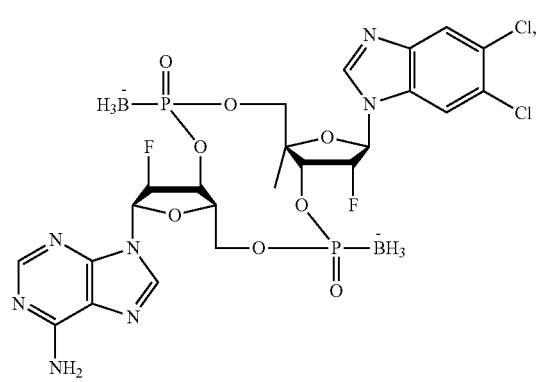

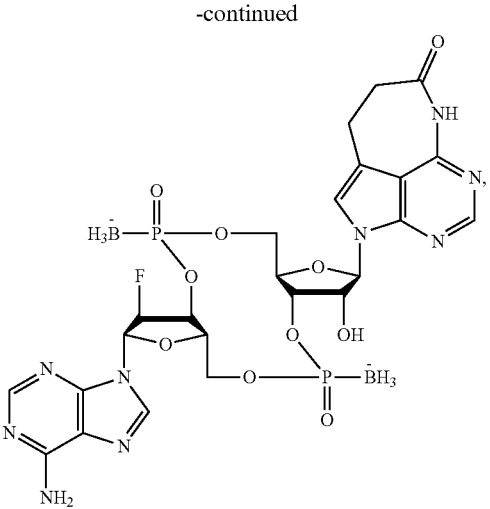
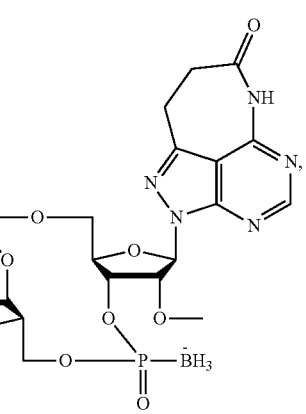
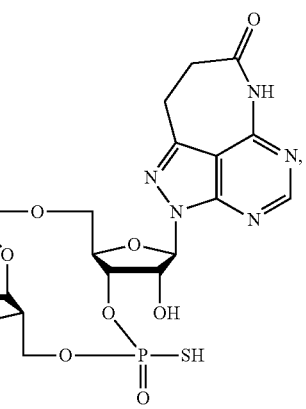

45
46
-continued
-continued
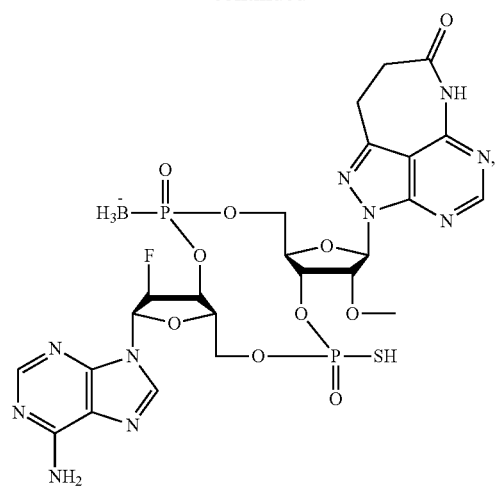
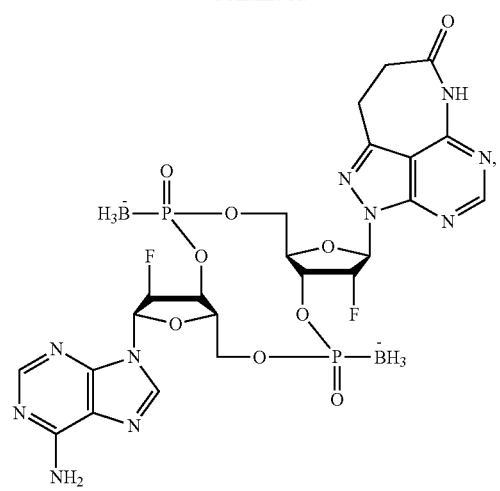
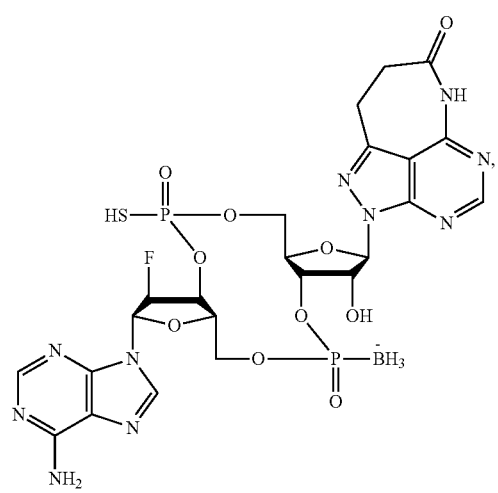
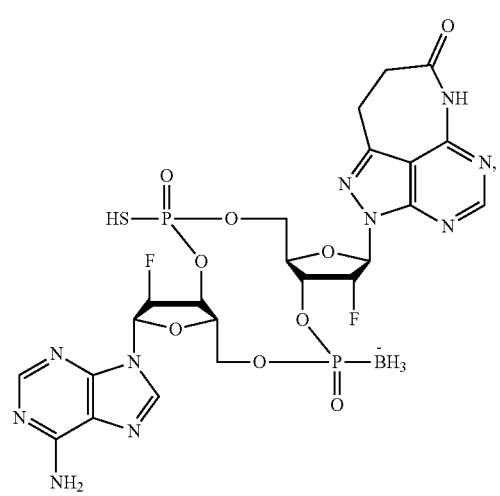
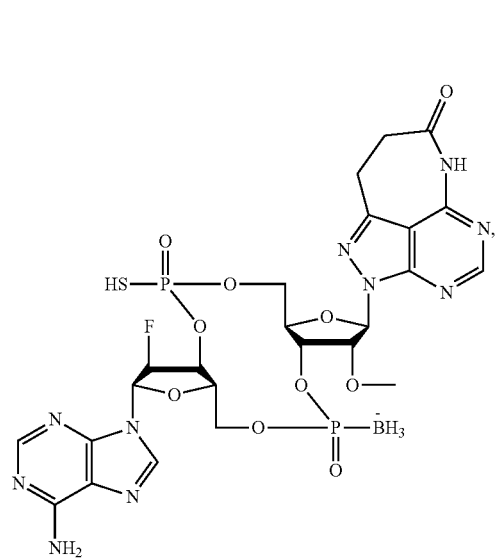
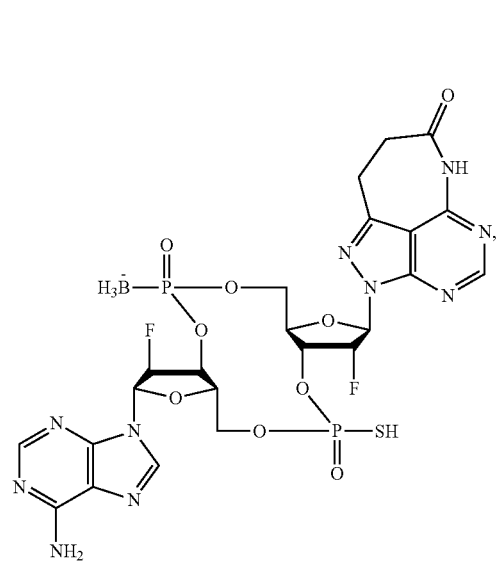

47
-continued
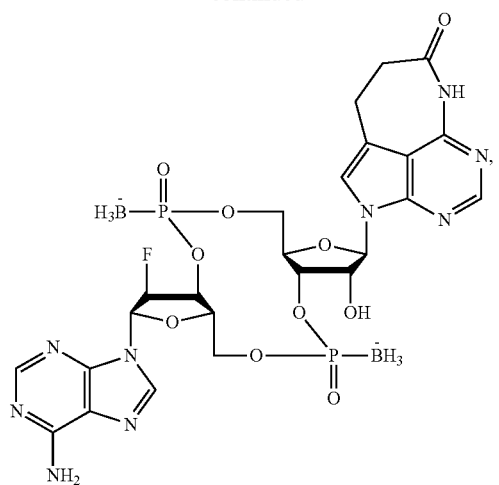
48
-continued
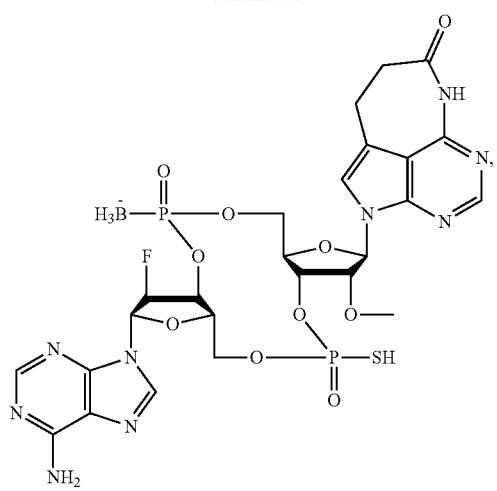
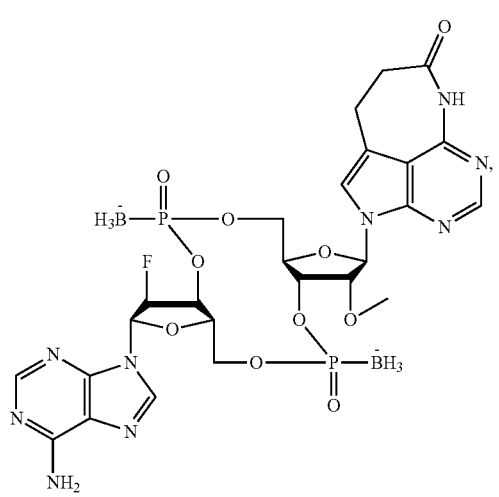
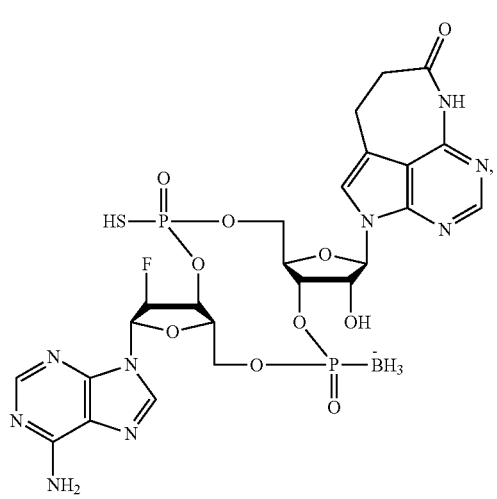
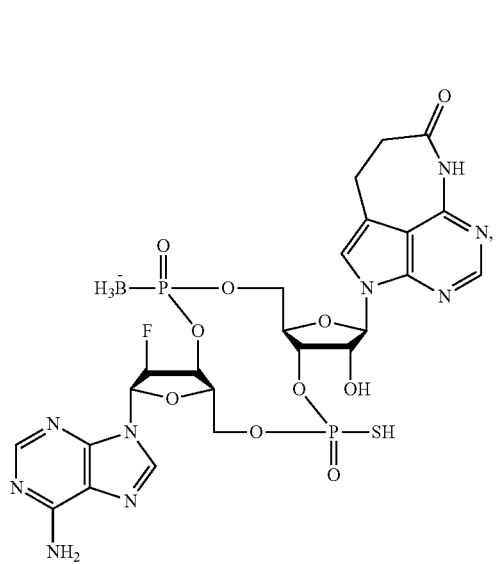
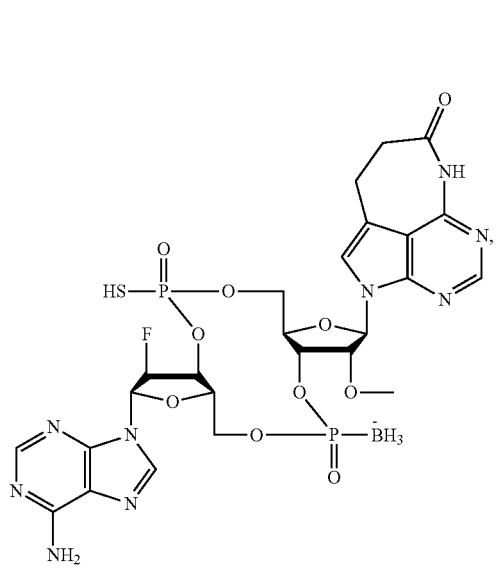

-continued
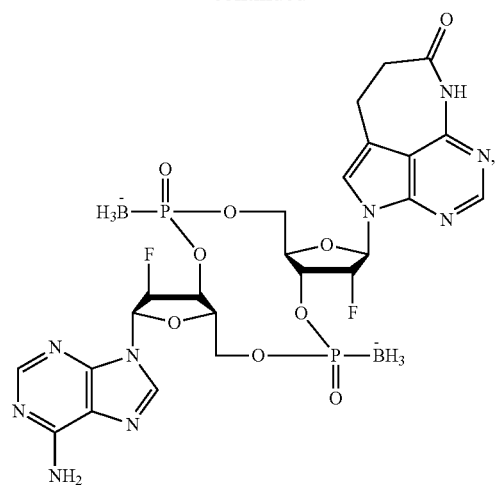
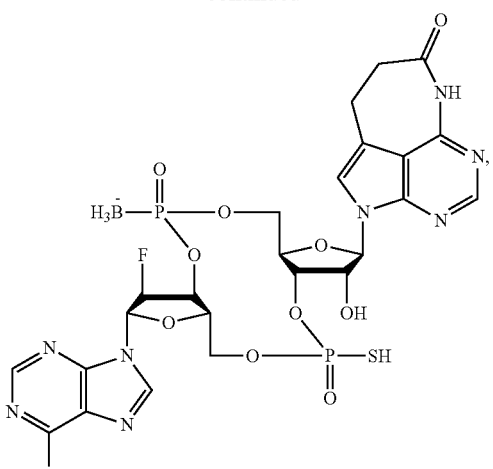
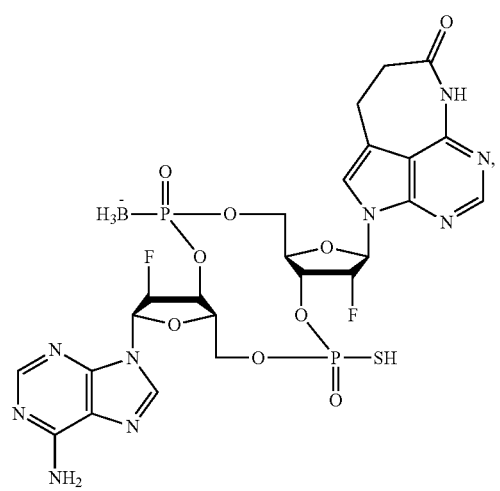
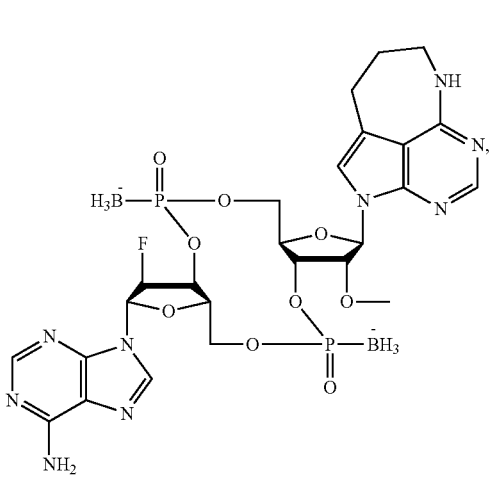
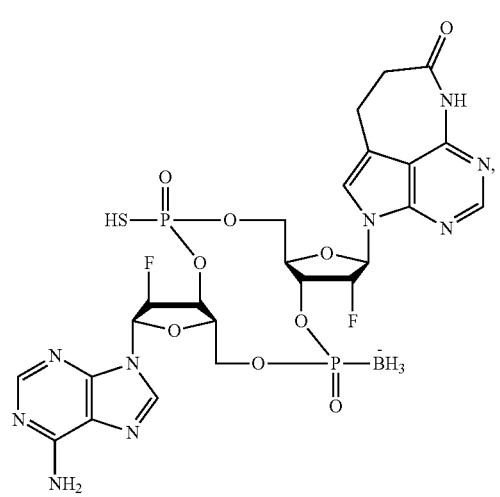
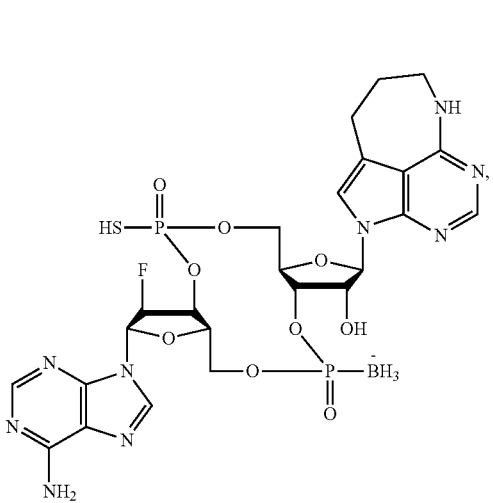

51
-continued
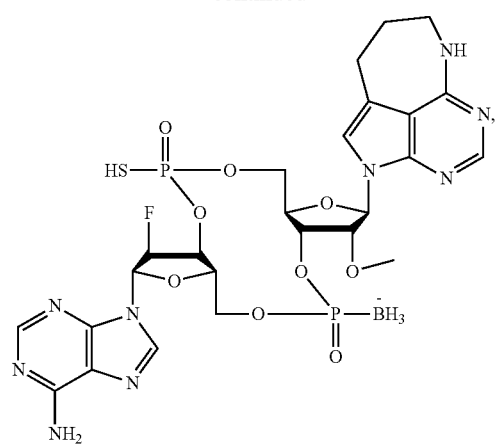
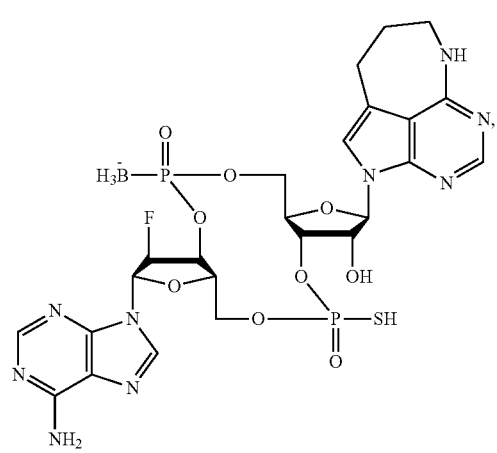
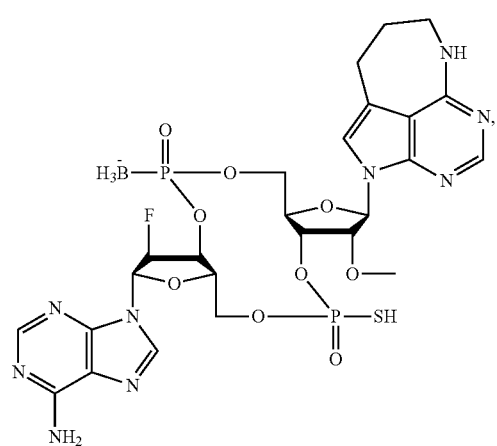
52
-continued
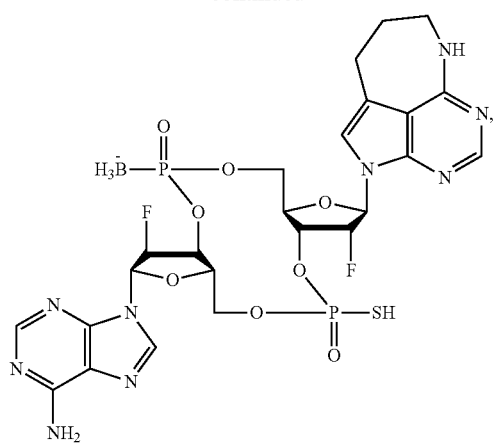
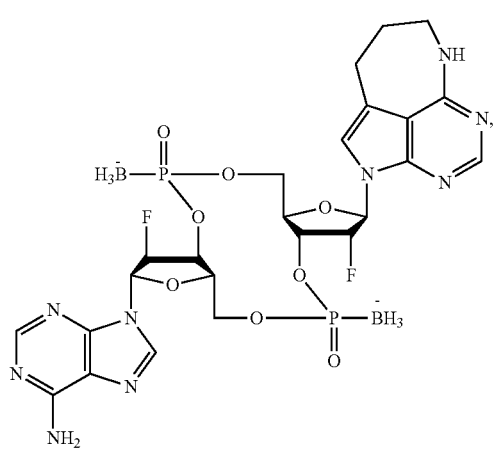
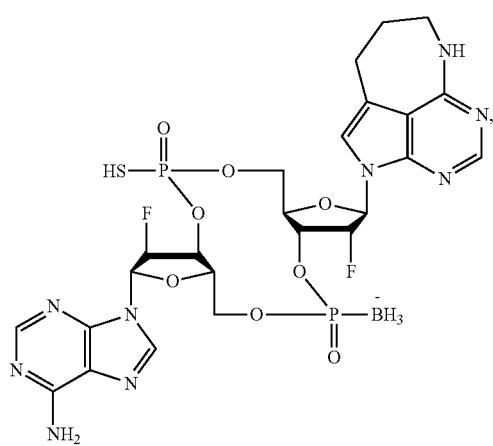

53
-continued
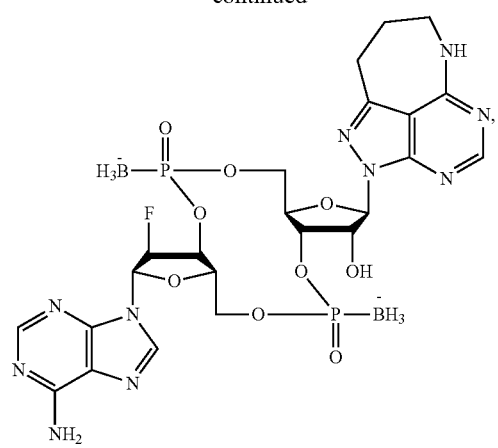
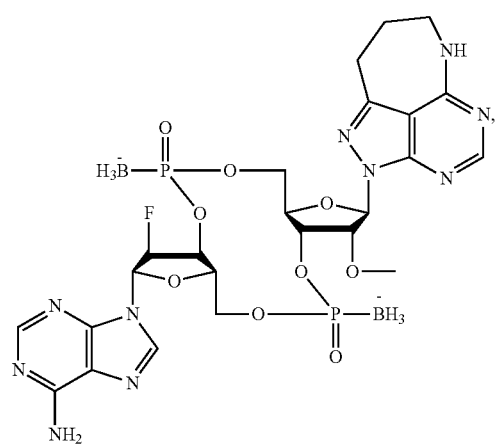
54
-continued
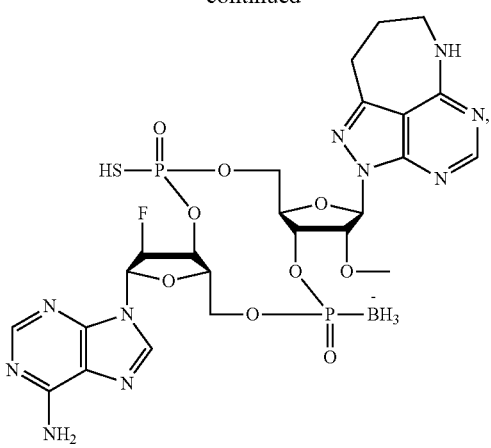
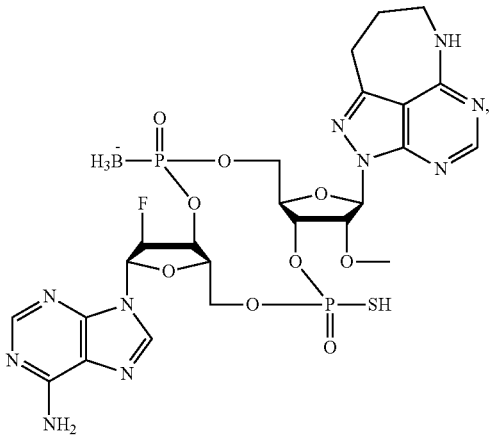

55
-continued
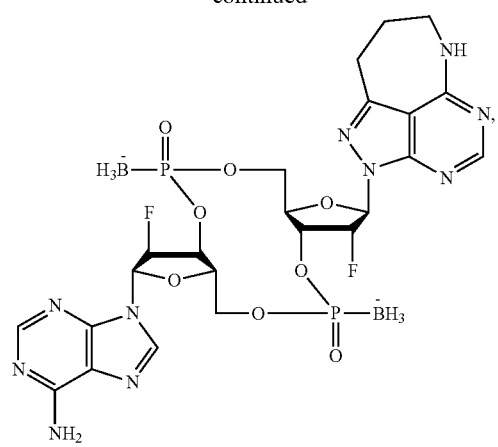
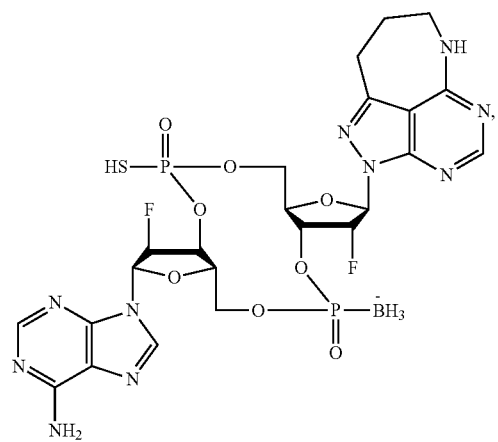
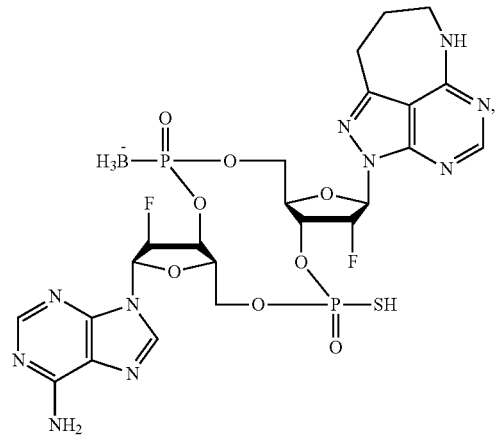
56
-continued
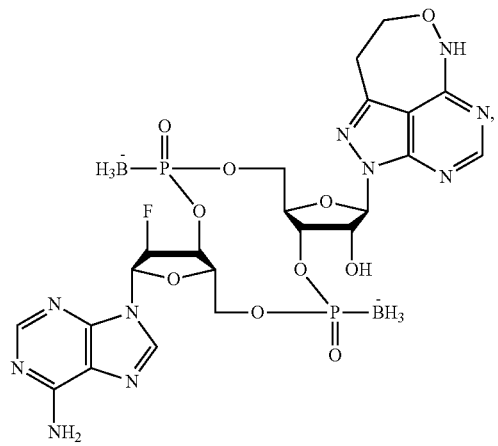
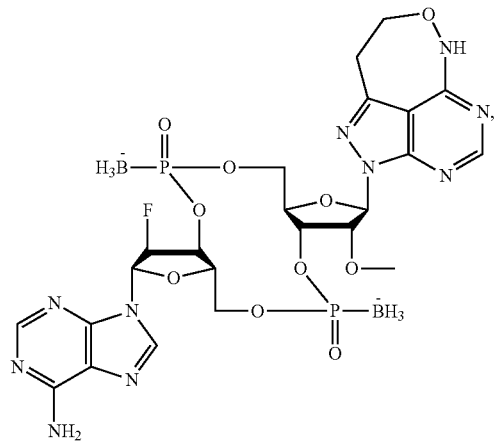
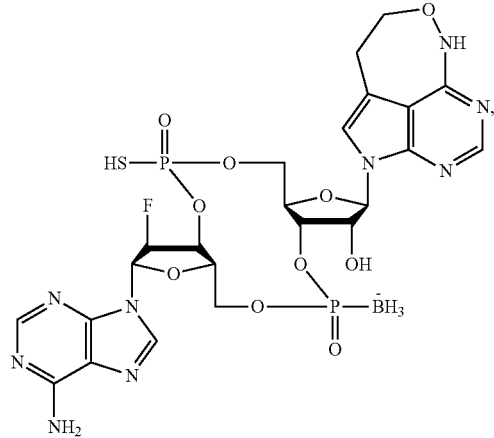

57
-continued
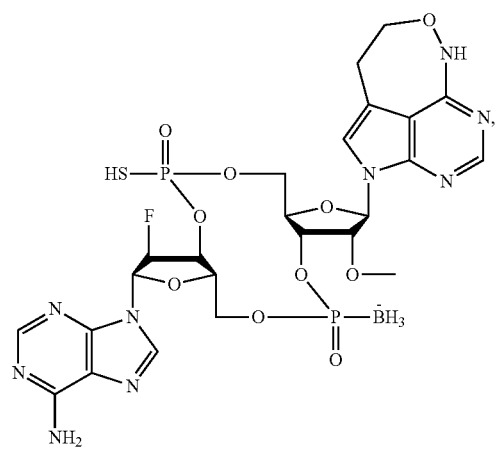
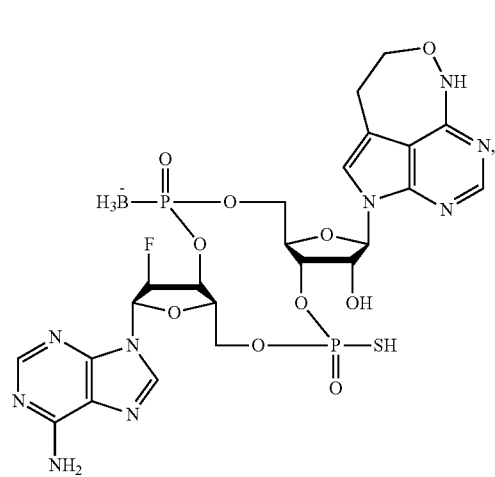
58
-continued
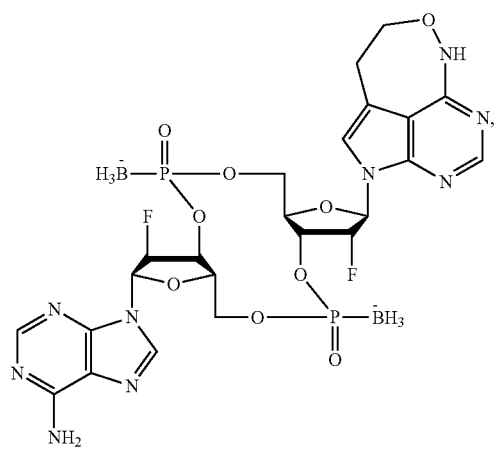
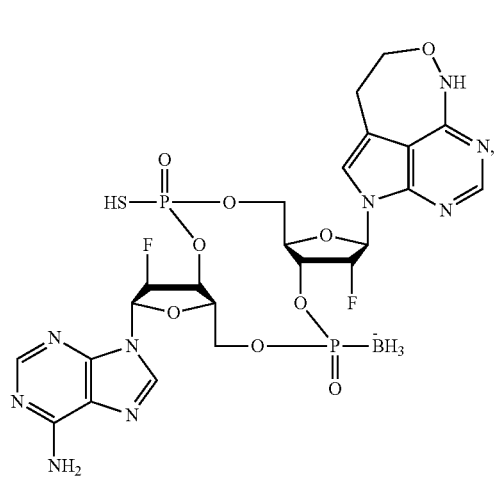
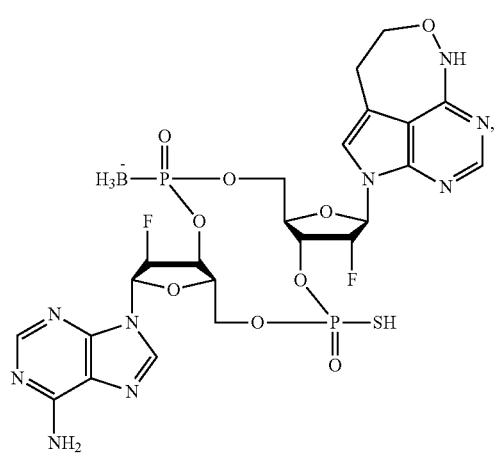

59
-continued
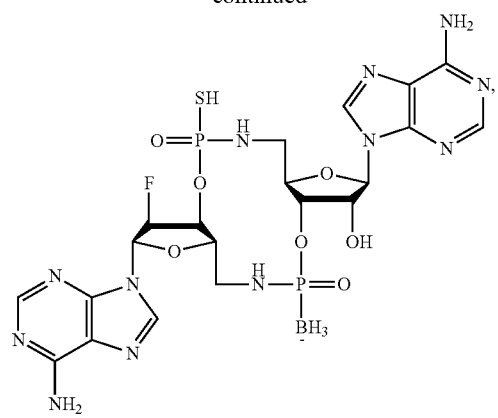
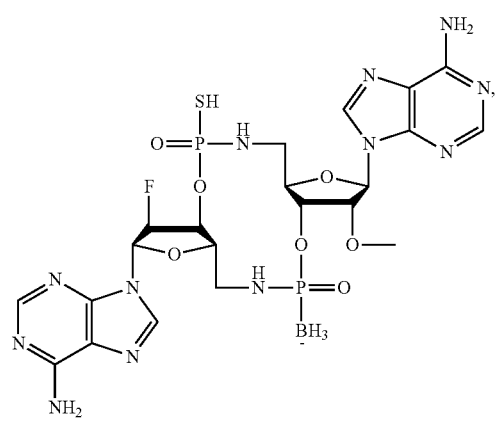
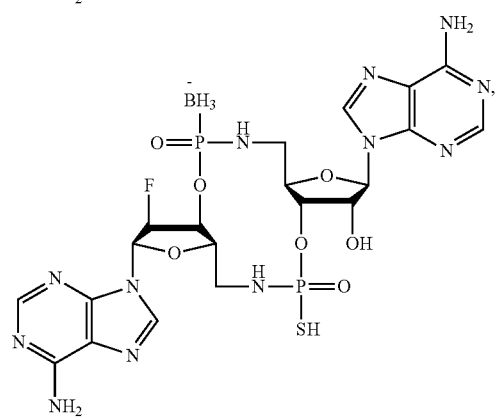
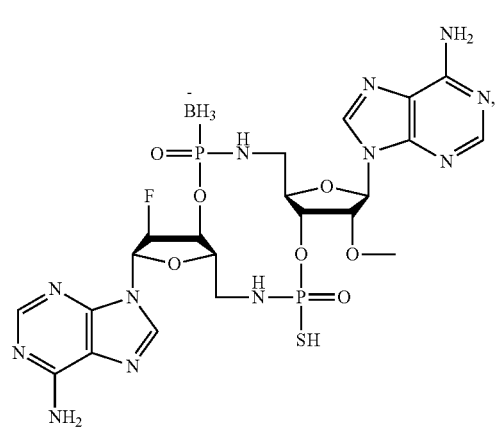
60
-continued
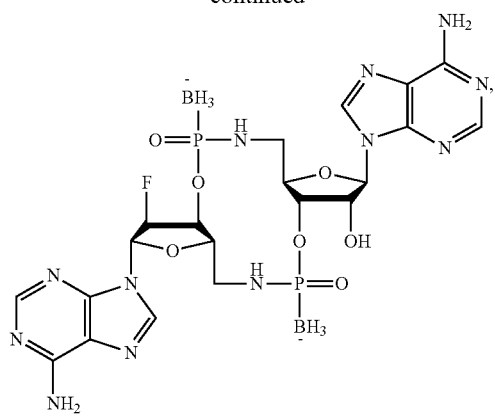
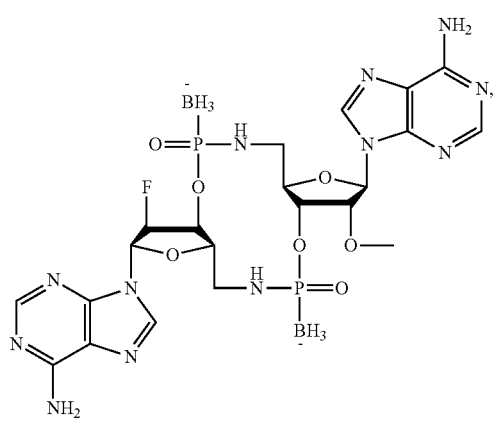
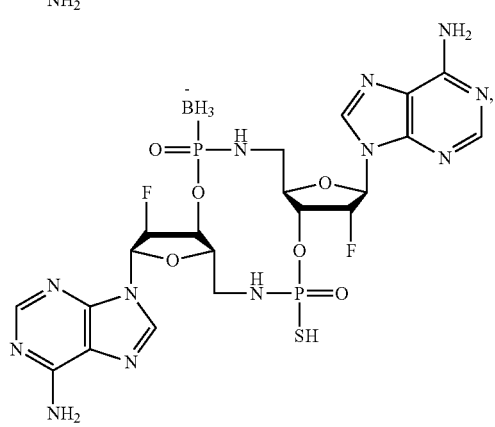
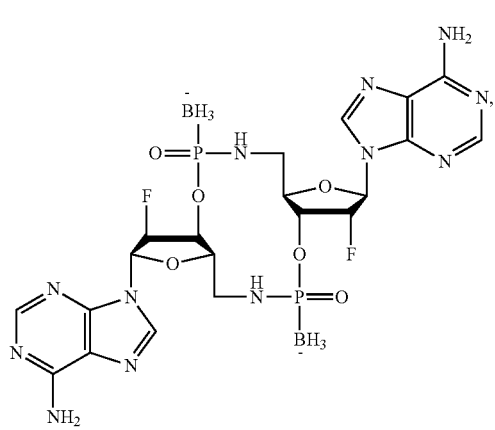

61
-continued
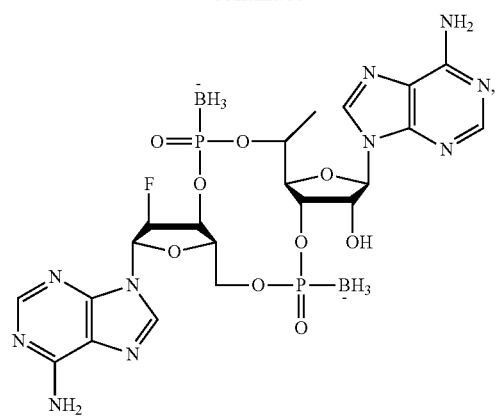
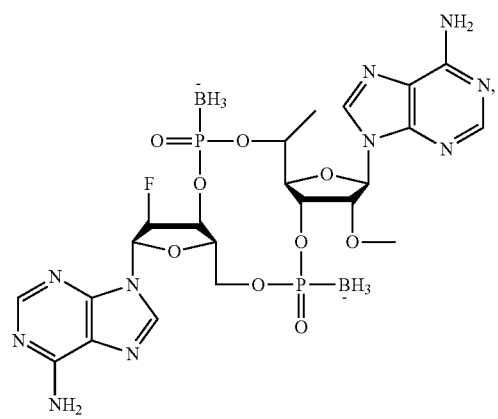
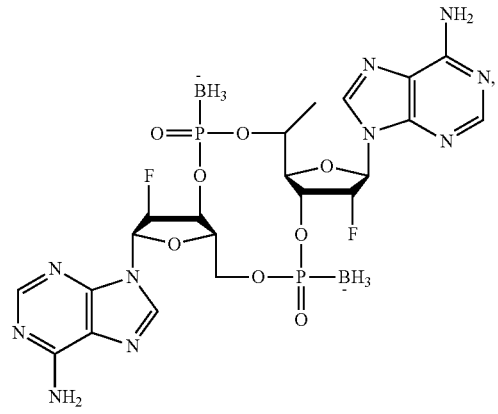
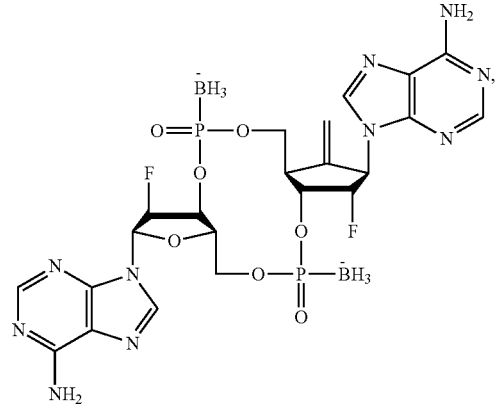
62
-continued
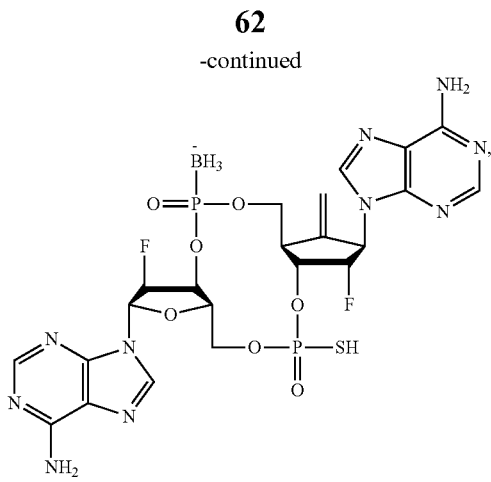
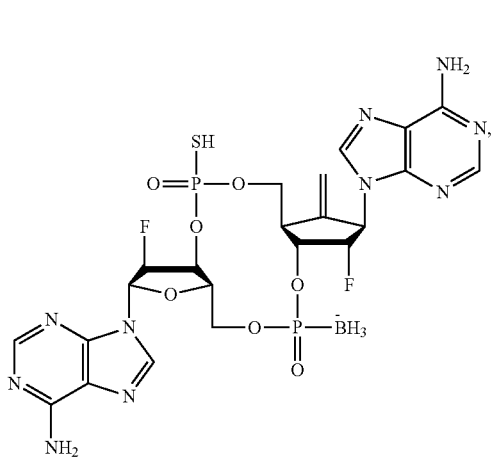
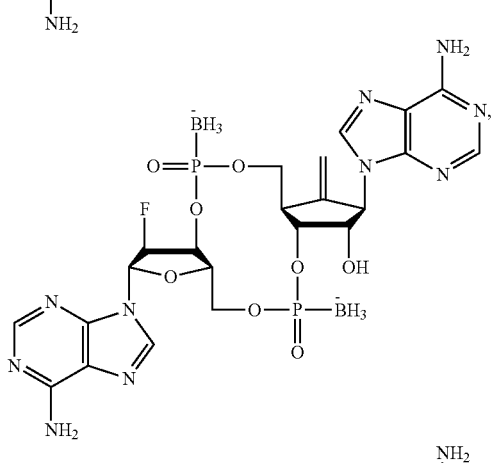
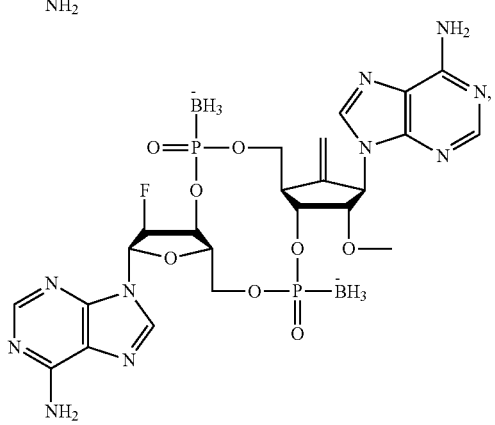

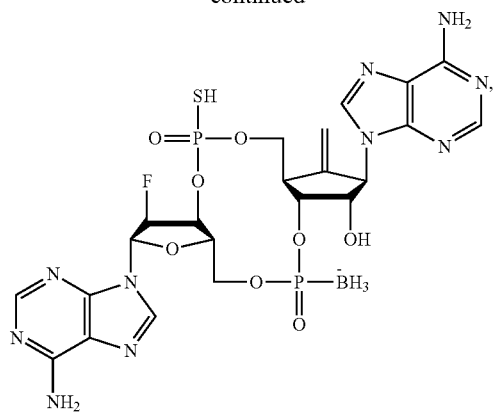
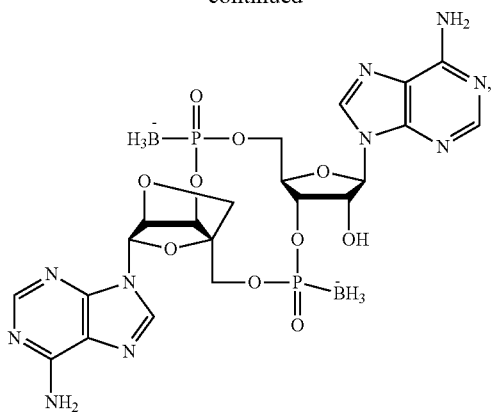
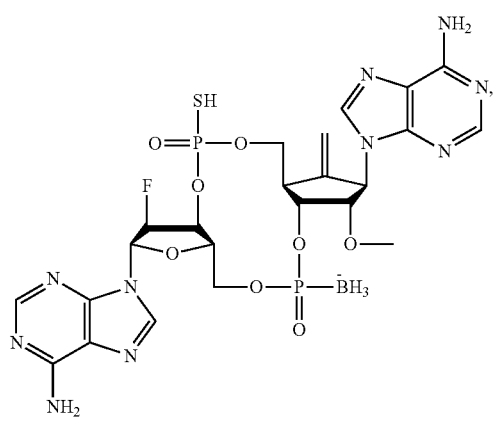
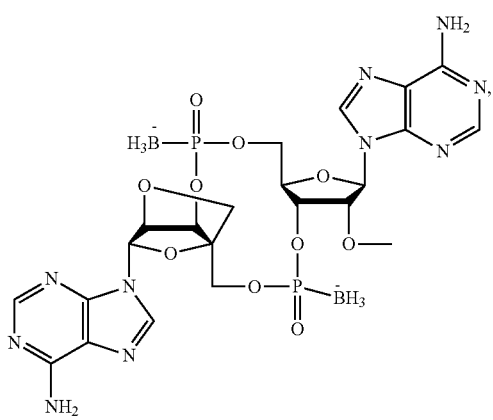
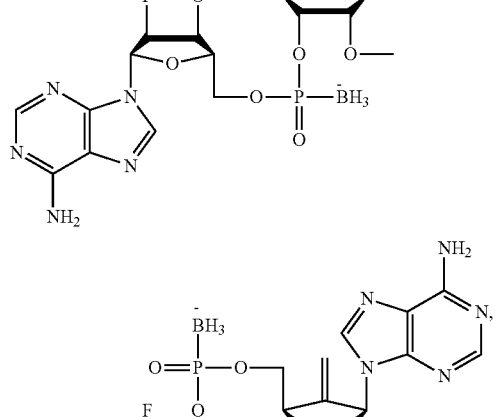
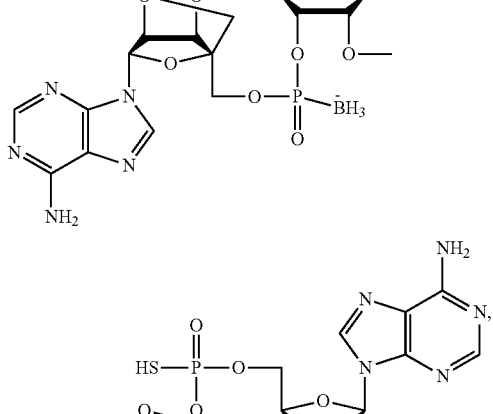
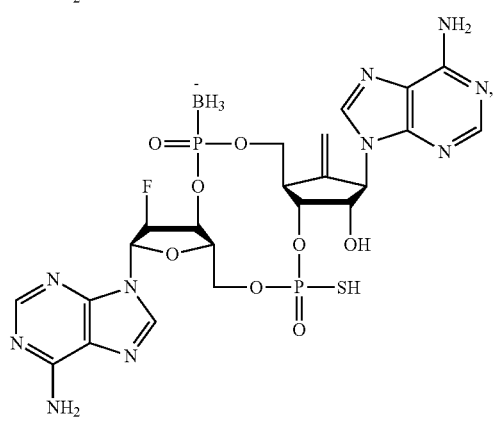
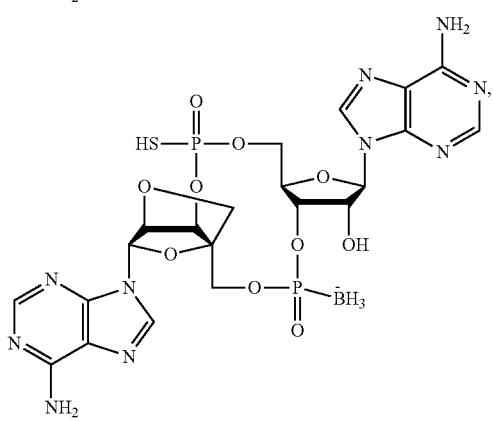
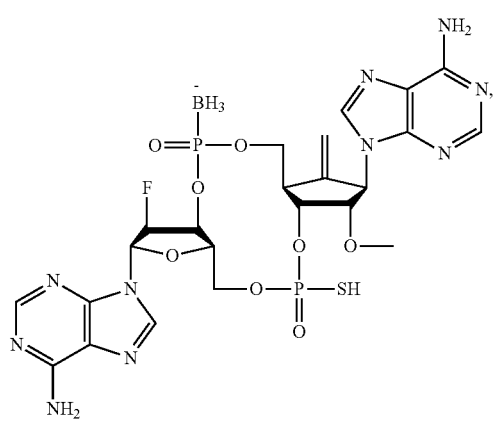
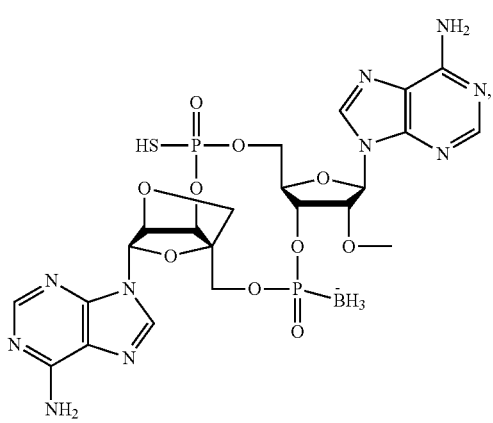

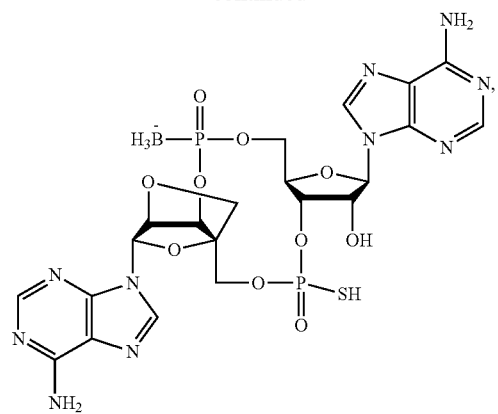
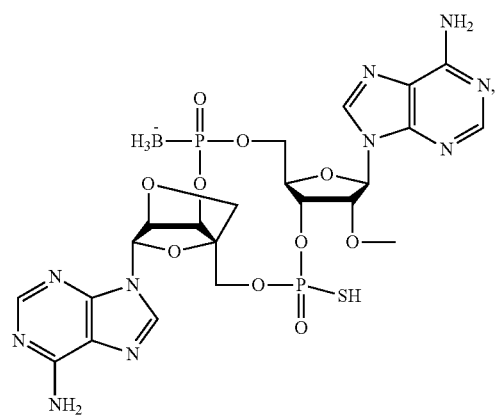
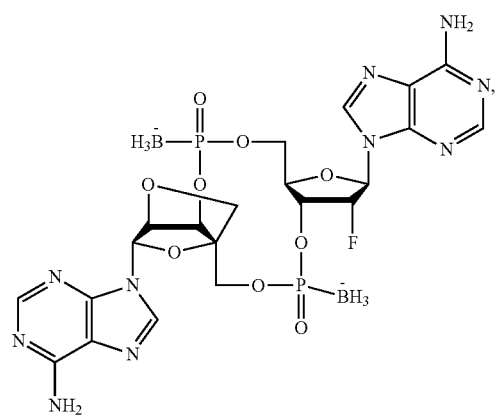
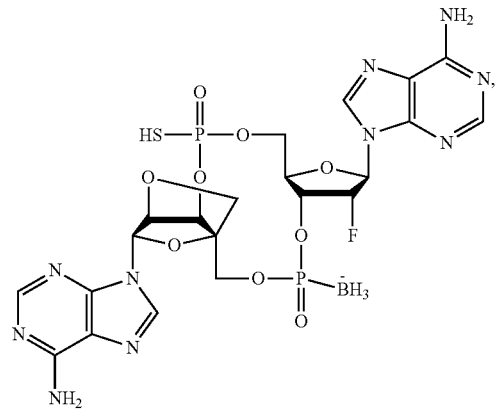
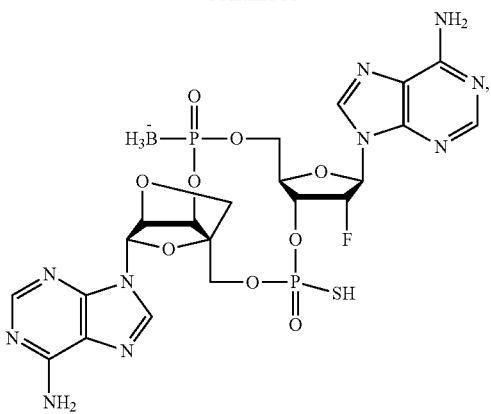
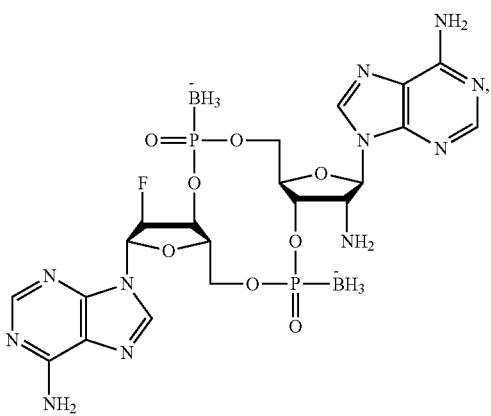
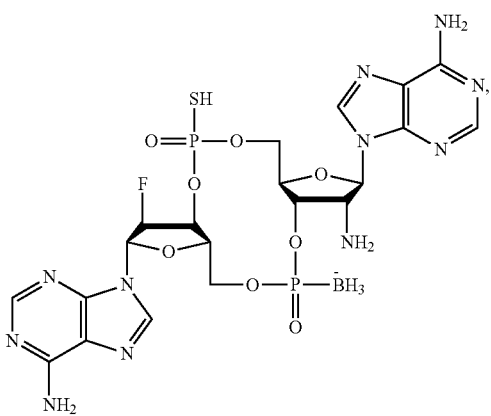
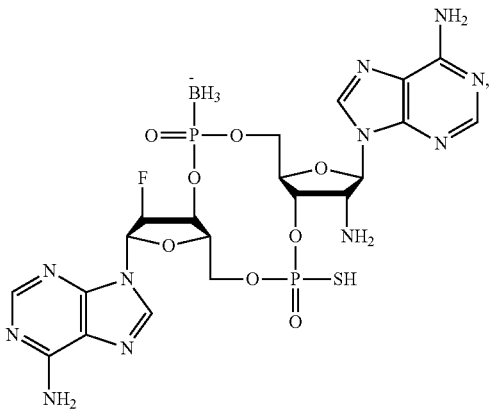

67
-continued
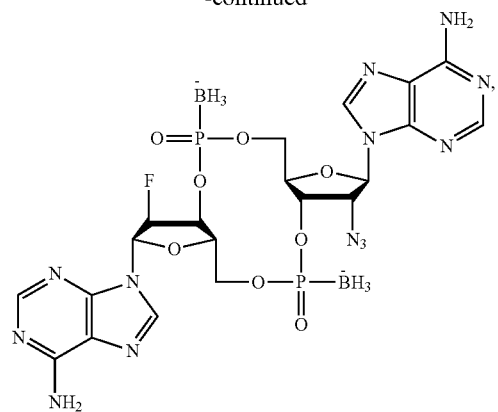
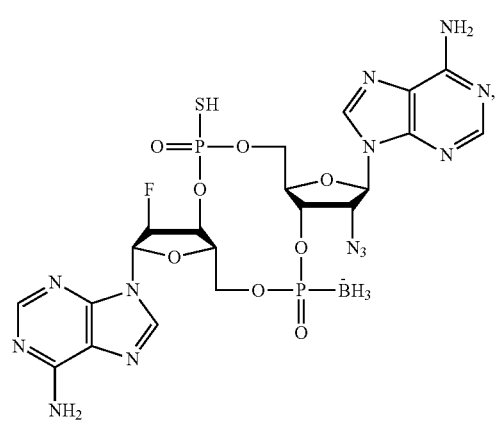
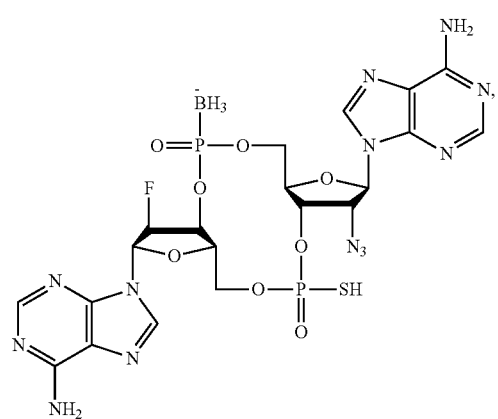
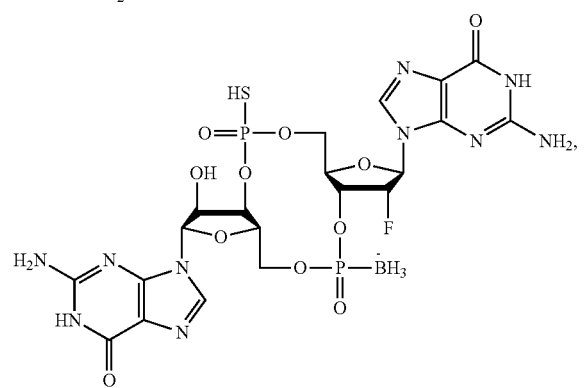
68
-continued
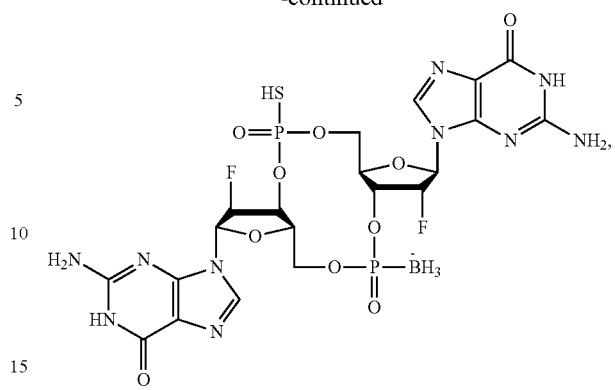
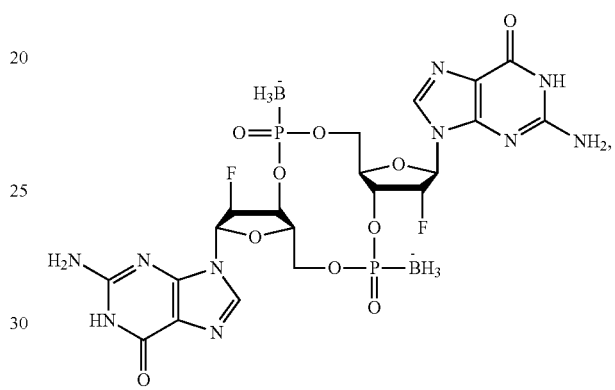
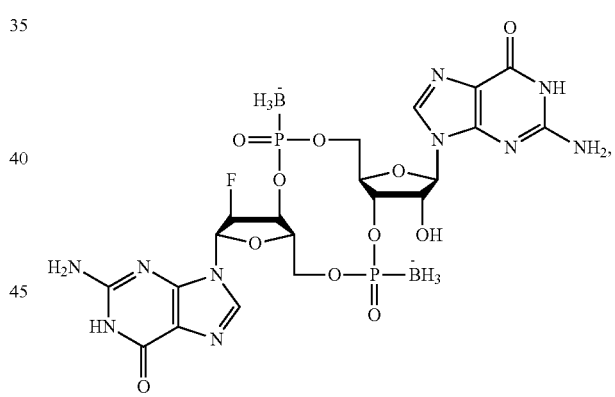
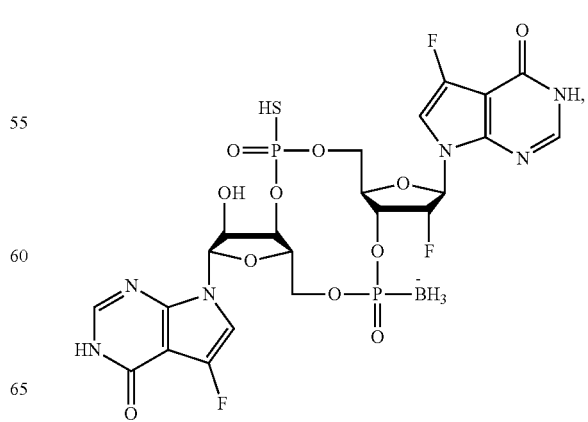

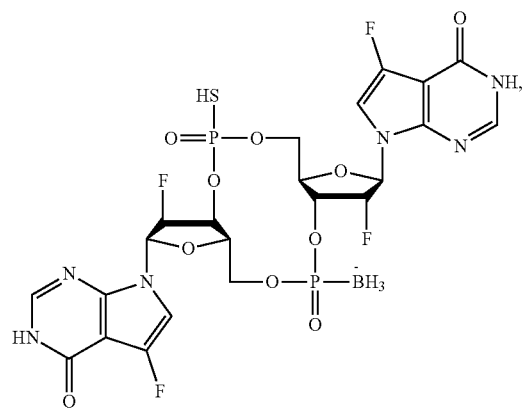
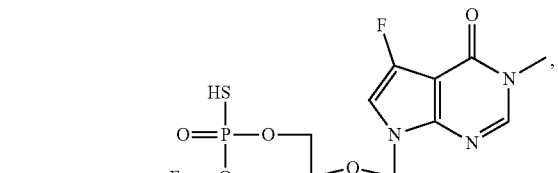
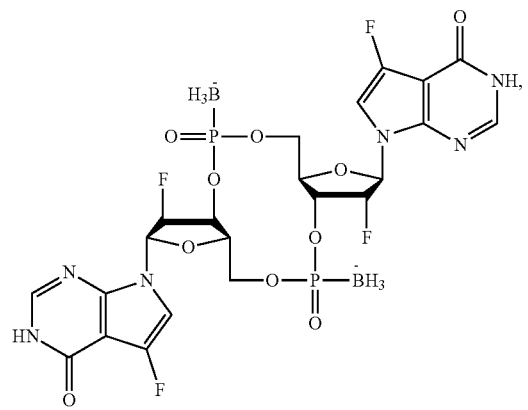
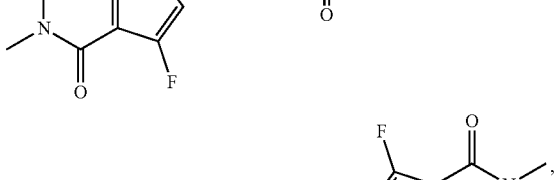
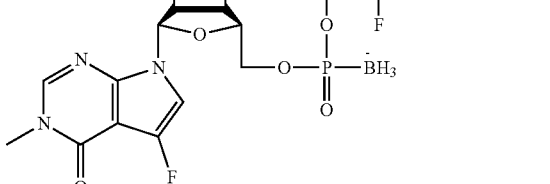
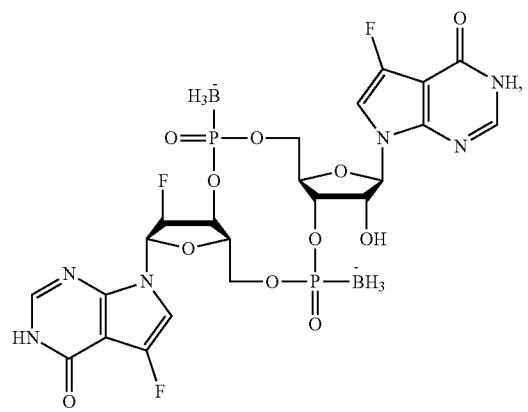
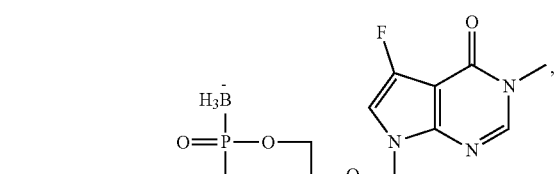
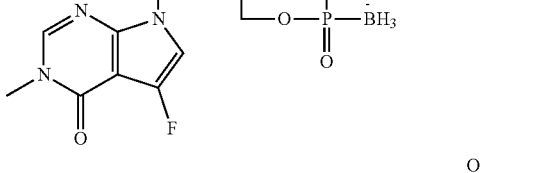
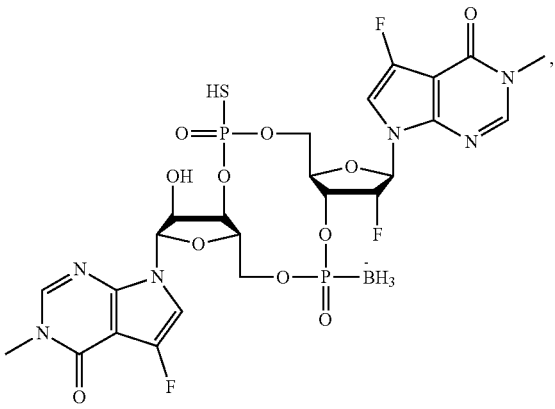
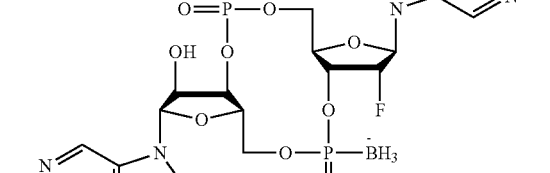
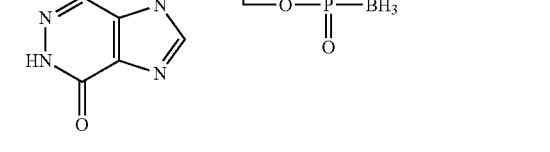

71
-continued
72
-continued
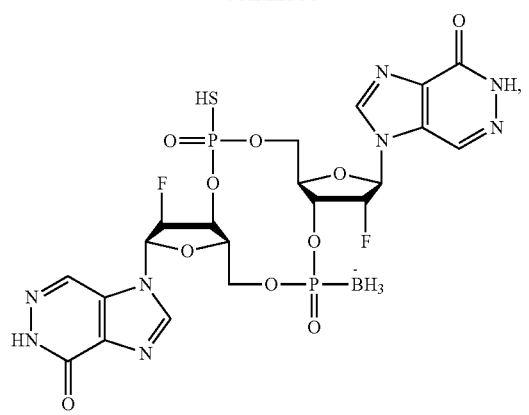
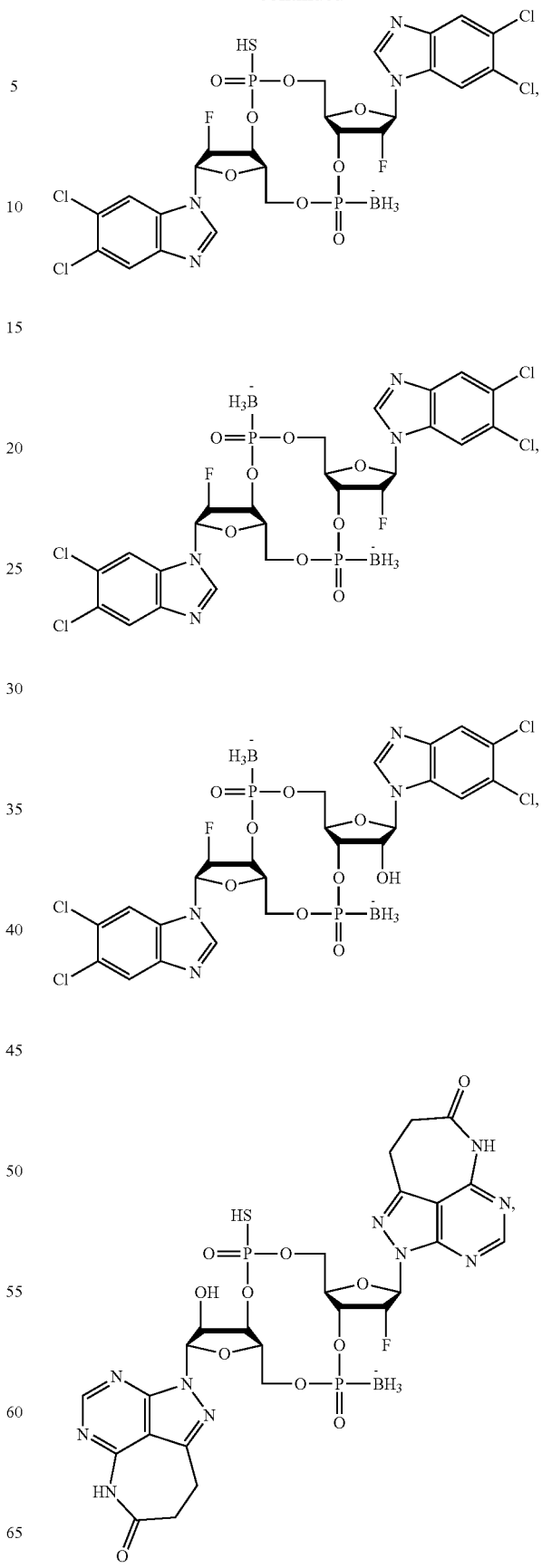

73
-continued
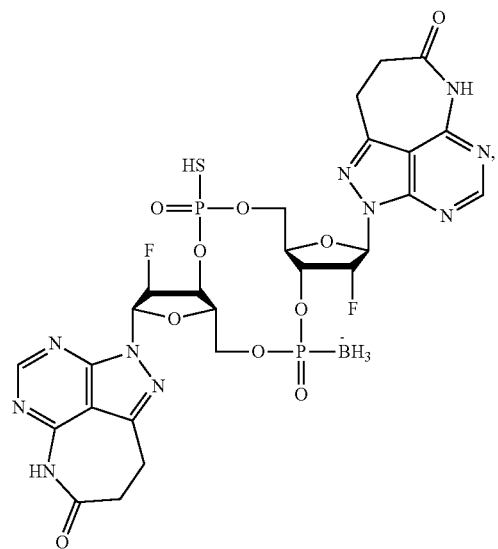
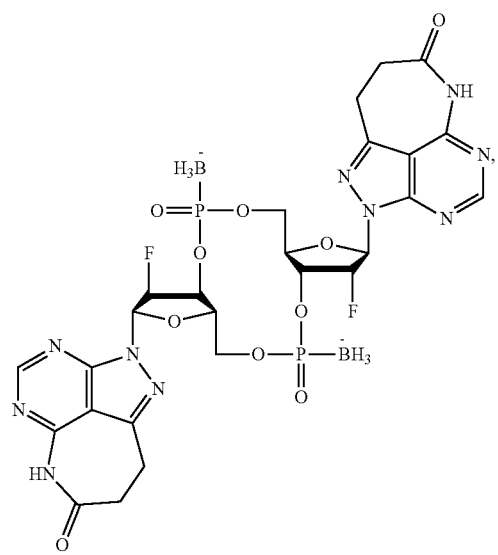
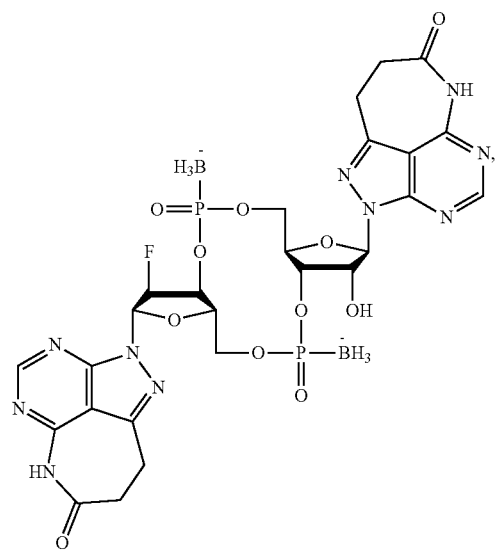
74
-continued
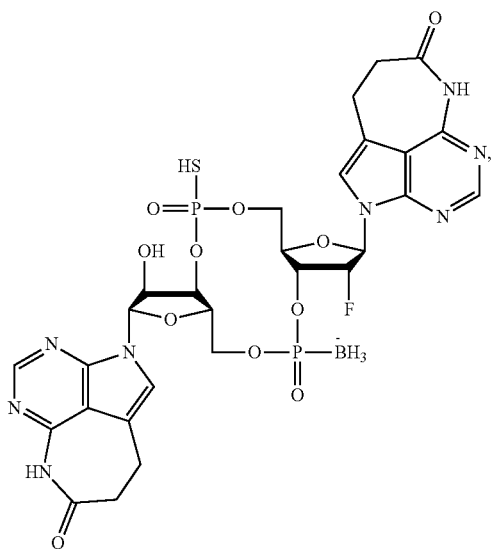
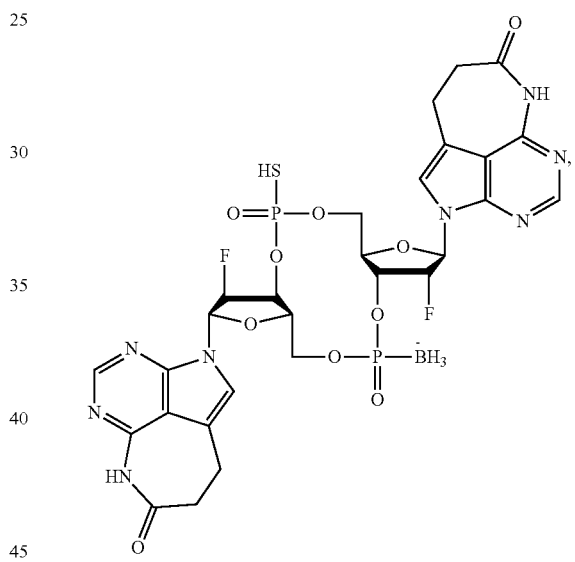
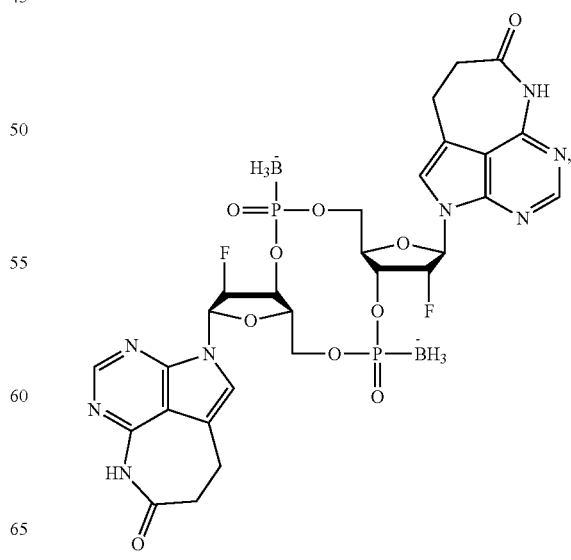

75
-continued
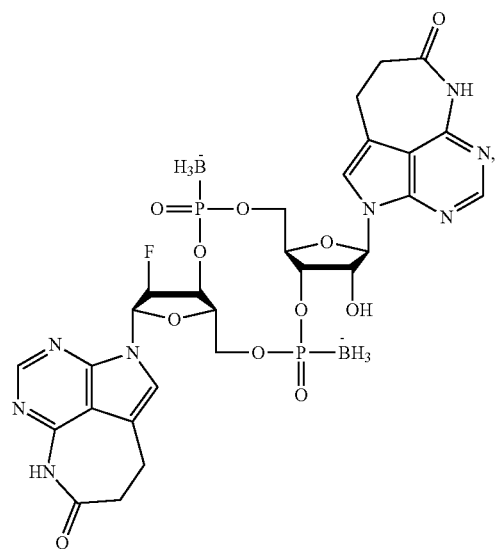
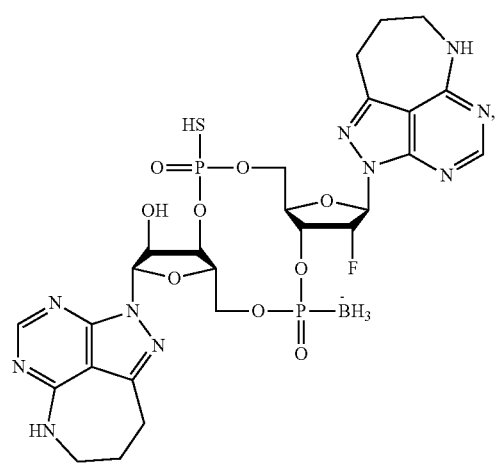
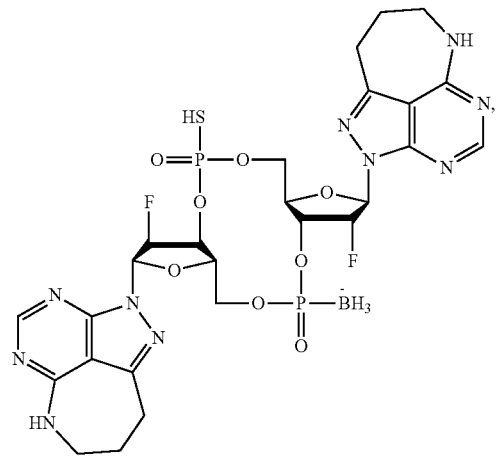
76
-continued
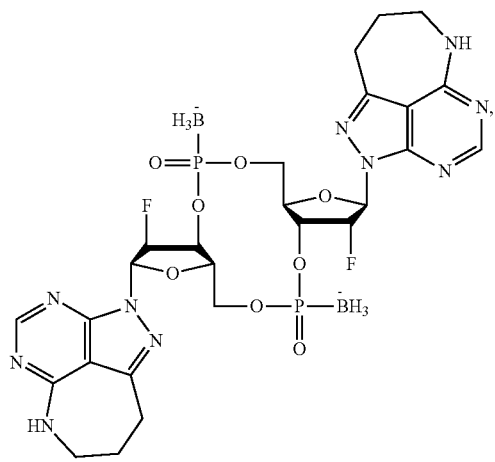
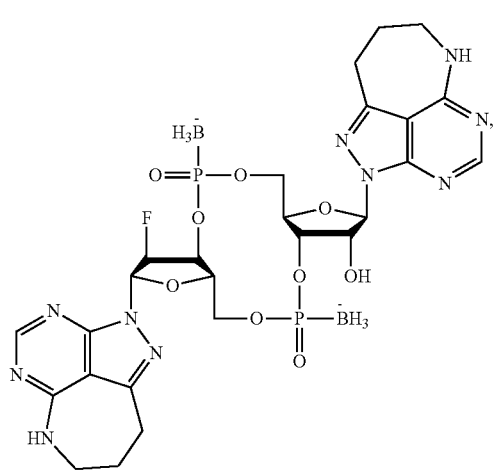
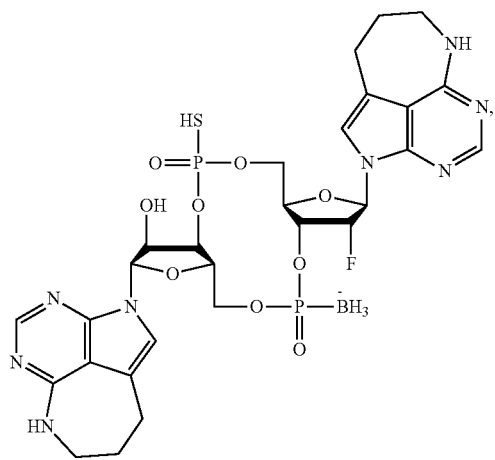

77
-continued
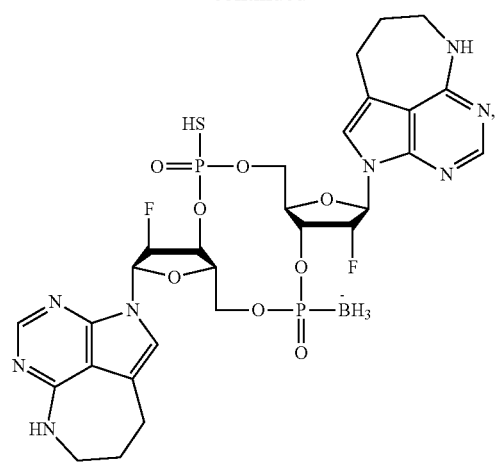
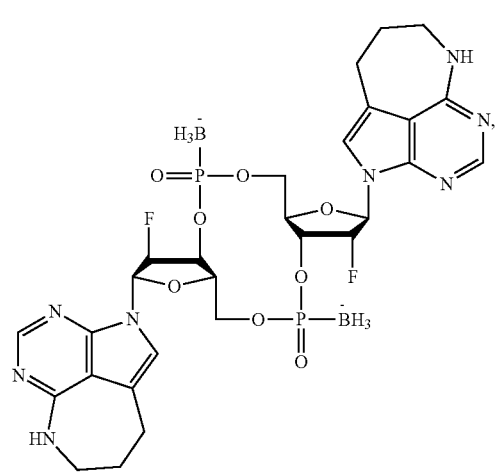
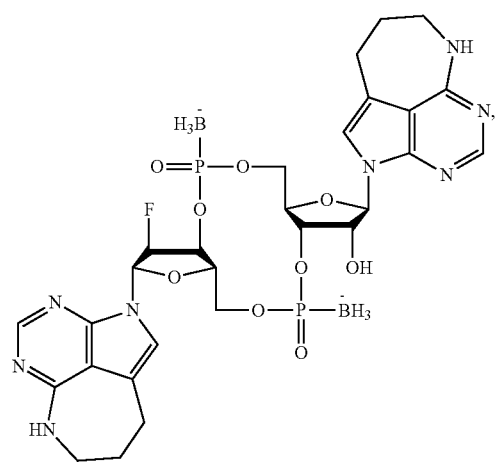
78
-continued
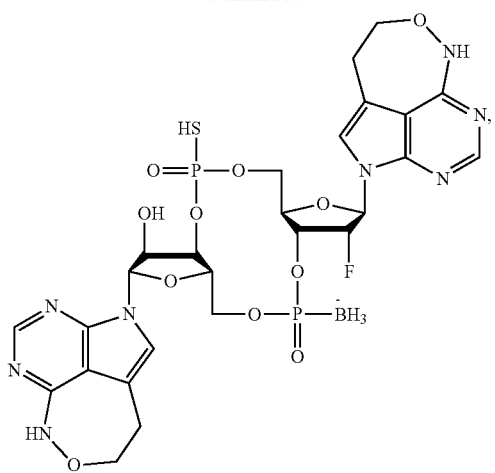
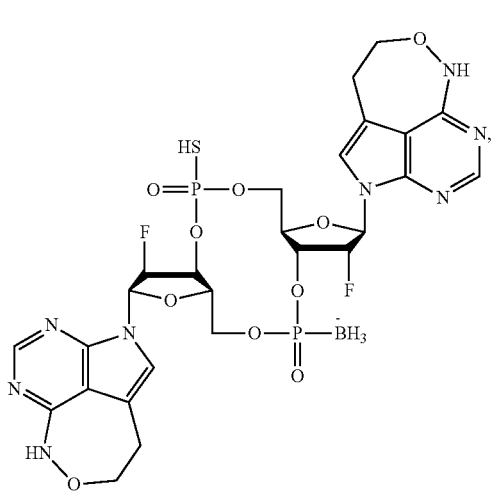
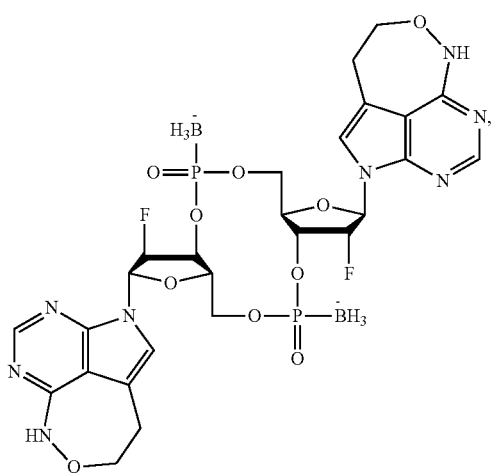

79
-continued
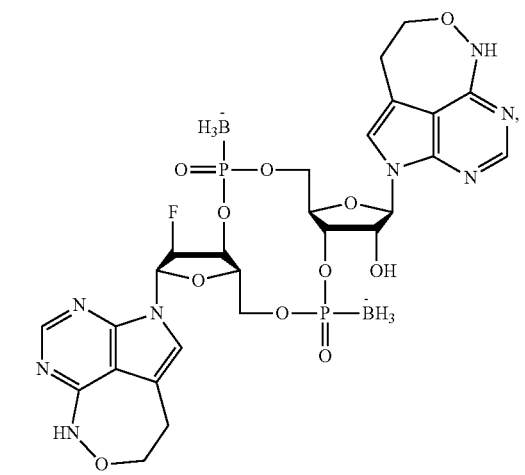
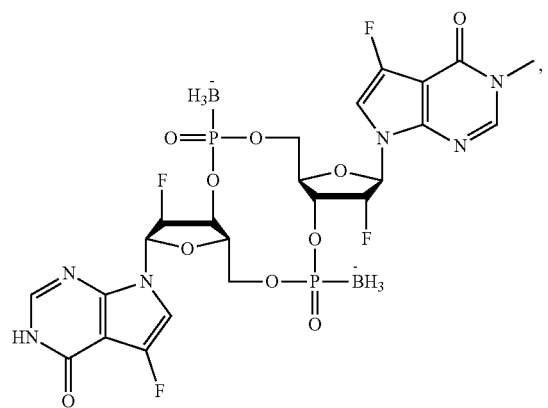
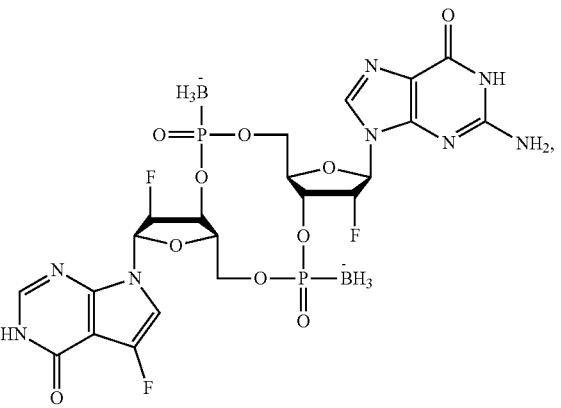
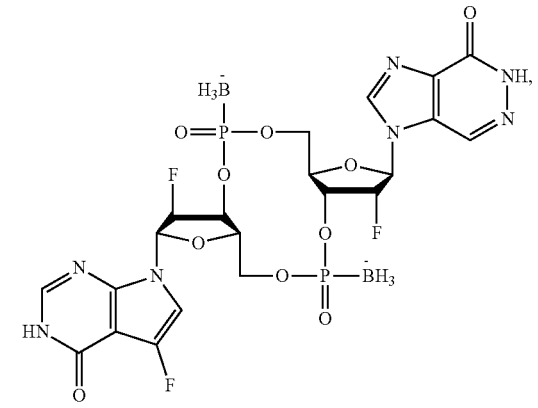
80
-continued
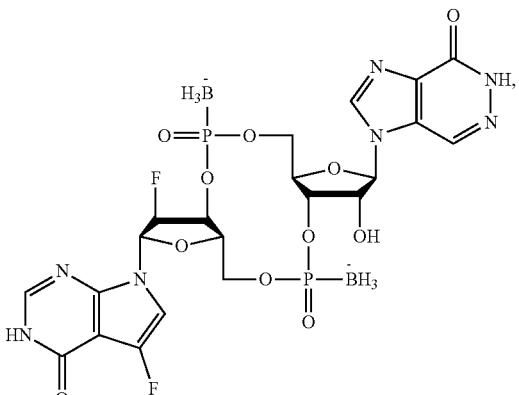
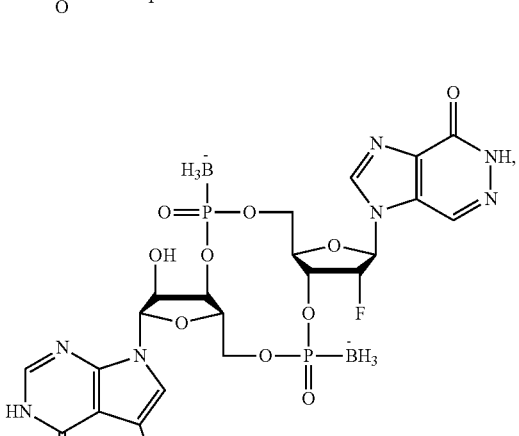
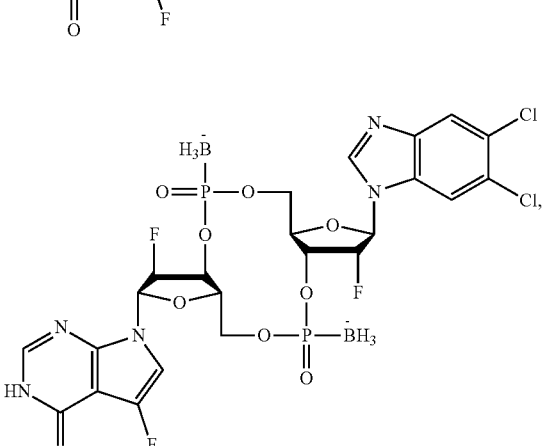
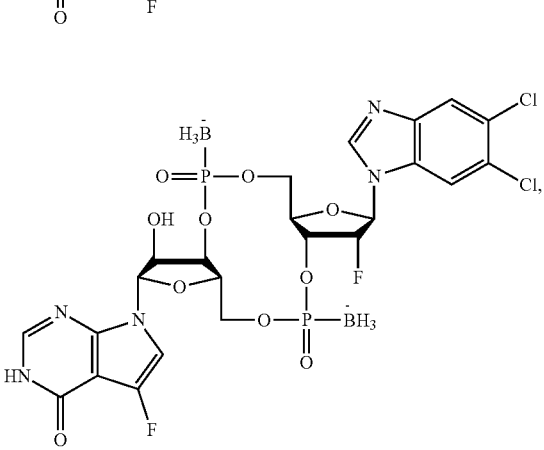

81
-continued
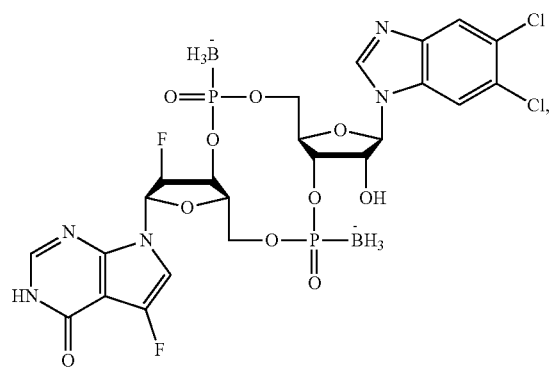
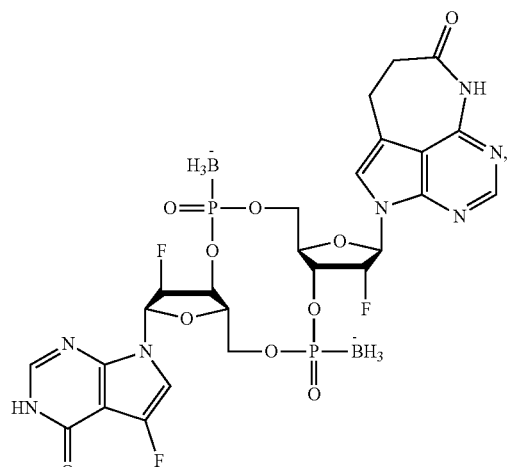
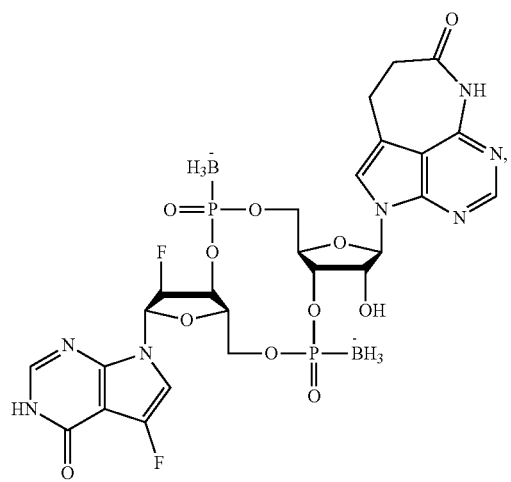
82
-continued
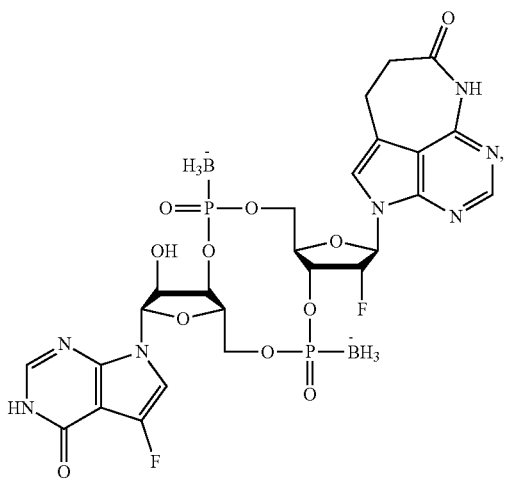
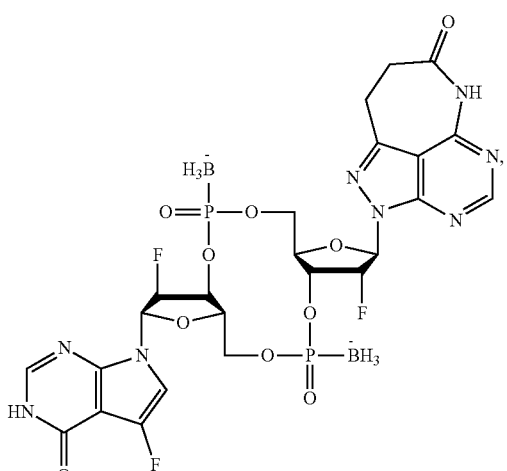
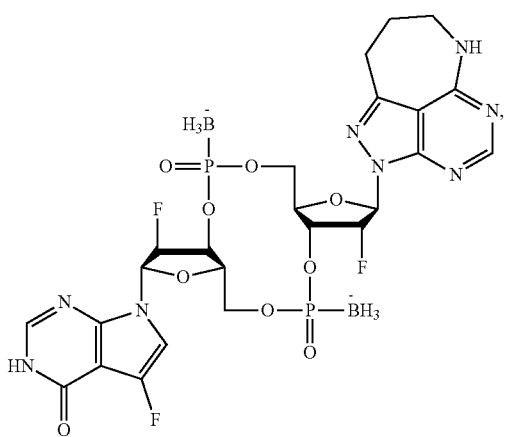

83
-continued
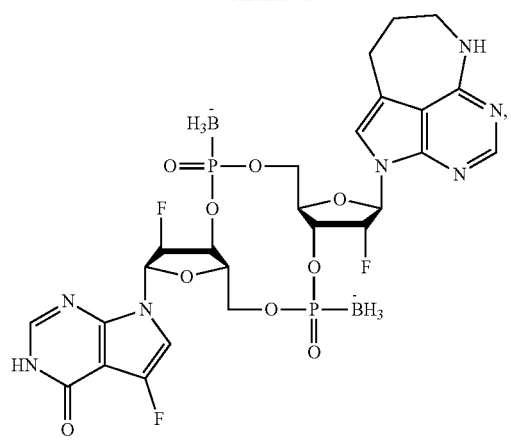
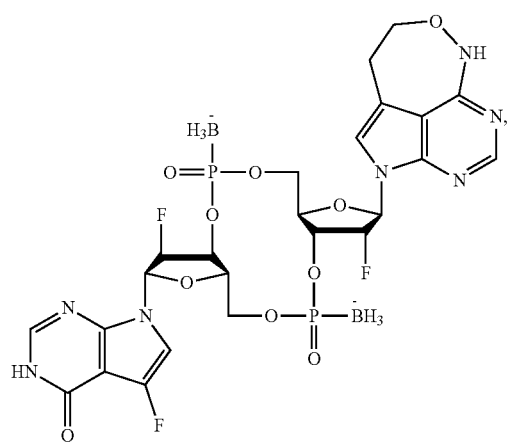
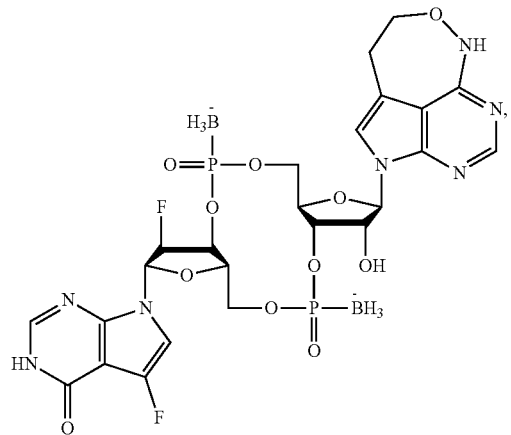
84
-continued
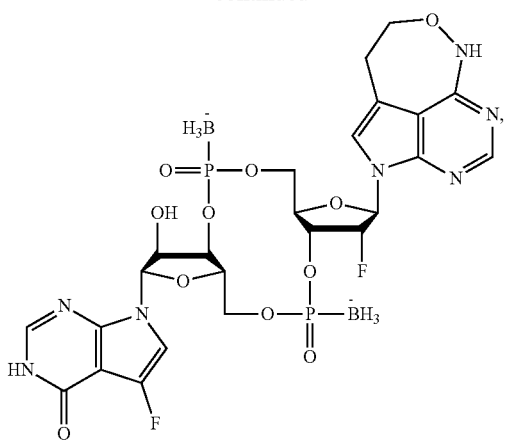
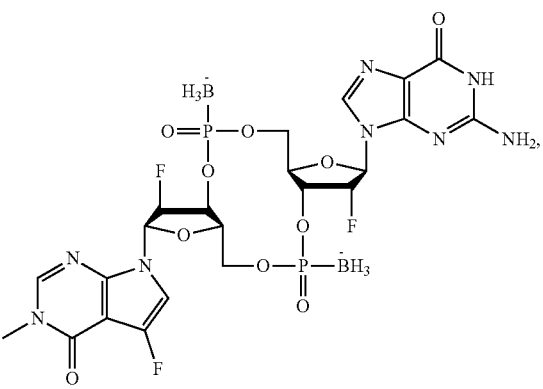
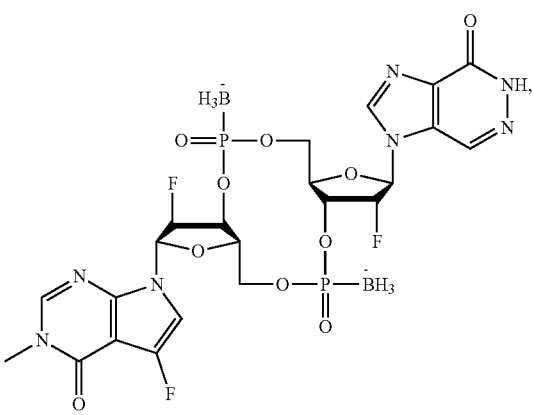
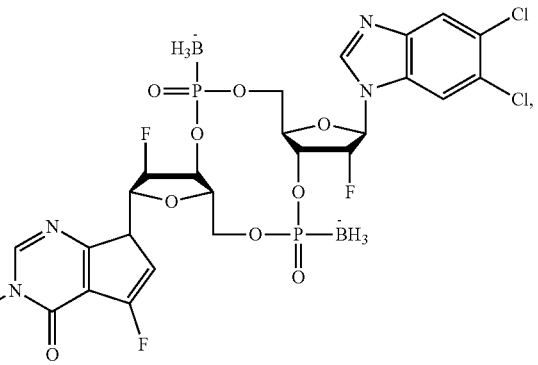

85
-continued
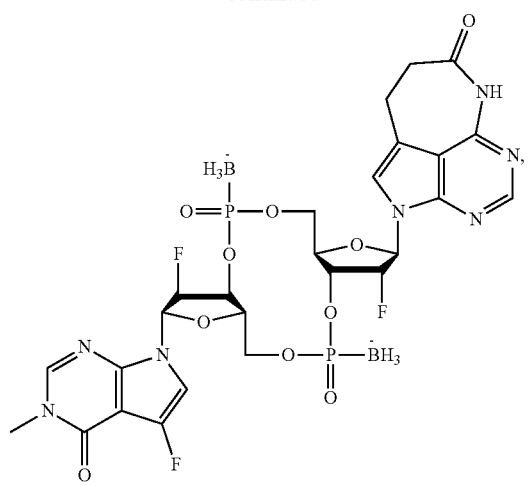
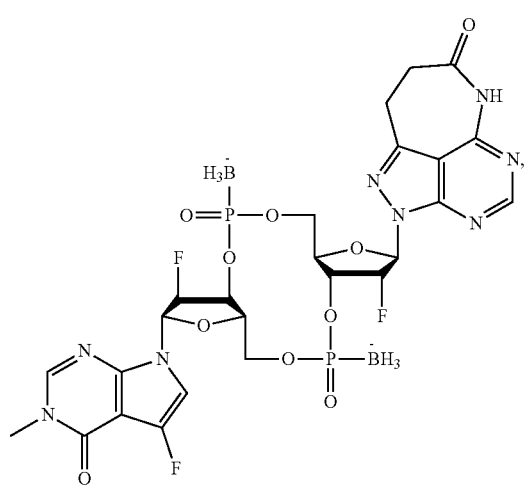
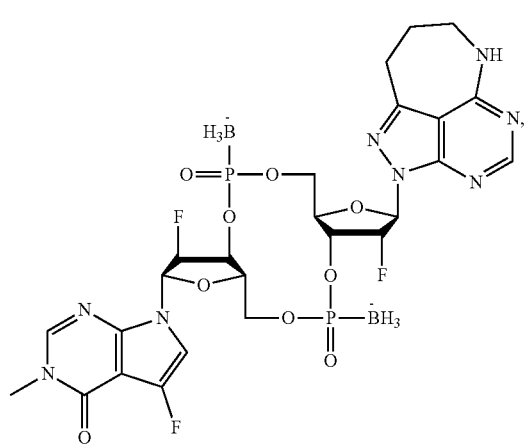
86
-continued
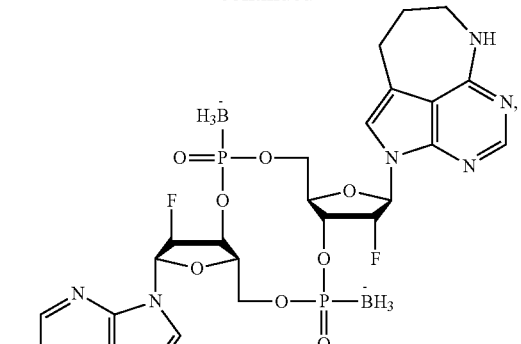
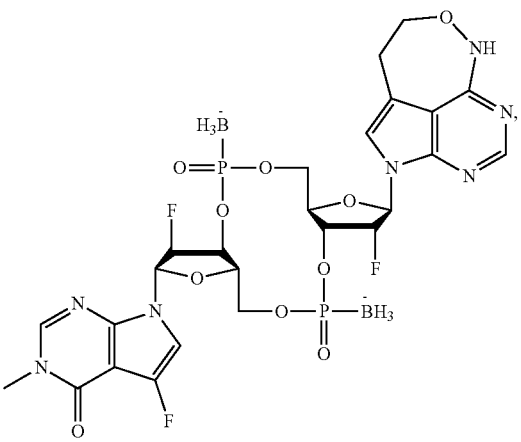
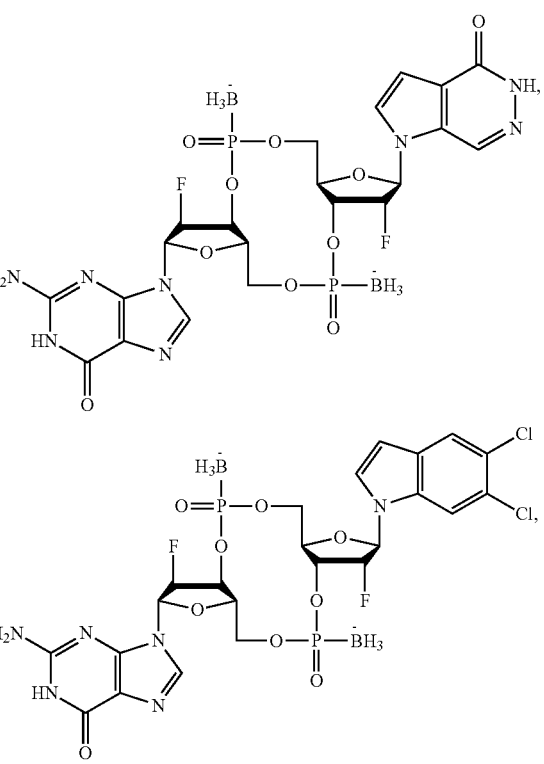

87
-continued
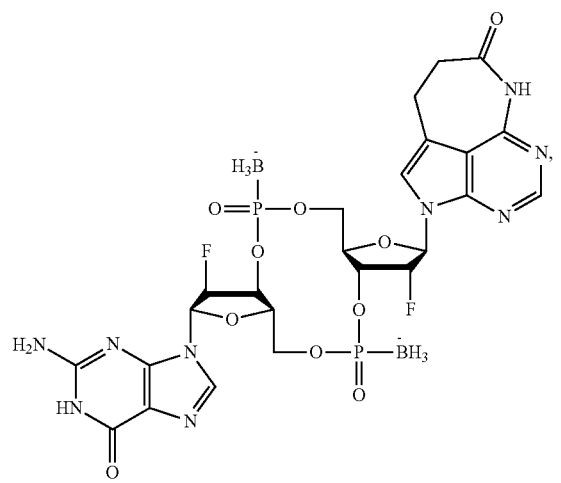
88
-continued
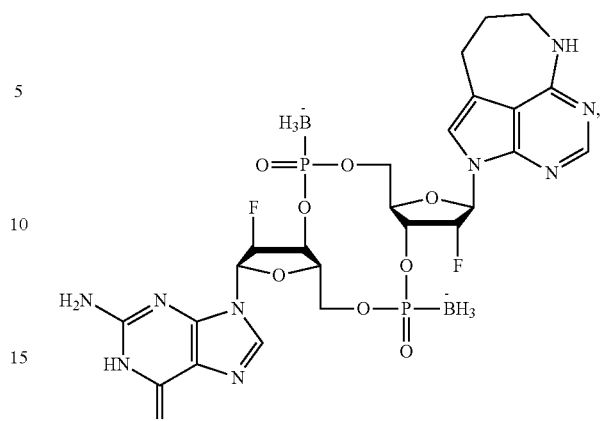
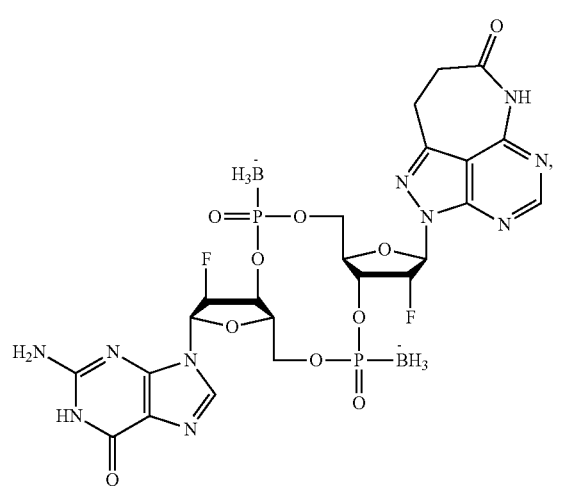
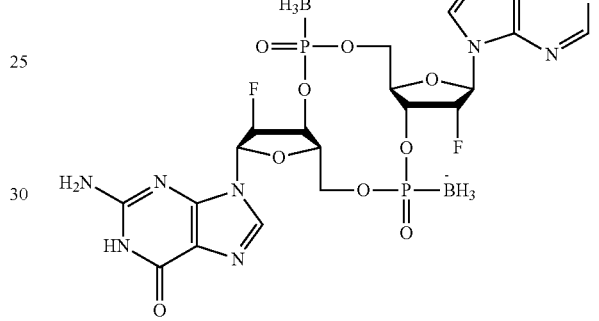
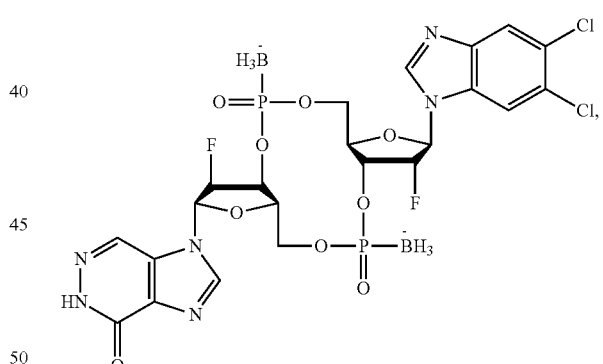
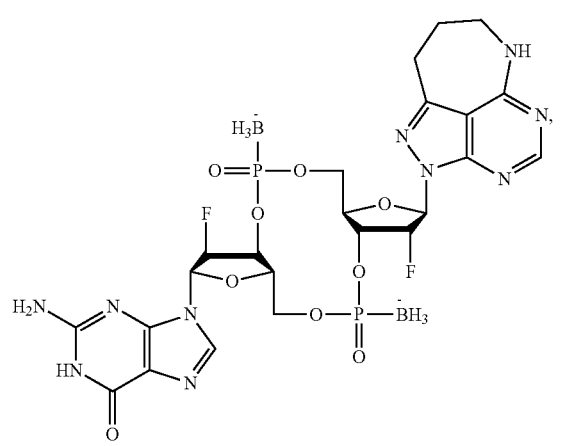
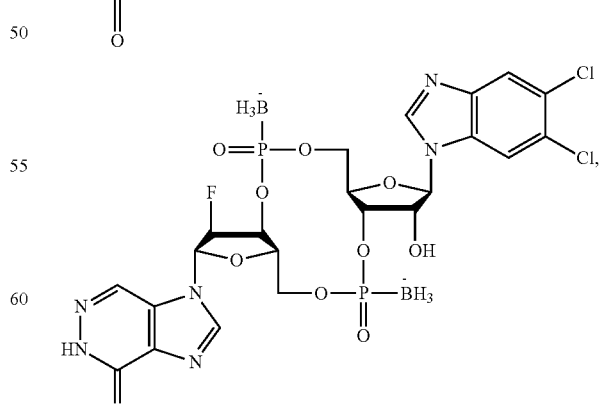

89
-continued
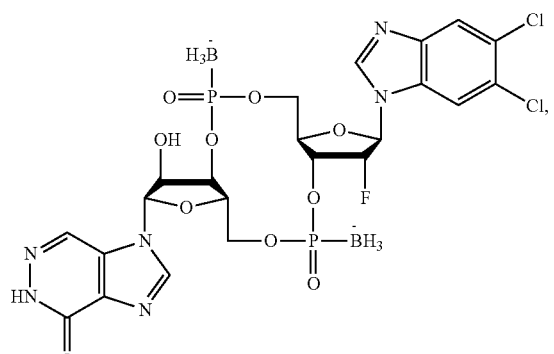
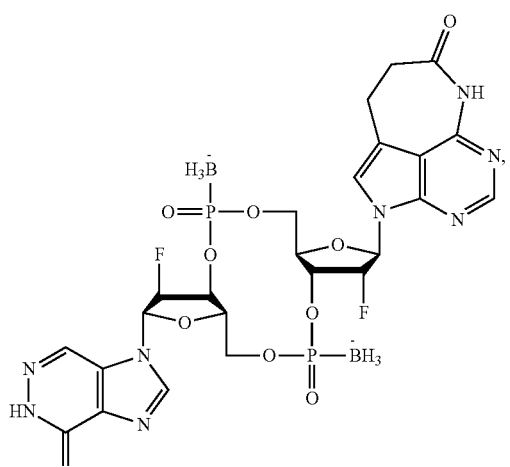
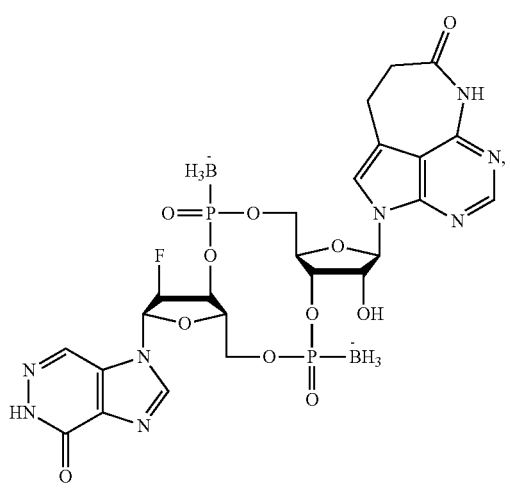
90
-continued
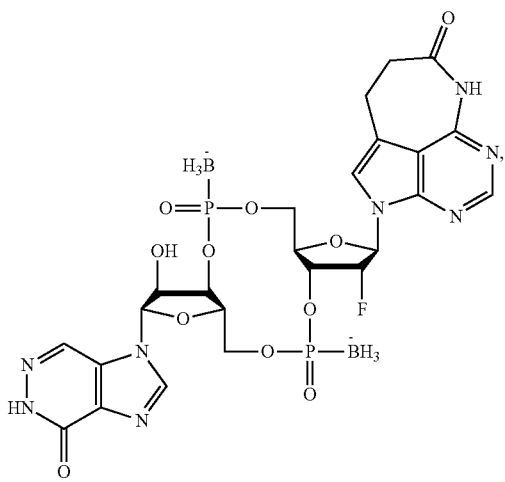
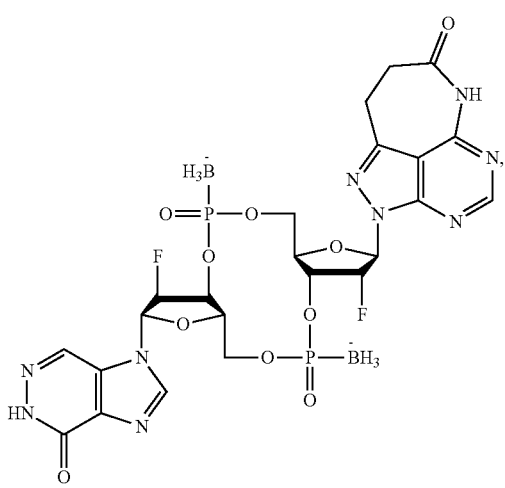
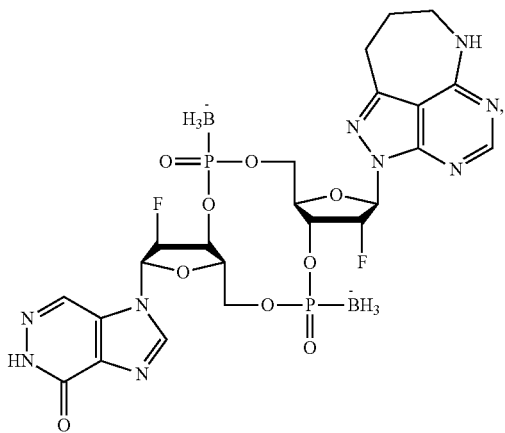

91
-continued
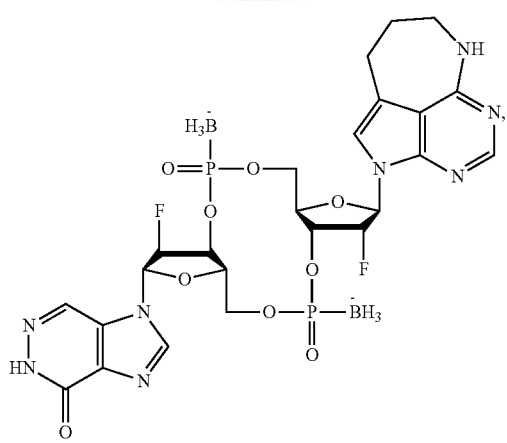
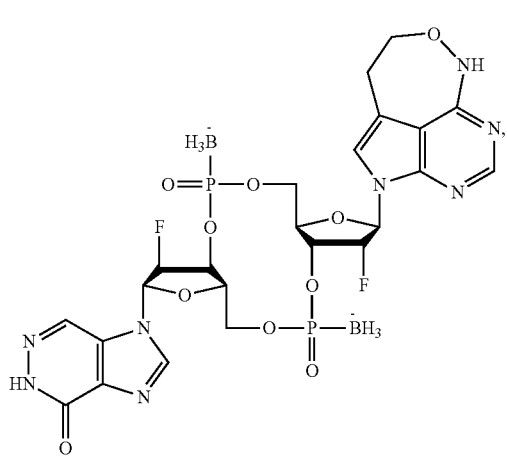
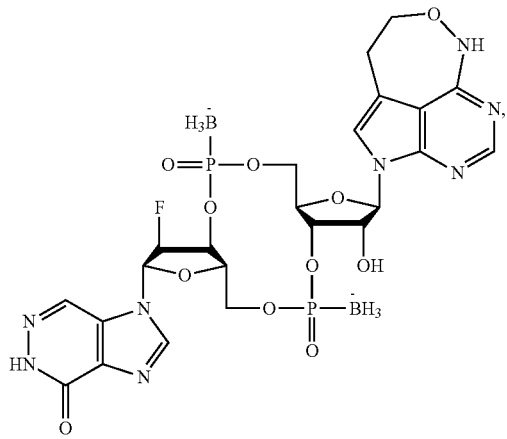
92
-continued
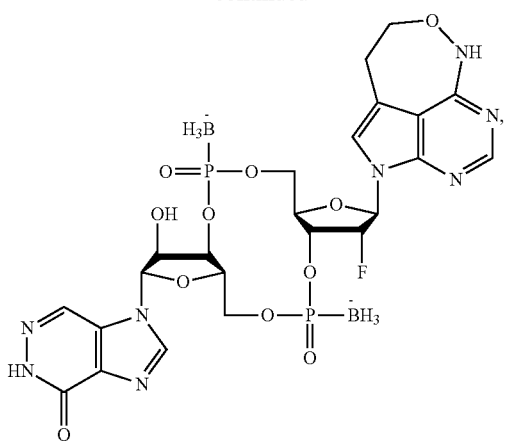
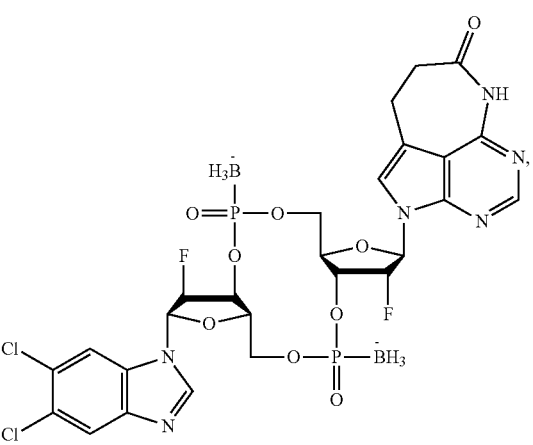
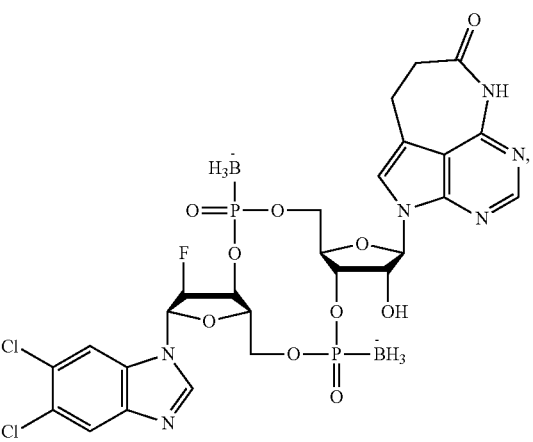

93
-continued
94
-continued
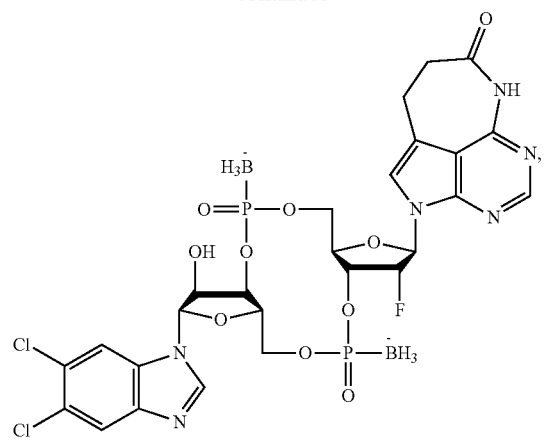
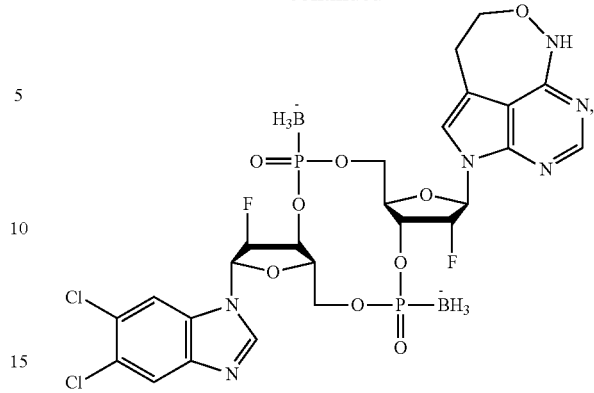
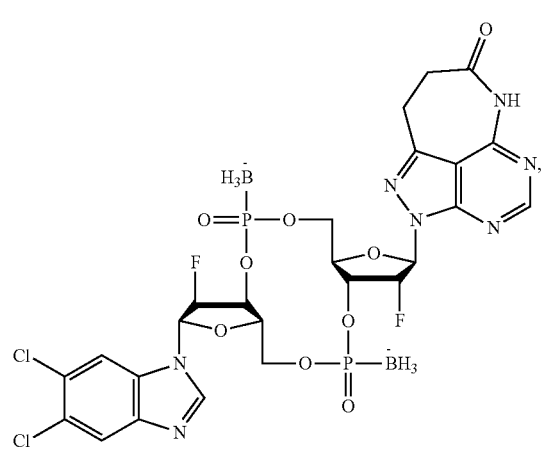
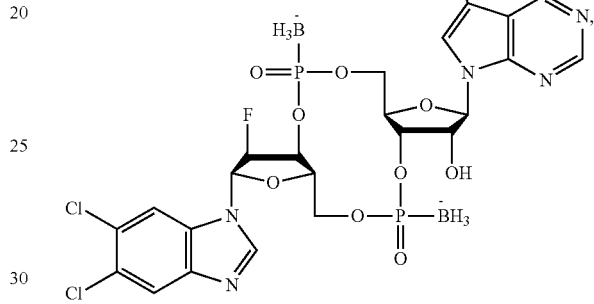
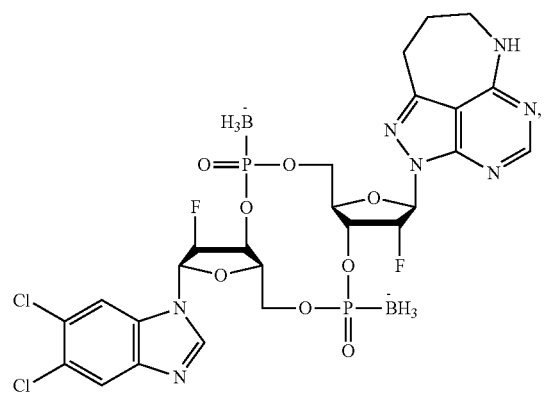
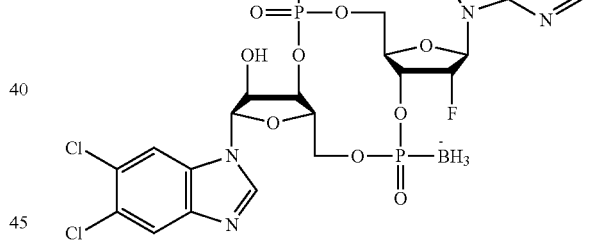
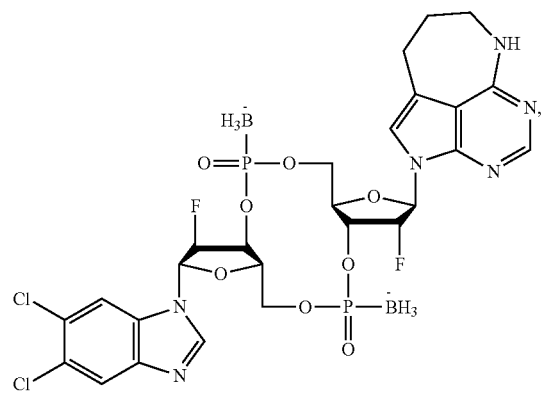
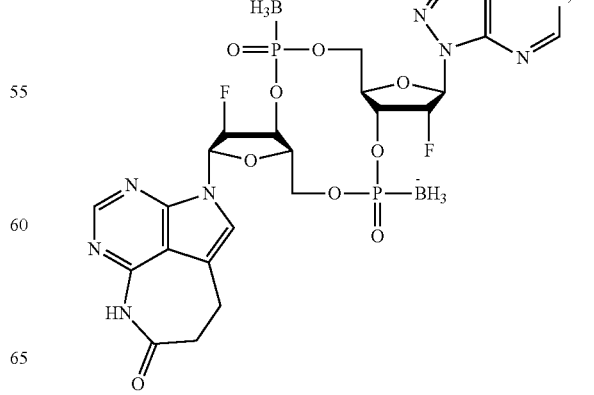

95
-continued
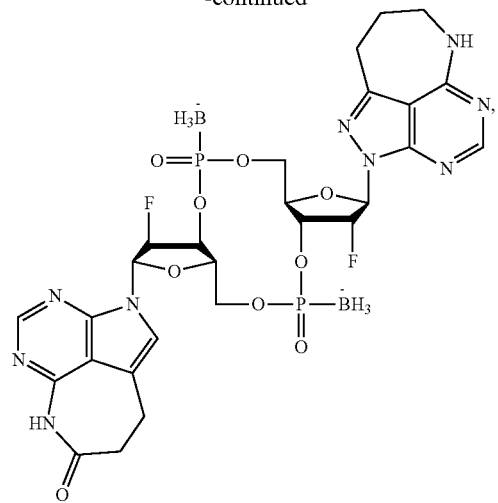
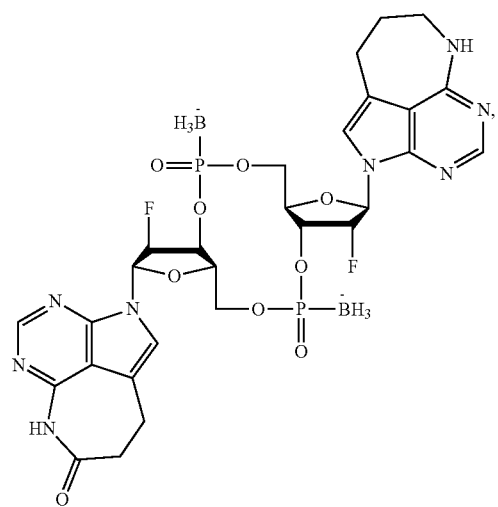
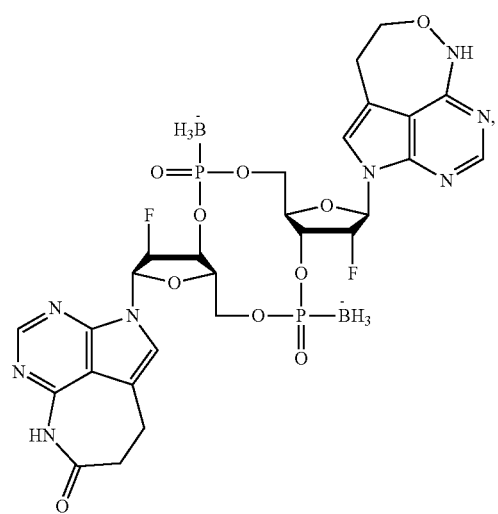
96
-continued
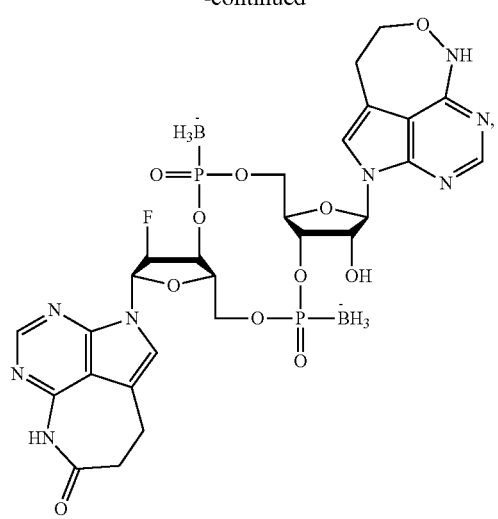
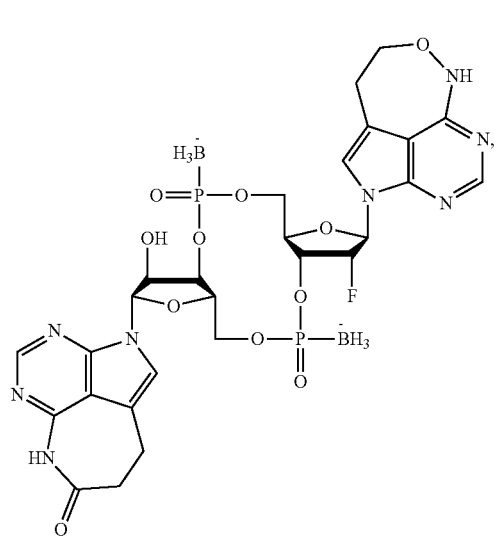
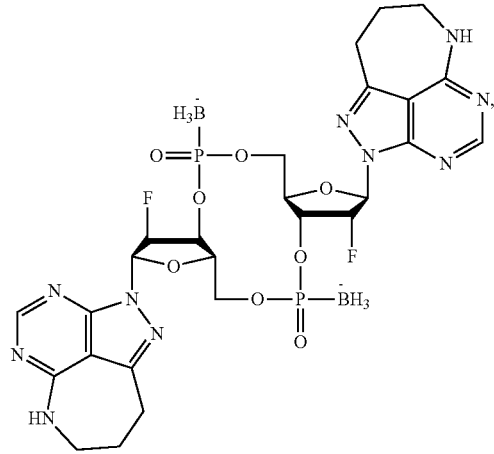

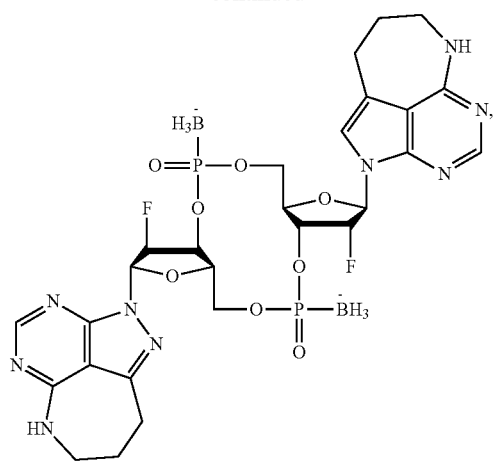

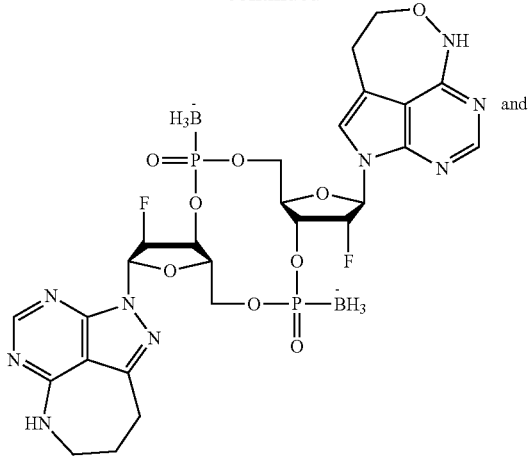

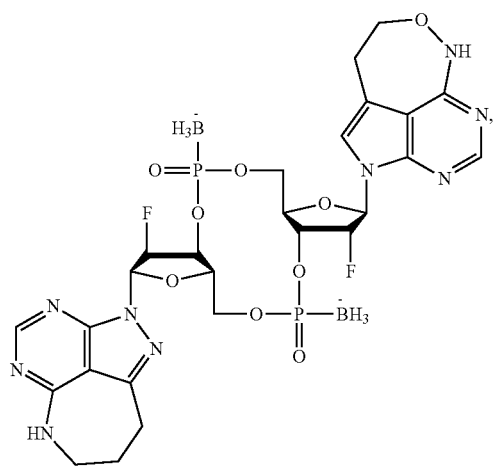

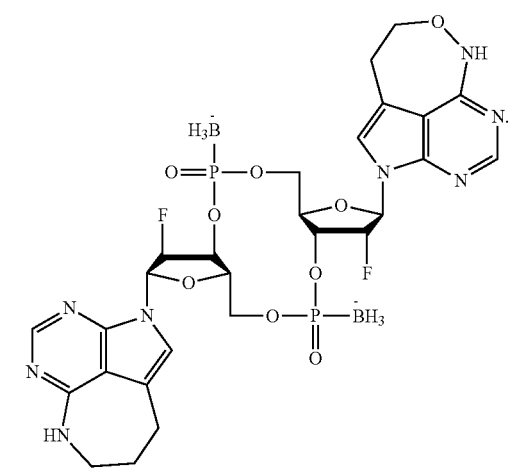

and

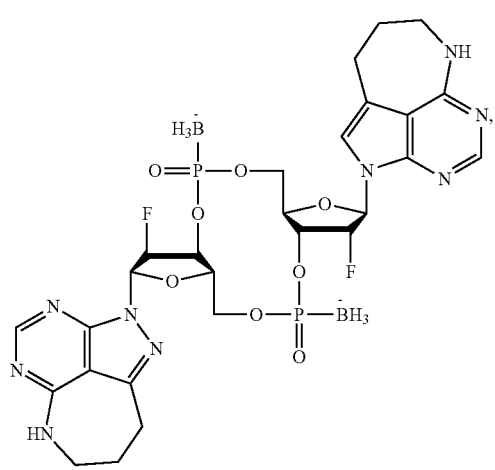

Definition and Description

Unless otherwise indicated, the following terms used in the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

The compound of the present disclosure may have a specific geometric or stereoisomeric form. The present disclosure contemplates all such compounds, including cis and trans isomer, (−)- and (+)-enantiomer, (R)- and (S)-enantiomer, diastereomer, (D)-isomer, (L)-isomer, and racemic mixture and other mixtures, for example, an enantiomer or diastereomer enriched mixture, all of which are encompassed within the scope of the present disclosure. The substituent such as alkyl can have an additional asymmetric carbon atom. All these isomers and mixtures thereof are encompassed within the scope of the present disclosure.

Unless otherwise specified, the absolute configuration of a stereogenic center is represented by a wedged solid bond (⬧) and a wedged dashed bond (⬧) and the relative configuration of a stereogenic center is represented by a straight solid bond (⬧) and a straight dashed bond (⬧), a wave line (⬧) represents a wedged solid bond (⬧) or a wedged dashed bond (⬧), or a wave line (⬧) represents a straight solid bond (⬧) or a straight dashed bond (⬧).

The compounds of the present disclosure may be present in particular. Unless otherwise indicated, the term "tautomer" or "tautomeric form" refer to the fact that the isomers with different functional groups are in dynamic equilibrium at room temperature and can be rapidly converted into each other. If tautomers are possible (e.g., in solution), the chemical equilibrium of the tautomers can be achieved. For example, proton tautomer (also known as prototropic tautomer) include interconversions by proton migration, such as keto-enol isomerization and imine-enamine isomerization. Valence tautomer include the mutual transformation caused by bonding electrons transfer. A specific example of keto-enol tautomerization is the interconversion between two tautomers pentane-2,4-dione and 4-hydroxypent-3-en-2-one, or an example of tautomerization between

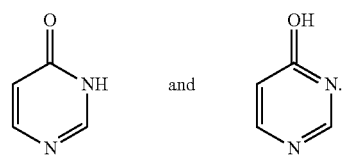

Unless otherwise specified, the term "enriched in one isomer", "isomer enriched", "enriched in one enantiomer" or "enantiomer enriched" refers to the content of one of the isomers or enantiomers is less than 100%, and the content of this isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomer, and, D and L isomer can be prepared using chiral synthesis or chiral reagents or other conventional techniques. If one kind of enantiomers of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form salts in the form of diastereomers which are then subjected to diastereomeric resolution through conventional methods in the art to give the pure enantiomer. In addition, the enantiomer or diastereomer is generally isolated through chromatography which uses a chiral stationary phase and optionally combines with a chemical derivative method (such as carbamate generated from amine). The compound of the present disclosure may contain an unnatural proportion of atomic isotope at one or more atoms that constitute the compound. For example, the compound can be radiolabeled with a radioactive isotope, such as tritium ($^3$H), iodine-125 ($^{125}$I) or C-14 ($^{14}$C). For another example, hydrogen can be replaced by heavy hydrogen to form a deuterated drug, and the bond formed by deuterium and carbon atoms is stronger than the bond formed by ordinary hydrogen and carbon atoms, compared with undeuterated drugs, deuterated drugs have advantages such as reduced side effects, increased drug stability, enhanced efficacy and prolonged biological half-life. All isotopic variations of the compound of the present disclosure, whether radioactive or not, are encompassed within the scope of the present disclosure. "Optional" or "optionally" means that the subsequent event or condition may occur but not requisite, that the term includes the instance in which the event or condition occurs and the instance in which the event or condition does not occur.

The term "substituted" means one or more than one hydrogen atoms on a specific atom are substituted with a substituent, including deuterium and hydrogen variants, as long as the valence of the specific atom is normal and the substituted compound is stable. When the substituent is an oxo (i.e., =O), it means two hydrogen atoms are substituted. Positions on an aromatic ring cannot be substituted with an oxo group. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two Rs, wherein the definition of R at each occurrence is independent. Moreover, a combination of the substituent and/or the variant thereof is allowed only when the combination results in a stable compound.

When an enumerative linking group does not indicate the direction for linking, the direction for linking is arbitrary, for example, the linking group L contained in

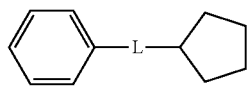

is -M-W—, then -M-W— can link benzene and cyclopentane to form

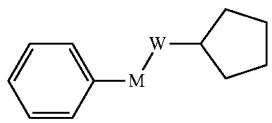

in the direction same as left-to-right reading order, and form

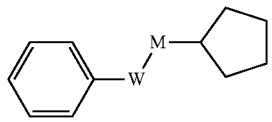

in the direction contrary to left-to-right reading order. A combination of linking group, substituents and/or variants thereof is allowed only when such combination can result in a stable compound.

Unless otherwise specified, the number of the atom on the ring is usually defined as the member of the ring, for example, a "5-6 membered ring" means that 5 to 6 atoms are arranged on the "ring".

Unless otherwise specified, "5-6 membered ring" means that there are 5 to 6 atoms arranging in a cycloalkyl, heterocycloalkyl, cycloalkenyl, heterocycloalkenyl, cycloalkynyl, heterocycloalkynyl, aryl or heteroaryl. The so-called ring includes a single ring, and also includes bicyclic systems, e.g., a spiro ring, a fused ring and a bridged ring. Unless otherwise specified, the ring optionally contains 1, 2 or 3 heteroatoms independently selected from O, S and N. The 5-6 membered ring includes 5-membered ring, 6-membered ring and so on. "5-6 membered ring" includes, for example, phenyl, pyridyl, and piperidinyl; on the other hand, the term "5-6 membered heterocycloalkyl" includes piperidyl, but excludes phenyl. The term "ring" also includes ring systems containing at least one ring, each ring of which independently conforms to the above definition.

Unless otherwise specified, the term "$C_{1-20}$ alkyl" refers to saturated hydrocarbon groups consisted of 1 to 20 carbon atoms with linear or branched chains. The $C_{1-20}$ alkyl includes $C_{1-10}$, $C_{1-9}$, $C_{1-8}$, $C_{1-6}$, $C_{1-5}$, $C_{1-4}$, $C_{1-3}$, $C_{1-2}$, $C_{2-16}$, $C_{2-4}$, $C_{10}$, $C_{8}$, $C_{7}$, $C_{6}$ and $C_{5}$ alkyl and the like; it can be monovalent (e.g. methyl), divalent (e.g., methylene) or multivalent (e.g., methylidyne). Examples of $C_{1-20}$ alkyl include methyl (Me), ethyl (Et), propyl (such as n-propyl and isopropyl), butyl (such as n-butyl, isobutyl, s-butyl and tert-butyl), pentyl (such as n-pentyl, isopentyl and neopentyl), hexyl, heptyl, octyl and the like.

Unless otherwise specified, the term "$C_{1-6}$ alkyl" refers to saturated hydrocarbon groups consisted of 1 to 6 carbon atoms with linear or branched chains. The $C_{1-6}$ alkyl includes $C_{1-5}$, $C_{1-4}$, $C_{1-3}$, $C_{1-2}$, $C_{2-6}$, $C_{2-4}$, $C_{6}$ and $C_{5}$ alkyl and the like; it can be monovalent (e.g. methyl), divalent (e.g., methylene) or multivalent (e.g., methylidyne). Examples of $C_{1-6}$ alkyl include methyl (Me), ethyl (Et), propyl (such as n-propyl and isopropyl), butyl (such as n-butyl, isobutyl, s-butyl and tert-butyl), pentyl (such as n-pentyl, isopentyl and neopentyl), hexyl and the like.

Unless otherwise specified, the term "$C_{1-3}$ alkyl" refers to saturated hydrocarbon groups consisted of 1 to 3 carbon atoms with linear or branched chains. The $C_{1-3}$ alkyl includes $C_{1-2}$ and $C_{2-3}$ alkyl and the like; it can be monovalent (e.g. methyl), divalent (e.g., methylene) or multivalent (e.g., methylidyne). Examples of $C_{1-3}$ alkyl include methyl (Me), ethyl (Et), propyl (such as n-propyl and isopropyl) and the like.

The term "heteroalkyl", by itself or in combination with another term, refers to a stable linear or branched chain alkylatomic group or a combination thereof having a specified number of carbon atoms and at least one heteroatom or heteroatomic group. In some embodiments, the heteroatom is selected from the group consisting of B, O, N and S, wherein the nitrogen and sulfur atoms are optionally oxidized and the nitrogen atom is optionally quaternized. In some other embodiments, the heteroatomic group is selected from the group consisting of —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl; in some other embodiments, the heteroalkyl is $C_{1-3}$ heteroalkyl. The heteroatom or heteroatomic group can be located at any interior position of the heteroalkyl, including the position where the alkyl attaches to the rest of the molecule, but the terms "alkoxy", "alkylamino" and "alkylthio" (or thioalkoxy) are used in their conventional meanings and refer to an alkyl group connected to the rest of the molecule via an oxygen atom, an amino or a sulfur atom respectively. Examples of the heteroalkyl include, but not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, —CH$_2$—CH$_2$—S(=O)$_2$—CH$_3$. Up to two consecutive heteroatoms can be present, such as, —CH$_2$—NH—OCH$_3$.

Unless otherwise specified, the term "$C_{1-6}$ alkoxy" refers to alkyl groups that contain 1 to 6 carbon atoms connected to the rest of the molecule via an oxygen atom. The $C_{1-6}$ alkoxy includes $C_{1-4}$, $C_{1-3}$, $C_{1-2}$, $C_{2-6}$, $C_{2-4}$, $C_{6}$, $C_{5}$, $C_{4}$ and $C_{3}$ alkoxy and the like. Examples of the $C_{1-6}$ alkoxy include, but not limited to, methoxy, ethoxy, propoxy (including n-propoxy and isopropoxy), butoxy (including n-butoxy, isobutoxy, sec-butoxy and tert-butoxy), pentyloxy (including n-pentyloxy, isopentoxy and neopentoxy), hexyloxy, etc.

Unless otherwise specified, the term "$C_{1-3}$ alkoxy" refers to alkyl groups that contain 1 to 3 carbon atoms connected to the rest of the molecule via an oxygen atom. The $C_{1-3}$ alkoxy includes $C_{1-2}$, $C_{2-3}$, $C_3$ and $C_2$ alkoxy and the like. Examples of the $C_{1-3}$ alkoxy include, but not limited to, methoxy, ethoxy, propoxy (including n-propoxy and isopropoxy, etc.)

Unless otherwise specified, the term "$C_{1-6}$ alkylamino" refers to alkyl groups that contain 1 to 6 carbon atoms connected to the rest of the molecule via an amino group. The $C_{1-6}$ alkylamino includes $C_{1-4}$, $C_{1-3}$, $C_{1-2}$ $C_{2-6}$, $C_{2-4}$, $C_6$, $C_5$, $C_4$, $C_3$ and $C_2$ alkylamino and the like. Examples of the $C_{1-6}$ alkylamino include, but not limited to, —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, etc.

Unless otherwise specified, the term "$C_{1-3}$ alkylamino" refers to alkyl groups that contain 1 to 3 carbon atoms connected to the rest of the molecule via an amino group. The $C_{1-3}$ alkylamino includes $C_{1-2}$, $C_3$ and $C_2$ alkylamino and the like. Examples of the $C_{1-3}$ alkylamino include, but not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, etc.

Unless otherwise specified, the term "$C_{1-6}$ alkylthiol" refers to alkyl groups that contain 1 to 6 carbon atoms connected to the rest of the molecule via a sulfur atom. The $C_{1-6}$ alkylthiol includes $C_{1-4}$, $C_{1-3}$, $C_{1-2}$ $C_{2-6}$, $C_{2-4}$, $C_6$, $C_5$, $C_4$, $C_3$ and $C_2$ alkylthiol and the like. Examples of the $C_{1-6}$ alkylthiol include, but not limited to, —SCH$_3$, —SCH$_2$CH$_3$, —SCH$_2$CH$_2$CH$_3$, —SCH$_2$(CH$_3$)$_2$, etc.

Unless otherwise specified, the term "$C_{1-3}$ alkylthiol" refers to alkyl groups that contain 1 to 3 carbon atoms connected to the rest of the molecule via a sulfur atom. The $C_{1-3}$ alkylthiol includes $C_{1-3}$, $C_{1-2}$ and $C_3$ alkylthiol and the like. Examples of the $C_{1-3}$ alkylthiol include, but not limited to, —SCH$_3$, —SCH$_2$CH$_3$, —SCH$_2$CH$_2$CH$_3$, —SCH$_2$(CH$_3$)$_2$, etc.

Unless otherwise specified, the term "$C_{2-6}$ alkynyl" refers to hydrocarbon groups composed of 2 to 6 carbon atoms that containing at least one carbon-carbon triple bond with linear or branched chains, and the carbon-carbon triple bonds can be located at any position of the group. The $C_{2-6}$ alkynyl includes $C_{2-4}$, $C_{2-3}$, $C_4$, $C_3$ and $C_2$ alkynyl and the like. It can be monovalent, divalent or multivalent. Examples of the $C_{2-6}$ alkynyl include, but not limited to, ethynyl, propynyl, butynyl, pentynyl and the like.

Unless otherwise specified, the term "5-6 membered heterocycloalkyl", by itself or in combination with another term, refers to saturated ring groups composed of 5 to 6 ring atoms respectively, the 1, 2, 3 or 4 ring atoms are heteroatoms independently selected from O, S and N, and the rest are carbon atoms, wherein the nitrogen atom is optionally quaternized, the nitrogen and sulfur heteroatoms can optionally be oxidized (i.e., NO and S(O)$_p$, p is 1 or 2). It includes monocyclic and bicyclic systems, wherein the bicyclic system includes spiro, fused, and bridged rings. In addition, in terms of the "5-6 membered heterocycloalkyl", the heteroatom can occupy the position through which the heterocycloalkyl is attached to the rest of the molecule. The 5-6 membered heterocycloalkyl includes 5-membered and 6-membered heterocycloalkyl. Examples of the 5-6 membered heterocycloalkyl include, but not limited to, pyrrolidinyl, pyrazolidinyl, imidazolidinyl, tetrahydrothiophenyl (including tetrahydrothiophen-2-yl and tetrahydrothiophen-3-yl etc.), tetrahydrofuranyl (including tetrahydrofuran-2-yl etc.), tetrahydropyranyl, piperidinyl (including 1-piperidinyl, 2-piperidinyl and 3-piperidinyl etc.), piperazinyl (including 1-piperazinyl and 2-piperazinyl etc.), morpholinyl (including 3-morpholinyl and 4-morpholinyl etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl.

Unless otherwise specified, the terms "$C_{6-10}$ aromatic ring" and "$C_{6-10}$ aryl" in the disclosure can be used interchangeably, the term "$C_{6-10}$ aromatic ring" or "$C_{6-10}$ aryl" refers to the cyclic hydrocarbon group with conjugated π electron system consisted of 6 to 10 carbon atoms, which can be monocyclic, fused bicyclic or fused tricyclic systems, where each ring is aromatic. It can be monovalent, divalent or multivalent, $C_{6-10}$ aryl includes $C_{6-9}$, $C_9$, $C_{10}$ and $C_6$ aryl and so on. Examples of the $C_{6-10}$ aryl include, but not limited to, phenyl, naphthyl (including 1-naphthyl, 2-naphthyl, etc.).

Unless otherwise specified, the terms "5-10 membered heteroaromatic ring" and "5-10 membered heteroaryl" in the disclosure can be used interchangeably, the term "5-10 membered heteroaryl" refers to the ring group with conjugated π electron system composed of 5 to 10 ring atoms, the 1, 2, 3 or 4 ring atoms are heteroatoms independently selected from O, S and N, and the rest are carbon atoms. It can be monocyclic, fused bicyclic or fused tricyclic systems, where each ring is aromatic. Wherein the nitrogen atom is optionally quaternized, the nitrogen and sulfur heteroatoms can optionally be oxidized (i.e., NO and S(O)$_p$, p is 1 or 2). The 5-10 membered heteroaryl can be connected to the rest of the molecule via a heteroatom or a carbon atom. The 5-10 membered heteroaryl includes 5-8 membered, 5-7 membered, 5-6 membered, 5-membered and 6-membered heteroaryl and the like. Examples of the 5-10 membered heteroaryl include, but not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thiophenyl (including 2-thiophenyl and 3-thiophenyl, etc.), pyridyl (including 2-pyridyl, 3-pyridyl and 4-pyridyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), benzoxazolyl, indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.), quinolinyl (including 3-quinolinyl and 6-quinolinyl, etc.).

Unless otherwise specified, $C_{n-n+m}$ or $C_n$—$C_{n+m}$ includes any specific case having n to n+m carbons, for example, $C_{1-6}$ includes $C_1$, $C_2$, $C_3$, $C_4$, $C_5$ and $C_6$, and also includes any range between n and n+m, for example, $C_{1-6}$ includes $C_{1-3}$, $C_{1-6}$, $C_{1-4}$, $C_{3-6}$, $C_{3-5}$, $C_{2-5}$ and $C_{1-5}$, and the like; similarly, n-membered to n+m-membered means that the number of atoms arranged on the ring is n to n+m, for example, 5- to 6-membered ring includes 5-membered ring and 6-membered ring.

The compound of the present disclosure can be prepared by a variety of synthetic methods well known to those skilled in the art, including the following enumerative embodiments, embodiments formed by the following enumerative embodiments in combination with other chemical synthesis methods and equivalent replacements well known to those skilled in the art. The preferred embodiments includes, but not limited to the embodiments of the present disclosure.

The HPLC detection conditions of the present disclosure are mainly as follows: chromatographic column: YMC-Pack ODS-A 150*4.6 mm, 5 μm, mobile phase: water (0.06875% trifluoroacetic acid)-acetonitrile (0.0625% trifluoroacetic acid); flow rate: 1.0 mL/min; detection wavelength: UV 220 nm & 215 nm & 254 nm; column temperature: 40° C.

The present disclosure adopts the abbreviating words as follows: "aq" refers to water; "CDCl$_3$" refers to deuterated chloroform; "CD$_3$OD" refers to methanol-d; "DMSO-d$_6$" refers to dimethyl sulfoxide-d$_6$, "DMF" refers to N,N-dimethylformamide; "Bz" refers to benzoyl group; "TBS" refers to tert-butyldimethylsilyl; "DMTr" refers to 4,4'-dimethoxytrityl; "CE" refers to cyanoethyl; "i-Pr" refers to isopropyl; "DMTrCl" refers to 4,4'-dimethoxytrityl chloride; "DDTT" refers to (E)-N,N-dimethyl-N'-(3-thioxo-3H-1,2,4-dithiazol-5-yl)formimidamide; "DCA" refers to 2,2'-dichloroacetic acid; "BSA" refers to N,O-bis(trimethylsilyl)acetamide; "ug" or "μg" refers to microgram.

DETAILED DESCRIPTION OF EMBODIMENT

Figure 1:
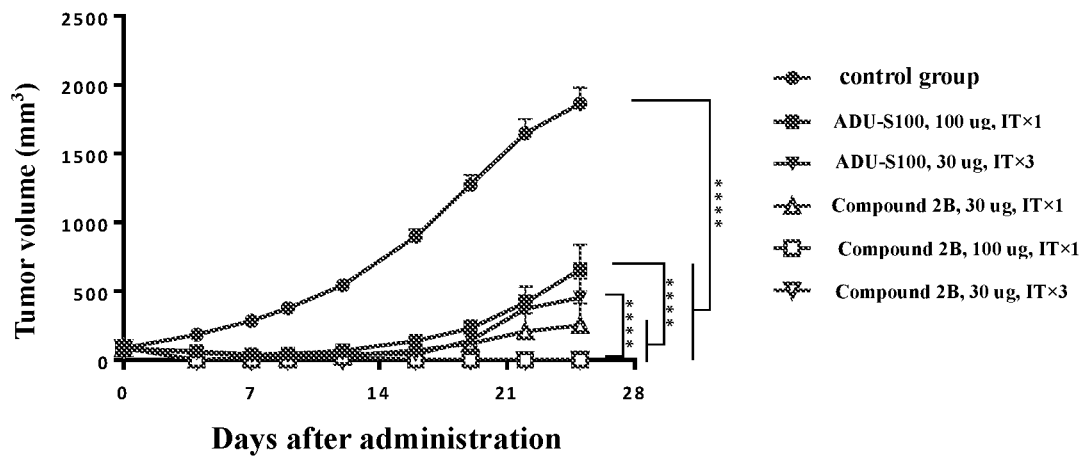
FIG. 1 shows the result of pharmacodynamic test on homologous mouse model of 4T1 breast cancer.

The following embodiments further illustrate the present disclosure, but it does not mean that there are any unfavorable restrictions on this application. The present disclosure has been described in detail herein, and specific embodiments thereof have also been disclosed. It will be apparent to those skilled in the art that various changes and modifications can be made to the specific embodiments of the present disclosure without departing from the spirit and scope of the present disclosure.

Embodiment 1: Preparation of Compounds 1A, 1B, 1C and 1D

Step 1: Preparation of Compound 1-2

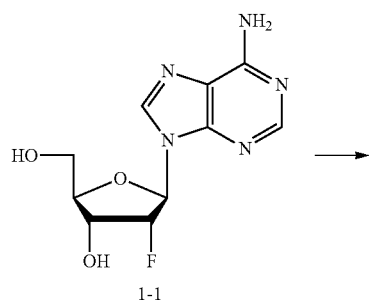

1-1

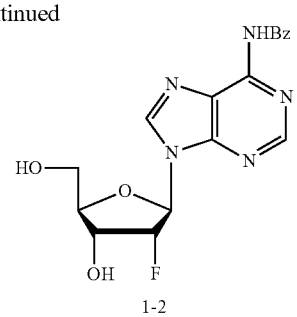

1-2

Under nitrogen atmosphere, trimethylchlorosilane (1.61 g, 14.86 mmol, 1.89 mL) was added dropwise to the solution of compound 1-1 (1 g, 3.71 mmol) in pyridine (20 mL). After reacting at 0° C. for 30 min, benzoyl chloride (605 mg, 4.30 mmol, 500.00 μL) was added to the reaction mixture. The reaction mixture was then heated to 15° C. and reacted for 3 hours. The reaction was terminated and cooled to 0° C., water (10 mL) and ammonia (5 mL) were successively added to quench the reaction. The reaction mixture was stirred for 10 min and extracted with ethyl acetate (25 mL×3). The organic phases were combined, dried over anhydrous sodium sulfate, filtered, and the filtrate was concentrated under reduced pressure, and the crude product was purified by silica gel column chromatography (dichloromethane/methanol (v/v)=9/1) to obtain compound 1-2.

MS (ESI) m/z (M+H)$^+$=374.1.

$^1$H NMR (400 MHz, DMSO-d$_6$) δ 11.26 (br s, 1H), 8.77 (s, 1H), 8.71 (s, 1H), 8.05 (d, J=7.3 Hz, 2H), 7.66 (t, J=7.6 Hz, 2H), 7.56 (t, J=7.6 Hz, 2H), 6.39 (dd, J=2.3, 17.3 Hz, 1H), 5.77 (d, J=6.3 Hz, 1H), 5.64-5.39 (m, 1H), 5.18 (t, J=5.4 Hz, 1H), 4.63-4.45 (m, 1H), 4.08-3.93 (m, 1H), 3.81-3.76 (m, 1H), 3.64-3.58 (m, 1H).

Step 2: Preparation of Compound 1-3

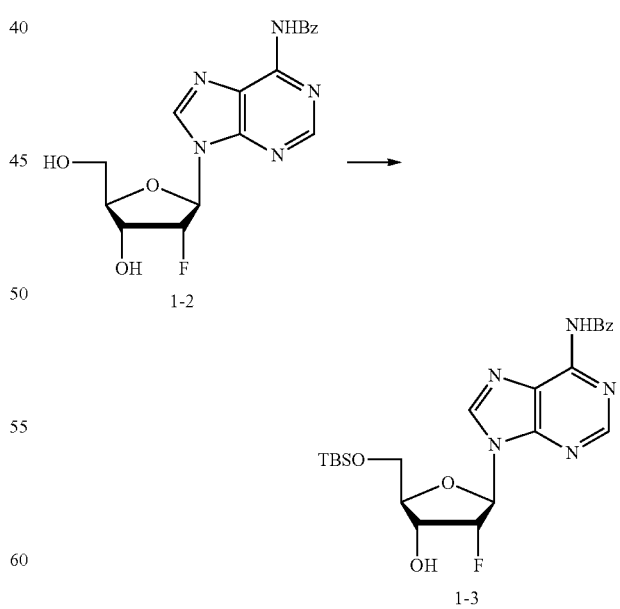

1-2

1-3

Compound 1-2 (1.5 g, 4.02 mmol) was dissolved in pyridine (15 mL), followed by successive addition of silver nitrate (2.73 g, 16.07 mmol) and tert-butyl dimethylchlorosilane (636 mg, 4.22 mmol, 517.07 μL). The reaction mixture was stirred at room temperature for 4 hours. The reaction mixture was quenched with water (50 mL), and extracted with ethyl acetate (40 mL×3). The organic phases were combined, dried over anhydrous sodium sulfate, filtered, and the filtrate was concentrated under reduced pressure to obtain the crude product, which was further purified by silica gel column chromatography (dichloromethane/methanol (v/v)=4/1) to obtain compounds 1-3.

MS (ESI) m/z (M+H)$^+$=488.1.

$^1$H NMR (400 MHz, DMSO-d$_6$) δ 11.29 (br s, 1H), 8.73 (br s, 1H), 8.58 (s, 1H), 8.01 (br d, J=7.3 Hz, 2H), 7.66-7.36 (m, 3H), 6.39 (br d, J=18.6 Hz, 1H), 5.82 (d, J=6.6 Hz, 1H), 5.66-5.39 (m, 1H), 4.73-4.50 (m, 1H), 4.08-4.02 (m, 1H), 4.00-3.94 (m, 1H), 3.85-3.80 (m, 1H), 0.83 (s, 9H), 0.03 (s, 3H), 0.00 (s, 3H).

Step 3: Preparation of Compound 1-4

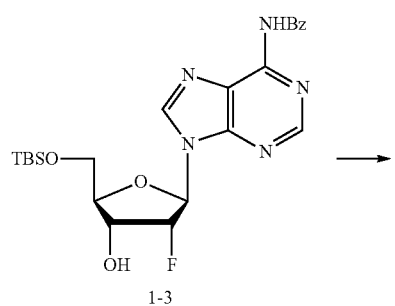

1-3

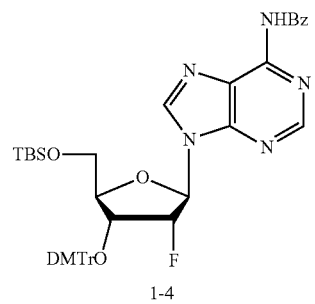

1-4

Compound 1-3 (1.8 g, 3.69 mmol) was dissolved in dichloromethane (20 mL), followed by successive addition 2, 4, 6-trimethylpyridine (3.30 g, 27.24 mmol, 3.60 mL) and 4,4'-dimethoxytrityl chloride (3.75 g, 11.07 mmol). The reaction mixture was stirred at room temperature for 16 hours. The reaction was quenched with water (20 mL), and extracted with ethyl acetate (20 mL×3). The organic phases were combined, dried over anhydrous sodium sulfate, filtered, and the filtrate was concentrated under reduced pressure to obtain the crude product, which was further purified by silica gel column chromatography (petroleum ether/ethyl acetate (v/v)=7/3) to obtain compound 1-4.

MS (ESI) m/z (M+H)$^+$=790.4.

$^1$H NMR (400 MHz, CDCl$_3$) δ 9.04 (s, 1H), 8.82 (s, 1H), 8.19 (s, 1H), 8.06 (d, J=7.2 Hz, 1H), 7.72-7.62 (m, 1H), 7.59-7.54 (m, 4H), 7.49-7.43 (m, 4H), 7.35-7.31 (m, 2H), 7.29-7.24 (m, 1H), 6.86-6.83 (m, 4H), 6.37 (dd, J=2.9, 15.2 Hz, 1H), 4.66-4.57 (m, 1H), 4.54-4.40 (m, 1H), 4.14 (br s, 1H), 3.81 (s, 3H), 3.80 (s, 3H), 3.79-3.70 (m, 1H), 3.49 (dd, J=3.2, 11.7 Hz, 1H), 0.83 (s, 9H), 0.01 (s, 3H), 0.00 (s, 3H).

Step 4: Preparation of Compound 1-5

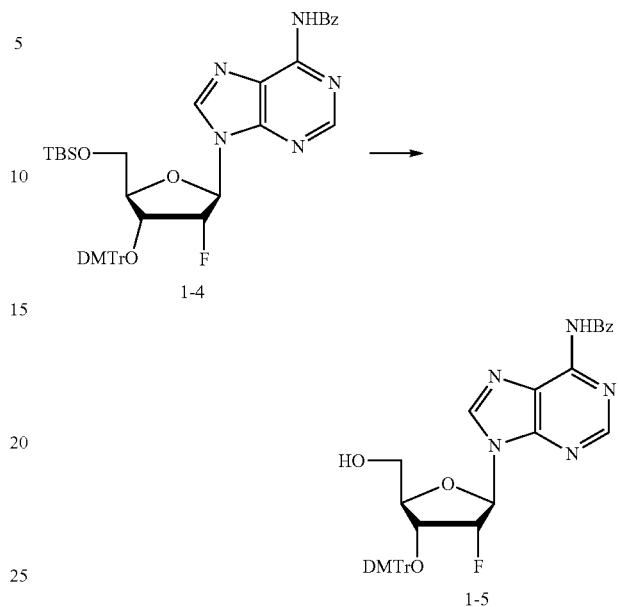

1-4

1-5

At 0° C., the tetrahydrofuran solution of tetrabutylammonium fluoride (1 M, 3.06 mL) was added into the solution of compound 1-4 (2.2 g, 2.78 mmol) in tetrahydrofuran (20 mL). After the addition was complete, the reaction mixture was heated to room temperature and stirred for 3 hours. The reaction mixture was then poured into a mixed system consisted of ethyl acetate (100 mL) and water (100 mL). The organic phase was successively washed with water (50 mL×3) and saturated brine (50 mL), dried over anhydrous sodium sulfate, filtered, and the filtrate was concentrated under reduced pressure to obtain the crude product, which was further purified by silica gel column chromatography (dichloromethane/methanol (v/v)=9/1) to obtain compound 1-5.

MS (ESI) m/z (M+H)$^+$=676.2.

$^1$H NMR (400 MHz, CDCl$_3$) δ 9.09 (s, 1H), 8.73 (s, 1H), 8.16 (s, 1H), 7.65-7.58 (m, 1H), 7.56-7.50 (m, 4H), 7.47-7.39 (m, 4H), 7.34-7.29 (m, 2H), 7.26-7.21 (m, 1H), 6.85 (d, J=8.3 Hz, 4H), 6.31 (dd, J=7.0, 11.4 Hz, 1H), 5.72-5.51 (m, 1H), 5.46-5.34 (m, 1H), 4.69 (br d, J=5.1 Hz, 1H), 3.79 (s, 3H), 3.78 (s, 3H), 3.53-3.44 (m, 1H), 3.37 (s, 1H), 3.03 (br t, J=12.1 Hz, 1H).

Step 5: Preparation of Compound 1-6

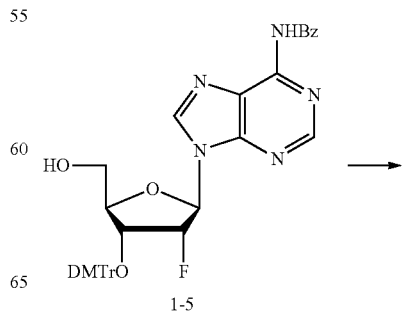

1-5

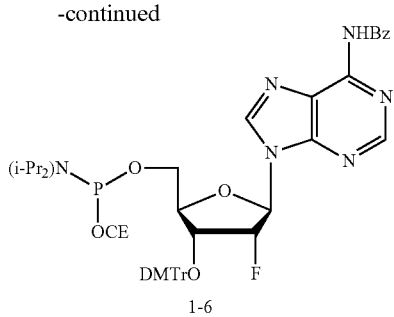

1-6

Under nitrogen atmosphere, 2-cyanoethyl-N,N-diisopropylchlorophosphinimide (525 mg, 2.22 mmol) was added dropwise to the solution of compound 1-5 (1 g, 1.48 mmol) and diisopropyl ethyl amine (742.00 mg, 5.74 mmol, 1.00 mL) in acetonitrile (10 mL). After the completion of the addition, the mixture was stirred at room temperature for 2 hours. The reaction was then terminated, and the reaction mixture was diluted with ethyl acetate (100 mL) and washed with saturated sodium bicarbonate solution (50 mL×3). The organic phase was washed with saturated brine (50 mL×2), dried over anhydrous sodium sulfate, filtered, and the filtrate was concentrated under reduced pressure to obtain compound 1-6.

MS (ESI) m z=793.4.

$^1$H NMR (400 MHz, CDCl$_3$) δ 9.04 (br d, J=12.0 Hz, 1H), 8.76 (d, J=4.6 Hz, 1H), 8.23 (d, J=16.9 Hz, 1H), 8.01 (br d, J=7.3 Hz, 2H), 7.65-7.56 (m, 1H), 7.55-7.48 (m, 4H), 7.44-7.37 (m, 4H), 7.31-7.26 (m, 2H), 7.24-7.20 (m, 1H), 6.83-6.77 (m, 4H), 6.44-6.19 (m, 1H), 4.64-4.50 (m, 1H), 4.31-4.00 (m, 2H), 3.76 (dd, J=3.7, 8.1 Hz, 6H), 3.65-3.29 (m, 5H), 2.80-2.71 (m, 1H), 2.67-2.59 (m, 1H), 2.53 (t, J=6.5 Hz, 1H), 1.13 (dd, J=3.4, 6.6 Hz, 6H), 1.05 (d, J=6.8 Hz, 3H), 0.99 (d, J=6.8 Hz, 3H).

$^{31}$P NMR (162 MHz, CDCl$_3$) δ 148.91, 148.74.

Step 6: Preparation of Compound 1-8

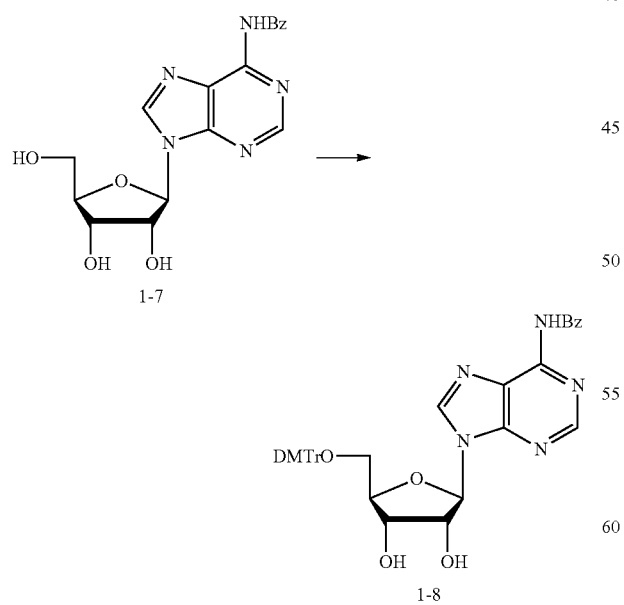

Compound 1-7 (10 g, 26.93 mmol) was dissolved in pyridine (150 mL), followed by dropwise addition of 4,4'-dimethoxytrityl chloride (11.86 g, 35.01 mmol). The reaction was performed at room temperature for 16 hours. The reaction mixture was quenched with water (100 mL), followed by addition of dichloromethane (200 mL). The solid was filtered off. The organic phase was separated, washed with water (100 mL×4), dried over anhydrous sodium sulfate, filtered, and the filtrate was concentrated under reduced pressure to obtain the solid, which was further purified by silica gel column chromatography (eluent: petroleum ether/ethyl acetate (v/v)=20/1-10/1; dichloromethane/methanol (v/v)=1/0-10/1) to obtain a crude product. The crude product was dissolved in dichloromethane (50 mL), then the solution was dropped into methyl tert-butyl ether (200 mL), and the solid was filtered out and dried in vacuum to obtain compound 1-8.

MS (ESI) m/z (M+H)$^+$=674.3.

$^1$H NMR (400 MHz, DMSO-d$_6$) δ 11.25 (s, 1H), 8.69 (s, 1H), 8.60 (s, 1H), 8.04 (d, J=7.6 Hz, 2H), 7.69-7.59 (m, 1H), 7.59-7.51 (m, 2H), 7.36 (d, J=7.6 Hz, 2H), 7.28-7.15 (m, 7H), 6.88-6.76 (m, 4H), 6.07 (d, J=4.8 Hz, 1H), 5.76 (s, 1H), 5.67 (d, J=5.6 Hz, 1H), 5.31 (d, J=5.6 Hz, 1H), 4.84-4.72 (m, 1H), 4.40-4.47 (m, 1H), 3.71 (d, J=1.2 Hz, 6H), 3.23 (d, J=4.8 Hz, 2H).

Step 7: Preparation of Compound 1-9B

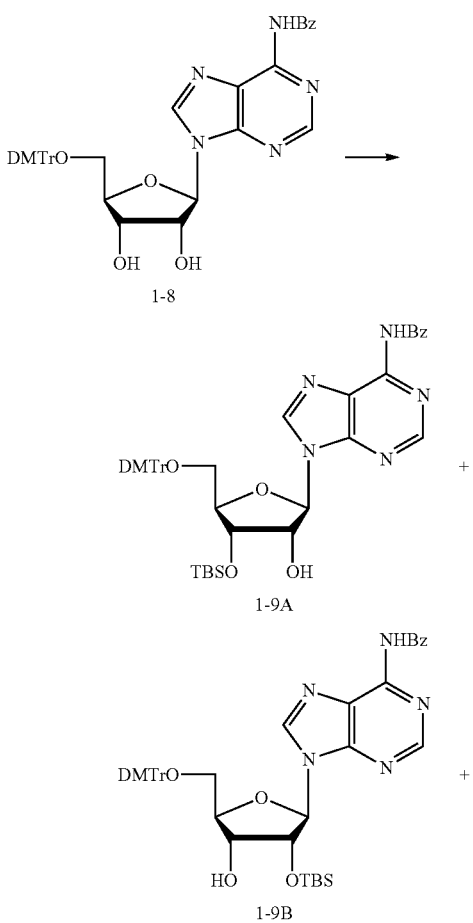

111

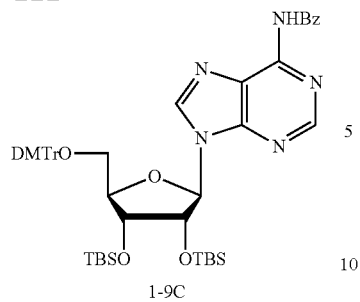

1-9C

Under nitrogen atmosphere, compound 1-8 (15 g, 22.26 mmol) and imidazole (4.55 g, 66.79 mmol) were dissolved in pyridine (60 mL), followed by addition of tert-butyl dimethylchlorosilane (5.03 g, 33.40 mmol, 4.09 mL). The reaction mixture was stirred at room temperature for 4 hours. The reaction solution was diluted with ethyl acetate (200 mL), and the white solid was filtered out. The solution was concentrated to dryness, redissolved in ethyl acetate (200 mL), washed with saturated brine (100 mL×4), dried over anhydrous sodium sulfate, filtered, and the filtrate was concentrated under reduced pressure to obtain the crude product, which was further purified by silica gel column chromatography (petroleum ether/ethyl acetate (v/v)=1/0-5/3/) to obtain compound 1-9A (6.00 g, yield: 29.3%, third peak), compound 1-9B (4.00 g, yield: 22.3%, second peak) and compound 1-9C (5.60 g, yield: 31.4%, first peak).

Compound 1-9A

MS (ESI) m/z (M+H)$^+$=788.4.

$^1$H NMR (400 MHz, CDCl$_3$) δ 9.03 (br s, 1H), 8.76 (s, 1H), 8.25 (s, 1H), 8.01 (br d, J=7.3 Hz, 2H), 7.63-7.55 (m, 1H), 7.55-7.47 (m, 2H), 7.37 (br d, J=7.1 Hz, 2H), 7.30-7.16 (m, 8H), 7.20-7.11 (m, 1H), 6.78 (br d, J=8.8 Hz, 4H), 6.06 (d, J=4.9 Hz, 1H), 4.78-4.74 (m, 1H), 4.62-4.55 (m, 1H), 4.18 (br d, J=3.9 Hz, 1H), 3.76 (s, 6H), 3.51 (dd, J=3.3, 10.6 Hz, 1H), 3.29-3.16 (m, 2H), 0.88 (s, 9H), 0.08 (s, 3H), 0.00 (s, 3H).

Compound 1-9B:

MS (ESI) m/z (M+H)$^+$=788.4.

$^1$H NMR (400 MHz, CDCl$_3$) δ 9.23 (s, 1H), 8.88 (s, 1H), 8.38 (s, 1H), 8.17 (br d, J=7.3 Hz, 2H), 7.79-7.70 (m, 1H), 7.67 (t, J=7.6 Hz, 2H), 7.59 (br d, J=7.6 Hz, 2H), 7.48 (br d, J=8.6 Hz, 4H), 7.44-7.30 (m, 4H), 6.96 (br d, J=8.8 Hz, 4H), 6.25 (d, J=5.1 Hz, 1H), 5.19-5.11 (m, 1H), 4.55-4.47 (m, 1H), 4.40-4.45 (m, 1H), 3.92 (s, 6H), 3.73-3.64 (m, 1H), 3.52-3.55 (m, 1H), 2.87 (d, J=3.9 Hz, 1H), 0.98 (s, 9H), 0.14 (s, 3H), 0.00 (s, 3H).

Step 8: Preparation of Compound 1-10

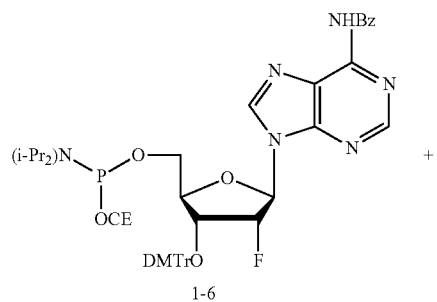

1-6

112

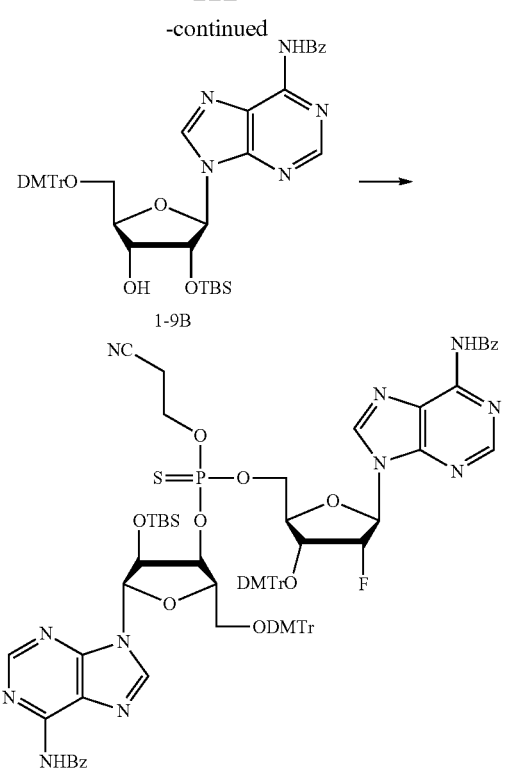

1-9B 1-10

Under nitrogen atmosphere, the solution of compound 1-6 (1.3 g, 1.48 mmol) in acetonitrile (5 mL) was added dropwise to the solution of compound 1-9B (1.16 g, 1.47 mmol), tetrazole (0.45 M acetonitrile solution, 32.98 mL) and 4 Å molecular sieve (2 g) in acetonitrile (20 mL), and reacted at room temperature. After 4 hours, (E)-N,N-dimethyl-N'-(3-thio-3H-1,2,4-dithiozol-5-yl) formamidine (1 g, 4.87 mmol) was added, and further stirred for 1 hour. The reaction mixture was filtered, and the filtrate was diluted with ethyl acetate (100 mL). The organic phase was successively washed with saturated sodium bicarbonate solution (50 mL×3) and saturated brine (50 mL×3), dried over anhydrous sodium sulfate, filtered, and the filtrate was concentrated under reduced pressure to obtain the crude product, which was further purified by silica gel column chromatography (dichloromethane/ethyl acetate (v/v)=9/1) to obtain compound 1-10.

MS (ESI) m/z (M/2+H)$^+$=798.4.

Step 9: Preparation of Compound 1-11

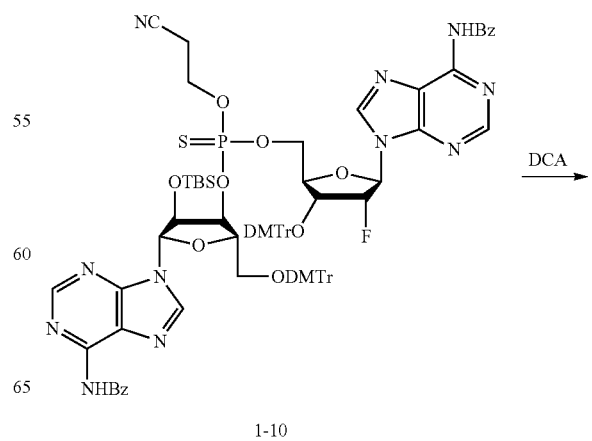

1-10

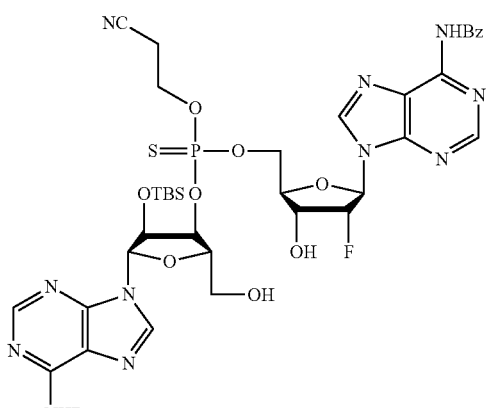

1-11

Compound 1-10 (2.1 g, 1.32 mmol) was dissolved in dichloromethane (10 mL), dichloroacetic acid (24.04 g, 5.27 mmol, 18 mL, 5% dichloromethane solution) and triethyl- silane (10.92 g, 93.91 mmol, 15 mL) were added dropwise, and the reaction mixture was stirred at room temperature for 1.5 hours. The reaction mixture was added with dichloromethane (100 mL), successively washed with water (100 mL), saturated sodium bicarbonate solution (100 mL×2) and saturated brine (100 mL), dried over anhydrous sodium sulfate, filtered, and the filtrate was concentrated under reduced pressure. The obtained solid was purified by silica gel column chromatography (dichloromethane/methanol (v/v)=20/1) to obtain compound 1-11.

MS (ESI) m/z (M+H)$^+$=990.3.

$^1$H NMR (400 MHz, CDCl$_3$) δ 9.24 (br s, 1H), 8.84-8.74 (m, 2H), 8.32-8.19 (m, 2H), 8.07-7.99 (m, 3H), 7.89-7.84 (m, 1H), 7.66-7.47 (m, 6H), 7.44-7.37 (m, 1H), 6.39-6.26 (m, 1H), 5.98 (d, J=7.6 Hz, 0.5H), 5.79 (d, J=7.8 Hz, 0.5H), 5.73 (t, J=5.3 Hz, 0.5H), 5.60 (t, J=5.3 Hz, 0.5H), 5.25-4.94 (m, 3H), 4.63-4.21 (m, 6H), 4.03-3.92 (m, 1H), 3.83-3.72 (m, 1H), 3.70-3.62 (m, 1H), 2.84-2.73 (m, 3H), 0.69 (d, J=2.4 Hz, 9H), −0.11--0.21 (m, 3H), −0.32--0.45 (m, 3H).

$^{31}$P NMR (162 MHz, CDCl$_3$) δ 68.00, 67.97.

Step 10: Preparation of Compound 1-12

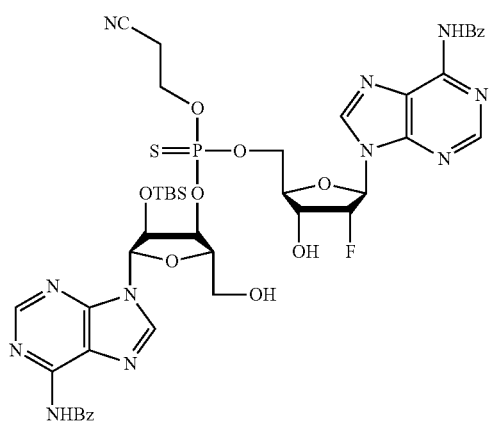

1-11

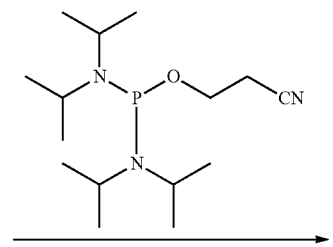

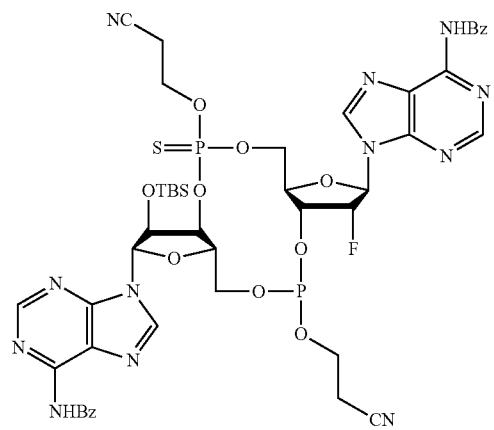

1-12

Under nitrogen atmosphere, compound 1-11 (1 g, 1.01 mmol), 4 Å molecular sieves (2 g) and tetrazole (0.45 M acetonitrile, 58 mL) were mixed with acetonitrile (15 mL), followed by dropwise addition of the solution of 2-cyanoethyl N,N,N',N'-tetraisopropylphosphorodiamidite (431.36 mg, 1.43 mmol, 454.55 μL) in acetonitrile (10 mL) within 30 minutes. The reaction mixture was stirred at room temperature for 1 hour. The reaction was terminated. The reaction mixture was filtered, and ethyl acetate (150 mL) was added to the filtrate for dilution. The organic phase was successively washed with saturated sodium bicarbonate solution (100 mL×3) and saturated brine solution (100 mL), dried over anhydrous sodium sulfate, filtered, and the filtrate was concentrated under reduced pressure. The obtained solid was purified by silica gel column chromatography (dichloromethane/methanol (v/v)=20/3) to obtain compound 1-12.

MS (ESI) m/z (M/2+H)$^+$=545.6.

Step 11: Preparation of Compound 1-13

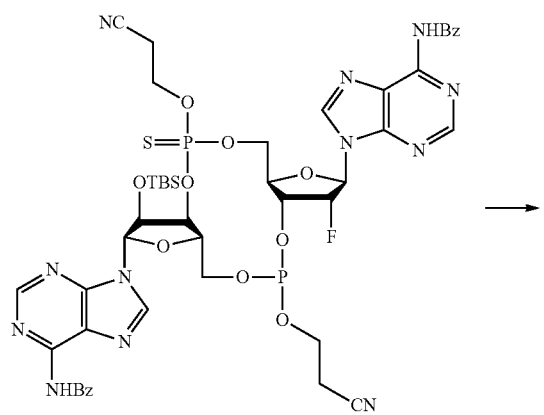

1-12

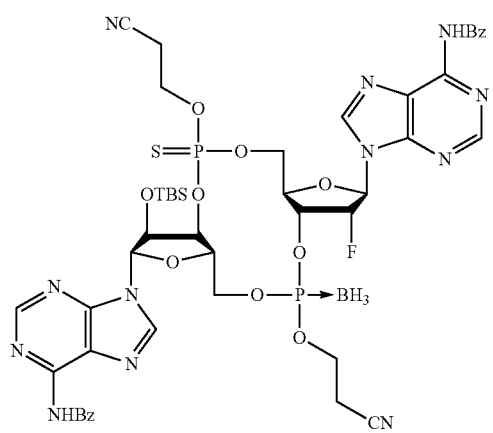

1-13

Under nitrogen atmosphere, at 0° C., borane dimethyl sulfide (2 M dichloromethane solution, 1.00 mL) was added dropwise to the solution of compound 1-12 (500 mg, 459.11 μmol) and 4 Å molecular sieve (500 mg) in dichloromethane (15 mL). After the completion of addition, the mixture was heated to 15° C. for 20 minutes. The reaction was terminated. The reaction mixture was quenched with water (5 mL), diluted with dichloromethane (40 mL), followed by filtration. The filtrate was washed with water (30 mL×3), dried over anhydrous sodium sulfate, followed by filtration. The filtrate was concentrated under reduced pressure to obtain compound 1-13, which can be directly used for the next reaction without further purification.

Step 12: Preparation of Compound 1-14

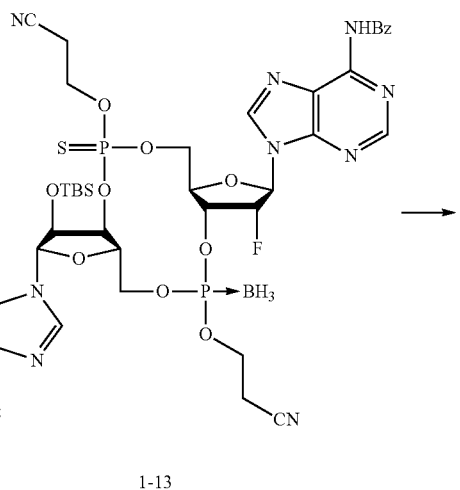

1-13

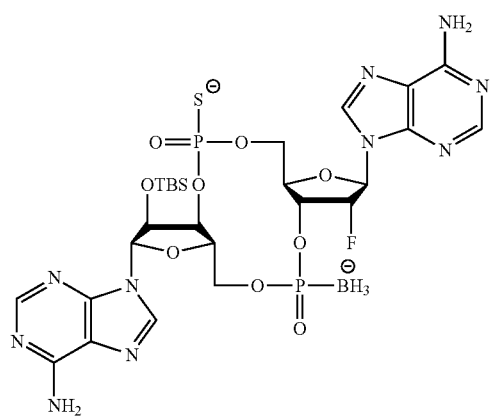

1-14

Compound 1-13 (480 mg, 435.22 μmol) was dissolved in 30% methylamine ethanol solution (15 mL), and the reaction mixture was stirred at room temperature for 12 hours. The reaction mixture was concentrated under reduced pressure, and the solid was dissolved in water (20 mL), extracted with ethyl acetate (10 mL), and lyophilized in aqueous phase to obtain compound 1-14.

Step 13: Preparation of Compounds 1-14A, 1-14B, 1-14C and 1-14D

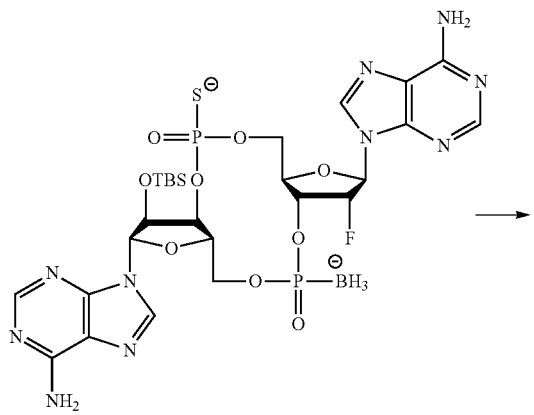

1-14

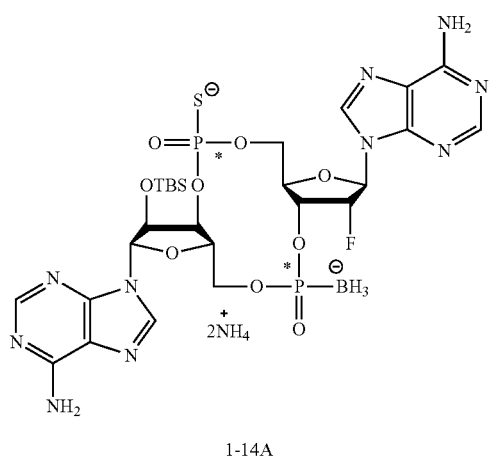

1-14A

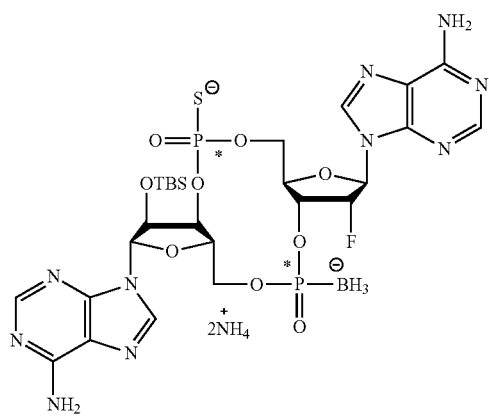

1-14B

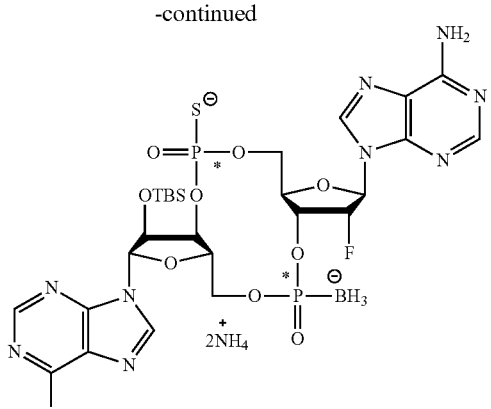

1-14C

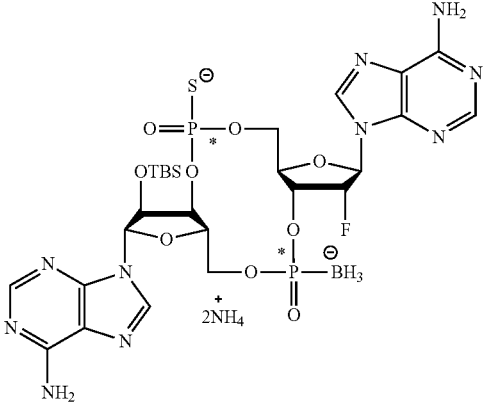

1-14D

Crude compound 1-14 was dissolved in water (10 mL), and separated by HPLC (separation conditions: chromatographic column: Xbridge 150*30 mm*10 μm; mobile phase: [water (10 mM ammonium bicarbonate)-acetonitrile]; acetonitrile %: 12%-32%, flow rate: 25 mL/min, 7 min).

Compound 1-14A (HPLC retention time 3.283 min)
Compound 1-14B (HPLC retention time 3.654 min)
Compound 1-14C (HPLC retention time 4.282 min)
Compound 1-14D (HPLC retention time 4.866 min)
Compound 1-14A:
MS (ESI) m/z (M+H)$^+$=789.2.
$^1$H NMR (400 MHz, DMSO-$d_6$) δ 8.64 (s, 1H), 8.52 (s, 1H), 8.24 (s, 1H), 8.22 (s, 1H), 8.11-7.41 (m, 4H), 6.37-6.27 (m, 1H), 5.96 (s, 1H), 5.25-5.02 (m, 1H), 4.98-4.62 (m, 3H), 4.41-4.18 (m, 4H), 3.98-3.80 (m, 2H), 0.94 (m, 9H), 0.51--0.16 (m, 9H).
$^{31}$P NMR (162 MHz, DMSO-$d_6$) δ 92.31-89.90, 52.80.
$^{19}$F NMR (376 MHz, DMSO-$d_6$) δ -201.02.
Compound 1-14B:
MS (ESI) m/z (M+H)$^+$=789.3.
$^1$H NMR (400 MHz, DMSO-$d_6$) δ 8.62-8.50 (m, 1H), 8.44-8.33 (m, 1H), 8.24 (br s, 1H), 8.19 (s, 1H), 8.13-7.38 (m, 4H), 6.38-6.23 (m, 1H), 5.96 (s, 1H), 5.47-5.14 (m, 1H), 4.91-4.68 (m, 2H), 4.51-4.17 (m, 5H), 3.87-3.69 (m, 2H), 0.95 (s, 9H), 0.25 (s, 3H), 0.24 (s, 3H), 0.13--0.44 (m, 3H).
$^{31}$P NMR (162 MHz, DMSO-$d_6$) δ 91.24-90.10, 53.03.
$^{19}$F NMR (376 MHz, DMSO-$d_6$) δ -201.36.
Compound 1-14C:
MS (ESI) m/z 775.5.
$^1$H NMR (400 MHz, DMSO-$d_6$) δ 8.98 (br s, 1H), 8.78 (br s, 1H), 8.59-8.39 (m, 1H), 8.29-8.05 (m, 2H), 7.82 (br s, 2H), 6.34 (br d, J=12.8 Hz, 1H), 6.13-5.89 (m, 1H), 5.58-5.32 (m, 1H), 5.17 (br s, 1H), 5.05-4.64 (m, 3H), 4.45-4.22 (m, 3H), 3.84-3.74 (m, 2H), 1.00 (s, 9H), 0.76--0.11 (m, 9H).

$^{31}$P NMR (162 MHz, DMSO-d$_6$) δ 92.51-90.91, 50.69.

$^{19}$F NMR (376 MHz, DMSO-d$_6$) δ -201.87.

Compound 1-14D:

MS (ESI) m/z 775.3.

$^1$H NMR (400 MHz, DMSO-d$_6$) δ 9.26 (s, 1H), 8.97 (s, 1H), 8.82-8.37 (m, 4H), 8.29 (s, 1H), 7.82 (s, 1H), 6.46-6.31 (m, 1H), 6.16 (s, 1H), 6.11-5.99 (m, 1H), 5.77-5.57 (m, 1H), 5.13-5.01 (m, 2H), 4.64 (br d, J=11.5 Hz, 1H), 4.55-4.37 (m, 2H), 3.93-3.79 (m, 2H), 1.14 (s, 9H), 0.95 (m, 6H), 0.74 (br s, 3H).

$^{31}$P NMR (162 MHz, DMSO-d$_6$) δ 91.98-90.66, 52.69.

$^{19}$F NMR (376 MHz, DMSO-d$_6$) δ -201.92.

Step 14: Preparation of Compound 1A

Xbridge 150*30 mm*10 μm; mobile phase: [water (10 mM ammonium bicarbonate)-acetonitrile]; acetonitrile %: 0%-20%, flow rate: 25 mL/min, 7 min) to obtain compound 1A (HPLC retention time 1.386 min).

MS (ESI) m/z (M+H)$^+$=674.8.

$^1$H NMR (400 MHz, D$_2$O) δ 8.42 (br s, 2H), 8.18 (br s, 1H), 8.06 (br s, 1H), 6.37 (br d, J=15.8 Hz, 1H), 6.13 (s, 1H), 5.62-5.36 (m, 1H), 5.05 (br s, 1H), 4.95-4.77 (m, 2H), 4.46 (br t, J=7.3 Hz, 2H), 4.40-4.26 (m, 2H), 4.08-3.93 (m, 2H), 0.10 (br s, 3H).

$^{31}$P NMR (162 MHz, D$_2$O) δ 93.99-91.82, 54.64.

$^{19}$F NMR (376 MHz, D$_2$O) δ -202.66.

Step 15: Preparation of Compounds 1B, 1C, 1D

Other optically active pure isomers 1B, 1C, 1D can be prepared from compounds 1-14B, 1-14C, 1-14D respectively according to the preparation method of compound 1A.

Compound 1B:

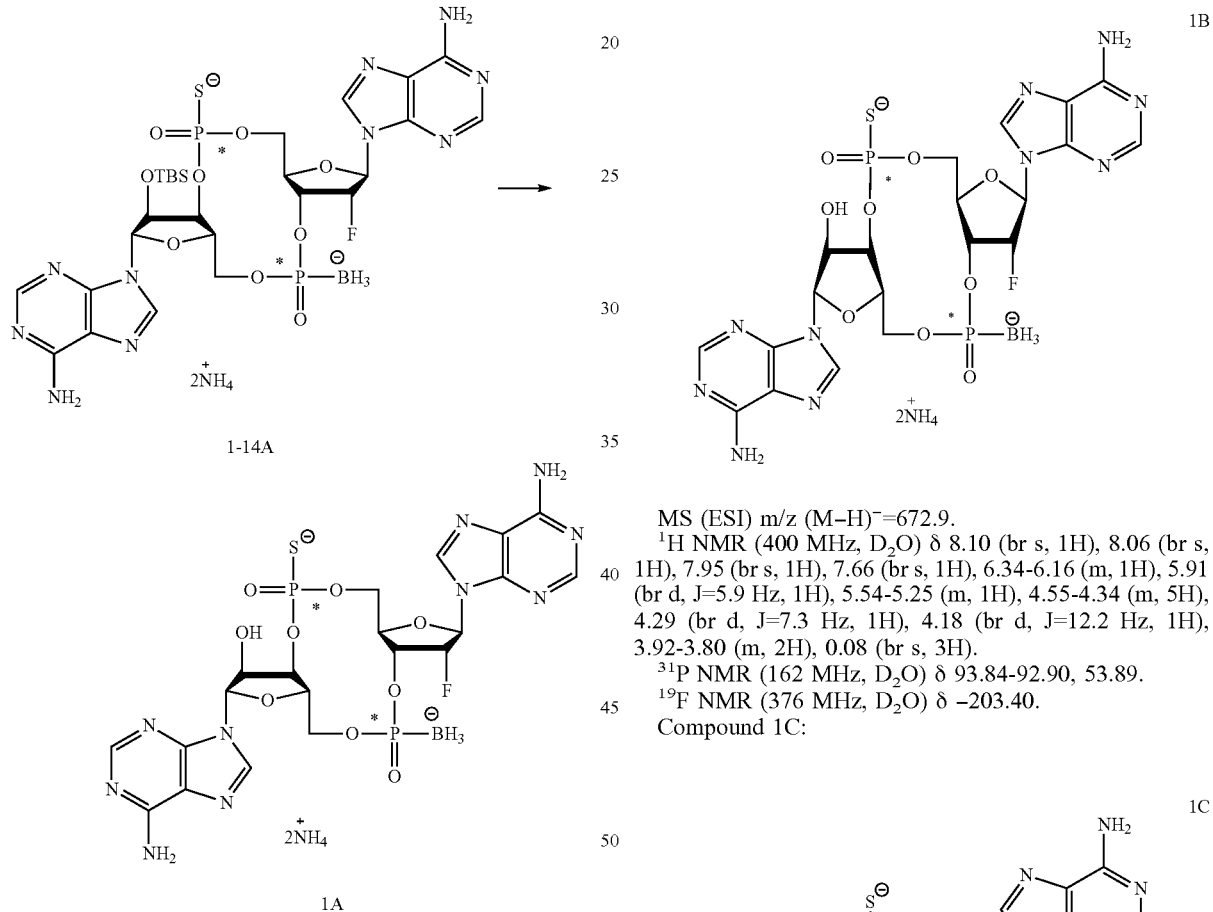

MS (ESI) m/z (M-H)$^-$=672.9.

$^1$H NMR (400 MHz, D$_2$O) δ 8.10 (br s, 1H), 8.06 (br s, 1H), 7.95 (br s, 1H), 7.66 (br s, 1H), 6.34-6.16 (m, 1H), 5.91 (br d, J=5.9 Hz, 1H), 5.54-5.25 (m, 1H), 4.55-4.34 (m, 5H), 4.29 (br d, J=7.3 Hz, 1H), 4.18 (br d, J=12.2 Hz, 1H), 3.92-3.80 (m, 2H), 0.08 (br s, 3H).

$^{31}$P NMR (162 MHz, D$_2$O) δ 93.84-92.90, 53.89.

$^{19}$F NMR (376 MHz, D$_2$O) δ -203.40.

Compound 1C:

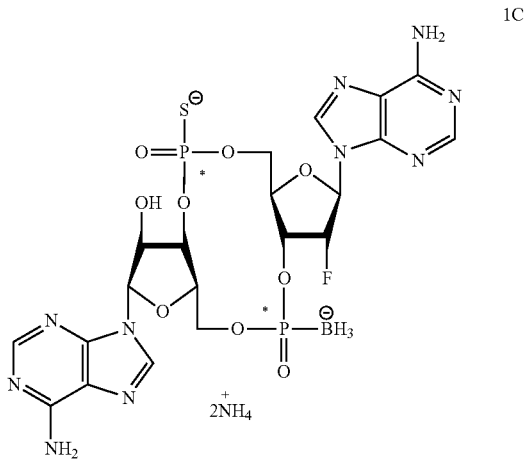

Optically active isomer compound 1-14A (20 mg, 24.31 μmol) was dissolved in pyridine (2 mL), followed by successive addition of triethylamine (290.80 mg, 2.87 mmol, 0.4 mL) and triethylamine trihydrofluoride (197.80 mg, 1.23 mmol, 0.2 mL). The reaction mixture was heated to 50° C., stirred for 14 h and then cooled to room temperature, followed by addition of isopropoxytrimethylsilane (745 mg, 5.63 mmol, 1 mL). The reaction was performed at room temperature for 4 hours. The reaction mixture was then concentrated under reduced pressure. The concentrated residue was dissolved in water (2 mL), and back-extracted with ethyl acetate (3 mL). The aqueous phase was separated by HPLC (separation conditions: chromatographic column:

MS (ESI) m/z (M−H)⁻=672.9.
¹H NMR (400 MHz, D₂O) 8.30-7.95 (m, 3H), 7.75 (br s, 1H), 6.24 (d, J=13.8 Hz, 1H), 6.08 (s, 1H), 5.35-5.06 (m, 1H), 4.97 (br d, J=3.3 Hz, 1H), 4.57-4.28 (m, 6H), 4.02-3.87 (m, 2H), 0.32 (br s, 3H).
³¹P NMR (162 MHz, D₂O) δ 95.59-93.68, 53.85.
¹⁹F NMR (376 MHz, D₂O) δ −202.82.
Compound 1D:

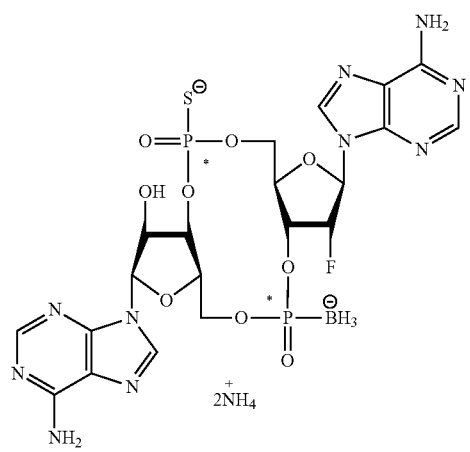

1D

MS (ESI) m/z (M−H)⁻=672.9.
¹H NMR (400 MHz, D₂O) δ 7.97 (br s, 1H), 7.83-7.75 (m, 3H), 6.23 (br d, J=11.2 Hz, 1H), 5.94 (br s, 1H), 5.24-4.97 (m, 1H), 4.44-4.17 (m, 7H), 3.75 (br s, 2H), 0.18 (br s, 3H).
³¹P NMR (162 MHz, D₂O) δ 94.34-93.26, 53.47.
¹⁹F NMR (376 MHz, D₂O) δ −203.12.

Embodiment 2: Preparation of Compounds 2A, 2B

Step 1: Preparation of Compound 2-2

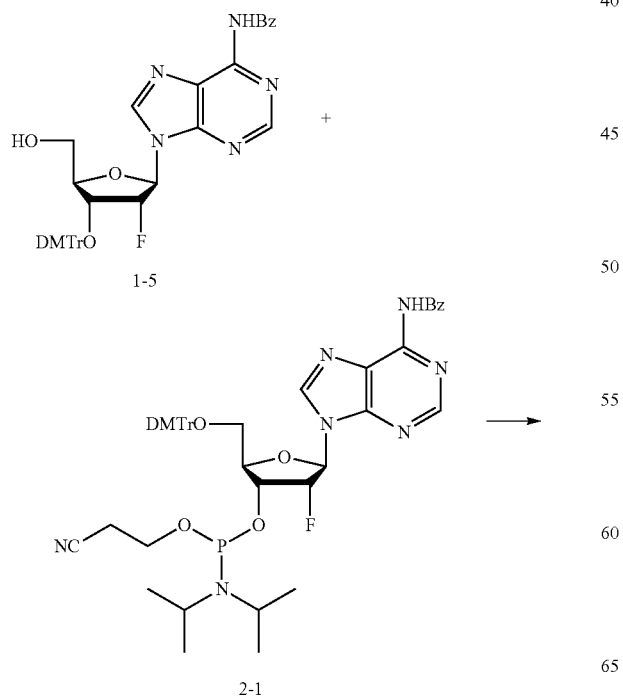

1-5

2-1

-continued

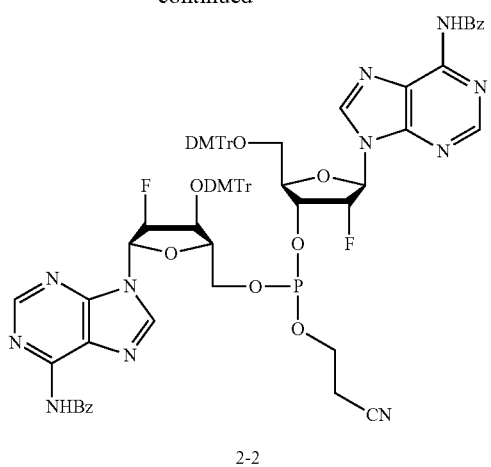

2-2

Under argon atmosphere, compound 1-5 (1.8 g, 2.66 mmol), 4 Å molecular sieve (2 g) and tetrazole (0.45 M acetonitrile solution, 88.80 mL) were dispersed in acetonitrile (10 mL). After stirring at room temperature for 10 minutes, the solution of compound 2-1 (2.33 g, 2.66 mmol) in acetonitrile (10 mL) was added. The reaction mixture was stirred at room temperature for 1 hour, and the reaction solution was diluted with ethyl acetate (50 mL) and filtered. The filtrate was washed with saturated sodium bicarbonate solution (40 mL×3) and saturated brine (10 mL), dried over anhydrous magnesium sulfate, and then concentrated and dried in vacuum to obtain compound 2-2.

MS (ESI) m/z (M/2+H)⁺=725.8.

Step 2: Preparation of Compound 2-3

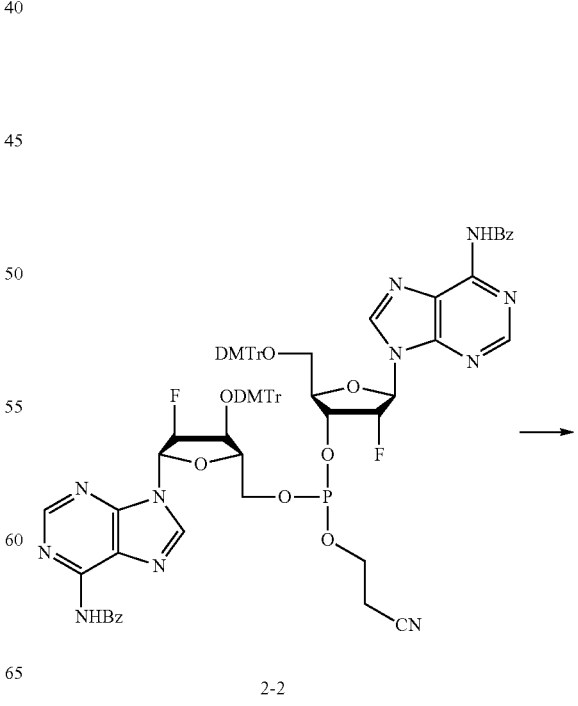

2-2

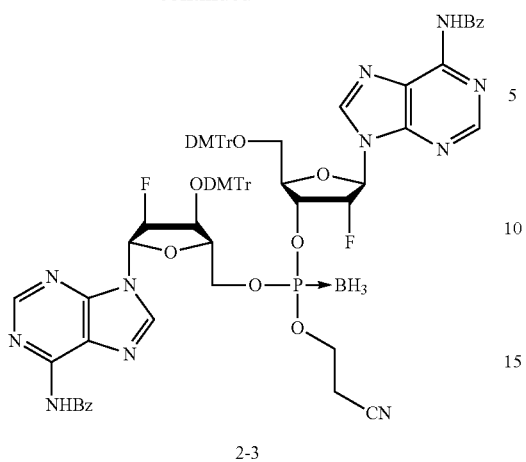

2-3

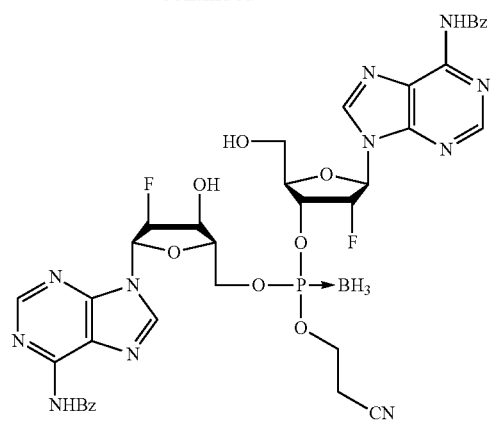

2-4

At 0° C., BH₃-Me₂S (2 M tetrahydrofuran solution, 3.31 mL) was slowly added to the mixed solution of compound 2-2 (3.2 g, 2.21 mmol) and 4 Å molecular sieve (3 g) in dichloromethane (35 mL). The reaction mixture was stirred at room temperature for 40 minutes and then filtered. The filter cake was washed with ethyl acetate (50 mL). Water (20 mL) was added to the filtrate, and then extracted with ethyl acetate (20 mL×3). The combined organic phases were dried over Na₂SO₄ and concentrated under reduced pressure to obtain compound 2-3, and the crude product was directly used in the next reaction.

Step 3: Preparation of Compound 2-4

Compound 2-3 (3.2 g, 2.19 mmol) was dissolved in the mixed solution of acetonitrile (9 mL) and acetic acid (80% aqueous solution, 27 mL), and the reaction solution was stirred at room temperature for 18 hours. The reaction mixture was diluted with ethyl acetate (20 mL), and then washed with saturated sodium bicarbonate solution (10 mL×3) and saturated brine (5 mL). The organic phase was dried over sodium sulfate, and filtered. The filtrate was concentrated in vacuum, and the residue was separated and purified by column chromatography (eluent: petroleum ether/ethyl acetate=0-100%, then dichloromethane/methanol=0-10%) to obtain compound 2-4.

MS (ESI) m/z (M+H)⁺=860.3.

$^1$H NMR (400 MHz, DMSO-d₆) δ 11.25 (s, H), 11.23 (s, 1H), 8.73-8.66 (m, 2H), 8.57 (s, 1H), 8.56 (s, 1H), 8.08-7.96 (m, 4H), 7.72-7.43 (m, 6H), 6.50-6.32 (m, 2H), 6.06-5.77 (m, 2H), 5.70-5.23 (m, 3H), 4.90-4.66 (m, 1H), 4.52-4.30 (m, 2H), 4.26-4.06 (m, 4H), 3.73-3.52 (m, 2H), 2.99-2.79 (m, 2H), 0.68-0.15 (br, 3H).

$^{31}$P NMR (162 MHz, DMSO-d₆) δ 114.2-115.2

$^{19}$F NMR (376 MHz, DMSO-d₆) δ −201.38−−201.75, −204.16−−204.3

Step 4: Preparation of Compound 2-5

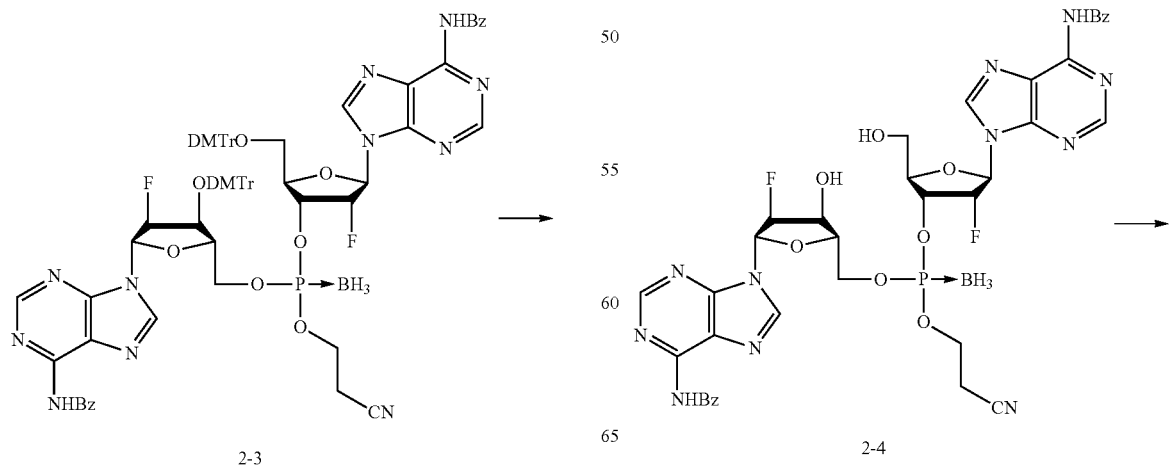

125 -continued

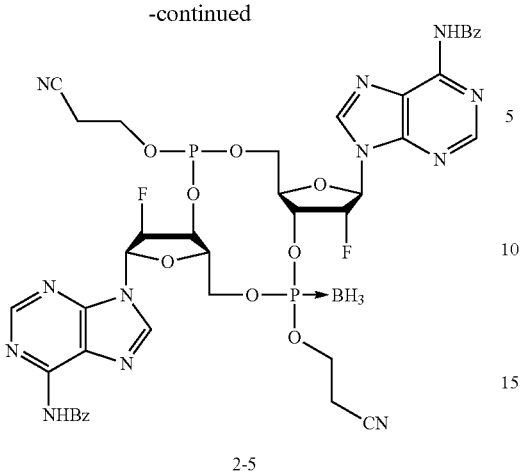

2-5

126 -continued

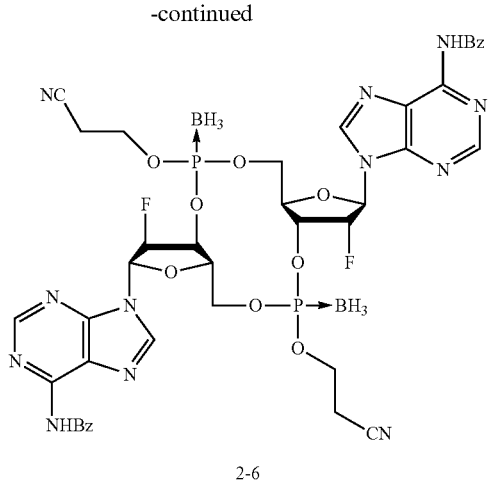

2-6

Under argon atmosphere, 4 Å molecular sieve (0.5 g) was added to the solution of compound 2-4 (200 mg, 232.68 μmol) in acetonitrile (1 mL), and tetrazole (0.45 M acetonitrile solution, 7.76 mL) was added at room temperature. The mixture was stirred at room temperature for 15 minutes, and then 2-cyanoethyl N,N,N',N'-tetraisopropylphosphorodiamidite (105.20 mg, 349.02 μmol) was added in batches. The reaction solution was stirred at room temperature for 1 hour. The molecular sieve was removed by filtration, and the filter cake was washed three times with ethyl acetate (5 mL). The filtrate was washed with saturated sodium bicarbonate solution (5 mL×3) and saturated brine (5 mL), dried over anhydrous sodium sulfate, and then concentrated and dried in vacuum to obtain compound 2-5. The product is directly used for the next reaction without purification.

MS (ESI) m/z (M+H)$^+$=959.4.

Step 5: Preparation of Compound 2-6

At 0° C., borane dimethyl sulfide (2 M tetrahydrofuran solution, 344.26 μL) was added dropwise to the solution of compound 2-5 (220 mg, 229.51 μmol) in dichloromethane (6 mL). The reaction solution was stirred at 0° C. for 20 minutes and then quenched with water (2 mL). After stirring for 10 minutes, the reaction solution was extracted with dichloromethane (5 mL×3). The organic phase was washed with saturated brine (5 mL), dried over anhydrous sodium sulfate, and dried in vacuum to obtain compound 2-6. The product is directly used for the next reaction without purification.

Step 6: Preparation of Compounds 2A, 2B and 2C

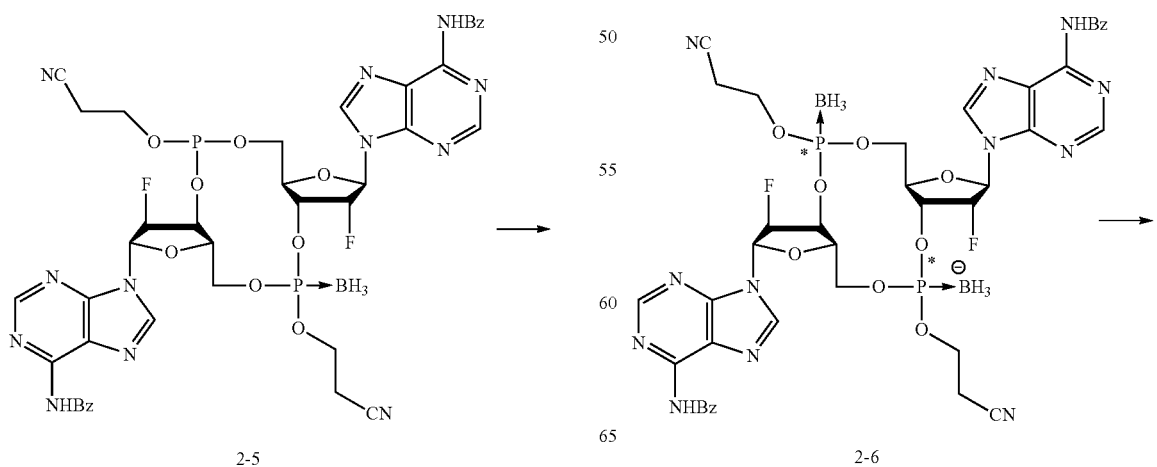

2-5 → 2-6 →

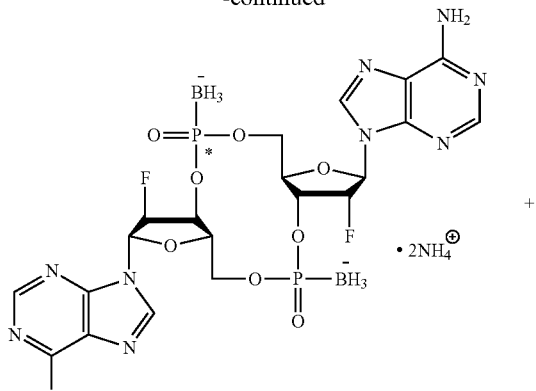

2A

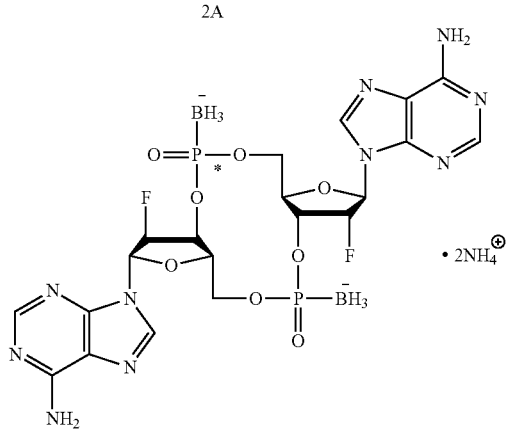

2B

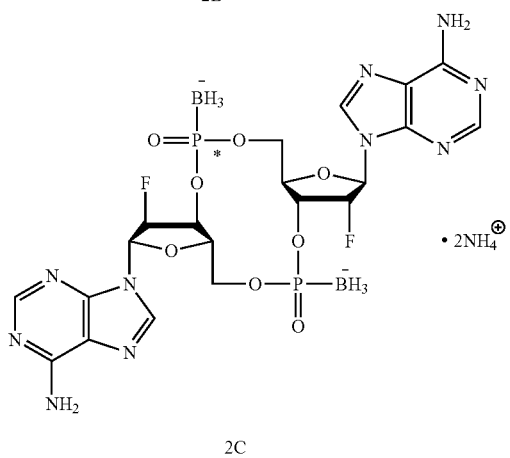

2C

Compound 2-6 (0.5 g, 0.502 mol) was dissolved in 30% methylamine ethanol solution (20 mL) and reacted at 35° C. with stirring for 72 hours. The reaction mixture was concentrated under reduced pressure, and the obtained solid was separated by HPLC (separation conditions: chromatographic column: Waters Xbridge Prep OBD C18 150*30 mm*10 μm; mobile phase: [water (10 mM ammonium bicarbonate)-acetonitrile]; acetonitrile %: 20%-90%, flow rate: 25 mL/min, 20 min).

Compound 2A (HPLC retention time: t=9.2 min).
MS (ESI) m/z (M−H)⁻=657.3.
¹H NMR (400 MHz, D₂O) δ 8.21 (s, 2H), 7.88 (s, 2H), 6.26 (s, 1H), 6.22 (s, 1H), 5.50 (s, 1H), 5.37 (s, 1H), 4.89-4.73 (m, 2H), 4.38-4.35 (m, 2H), 4.18-4.15 (m, 2H), 3.92-3.85 (m, 2H), 0.45--0.2 (br, 6H).
³¹P NMR (162 MHz, D₂O) δ 93.43-92.29
¹⁹F NMR (376 MHz, D₂O) δ −203.09, Compound 2B (HPLC retention time: t=11.1 min).
MS (ESI) m/z (M+H)⁺=659.2.
¹H NMR (400 MHz, D₂O) δ 8.16 (s, 1H), 8.03 (s, 2H), 7.62-7.75 (m, 1H), 6.35-6.30 (m, 1H), 6.18-6.14 (m, 2H), 5.42-5.25 (m, 2H), 5.19-5.07 (m, 2H), 4.48-4.35 (m, 2H), 4.36-4.26 (m, 2H), 4.26-4.17 (m, 2H), 3.85-3.81 (m, 2H), 0.55--0.15 (br, 6H)
³¹P NMR (162 MHz, D₂O) δ 92.77-90.51
¹⁹F NMR (376 MHz, D₂O) δ −202.63

Compound 2C (HPLC retention time: t=17.0 min).
MS (ESI) m/z (M+H)⁺=659.4.
¹H NMR (400 MHz, D₂O) δ 8.12 (s, 2H), 7.84 (s, 2H), 6.15 (s, 1H), 6.11 (s, 1H), 5.42-5.26 (m, 2H), 5.09-5.03 (m, 2H), 4.35-4.28 (m, 4H), 3.89-3.84 (m, 2H), 0.55--0.1 (br, 6H)
³¹P NMR (162 MHz, D₂O) δ 95.02-92.41
¹⁹F NMR (376 MHz, D₂O) δ −201.85

Step 7: Preparation of Compound 2D

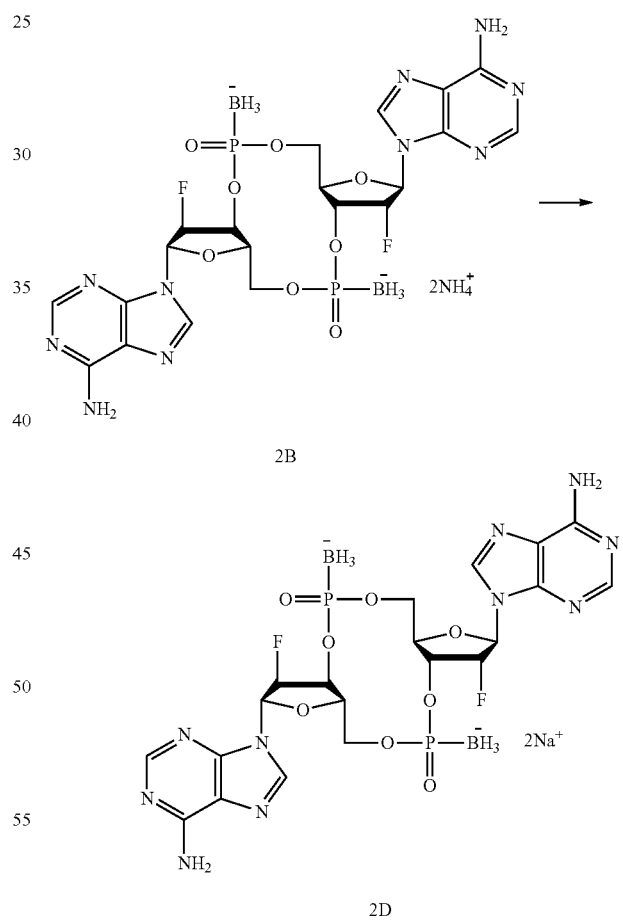

Dowex-50W ion exchange resin (20 g) was placed in a beaker, washed with deionized water (10 mL), then added with sulfuric acid (15% deionized water solution), and stirred for 5 minutes. The liquid was poured out, and the resin was transferred to a chromatographic column, and successively washed with sulfuric acid (15% deionized water solution, 4 CV) and deionized water to pH=7.0. The treated resin was transferred into a beaker, followed by addition of sodium hydroxide (15% deionized water solution), and stirred for 5 minutes. The liquid was poured out, and the resin was transferred to a chromatographic column, and successively washed with sodium hydroxide (15% deionized water solution) and water in turn to pH=7.0. Compound 2B (140 mg, 202.28 umol, 2NH$_4$) was dissolved in water (2 mL) and purified by the above-mentioned chromatographic column to obtain compound 2D.

MS (ESI) m/z (M+H)$^+$=659.3.

$^1$H NMR (400 MHz, D$_2$O) δ 8.27 (s, 1H), 8.23 (s, 1H), 8.05 (s, 1H), 7.78 (s, 1H), 6.33-6.25 (m, 2H), 5.55-5.42 (m, 2H), 5.05-4.90 (m, 2H), 4.44-4.36 (m, 3H), 4.29-4.25 (m, 1H), 4.02-3.96 (m, 2H), 0.55--0.2 (br, 6H).

$^{31}$P NMR (162 MHz, D$_2$O) δ 93.43-92.29

$^{19}$F NMR (376 MHz, D$_2$O) δ -203.09

Embodiment 3: Preparation of Compounds 3A, 3B, 3C, 3D

Step 1: Preparation of Compound 3-2

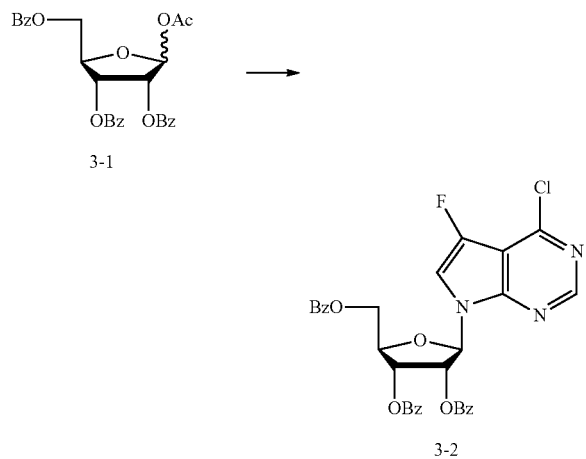

Under argon atmosphere, 4-chloro-5-fluoro-7H-pyrrolo[2,3-d]-pyrimidine (1.03 g, 6.0 mmol) was dissolved in acetonitrile (40 mL), followed by addition of BSA (1.76 mL, 7.2 mmol). After stirring for 5 minutes, compound 3-1 (3.0 g, 6.0 mmol) and trimethylsilyl trifluoromethanesulfonate (1.32 mL, 7.2 mmol) was successively added. After reacting at 25° C. for 30 minutes, the reaction mixture was heated to 80° C. for 3 hours. Water (100 mL) was added to quench the reaction, then the reaction mixture was extracted with ethyl acetate (100 mL×3). The organic phases were combined, washed with saturated brine (100 mL), dried over anhydrous sodium sulfate, filtered, and the filtrate was concentrated under reduced pressure to obtain the crude product, which was further purified by silica gel column chromatography (petroleum ether/ethyl acetate (v/v=5/1)) to obtain compound 3-2.

MS (ESI) m/z (M+H)$^+$=616.1

$^1$H NMR (400 MHz, CDCl$_3$) δ 8.59 (s, 1H), 8.11 (d, J=8.0 Hz, 2H), 8.01 (d, J=8.0 Hz, 2H), 7.91 (d, J=8.0 Hz, 2H), 7.65-7.38 (m, 9H), 7.18 (s, 1H), 6.69 (d, J=8 Hz, 1H), 6.15-6.07 (m, 2H), 4.91-4.66 (m, 3H).

Step 2: Preparation of Compound 3-3

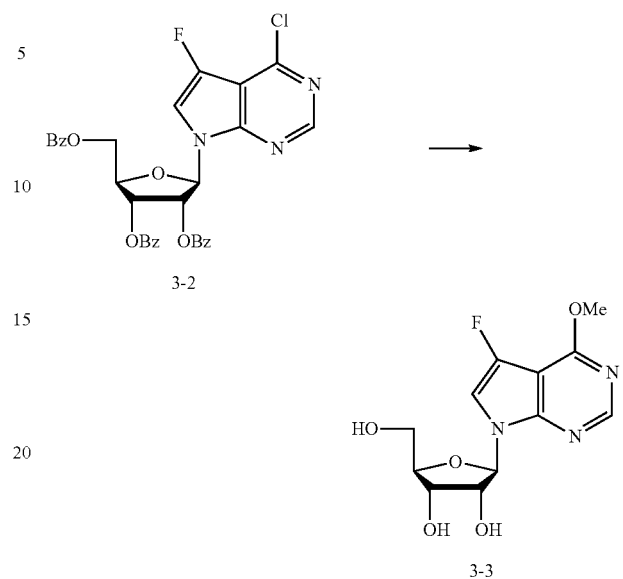

Under argon atmosphere, compound 3-2 (200 mg, 0.32 mmol) was added to the solution of sodium methoxide (4 mL, 0.5 mol/L, 1.92 mmol) in methanol. The reaction was performed at 25° C. for 1 hour. The pH of reaction mixture was adjusted to 7.0 with acetic acid, and then concentrated to obtain crude product, which was purified by silica gel column chromatography (dichloromethane/methanol (v/v)=10/1) to obtain compound 3-3.

MS (ESI) m/z (M+H)$^+$=300.1

$^1$H NMR (400 MHz, DMSO-d$_6$) δ 8.45 (s, 1H), 7.66 (s, 1H), 6.18 (d, J=4.0 Hz, 1H), 5.35 (d, J=4.0 Hz, 1H), 5.16 (d, J=4.0 Hz, 1H), 5.10-5.06 (m, 1H), 4.35-4.31 (m, 1H), 4.11-4.09 (m, 1H), 4.07 (s, 3H), 3.92-3.88 (m, 1H), 3.65-3.51 (m, 2H).

Step 3: Preparation of Compound 3-4

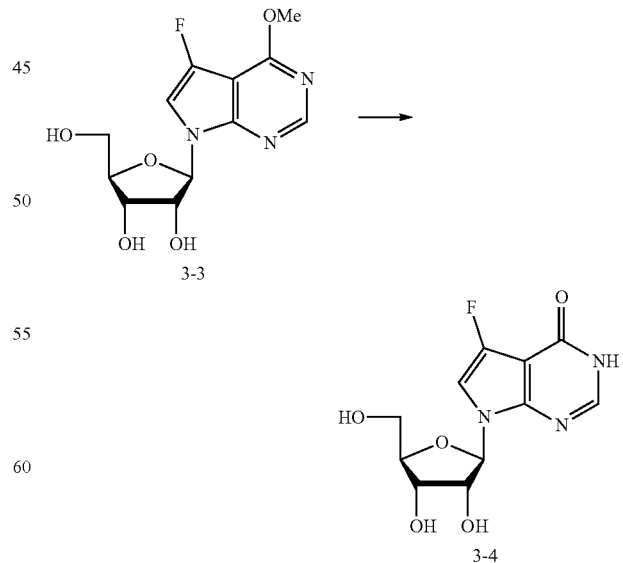

Under argon atmosphere, compound 3-3 (100 mg, 0.34 mmol) was dissolved in acetonitrile (10 mL), followed by successive addition of sodium iodide (250 mg, 1.68 mmol) and trimethyliodosilane (0.2 mL, 1.56 mmol). The reaction mixture was stirred at 25° C. for 3 hours, and concentrated under reduced pressure. The crude product was purified by silica gel column chromatography (dichloromethane/methanol (v/v)=8/1) to obtain compound 3-4.

MS (ESI) m/z (M+H)=286.0

$^1$H NMR (400 MHz, DMSO-d$_6$) δ 12.1 (s, 1H), 7.92 (d, J=3.2 Hz, 1H), 7.35 (d, J=3.2 Hz, 1H), 6.06 (dd, J=8.0 Hz, 3.2 Hz, 1H), 5.35-5.02 (m, 3H), 4.23 (s, 1H), 4.06-4.04 (m, 1H), 3.88-3.86 (m, 1H), 3.62-3.51 (m, 2H).

Step 4: Preparation of Compound 3-5

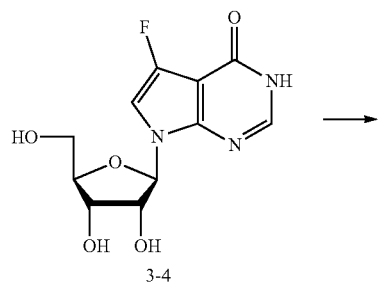

3-4

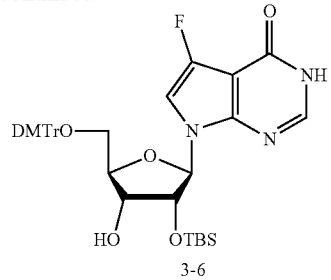

3-6

Under nitrogen atmosphere, compound 3-5 (0.85 g, 1.45 mmol) was dissolved in pyridine (8 mL), followed by successive addition of imidazole (200 mg, 2.94 mmol) and tert-butyl dimethylchlorosilane (265 mg, 1.76 mmol). The reaction mixture was stirred at 25° C. for 12 hours. Most of solvent was removed under reduced pressure, and the reaction solution was poured into ethyl acetate (30 mL). The organic phase was washed with saturated brine (10 mL×3), dried over anhydrous sodium sulfate, filtered, and the filtrate was concentrated under reduced pressure to obtain the crude product, which was further purified by silica gel column chromatography (petroleum ether/ethyl acetate (v/v)=2/1) to obtain compound 3-6.

MS (ESI) m/z (M+H)$^+$=702.3.

$^1$H NMR (400 MHz, DMSO-d$_6$) 12.14 (br s, 1H), 7.92 (br s, 1H), 7.39 (br s, 2H), 7.33-7.21 (m, 7H), 7.13 (br s, 1H), 6.88 (br s, 4H), 6.11 (br s, 1H), 5.10 (br s, 1H), 4.40 (br d, J=4.4 Hz, 1H), 4.16-3.94 (m, 3H), 3.78-3.68 (m, 6H), 3.23 (br d, J=9.3 Hz, 1H), 0.79-0.70 (m, 9H), −0.03 (br d, J=2.2 Hz, 3H), −0.10--0.17 (m, 3H).

Step 6: Preparation of Compound 3-7

Under argon atmosphere, DMTrCl (2.57 g, 7.57 mmol) was slowly added to pyridine (10 mL) solution of compound 3-4 (1.8 g, 6.31 mmol), and the reaction mixture was stirred at 25° C. for 12 hours. Concentrated under reduced pressure to dryness, redissolved in ethyl acetate (50 mL), the organic phase was washed with saturated brine (20 mL×5), dried over anhydrous sodium sulfate, filtered, and the filtrate was concentrated under reduced pressure, the crude product was purified by silica gel column chromatography (dichloromethane/methanol (v/v)=20/1) to obtain compound 3-5.

MS (ESI) m/z (M+H)$^+$=588.3.

$^1$H NMR (400 MHz, DMSO-d$_6$) 12.15 (br s, 1H), 7.93 (d, J=2.9 Hz, 1H), 7.41-7.34 (m, 2H), 7.32-7.14 (m, 8H), 6.86 (dd, J=2.0, 8.8 Hz, 4H), 6.08 (d, J=3.7 Hz, 1H), 5.50 (d, J=5.9 Hz, 1H), 5.19 (d, J=5.6 Hz, 1H), 4.34-4.25 (m, 1H), 4.12 (q, J=5.1 Hz, 2H), 3.99 (q, J=4.5 Hz, 1H), 3.73 (s, 6H).

Step 5: Preparation of Compound 3-6

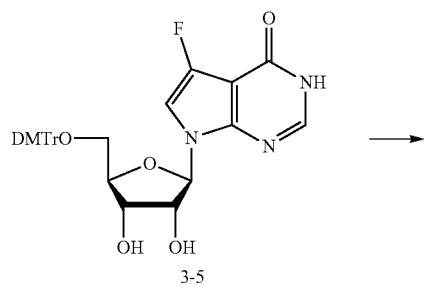

3-5

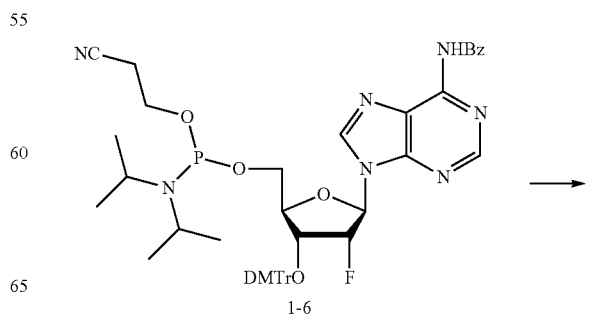

1-6

133

-continued

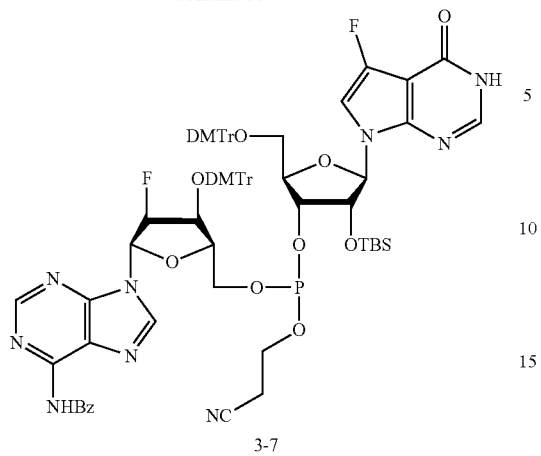

3-7

Compound 1-6 (0.7 g, 997.36 μmol) was dissolved in tetrahydrofuran (4 mL), followed by successive addition of 4 Å molecular sieve (1 g) and tetrazole (0.45 M acetonitrile solution, 33.25 mL). Compound 3-6 (1.05 g, 1.20 mmol) in acetonitrile (6 mL) was then added dropwise to the reaction mixture at 25° C. under argon atmosphere, and stirred for 1 hour. The reaction mixture was diluted with ethyl acetate (50 mL), followed by filtration. The filtrate was successively washed with saturated sodium bicarbonate solution (50 mL×3) and saturated brine (50 mL) in turn, dried over anhydrous sodium sulfate, followed by filtration. The filtrate was concentrated under reduced pressure to obtain the crude product, which was further purified by flash column chromatography (dichloromethane/methanol (v/v)=10/1) to obtain compound 3-7.

$^{31}$P NMR (162 MHz, CDCl$_3$) δ 138.84, 138.40.

$^{19}$F NMR (376 MHz, CDCl$_3$) δ −163.24, −196.85-−198.69.

Step 7: Preparation of Compound 3-8

134

-continued

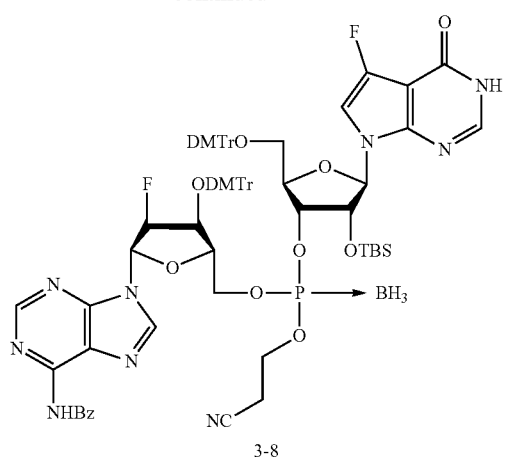

3-8

At 0° C. under argon atmosphere, compound 3-7 (1.8 g, 1.22 mmol) was dissolved in dichloromethane (30 mL), followed by successive addition of 4 Å molecular sieve (2 g) and borane dimethyl sulfide complex (2 M tetrahydrofuran solution, 2.44 mL). The reaction mixture was stirred at 20° C. for 30 minutes. The reaction mixture was quenched with water (5 mL), diluted with dichloromethane (40 mL), filtered, and the filtrate was washed with water (30 mL×3). The organic phase was dried over anhydrous sodium sulfate, filtered, and the filtrate was concentrated under reduced pressure to obtain crude product 3-8, which was directly used for the next reaction without further purification.

Step 8: Preparation of Compound 3-9

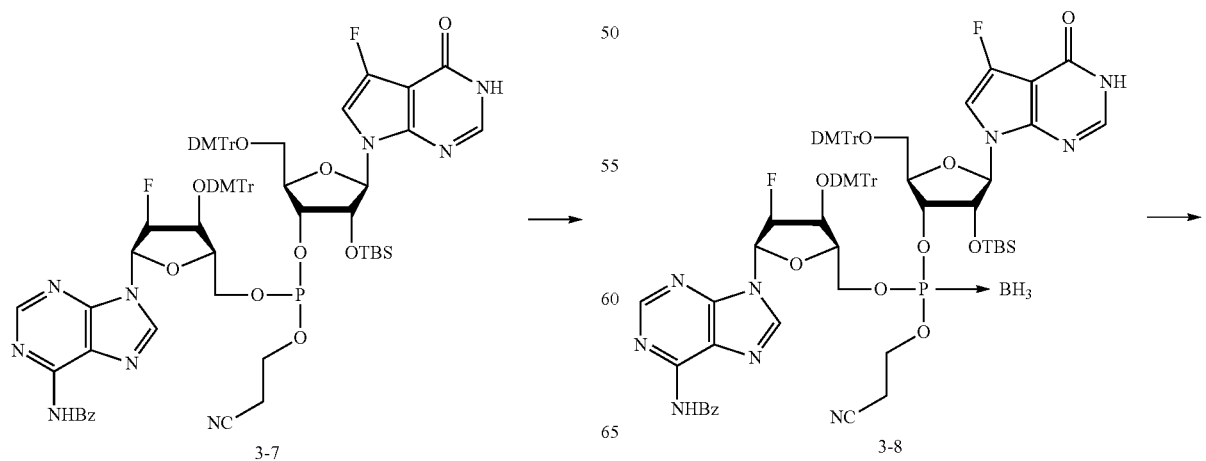

3-7 → 3-8 →

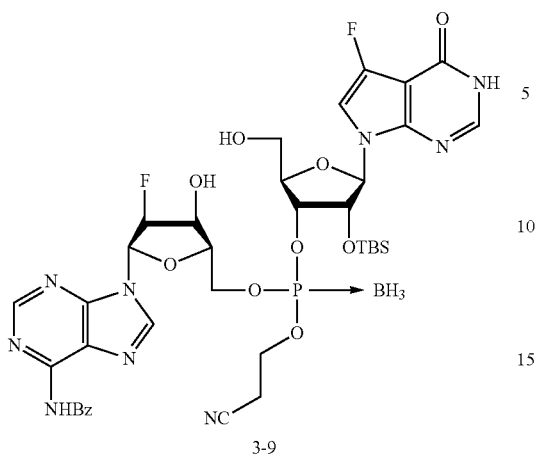

3-9

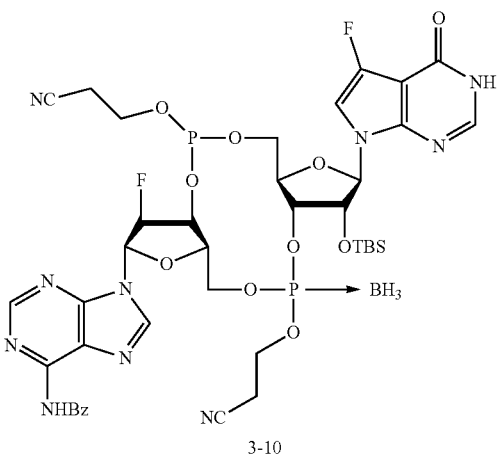

3-10

Compound 3-8 (1.6 g, 1.07 mmol) was dissolved in dichloromethane (20 mL), followed by successive addition of 2,2-dichloroacetic acid (1.23 g, 5.37 mmol, 5% dichloromethane solution) and triethylsilane (14.56 g, 125.22 mmol, 20 mL). After completion of addition, the reaction mixture was stirred at 25° C. for 1 hour. The reaction was diluted with dichloromethane (50 mL). The organic phase was successively washed with water (50 mL), saturated sodium bicarbonate solution (50 mL×2) and saturated brine (50 mL), dried over anhydrous sodium sulfate, filtered, and the filtrate was concentrated under reduced pressure to obtain the crude product, which was further purified by silica gel column chromatography (dichloromethane/methanol (v/v)=9/1), and separated by HPLC (separation conditions: chromatographic column: Xbridge Prep OBD C18 150*30 mm 5 μm; mobile phase: [water (10 mM ammonium bicarbonate)-acetonitrile]; acetonitrile %: 45%-45%, flow rate: 25 mL/min, 8 min) in turn to obtain compound 3-9 (HPLC retention time: 3.488 min).

MS (ESI) m/z (M+H)$^+$=886.2

Step 8: Preparation of Compound 3-10

At 20° C. under argon atmosphere, compound 3-9 (180 mg, 203.23 μmol) was dissolved in acetonitrile (2 mL), followed by successive addition of the solution of 4 Å molecular sieve (0.5 g) and 1H-tetrazole in acetonitrile (0.45 M, 9.03 mL), and 2-cyanoethyl N,N,N',N'-tetraisopropylphosphorodiamidite (91.88 mg, 304.85 μmol, 96.82 μL) was added dropwise. The reaction mixture was stirred for 1 hour, filtered, and the filtrate was diluted with ethyl acetate (30 mL). The organic phase was washed with saturated sodium bicarbonate solution (20 mL×2), dried over anhydrous sodium sulfate, concentrated under reduced pressure, and the crude product was purified by silica gel column chromatography (dichloromethane/methanol (v/v)=15/1) to obtain compound 3-10.

$^{31}$P NMR (162 MHz, CD$_3$CN) δ 139.33, 138.84, 137.41, 136.85.

$^{19}$F NMR (376 MHz, CD$_3$CN) δ −165.95, 166.02, −199.48--201.40.

Step 9: Preparation of Compound 3-11

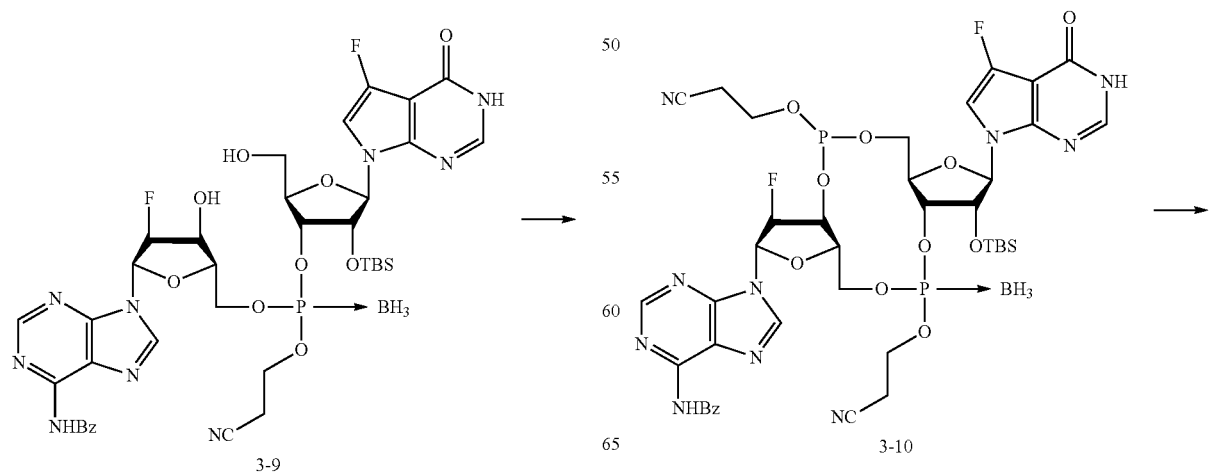

3-9        3-10

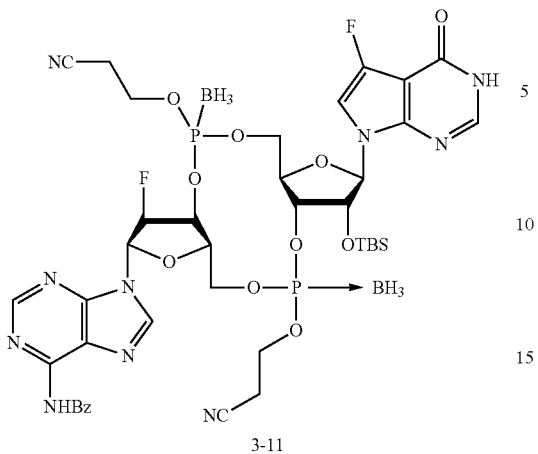

3-11

At 0° C., under argon atmosphere, borane dimethyl sulfide complex (2 M tetrahydrofuran solution, 243.72 μL) was added dropwise to the solution of compound 3-10 (160 mg, 162.48 μmol) and 4 Å molecular sieve (200 mg) in dichloromethane (5 mL). After the completion of addition, the reaction mixture was stirred at 15° C. for 30 minutes. The reaction mixture was then quenched with water (5 mL), diluted with dichloromethane (40 mL), filtered, and the filtrate was washed with water (30 mL). The organic phase was dried over anhydrous sodium sulfate, filtered, and the filtrate was concentrated to obtain crude product 3-11, which was directly used for the next reaction without further purification.

Step 10: Preparation of Compounds 3-12A, 3-12B, 3-12C, 3-12D

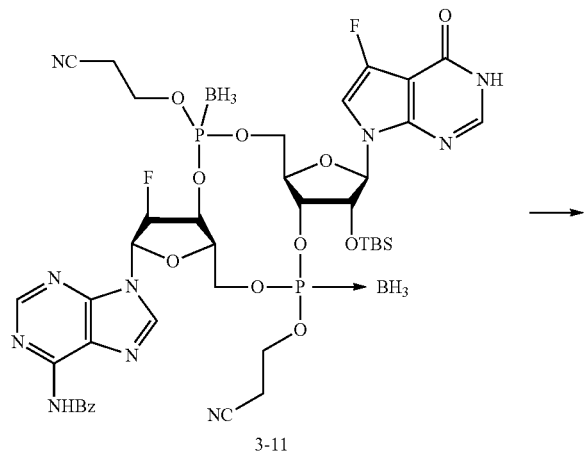

3-11

⟶

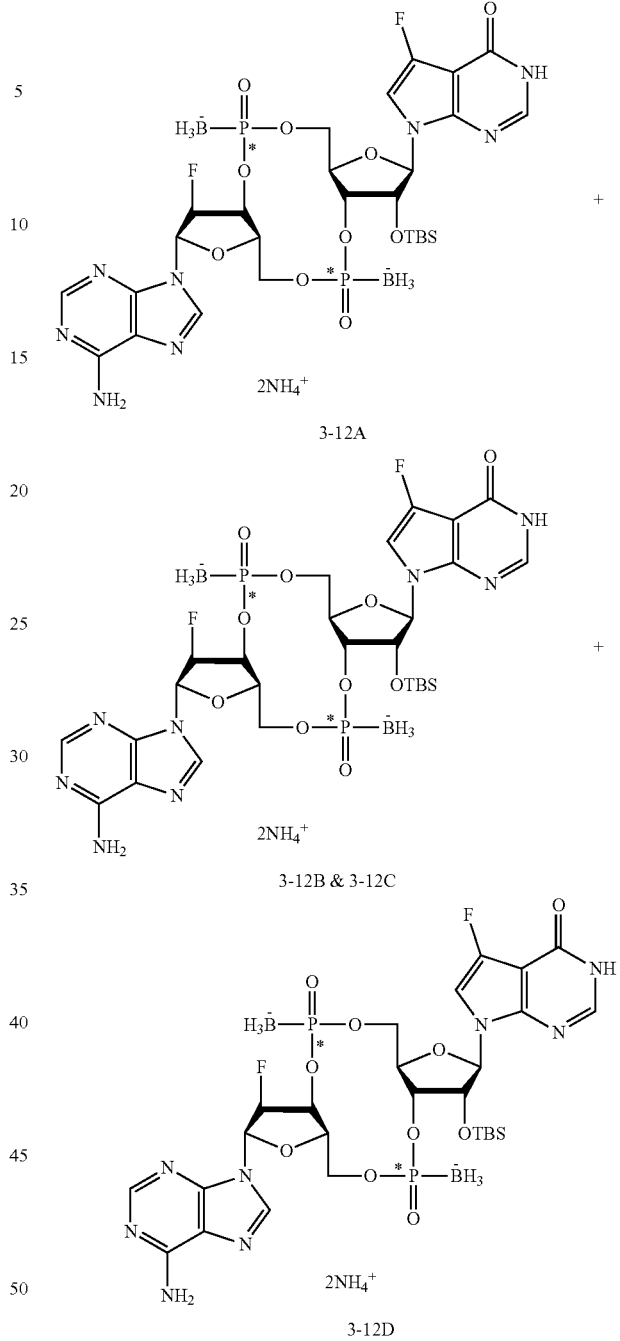

Compound 3-11 (140 mg, 140.20 μmol) was dissolved in 30% methylamine ethanol solution (5 mL) and reacted at 20° C. with stirring for 72 hours. The reaction mixture was concentrated under reduced pressure, and the residue was dissolved in water (10 mL), and back-extracted with ethyl acetate (10 mL). The aqueous phase was lyophilized to obtain the crude product, which was separated by HPLC (separation conditions: chromatographic column: Xbridge Prep OBD C18 150*30 mm 5 μm; mobile phase: [water (0.04% ammonia water+10 mM ammonium bicarbonate)-acetonitrile]; acetonitrile %: 5%-45%, flow rate: 25 mL/min, 7 min) to obtain: Compound 3-12A (HPLC retention time 2.143 min)

Mixture of compounds 3-12B and 3-12C (HPLC retention time 2.304 min)
Compound 3-12D (HPLC retention time 2.596 min)
  Compound 3-12A:
    MS (ESI) m/z (M+H)$^+$=789.3.
    $^1$H NMR (400 MHz, CD$_3$OD) δ 8.74 (s, 1H), 8.29 (s, 1H), 7.84 (d, J=1.5 Hz, 1H), 7.59 (s, 1H), 6.40 (d, J=15.4 Hz, 1H), 6.21 (s, 1H), 5.62-5.40 (m, 1H), 5.31-5.08 (m, 1H), 4.55-4.24 (m, 6H), 4.03-3.97 (m, 2H), 0.99 (s, 9H), 0.83--0.35 (m, 12H).
    $^{31}$P NMR (162 MHz, DMSO-d$_6$) δ 93.38-90.01.
    $^{19}$F NMR (376 MHz, DMSO-d$_6$) δ −165.43, −200.43--200.57.
  Mixture of compounds 3-12B and 3-12C:
    MS (ESI) m/z (M+H)$^+$=789.3.
    $^{31}$P NMR (162 MHz, DMSO-d$_6$) δ 93.82-90.37.
    $^{19}$F NMR (376 MHz, DMSO-d$_6$) δ −164.75, −165.44, −199.67--200.85.
  Compound 3-12D:
    MS (ESI) m/z (M+H)$^+$=789.3.
    $^1$H NMR (400 MHz, CD$_3$OD) δ 8.62 (br s, 1H), 8.21 (br s, 1H), 7.86-7.61 (m, 1H), 7.42 (br s, 1H), 6.37 (br d, J=16.6 Hz, 1H), 6.07 (br s, 1H), 5.58-5.32 (m, 1H), 5.28-5.08 (m, 1H), 4.59-4.26 (m, 6H), 4.02-3.80 (m, 2H), 1.07-0.85 (m, 9H), 0.73-0.05 (m, 12H).
    $^{31}$P NMR (162 MHz, DMSO-d$_6$) δ 94.76-91.59.
    $^{19}$F NMR (376 MHz, DMSO-d$_6$) δ −165.15, −200.66--200.94.
Step 11: Preparation of Compound 3A Compound 3-12A (10 mg, 12.69 μmol) was dissolved in pyridine (1 mL), followed by successive addition of triethylamine (73.83 mg, 729.59 μmol, 101.55 μL) and triethylamine trihydrofluoride (49.01 mg, 304.00 μmol, 49.55 μL). The reaction mixture was heated to 50° C. and stirred for 48 hours. The reaction mixture was cooled to 25° C., then isopropoxy trimethylsilane (193.01 mg, 1.46 mmol, 259.08 μL) was added, and the reaction mixture was stirred at 25° C. for 4 hour and concentrated under reduced pressure. The residue was dissolved in water (3 mL), and back-extracted with ethyl acetate (3 mL). The aqueous phase was collected, and separated by HPLC (separation conditions: chromatographic column: Xbridge Prep OBD C18 150*30 mm 5 μm; mobile phase: [water (10 mM ammonium bicarbonate)-acetonitrile]; acetonitrile %: 0%-30%, flow rate: 25 mL/min, 7 min) to obtain compound 3A.

MS (ESI) m/z (M−H)$^+$=672.8.

$^1$H NMR (400 MHz, D$_2$O) δ 8.23 (br s, 1H), 7.95 (br s, 1H), 7.77 (br s, 1H), 7.08 (br s, 1H), 6.23 (br d, J=16.1 Hz, 1H), 6.05 (br s, 1H), 5.64-5.36 (m, 1H), 5.01-4.74 (m, 1H), 4.57 (br s, 1H), 4.44-4.30 (m, 2H), 4.20 (br d, J=8.8 Hz, 1H), 4.15-4.03 (m, 2H), 3.84 (t, J=12.2 Hz, 2H), 0.02 (br s, 6H).

$^{31}$P NMR (162 MHz, D$_2$O) δ 94.63-92.15.

$^{19}$F NMR (376 MHz, D$_2$O) δ −165.60, −203.17--203.42.

Step 12: Preparation of Compounds 3B and 3C

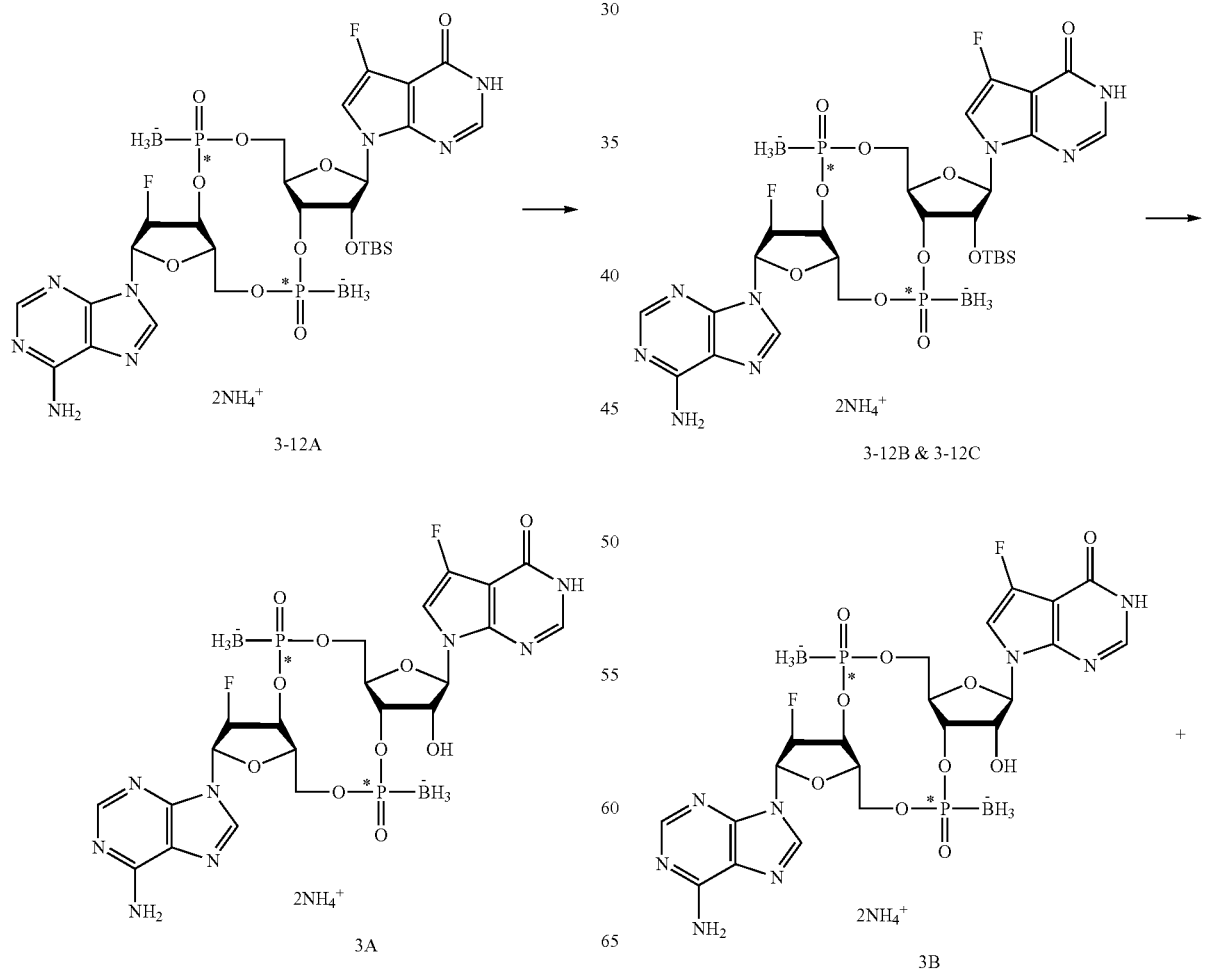

3-12A 3-12B & 3-12C

3A

3B

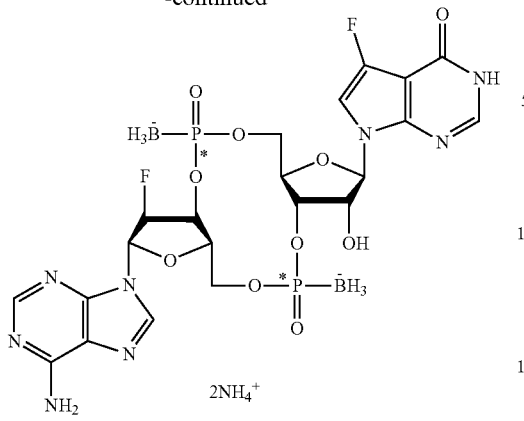

3C

Step 13: Preparation of Compound 3D

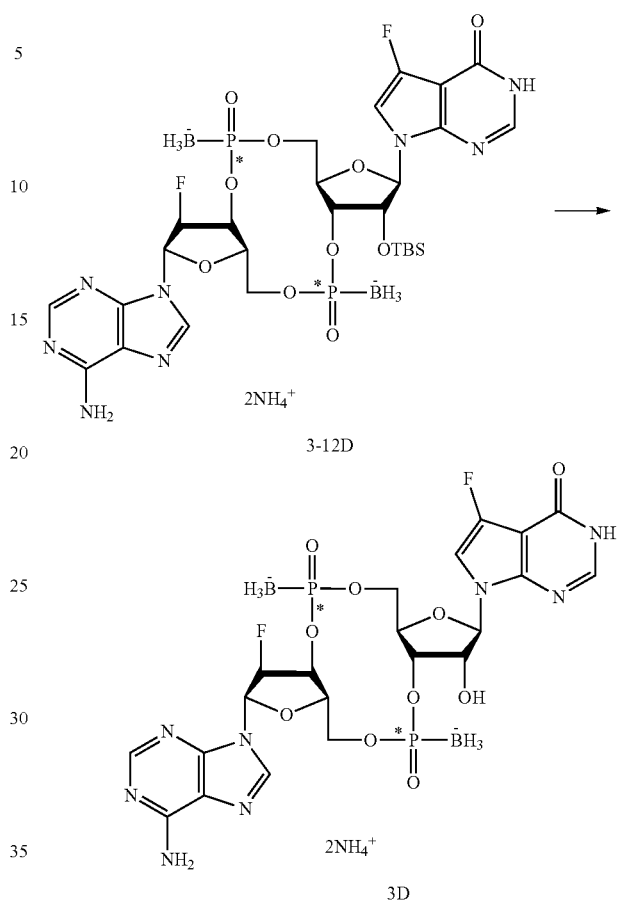

3-12D

3D

The mixture of compounds 3-12B and 3-12C (20 mg, 24.32 μmol, 2NH$_4^+$) was dissolved in pyridine (1 mL), followed by successive addition of triethylamine (147.65 mg, 1.46 mmol, 203.10 μL) and triethylamine trihydrofluoride (117.62 mg, 729.59 μmol, 118.92 μL). The reaction mixture was heated to 50° C. and stirred for 48 hours, and then cooled to 25° C., followed by addition of isopropoxy trimethylsilane (386.03 mg, 2.92 mmol, 518.16 μL). The reaction mixture was stirred at 25° C. for 4 hours, and concentrated under reduced pressure. The residue was dissolved in water (3 mL), and back-extracted with ethyl acetate (3 mL). The aqueous phase was collected, and separated by HPLC (separation conditions: chromatographic column: Xbridge Prep OBD C18 150*30 mm 5 μm; mobile phase: [water (0.04% ammonia water+10 mM ammonium bicarbonate)-acetonitrile]; acetonitrile %: 0%-30%, flow rate: 25 mL/min, 7 min) to obtain compound 3B (HPLC retention time 6.24 min) and compound 3C (HPLC retention time 6.27 min).

Compound 3B:

MS (ESI) m/z (M–H)$^-$=672.9.

$^1$H NMR (400 MHz, D$_2$O) δ 8.29 (s, 1H), 7.97 (s, 1H), 7.78 (s, 1H), 7.08 (d, J=1.8 Hz, 1H), 6.25 (d, J=16.6 Hz, 1H), 6.07 (s, 1H), 5.42-5.17 (m, 1H), 5.14-4.97 (m, 1H), 4.64-4.58 (m, 1H), 4.36-4.26 (m, 2H), 4.13 (br d, J=10.0 Hz, 3H), 3.86 (dd, J=5.3, 12.0 Hz, 1H), 3.78 (br dd, J=5.1, 11.2 Hz, 1H), 0.00 (br s, 3H), −0.17 (br s, 3H).

$^{31}$P NMR (162 MHz, D$_2$O) δ 94.34-93.23.

$^{19}$F NMR (376 MHz, D$_2$O) δ −164.48, −201.40.

Compound 3C:

MS (ESI) m/z (M–H)$^-$=672.9.

$^1$H NMR (400 MHz, D$_2$O) δ 8.30 (br s, 1H), 8.05 (br s, 1H), 7.77 (br s, 1H), 7.12 (br s, 1H), 6.27 (br d, J=15.4 Hz, 1H), 6.09 (br s, 1H), 5.62-5.23 (m, 1H), 4.92-4.69 (m, 3H), 4.40-4.23 (m, 3H), 4.18 (br d, J=9.0 Hz, 1H), 4.07 (br d, J=11.7 Hz, 1H), 3.86 (br d, J=8.3 Hz, 2H), 0.06 (br s, 6H).

$^{31}$P NMR (162 MHz, D$_2$O) δ 93.82-89.83.

$^{19}$F NMR (376 MHz, D$_2$O) δ −165.87, −202.61--203.31.

Compound 3-12D (10 mg, 12.16 μmol, 2NH$_4^+$) was dissolved in pyridine (1 mL), followed by successive addition of triethylamine (73.83 mg, 729.59 μmol, 101.55 μL) and triethylamine trihydrofluoride (49.01 mg, 304.00 μmol, 49.55 μL). The reaction mixture was heated to 50° C. and stirred for 48 hours. The reaction mixture was cooled to 25° C., followed by addition of isopropoxy trimethylsilane (193.01 mg, 1.46 mmol, 259.08 μL). The reaction mixture was then stirred at 25° C. for 4 hours, and concentrated under reduced pressure. The residue was dissolved in water (3 mL), and back-extracted with ethyl acetate (3 mL). The aqueous phase was collected, and separated by HPLC (separation conditions: chromatographic column: Xbridge Prep OBD C18 150*30 mm 5 μm; mobile phase: [water (0.04% ammonia water+10 mM ammonium bicarbonate)-acetonitrile]; acetonitrile %: 0%-30%, flow rate: 25 mL/min, 7 min) to obtain compound 3D.

MS (ESI) m/z (M–H)$^-$=672.8.

$^1$H NMR (400 MHz, D$_2$O) δ 8.30 (br s, 1H), 8.12 (br s, 1H), 7.69 (br s, 1H), 7.15 (br s, 1H), 6.29 (br dd, J=3.3, 16.1 Hz, 1H), 6.04 (br d, J=7.0 Hz, 1H), 5.76-5.50 (m, 1H), 5.24-5.09 (m, 1H), 4.97-4.92 (m, 1H), 4.49-4.43 (m, 2H), 4.40 (br d, J=12.0 Hz, 1H), 4.31 (br d, J=8.0 Hz, 2H), 4.02-3.85 (m, 2H), 0.29 (br s, 6H).

$^{31}$P NMR (162 MHz, D$_2$O) δ 94.73-93.43.

$^{19}$F NMR (376 MHz, D$_2$O) δ −164.94, −201.79.

Embodiment 4: Preparation of Compounds 4A, 4B, 4C, 4D

Step 1: Preparation of Compound 4-1

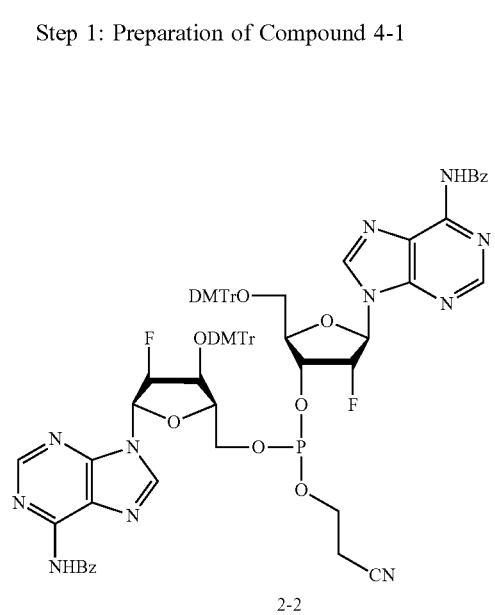

2-2

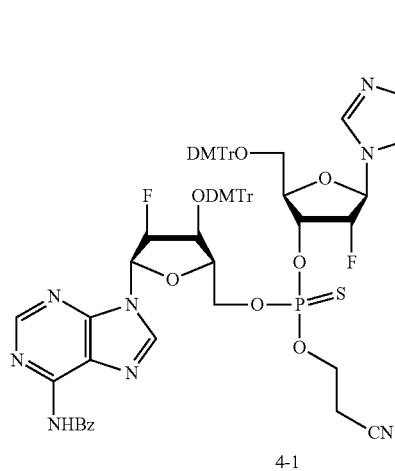

4-1

Compound 2-2 (2.3 g, 1.59 mmol) was dissolved in pyridine at 15° C. under argon atmosphere, then DDTT (976.77 mg, 4.76 mmol) was added and the reaction mixture was stirred for 2 hours. The obtained brown reaction mixture was diluted with ethyl acetate (200 mL), successively washed with saturated sodium bicarbonate solution (50×3 mL) and saturated brine. The organic phase was separated, dried over anhydrous sodium sulfate, filtered, and the filtrate was concentrated to obtain a crude product, which was purified by silica gel column chromatography (petroleum ether/ethyl acetate (v/v)=1/0-1/4) to obtain compound 4-1.

MS (ESI) m/z (M/2+H)⁺=742.1

Step 2: Preparation of Compound 4-2

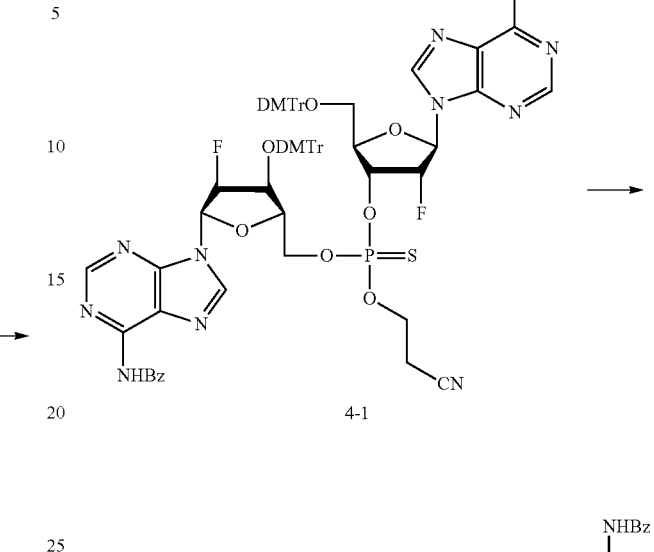

4-1

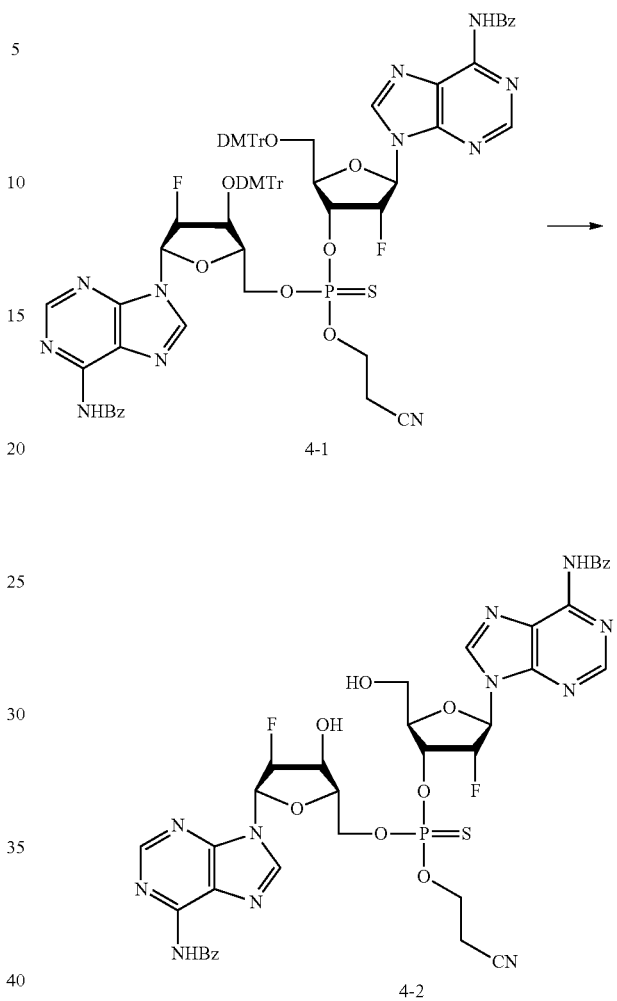

4-2

Compound 4-1 (2 g, 1.21 mmol) was added to the mixed solution of 80% acetic acid (36 mL) and acetonitrile (10 mL), and the mixture was stirred at 40° C. for 20 hours. The reaction mixture was then diluted with ethyl acetate (300 mL), and the saturated sodium bicarbonate solution was carefully added thereto to adjust the pH to 9.0. The organic phase was separated, washed with saturated brine (20 mL), dried over anhydrous sodium sulfate, and concentrated under reduced pressure. The crude product was slurried with ethyl acetate (10 mL), followed by filtration. The filter cake was washed with ethyl acetate (2×2 mL), and dried in vacuum to obtain compound 4-2.

MS (ESI) m/z (M+H)⁺=878.3.

$^{1}$H NMR (400 MHz, DMSO-d$_6$) δ 8.74-8.25 (m, 4H), 8.08-8.02 (m, 5H), 7.57-7.48 (m, 7H), 6.44-6.37 (m, 2H), 5.82-5.69 (m, 1H), 5.56-5.51 (m, 2H), 5.05-4.95 (m, 1H), 4.55-4.43 (m, 2H), 4.35-4.25 (m, 4H), 3.84-3.64 (m, 2H), 2.88-2.84 (m, 2H).

$^{31}$P NMR (162 MHz, DMSO-d$_6$) δ 69.59-67.63

$^{19}$F NMR (376 MHz, DMSO-d$_6$) δ −203--207

Step 3: Preparation of Compound 4-3

Step 4: Preparation of Compound 4-4

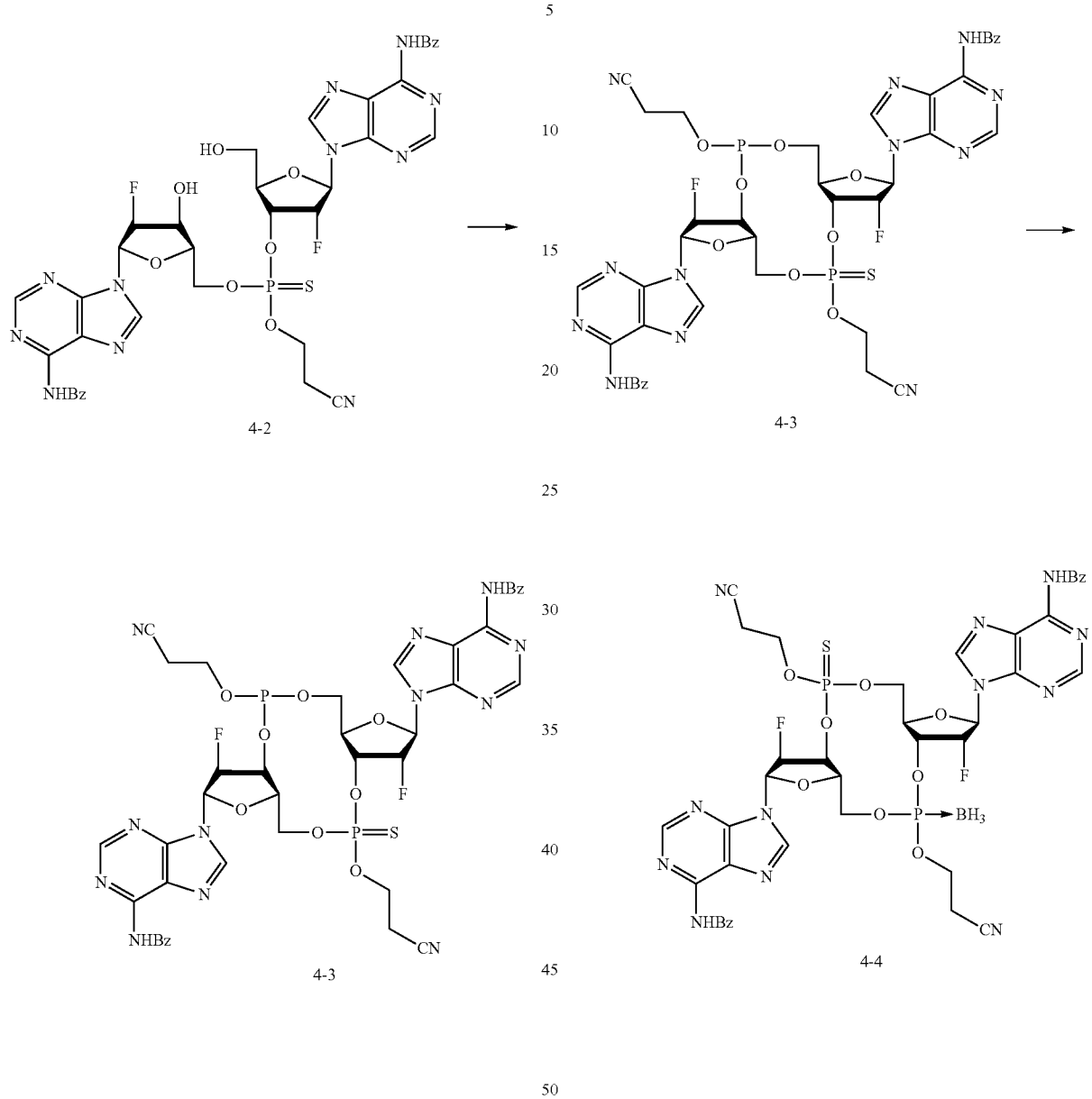

Compound 4-2 (400 mg, 455.70 μmol) was dissolved in acetonitrile (2 mL), followed by successive addition of 4 Å molecular sieve (0.3 g) and tetrazole (0.45 M acetonitrile solution, 10.13 mL). The obtained reaction mixture was bubbled with argon for 4 minutes, and then 2-cyanoethyl N,N,N',N'-tetraisopropylphosphorodiamidite was added dropwise, and stirred for 1 hour. The reaction mixture was diluted with ethyl acetate (60 mL), followed by filtration. The organic phase was successively washed with saturated sodium bicarbonate solution (20 mL×3) and saturated brine (10 mL), dried over anhydrous sodium sulfate, filtered, and the filtrate was concentrated under reduced pressure to obtain crude product 4-3.

MS (ESI) m/z (M+H)$^+$=977.2.

Compound 4-3 (0.43 g, 440.21 μmol) was dissolved in dichloromethane (30 mL), and the obtained mixture was bubbled with argon for 4 minutes, stirred at 15° C. for 10 minutes, and then cooled to 0° C., followed by dropwise addition of borane dimethyl sulfide complex (2 M tetrahydrofuran solution, 660.32 μL). The reaction mixture was then heated to 15° C. and stirred for 30 minutes. The reaction was quenched with water (20 mL), diluted with dichloromethane (50 mL), and stirred at room temperature for 30 minutes. The aqueous phase was separated, and the organic phase was washed with saturated brine (10 mL), dried over anhydrous magnesium sulfate, filtered, and the filtrate was concentrated under reduced pressure to obtain crude product 4-4, which can be directly used for the next reaction without further purification.

Step 5: Preparation of Compound 4-5

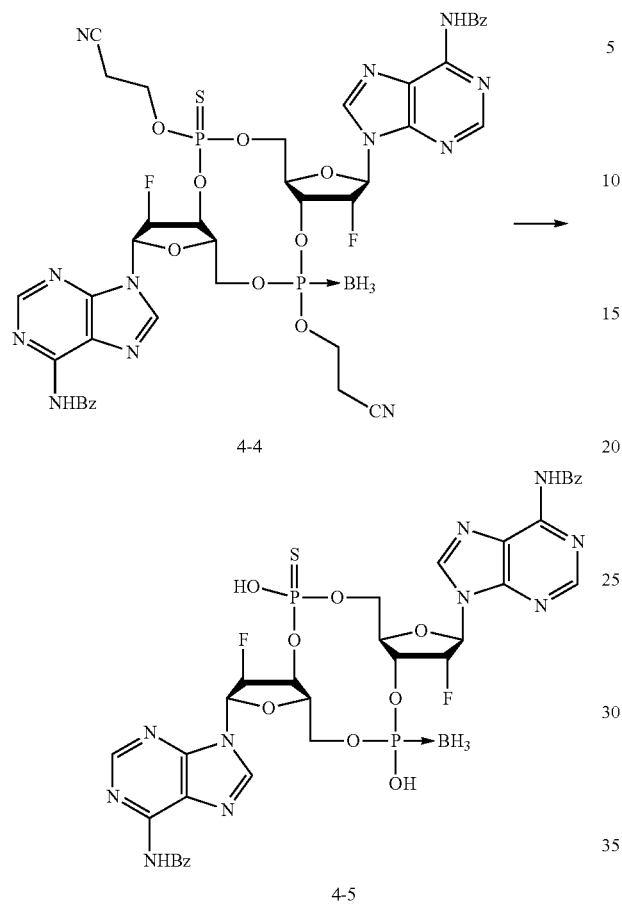

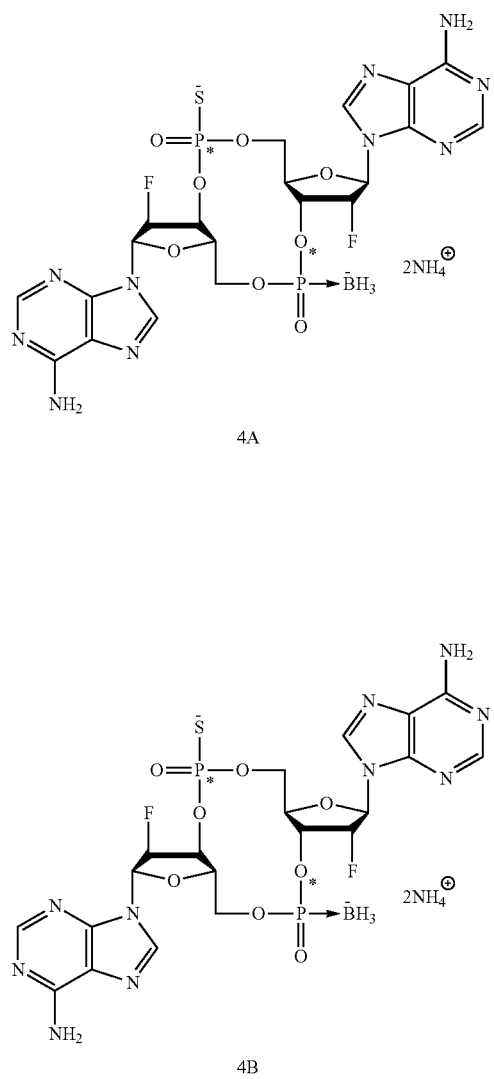

Compound 4-4 (420 mg, 423.97 μmol) was dissolved in the mixed solution of ethanol (3 mL) and acetonitrile (3 mL), followed by addition of tert-butylamine (6 mL). The reaction mixture was stirred at room temperature for 3 hours, and then concentrated under reduced pressure to obtain crude product 4-5, which was directly used for the next reaction without further purification.

Step 6: Preparation of Compounds 4A, 4B, 4C and 4D

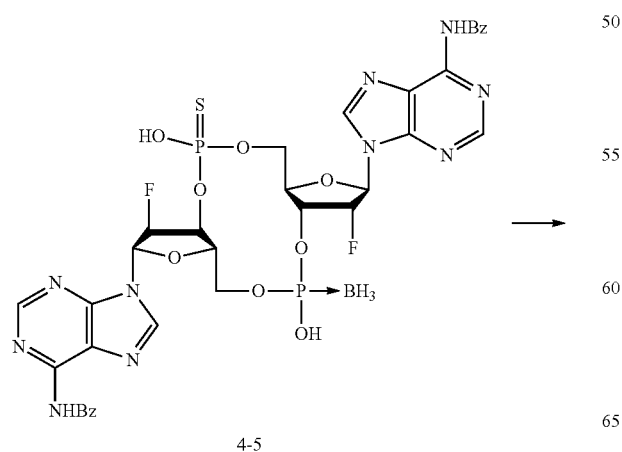

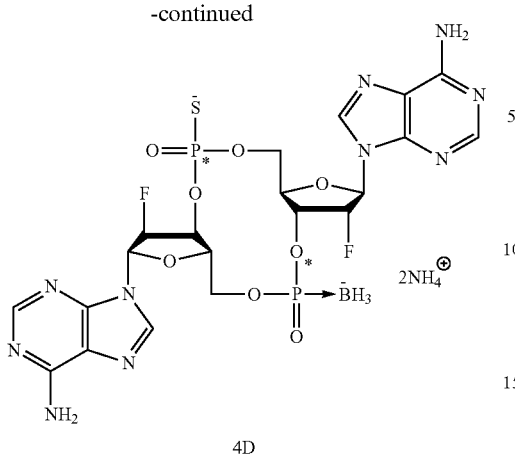

4D

Compound 4-5 (350 mg, 395.70 μmol) was dissolved in 30% methylamine ethanol solution (40 mL), and the reaction mixture was stirred at room temperature for 24 hours. The reaction mixture was then concentrated under reduced pressure. The residue was dissolved in water (10 mL), and back-extracted with ethyl acetate (5 mL×3). The aqueous phase was concentrated under reduced pressure and separated by HPLC (separation conditions: chromatographic column: Xbridge Prep OBD C18 150*30 mm 10 μm; mobile phase: [water (10 mM ammonium bicarbonate)-acetonitrile]; acetonitrile %: 0%-30%, flow rate: 25 mL/min, 20 min) to obtain:
Compound 4A (HPLC retention time 5.4 min)
Compound 4B (HPLC retention time 5.9 min)
Compound 4C (HPLC retention time 6.7 min)
Compound 4D (HPLC retention time 7.4 min)

Compound 4A:
MS (ESI) m/z (M+H)⁺=677.2.
$^1$H NMR (400 MHz, D$_2$O) δ 8.36 (s, 1H), 8.27 (s, 1H), 7.96 (s, 1H), 7.91 (s, 1H), 6.29-6.23 (m, 2H), 5.80 (d, J=51.2 Hz, 1H), 5.45 (d, J=51.2 Hz, 1H), 4.85-4.72 (m, 2H), 4.38-4.32 (m, 2H), 4.24-4.15 (m, 1H), 3.91-3.87 (m, 2H), 0.50--0.20 (br, 3H).
$^{31}$P NMR (162 MHz, D$_2$O) δ 96.2-91.9, 54.5.
$^{19}$F NMR (376 MHz, D$_2$O) δ -202.7--203.0.

Compound 4B:
MS (ESI) m/z (M+H)⁺=677.2.
$^1$H NMR (400 MHz, D$_2$O) δ 8.01 (s, 1H), 7.98 (s, 1H), 7.86 (br s, 1H), 7.46 (br s, 1H), 6.37 (d, J=13.6 Hz, 1H), 6.16 (d, J=14.0 Hz, 1H), 5.38-5.07 (m, 2H), 4.42-4.32 (m, 2H), 4.32-4.25 (m, 1H), 4.25-4.18 (m, 1H), 3.87-3.79 (m, 2H), 0.25--0.30 (br, 3H).
$^{31}$P NMR (162 MHz, D$_2$O) δ 94.7-91.5, 54.062.
$^{19}$F NMR (376 MHz, D$_2$O) δ -202.5--204.1.

Compound 4C:
MS (ESI) m/z (M+H)⁺=677.2.
$^1$H NMR (400 MHz, D$_2$O) δ 8.20 (s, 1H), 8.07 (s, 1H), 7.92 (s, 1H), 7.75 (s, 1H), 6.16-6.08 (m, 2H), 5.81 (d, J=50.8 Hz, 1H), 5.40 (d, J=51.2 Hz, 1H), 5.03-4.81 (m, 2H), 4.38-4.28 (m, 4H), 3.96-3.88 (m, 2H), 0.50--0.20 (br, 3H).
$^{31}$P NMR (162 MHz, D$_2$O) δ 94.3-91.1, 54.033.
$^{19}$F NMR (376 MHz, D$_2$O) δ -201.377--202.447.

Compound 4D:
MS (ESI) m/z (M+H)⁺=677.1.
$^1$H NMR (400 MHz, D$_2$O) δ 8.01 (s, 1H), 7.92 (s, 2H), 7.77 (s, 2H), 6.19-6.16 (m, 2H), 5.31-5.18 (m, 2H), 4.81-4.72 (m, 2H), 4.38-4.27 (m, 4H), 3.85-3.77 (m, 2H), 0.50--0.10 (br, 3H).

$^{31}$P NMR (162 MHz, D$_2$O) δ 94.8-91.5, 54.011.
$^{19}$F NMR (376 MHz, D$_2$O) δ -202.724--202.889.

Embodiment 5: Preparation of Compounds 5A, 5B, 5C, 5D

Step 1: Preparation of Compound 5-2

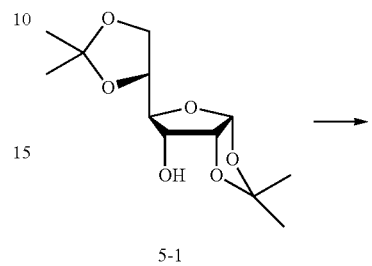

5-1

5-2

At 0° C., compound 5-1 (20 g, 76.84 mmol) was dissolved in acetonitrile (300 mL), and sodium hydride (4.61 g, 115.26 mmol, 60%) was added. After stirring for 0.5 hour, benzyl bromide (13.14 g, 76.84 mmol) was added, and the reaction mixture was heated to 20° C. and stirred for 3 hours. The reaction mixture was quenched with methanol, followed by addition of water (100 mL) and ethyl acetate (150 mL). The organic phase was separated, dried over anhydrous sodium sulfate. The solid was filtered off, and the filtrate was concentrated to obtain the crude product, which was slurried with petroleum ether, and the solid was separated to obtain compound 5-2.

$^1$H NMR (400 MHz, CDCl$_3$) δ 7.41-7.30 (m, 5H), 5.74 (d, J=3.8 Hz, 1H), 4.76 (d, J=11.8 Hz, 1H), 4.60-4.55 (m, 2H), 4.35 (dt, J=3.2, 7.0 Hz, 1H), 4.13 (dd, J=3.2, 8.8 Hz, 1H), 4.02-3.92 (m, 2H), 3.87 (dd, J=4.6, 8.8 Hz, 1H), 1.58 (s, 3H), 1.37 (s, 3H), 1.35 (d, J=4.4 Hz, 6H)

Step 2: Preparation of Compound 5-3

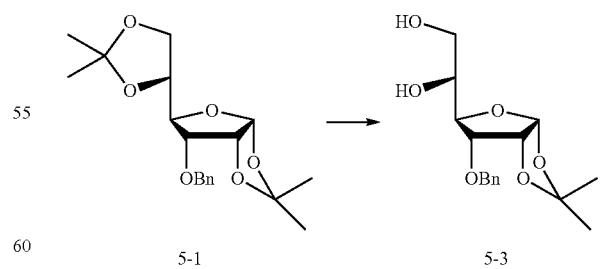

5-1

5-3

Compound 5-2 (51 g, 145.55 mmol) was dissolved in water (42 mL) and acetic acid (179.55 g, 2.99 mol, 171 mL), and reacted at 20° C. with stirring for 72 hours. The reaction mixture was neutralized with 1.0 M sodium hydroxide solution, and extracted with ethyl acetate (300 mL×3). The organic phases were combined, dried over anhydrous sodium sulfate. The solid was filtered off, and the filtrate was concentrated to obtain crude product 5-3, which was directly used for the next reaction without further purification.

$^1$H NMR (400 MHz, CDCl$_3$) δ 7.40-7.32 (m, 5H), 5.74 (d, J=3.8 Hz, 1H), 4.77 (d, J=11.2 Hz, 1H), 4.59 (t, J=4.0 Hz, 1H), 4.54 (d, J=11.2 Hz, 1H), 4.14-4.06 (m, 2H), 3.91 (dd, J=8.8, 4.4 Hz, 1H), 3.72-3.61 (m, 2H), 2.56 (br s, 2H), 1.57 (s, 3H), 1.34 (s, 3H).

Step 3: Preparation of Compound 5-4

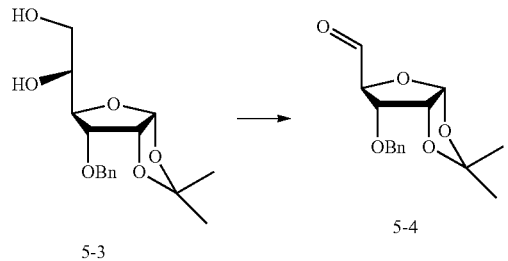

The solution of compound 5-3 (20 g, 64.45 mmol) in water (200 mL) was added to the solution of sodium periodate (15.99 g, 74.76 mmol) in water (100 mL). The reaction mixture was stirred at 0° C. for 1 hour, followed by addition of ethylene glycol (2.60 g, 41.89 mmol, 2.34 mL), and stirred for another 20 minutes. The reaction mixture was extracted with ethyl acetate (170 mL×3). The organic phases were combined, and dried over anhydrous sodium sulfate. The solid was filtered off, and the filtrate was concentrated to obtain crude product 5-4, which was directly used for the next reaction without further purification.

$^1$H NMR (400 MHz, CDCl$_3$) δ 9.60 (d, J=1.8 Hz, 1H), 7.35-7.32 (m, 5H), 5.80 (d, J=3.6 Hz, 1H), 4.76-4.70 (m, 1H), 4.65-4.60 (m, 1H), 4.58 (t, J=3.8 Hz, 1H), 4.47 (dd, J=9.0, 1.6 Hz, 1H), 3.83 (dd, J=9.4, 4.4 Hz, 1H), 1.59 (s, 3H), 1.36 (s, 3H).

Step 4: Preparation of Compound 5-5

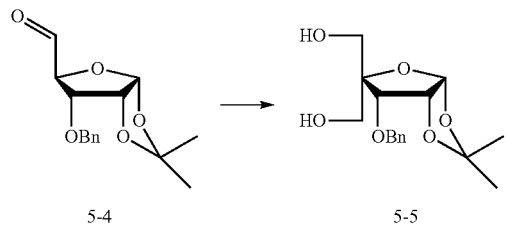

At 0° C., compound 5-4 (17.94 g, 64.46 mmol) was dissolved in dioxane (45 mL) and water (40 mL), then formalin (36 mL, 483.54 mmol, 37% aqueous solution) and sodium hydroxide (1 M aqueous solution, 176 mL) were added, and the reaction mixture was heated to 20° C. and stirred for 48 hours. The reaction mixture was then extracted with ethyl acetate (200 mL×3). The organic phases were combined, and dried over anhydrous sodium sulfate. The solid was filtered off, and the filtrate was concentrated to obtain crude product 5-5, which was directly used for the next reaction without further purification.

$^1$H NMR (400 MHz, CDCl$_3$) δ 7.38-7.31 (m, 5H), 5.78-5.72 (m, 1H), 4.83-4.76 (m, 1H), 4.66-4.61 (m, 1H), 4.55 (d, J=11.7 Hz, 1H), 4.22-4.16 (m, 1H), 3.95-3.85 (m, 2H), 3.80-3.74 (m, 1H), 3.62-3.50 (m, 1H), 2.37 (t, J=6.9 Hz, 1H), 1.88 (dd, J=3.7, 9.6 Hz, 1H), 1.62 (s, 3H), 1.32 (s, 3H).

Step 5: Preparation of Compound 5-6

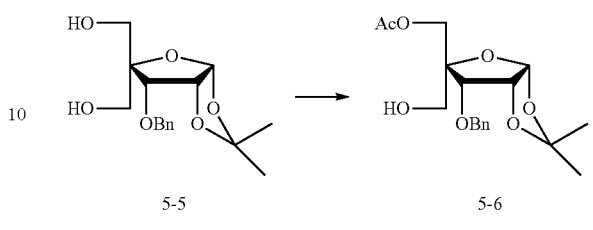

Compound 5-5 (19 g, 61.22 mmol) was dissolved in diisopropyl ether (350 mL), followed by addition of lipase Novozyme-435 (1.5 g, 61.22 mmol) and vinyl acetate (5.27 g, 61.22 mmol, 5.67 mL), and the reaction mixture was heated to 50° C. and stirred for 16 hours. The reaction mixture was extracted with ethyl acetate (200 mL×3). The organic phases were combined, and dried over anhydrous sodium sulfate. The solid was filtered off, and the filtrate was concentrated to obtain the crude product, which was purified by silica gel column chromatography (petroleum ether/ethyl acetate (v/v)=1/0-0/1) to obtain compound 5-6.

$^1$H NMR (400 MHz, CDCl$_3$) δ 7.34 (m, 5H), 5.75 (d, J=4.0 Hz, 1H), 4.80 (d, J=11.8 Hz, 1H), 4.65 (t, J=4.6 Hz, 1H), 4.51 (d, J=11.8 Hz, 1H), 4.25 (d, J=11.8 Hz, 1H), 4.12-4.06 (m, 1H), 4.00 (d, J=5.4 Hz, 1H), 3.93 (br d, J=6.8 Hz, 2H), 2.36 (t, J=6.8 Hz, 1H), 2.01-1.97 (m, 3H), 1.62 (s, 3H), 1.33 (s, 3H).

Step 6: Preparation of Compound 5-7

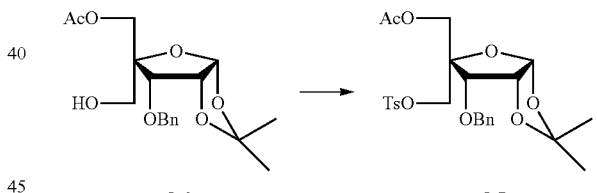

Compound 5-6 (5 g, 14.19 mmol) was dissolved in pyridine (21 mL), followed by addition of dichloromethane (83 mL), and p-toluenesulfonyl chloride (2.98 g, 15.61 mmol), the reaction mixture was stirred at 15° C. for 24 hours. The reaction mixture was then quenched with 10% hydrochloric acid solution, and extracted with dichloromethane (40 mL×3). The organic phases were combined, and dried over anhydrous sodium sulfate. The solid was filtered off, and the filtrate was concentrated to obtain the crude product, which was purified by silica gel column chromatography (petroleum ether/ethyl acetate (v/v)=1/0-1/1) to obtain compound 5-7.

$^1$H NMR (400 MHz, CDCl$_3$) δ 7.79 (br d, J=7.9 Hz, 2H), 7.37-7.30 (m, 7H), 5.68 (d, J=3.6 Hz, 1H), 4.69 (br d, J=12.1 Hz, 1H), 4.56 (br t, J=4.2 Hz, 1H), 4.54-4.45 (m, 2H), 4.33 (d, J=10.6 Hz, 1H), 4.16 (d, J=11.8 Hz, 1H), 4.12-4.08 (m, 1H), 4.00-3.93 (m, 2H), 2.41 (s, 3H), 1.89 (s, 3H), 1.34 (s, 3H), 1.26 (s, 3H).

Step 7: Preparation of Compound 5-8

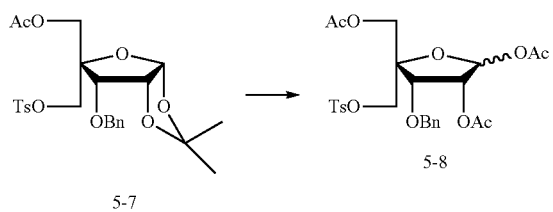

At 0° C., compound 5-7 (20 g, 40.61 mmol) was dissolved in acetic acid (200 mL), followed by addition of acetic anhydride (38.03 mL, 406.06 mmol) and sulfuric acid (216.44 µL, 4.06 mmol), and the reaction mixture was heated to 20° C. and stirred for 6 hours. The reaction mixture was poured into water (600 mL), neutralized to pH=7 with sodium hydroxide solution, and extracted with ethyl acetate (200 mL×3). The organic phases were combined, washed with saturated brine (200 mL), and dried over anhydrous sodium sulfate. The solid was filtered off, and the filtrate was concentrated to obtain crude product 5-8, which was directly used for the next reaction without further purification.

Step 8: Preparation of Compound 5-9

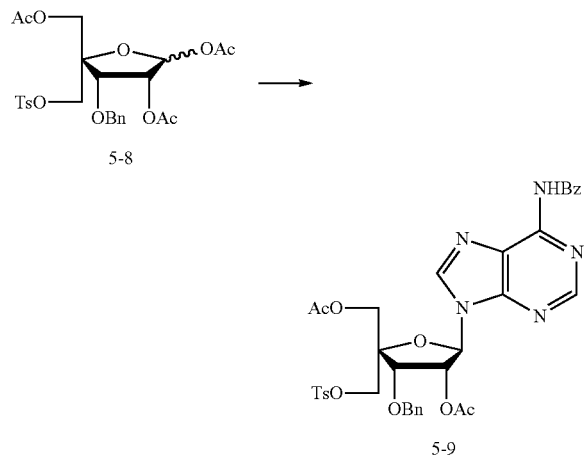

N-(5H-purin-6-yl)benzamide (5.87 g, 24.52 mmol) was dissolved in dichloroethane (200 mL), followed by addition of N,O-bis(trimethylsilyl)acetamide (16.16 mL, 65.39 mmol). The reaction mixture was heated to 80° C. and stirred for 0.5 hour, and then cooled to 0° C., followed by addition of compound 5-8 (9.0 g, 16.35 mmol) and trimethylsilyl trifluoromethanesulfonate (4.73 mL, 26.15 mmol). The reaction mixture was then heated to 80° C. and stirred for 1 hour, and then cooled to room temperature. The reaction mixture was poured into saturated sodium bicarbonate solution (200 mL), and extracted with ethyl acetate (200 mL×2). The organic phase was washed with saturated brine (200 mL), dried over anhydrous sodium sulfate, filtered, and the filtrate was concentrated under reduced pressure to obtain the crude product, which was purified by silica gel column chromatography (petroleum ether/ethyl acetate (v/v)=1/0-0/1) to obtain compound 5-9.

MS (ESI) m/z (M+H)$^+$=730.3.

Step 9: Preparation of Compound 5-10

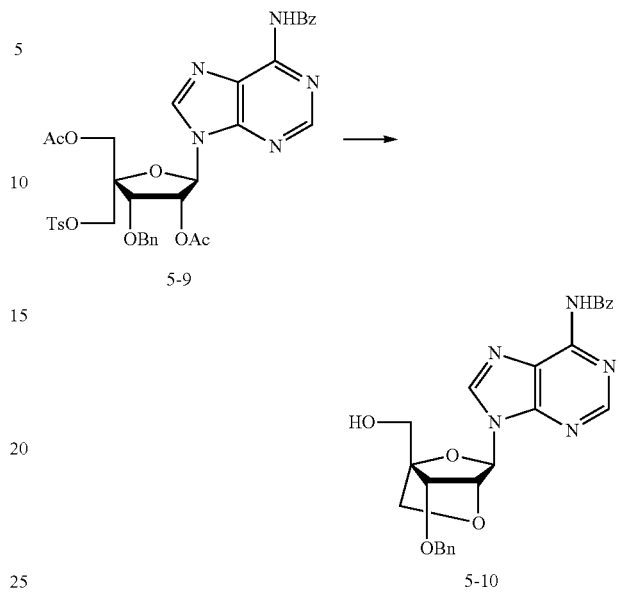

Compound 5-9 (11 g, 10.85 mmol) was dissolved in water (24 mL) and dioxane (24 mL), followed by addition of ammonia water (33.44 mL, 217.06 mmol, 25-28%) and 2.0 M sodium hydroxide aqueous solution (31.68 mL), and the reaction mixture was stirred at 25° C. for 18 hours. The reaction solution was poured into water (100 mL), and extracted with ethyl acetate (40 mL×3). The organic phase was washed with saturated brine (50 mL), dried over anhydrous sodium sulfate, filtered, and the filtrate was concentrated under reduced pressure to obtain the crude product, which was purified by silica gel column chromatography (dichloromethane/methanol (v/v)=1/0-10/1) to obtain compound 5-10.

MS (ESI) m/z (M+H)$^+$=474.1.

Step 10: Preparation of Compound 5-11

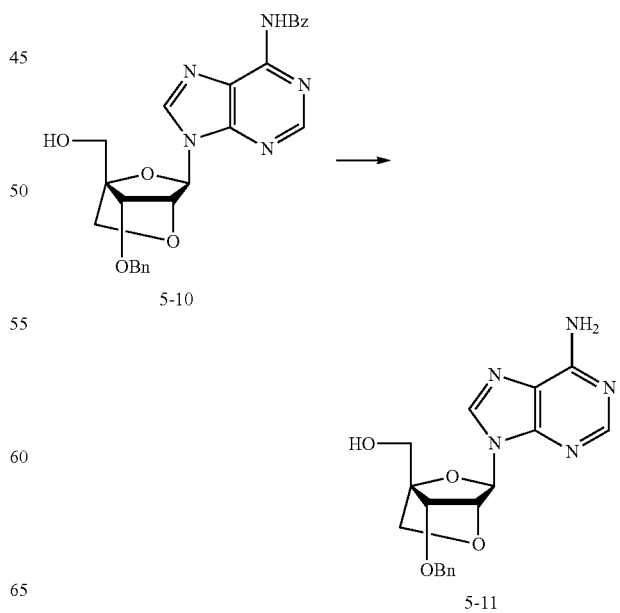

Compound 5-10 (1.68 g, 3.38 mmol) was dissolved in ammonia water (19.31 mL). The reaction mixture was stirred at 30° C. for 24 hours, and then concentrated under reduced pressure to obtain the crude product, which was purified by silica gel column chromatography (dichloromethane/methanol (v/v)=1/0-10/1) to obtain compound 5-11.

MS (ESI) m/z (M+H)$^+$=370.2

Step 11: Preparation of Compound 5-12

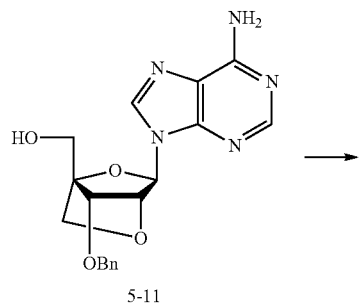

5-11

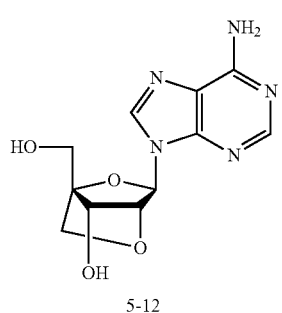

5-12

Compound 5-11 (1.4 g, 3.79 mmol) was dissolved in methanol (140 mL), followed by addition of palladium hydroxide/carbon (0.45 g, 640.84 μmol, 20% wet). The reaction mixture was stirred at 60° C. under hydrogen atmosphere for 2 hours, followed by addition of ammonium formate (1.91 g, 30.32 mmol). The reaction mixture was stirred for another 15 hours, followed by filtration to remove the catalyst, and the filtrate was concentrated under reduced pressure to obtain crude product 5-12, which can be directly used for the next reaction without further purification.

$^1$H NMR (400 MHz, DMSO-d$_6$) δ 8.22 (s, 1H), 8.14 (s, 1H), 7.32 (s, 2H), 5.89 (s, 1H), 4.55 (s, 1H), 4.40 (s, 1H), 4.25 (s, 1H), 3.93-3.91 (m, 1H), 3.81-3.74 (m, 4H)

Step 12: Preparation of Compound 5-13

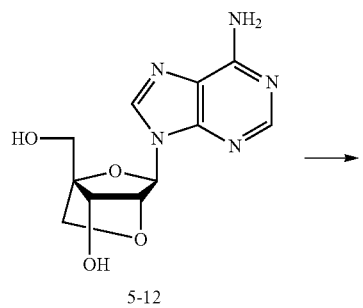

5-12

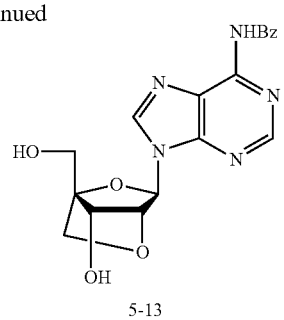

5-13

At 0° C., compound 5-12 (1 g, 3.58 mmol) was dissolved in pyridine (20 mL), followed by addition of N,N-dimethylformamide (10 mL), and trimethylchlorosilane (1.97 g, 18.12 mmol, 2.3 mL). After stirring for 30 min, benzoyl chloride (968.00 mg, 6.89 mmol, 0.8 mL) was added, and the reaction mixture was stirred at 20° C. for 3 hours. The reaction mixture was then quenched with water (10 mL) and ammonia water (10 mL), stirred for 30 minutes, and then extracted with ethyl acetate (20 mL×3). The organic phase was dried over anhydrous sodium sulfate, filtered, and the filtrate was concentrated under reduced pressure to obtain the crude product, which was purified by silica gel column chromatography (ethyl acetate/methanol (v/v)=20/3) to obtain compound 5-13.

MS (ESI) m/z (M+H)$^+$=384.0

$^1$H NMR (400 MHz, CDCl$_3$) δ 9.24 (br s, 1H), 8.71 (s, 1H), 8.41 (s, 1H), 7.99 (br d, J=7.5 Hz, 2H), 7.65-7.59 (m, 1H), 7.52 (t, J=7.5 Hz, 2H), 6.12 (s, 1H), 4.68-4.62 (m, 2H), 4.09-4.05 (m, 1H), 3.99 (s, 2H), 3.89 (d, J=8.0 Hz, 1H).

Step 13: Preparation of Compound 5-14

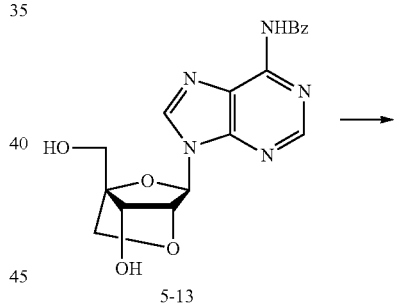

5-13

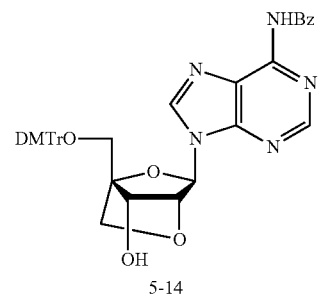

5-14

Compound 5-13 (500 mg, 1.30 mmol) was dissolved in pyridine (10 mL) at 20° C. under argon atmosphere, and DMTrCl (530 mg, 1.56 mmol) was added and stirred for 16 hours. The reaction mixture was quenched with methanol (10 mL) and concentrated under reduced pressure to obtain the crude product, which was purified by silica gel column chromatography (dichloromethane/methanol (v/v)=20/1-10/1) to obtain compound 5-14.

MS (ESI) m/z (M+H)$^+$=686.2

Step 14: Preparation of Compound 5-15

Step 15: Preparation of compound 5-16

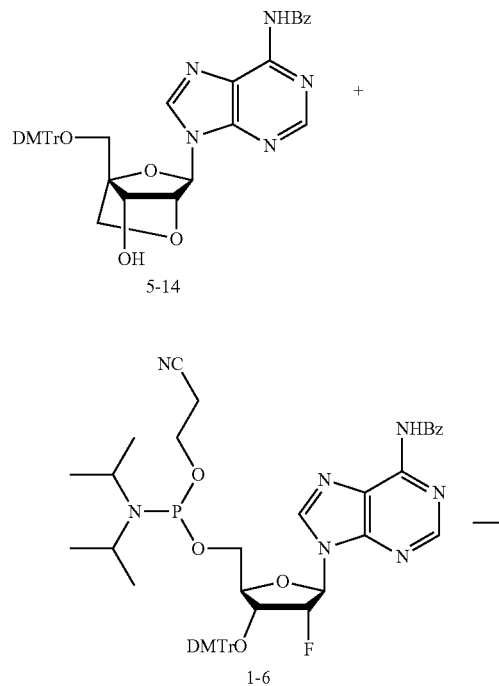

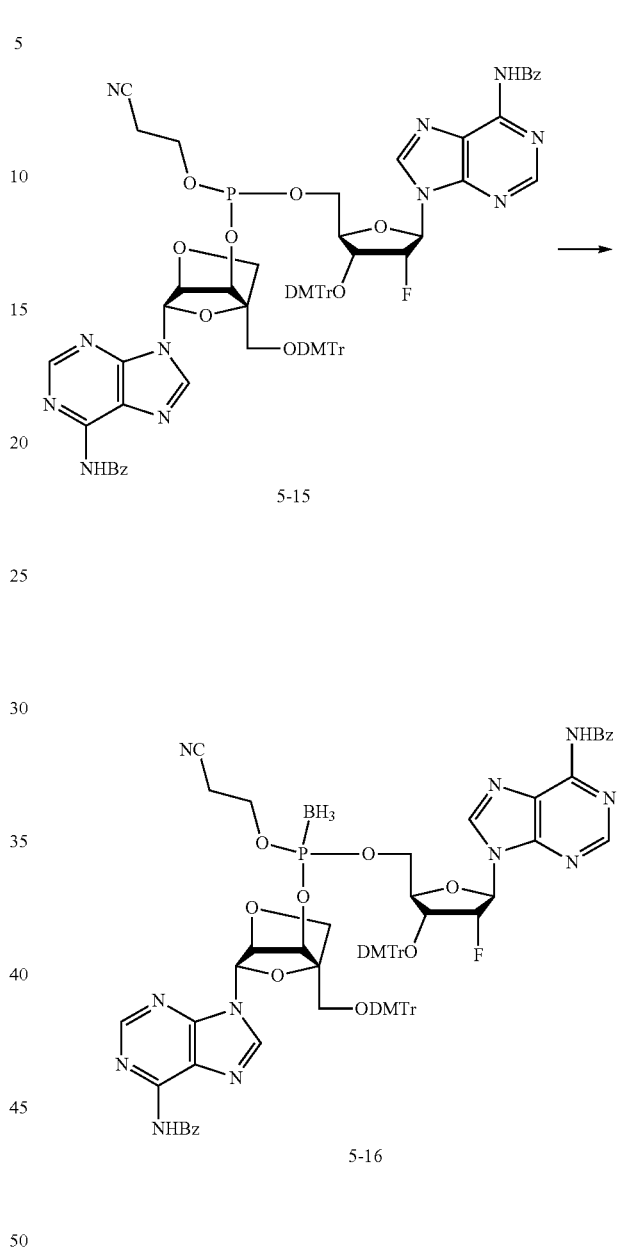

At 20° C., compound 5-14 (500 mg, 729.16 μmol), tetrazole (0.45 M acetonitrile solution, 25.00 mL) and 4 Å molecular sieve were dispersed in acetonitrile (4 mL), followed addition of the solution of compound 1-6 (836.68 mg, 955.20 μmol) in acetonitrile (2 mL), and stirred for 1 hour. The molecular sieve was then filtered out from the reaction mixture, and the reaction mixture was diluted with ethyl acetate (50 mL). The organic phase was successively washed with saturated sodium bicarbonate solution (50 mL×2) and saturated brine (50 mL), dried over anhydrous sodium sulfate, filtered, and the filtrate was concentrated under reduced pressure to obtain the crude product, which was purified by silica gel column chromatography (petroleum ether/ethyl acetate (v/v)=100/3) to obtain compound 5-15.

MS (ESI) m/z (M/2+H)$^+$=731.0.

Compound 5-15 (1.3 g, 890.13 μmol) and 4 Å molecular sieve (300 mg) were dispersed in dichloromethane (30 mL) at 0° C. under argon atmosphere, followed dropwise addition of borane dimethyl sulfide (2 M tetrahydrofuran solution, 1.34 mL). The reaction mixture was stirred at 0° C. for 15 minutes, and then diluted with dichloromethane (50 mL). The molecular sieve was filtered out, and the filtrate was successively washed with water (50 mL) and saturated brine (50 mL), dried over anhydrous sodium sulfate, filtered, and the filtrate was concentrated under reduced pressure to obtain the crude product, which was purified by silica gel column chromatography (dichloromethane/ethyl acetate (v/v)=1/1) to obtain compounds 5-16.

Step 16: Preparation of Compound 5-17

Step 17: Preparation of Compound 5-18

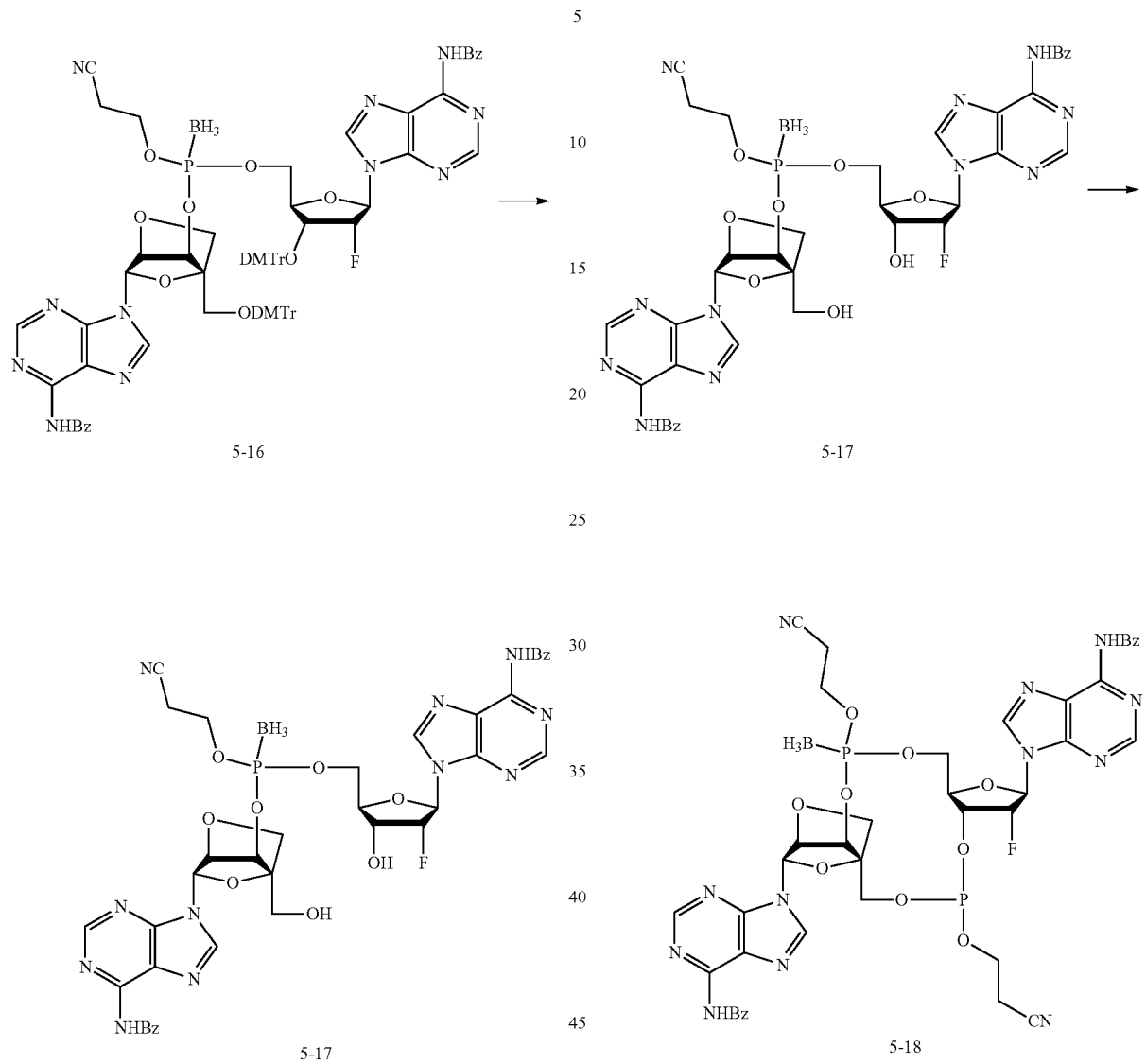

Compound 5-16 (850 mg, 576.55 μmol) was dissolved in dichloromethane (10 mL), followed addition of the solution of 2,2-dichloroacetic acid (10.53 g, 2.31 mmol, 2 mL, 5%) in dichloromethane. The reaction mixture was stirred for 0.5 hour, and diluted with dichloromethane (50 mL). The organic phase was washed with saturated sodium bicarbonate solution (20 mL×2), dried over anhydrous sodium sulfate, filtered, and the filtrate was concentrated under reduced pressure to obtain the crude product, which was separated and purified by thin layer chromatography (dichloromethane/methanol (v/v)=10/1) to obtain compound 5-17.

MS (ESI) m/z (M-14+H)$^+$=856.4.

At 20° C. under argon atmosphere, compound 5-17 (400 mg, 467.44 μmol), 4 Å molecular sieve (1 g) and tetrazole (0.45 M acetonitrile solution, 16 mL) were dispersed in acetonitrile (2 mL) and tetrahydrofuran (3 mL), followed by dropwise addition of 2-cyanoethyl N,N,N',N'-tetraisopropylphosphorodiamidite (189.80 mg, 629.71 μmol, 0.2 mL) in acetonitrile (0.5 mL). The reaction mixture was stirred for 1 hour, and filtered to remove molecular sieve. The filtrate was diluted with ethyl acetate (20 mL). The organic phase was successively washed with saturated sodium bicarbonate solution (20 mL×2) and saturated brine (20 mL), dried over anhydrous sodium sulfate, filtered, and the filtrate was concentrated under reduced pressure to obtain the crude product, which was separated and purified by thin layer chromatography (dichloromethane/methanol (v/v)=15/1) to obtain compound 5-18.

Step 18: Preparation of Compound 5-19

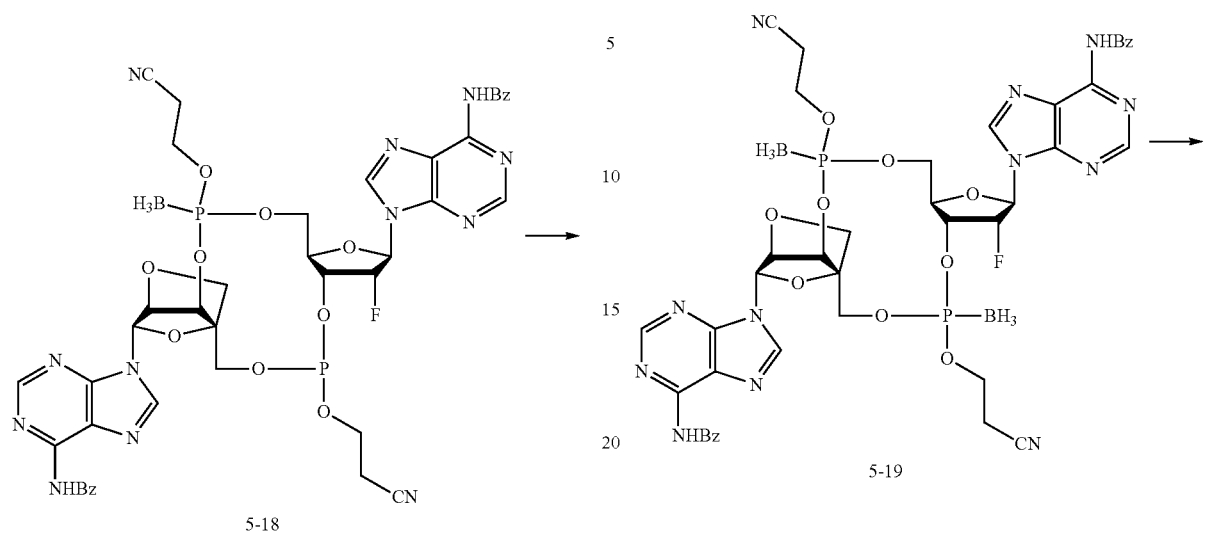

5-18

5-19

At 0° C. under argon atmosphere, compound 5-18 (230 mg, 237.46 μmol), 4 Å molecular sieve (100 mg) were dispersed in tetrahydrofuran (3 mL) and dichloromethane (2 mL), followed by dropwise addition of borane dimethyl sulfide (2 M tetrahydrofuran solution, 460.00 μL). The reaction mixture was heated to 15° C. and stirred for 10 minutes. The reaction mixture was then diluted with dichloromethane (20 mL), followed by filtration. The filtrate was washed with water (30 mL), dried over anhydrous sodium sulfate, followed by filtration. The filtrate was concentrated under reduced pressure to obtain crude product 5-19, which was directly used for the next reaction without further purification.

Step 19: Preparation of Compound 5A, 5B, 5C and 5D

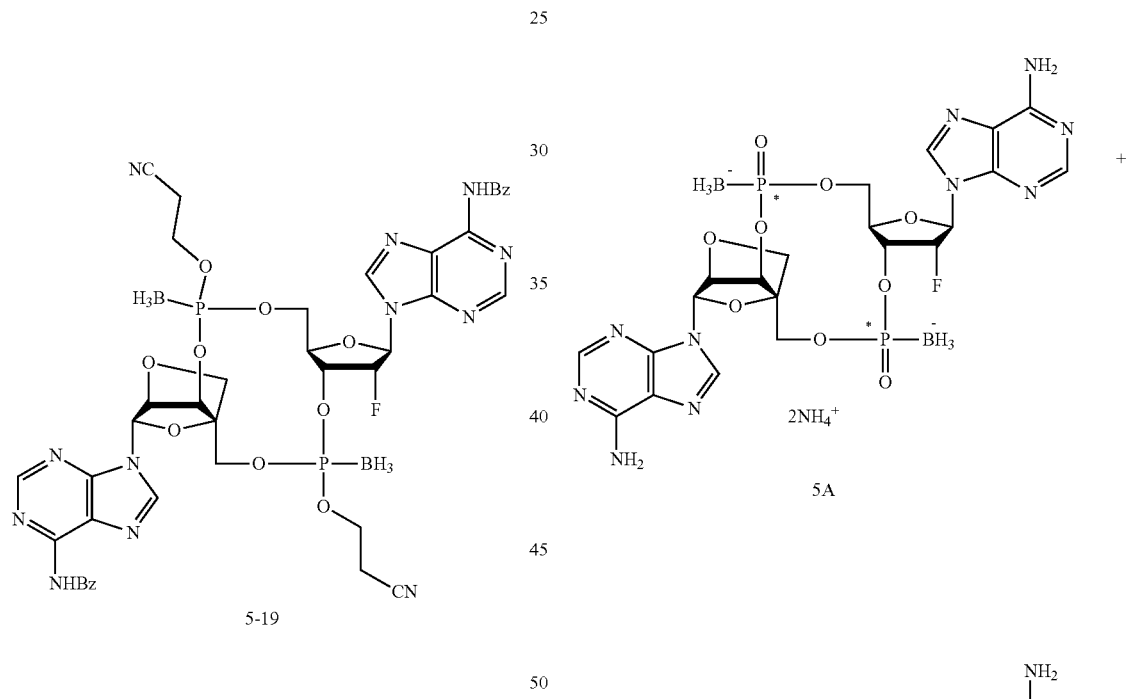

5-19

5A

5B

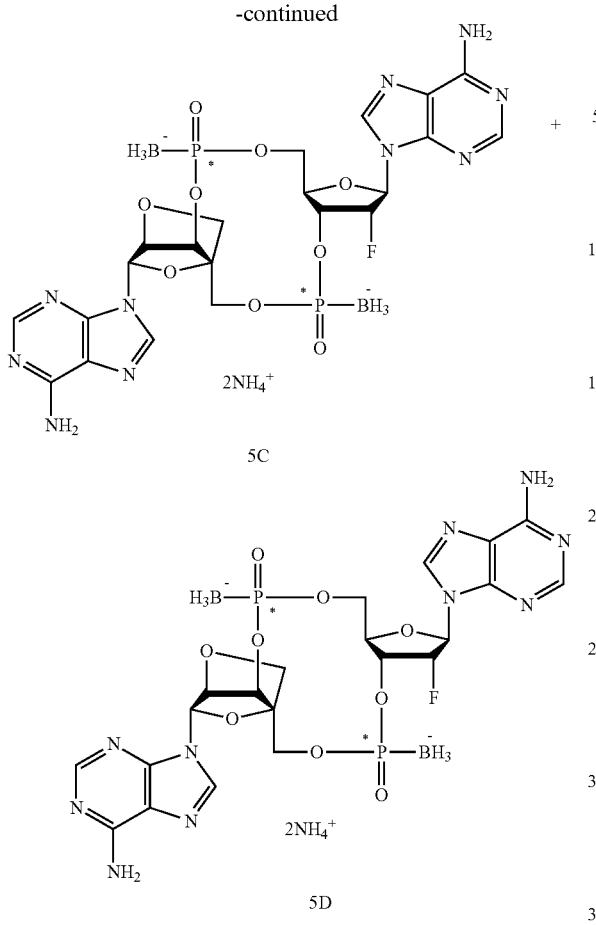

5C

5D

Compound 5-19 (200 mg, 203.58 μmol) was dissolved in methylamine aqueous solution (10 mL, 33%), and stirred at 20° C. for 24 hours. The reaction mixture was extracted with ethyl acetate (30 mL). The aqueous phase was lyophilized, and the crude product was separated by HPLC (separation conditions: chromatographic column: Xbridge Prep OBD C18 150*40 mm 10 μm; mobile phase: [water (10 mM ammonium bicarbonate)-acetonitrile]; acetonitrile %: 0%-20%, flow rate: 25 mL/min, 25 min) to obtain:
Compound 5A (HPLC retention time 5.59 min)
Compound 5B (HPLC retention time 5.87 min)
Compound 5C (HPLC retention time 6.16 min)
Compound 5D (HPLC retention time 7.44 min)

Compound 5A:
MS (ESI) m/z (M−H)⁻=666.8
$^1$H NMR (400 MHz, D$_2$O) δ 8.11 (s, 2H), 8.02 (s, 1H), 7.99 (s, 1H), 6.27 (d, J=16.1 Hz, 1H), 6.01 (s, 1H), 5.58-5.42 (m, 1H), 4.84-4.72 (m, 1H), 4.67 (br s, 1H), 4.46 (br d, J=10.5 Hz, 1H), 4.35 (br d, J=9.0 Hz, 1H), 4.20-4.10 (m, 2H), 4.07-3.88 (m, 4H), 0.52--0.57 (m, 6H).
$^{19}$F NMR (376 MHz, D$_2$O) −202.51--202.65.
$^{31}$P NMR (162 MHz, D$_2$O) δ 94.12-90.98.

Compound 5B:
MS (ESI) m/z (M−H)⁻=667.1
$^1$H NMR (400 MHz, D$_2$O) δ 8.26 (s, 1H), 8.15-8.09 (m, 1H), 8.07 (s, 1H), 7.96 (s, 1H), 6.30 (d, J=16.4 Hz, 1H), 6.05 (s, 1H), 5.48-5.42 (m, 0.5H), 5.33 (br s, 0.5H), 5.02-4.86 (m, 1H), 4.75 (s, 1H), 4.51 (br d, J=10.5 Hz, 1H), 4.33 (br d, J=9.0 Hz, 1H), 4.23 (br d, J=12.0 Hz, 1H), 4.15 (br d, J=12.2 Hz, 1H), 4.04 (br d, J=5.4 Hz, 1H), 3.95-4.02 (m, 2H), 3.91 (d, J=8.1 Hz, 1H), 0.46--0.33 (m, 6H).

$^{19}$F NMR (376 MHz, D$_2$O) −201.02--201.20.
$^{31}$P NMR (162 MHz, D$_2$O) δ 94.86-93.72.

Compound 5C:
MS (ESI) m/z (M−H)⁻=666.8.
$^1$H NMR (400 MHz, D$_2$O) δ 8.40 (s, 1H), 7.89 (s, 1H), 7.82 (br s, 1H), 7.75 (br s, 1H), 6.29 (br d, J=13.7 Hz, 1H), 6.02 (s, 1H), 5.59-5.23 (m, 1H), 4.73 (br s, 1H), 4.71-4.68 (m, 2H), 4.39-4.28 (m, 2H), 4.21-4.08 (m, 1H), 4.07-3.90 (m, 3H), 3.88 (br d, J=7.3 Hz, 1H), 0.18 (br s, 6H).
$^{19}$F NMR (376 MHz, D$_2$O) −204.17--204.48.
$^{31}$P NMR (162 MHz, D$_2$O) δ 96.82-89.33.

Compound 5D:
MS (ESI) m/z (M−H)⁻=666.8.
$^1$H NMR (400 MHz, D$_2$O) δ 8.45 (s, 1H), 8.32 (s, 1H), 8.07 (br s, 1H), 8.05 (br s, 1H), 6.46 (d, J=14.7 Hz, 1H), 6.17 (s, 1H), 5.64-5.39 (m, 1H), 5.18-5.05 (m, 1H), 4.98 (br d, J=8.8 Hz, 1H), 4.90 (s, 1H), 4.53-4.36 (m, 3H), 4.19-4.14 (m, 2H), 4.10 (br dd, J=5.6, 12.0 Hz, 1H), 4.02 (br d, J=8.1 Hz, 1H), 0.61-0.11 (m, 6H).
$^{19}$F NMR (376 MHz, D$_2$O) −201.73--202.52.
$^{31}$P NMR (162 MHz, D$_2$O) δ 95.28-93.68.

Embodiment 6: Preparation of Compounds 6A, 6B, 6C, 6D

Step 1: Preparation of Compound 6-1

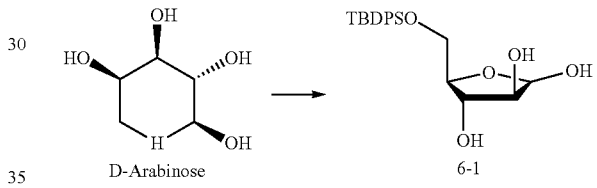

At 20° C., compound D-arabinose (25 g, 166.5 mmol) was dissolved in DMF (250 mL), followed by addition of imidazole (17 g, 249.8 mmol) and tert-butyl diphenyl chlorosilane (45.8 g, 166.5 mmol), and stirred for 2 hours. The reaction mixture was poured into water (2.5 L), extracted with ethyl acetate (1000 mL), dried over anhydrous sodium sulfate, filtered, and the filtrate was concentrated under reduced pressure to obtain crude product 6-1, which was directly used for the next reaction without further purification.
MS (ESI) m/z (M+Na)⁺=411.2.

Step 2: Preparation of Compound 6-2

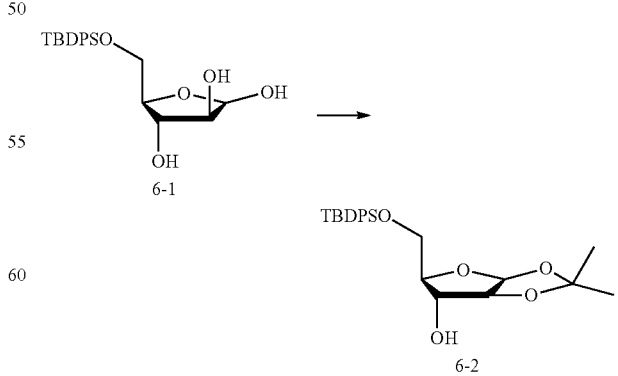

Compound 6-1 (17.5 g, 45.0 mmol) was dissolved in anhydrous acetone (150 mL, 2.04 mol), followed by successive addition of anhydrous copper sulfate (20 g, 125.3 mmol) and sulfuric acid (0.8 mL, 98%). The reaction mixture was stirred at 20° C. for 17 hours, followed by filtration. The filtrate was neutralized with calcium hydroxide, followed by filtration. The filtrate was concentrated under reduced pressure to obtain the crude product, which was purified by silica gel column chromatography (petroleum ether/ethyl acetate (v/v)=1/0-7/3) to obtain compound 6-2.

MS (ESI) m/z (M+Na)$^+$=451.2.

$^1$H NMR (400 MHz, CDCl$_3$) 7.70-7.65 (m, 4H), 7.45-7.37 (m, 6H), 5.89 (d, J=4.2 Hz, 1H), 4.56 (d, J=4.2 Hz, 1H), 4.45-4.44 (m, 1H), 4.09-4.04 (m, 1H), 3.85-3.81 (m, 2H), 1.33 (s, 3H), 1.30 (s, 3H), 1.07 (s, 9H).

Step 3: Preparation of Compound 6-3

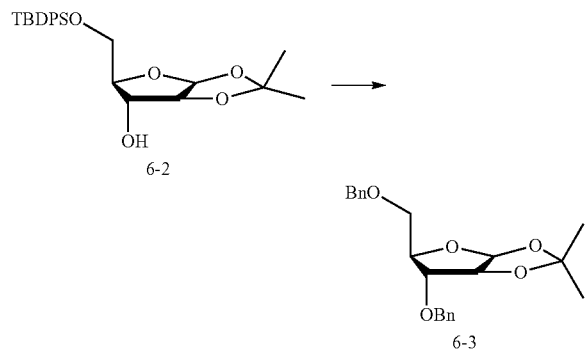

Under nitrogen atmosphere, compound 6-2 (27 g, 63.0 mmol) was dissolved in tetrahydrofuran (300 mL), followed by successive addition of benzyl bromide (44 mL, 370.8 mmol) and potassium hydroxide (31.8 g, 565.9 mmol). The reaction mixture was heated to 70° C. and stirred for 17 hours, and then cooled to room temperature, followed by filtration. The filter residue was washed with tetrahydrofuran (20 mL×3), and the combined filtrate was concentrated under reduced pressure to obtain the crude product, which was purified by silica gel column chromatography (petroleum ether/ethyl acetate (v/v)=1/0-9/1) to obtain compound 6-3.

MS (ESI) m/z (M+Na)$^+$=393.1.

$^1$H NMR (400 MHz, CDCl$_3$) 7.38-7.28 (m, 10H), 5.92 (d, J=3.9 Hz, 1H), 4.66 (d, J=4.2 Hz, 1H), 4.62-4.55 (m, 4H), 4.29-4.28 (m, 1H), 4.04 (d, J=2.9 Hz, 1H), 3.65 (d, J=6.1 Hz, 2H), 1.45 (s, 3H), 1.33 (s, 3H).

Step 4: Preparation of Compound 6-4

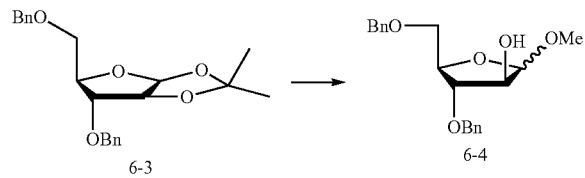

Compound 6-3 (33.5 g, 90.4 mmol) was dissolved in methanol (250 mL), followed by successive addition of D-camphorsulfonic acid (0.1 g, 399.5 μmol). The reaction mixture was heated to 70° C. and stirred for 12 hour, and then cooled to room temperature, followed by addition of 30 drops of triethylamine. The reaction mixture was concentrated under reduced pressure to obtain the crude product, which was purified by silica gel column chromatography (petroleum ether/ethyl acetate (v/v)=1/0-7/3) to obtain compound 6-4.

MS (ESI) m/z (M+Na)$^+$=367.0.

$^1$H NMR (400 MHz, CDCl$_3$) 7.39-7.23 (m, 10H), 4.92 (s, 0.6H), 4.87 (d, J=4.6 Hz, 0.4H), 4.79-4.44 (m, 4H), 4.28 (q, J=2.2 Hz, 1H), 4.16-4.09 (m, 1H), 3.89-3.82 (m, 1H), 3.66-3.65 (m, 0.6H), 3.54 (d, J=5.6 Hz, 0.7H), 3.45-3.44 (m, 0.4H), 3.44-3.41 (s, 3H), 3.37-3.36 (m, 0.6H), 2.61-2.59 (m, 0.3H).

Step 5: Preparation of Compound 6-5

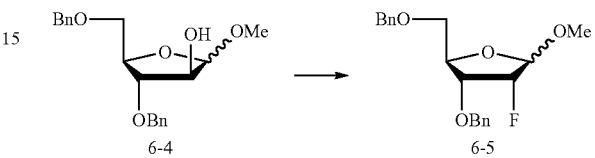

At 0° C., compound 6-4 (1.24 g, 3.6 mmol) was dissolved in dichloromethane (40 mL), followed by successive addition of pyridine (2.7 mL 33.5 mmol) and trifluoromethanesulfonic anhydride (0.8 mL, 4.9 mmol). After 20 minutes, the reaction mixture was quenched with water (10 mL). The aqueous phase was separated, and the organic phase was dried over anhydrous sodium sulfate, and concentrated under reduced pressure to obtain a crude product. The crude product was dissolved in tetrahydrofuran (25 mL), cooled to 0° C., followed by addition of tetrabutylammonium fluoride (1 M tetrahydrofuran solution, 18 mL), then heated to 20° C. and stirred for 12 hours. The reaction mixture was concentrated under reduced pressure to obtain the crude product, which was purified by silica gel column chromatography (petroleum ether/ethyl acetate (v/v)=1/0-9/1) to obtain compound 6-5.

MS (ESI) m/z (M+Na)$^+$=369.2.

$^1$H NMR (400 MHz, CDCl$_3$) 7.40-7.28 (m, 10H), 5.05-4.99 (m, 1H), 4.74-4.47 (m, 5H), 4.32 (m, 1H), 4.16-4.04 (m, 1H), 3.69-3.63 (m, 1H), 3.58-3.51 (m, 1H), 3.34 (s, 3H).

$^{19}$F NMR (376 MHz, CDCl$_3$) −209.4.

Step 6: Preparation of Compound 6-6

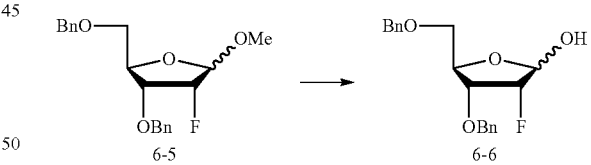

At 20° C., compound 6-5 (8.4 g, 24.2 mmol) was dissolved in trifluoroacetic acid (90 mL, 1.2 mol) and water (10 mL, 555.1 mmol). After stirring for 12 hours, water (150 mL) and dichloromethane (200 mL) were added to the reaction mixture, and the pH of aqueous phase was adjusted to 7 with 10 M sodium hydroxide. The organic phase was separated, and the aqueous phase was extracted with dichloromethane (50 mL×2). The organic phases were combined, dried over anhydrous sodium sulfate, filtered, and the filtrate was concentrated under reduced pressure to obtain a crude product, which was purified by silica gel column chromatography (petroleum ether/ethyl acetate (v/v)=1/0-7/3) to obtain compound 6-6.

MS (ESI) m/z (M+Na)$^+$=355.0.

$^{19}$F NMR (376 MHz, CDCl$_3$) −206.8.

Step 7: Preparation of Compound 6-7

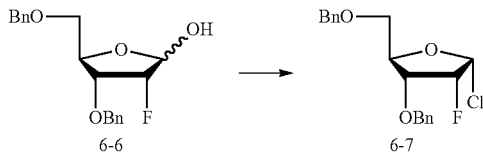

At −50° C. under argon atmosphere, compound 6-6 (5.9 g, 17.8 mmol) and carbon tetrachloride (7.7 mL 80.3 mmol) were dissolved in toluene (70 mL), followed by dropwise addition of the solution of tris(dimethylamino)phosphine (3.49 g, 21.41 mmol, 3.89 mL) in toluene (5 mL). The reaction mixture was heated to 0° C. and stirred for 3 hours, then cooled to −20° C., diluted with cold toluene (30 mL), and quenched with cold saturated brine (30 mL). The organic phase was separated, dried over anhydrous sodium sulfate, filtered, and the filtrate was concentrated under reduced pressure to obtain crude product 6-7, which was directly used for the next reaction without further purification.

MS (ESI) m/z (M+NH$_4$)$^+$=369.1.

$^1$H NMR (400 MHz, CDCl$_3$) 7.27-7.26 (m, 10H), 6.30-6.29 (m, 1H), 5.16-4.95 (m, 1H), 4.89-4.85 (m, 1H), 4.72-4.43 (m, 4H), 4.12-4.11 (m, 1H), 3.80-3.50 (m, 2H).

$^{19}$F NMR (376 MHz, CDCl$_3$) −200.5-−200.6.

Step 8: Preparation of Compound 6-8

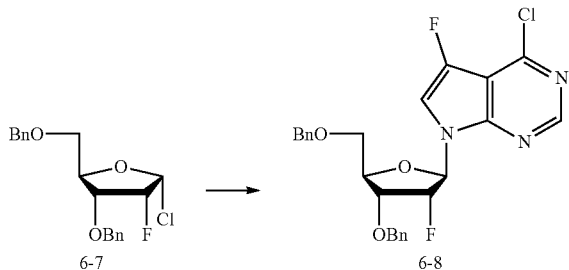

At 20° C., under argon atmosphere, compound 6-7 (6.5 g, 18.5 mmol), 4-chloro-5-fluoro-7H-pyrrolo[2,3-d]pyrimidine (3.2 g, 18.5 mmol) were dissolved in acetonitrile (100 mL), followed by successive addition of potassium hydroxide (3.1 g, 55.6 mmol) and tris(3,6-dioxaheptyl)amine (599.3 mg, 1.9 mmol). After stirring for 12 hours, the reaction solution was concentrated. The crude product was dissolved in ethyl acetate (150 mL) and water (60 mL). The aqueous phase was separated and extracted with ethyl acetate (20 mL×2). The organic phases were combined, dried over anhydrous sodium sulfate, filtered, and the filtrate was concentrated under reduced pressure to obtain the crude product, which was purified by silica gel column chromatography (petroleum ether/ethyl acetate (v/v)=1/0-4/1) to obtain compound 6-8.

MS (ESI) m/z (M+H)$^+$=486.1.

$^1$H NMR (400 MHz, CDCl$_3$) 8.61 (s, 1H), 7.41-7.30 (m, 11H), 6.67-6.60 (m, 1H), 4.81-4.74 (m, 1H), 4.65-4.50 (m, 4H), 4.43-4.33 (m, 2H), 3.92-3.84 (m, 1H), 3.68-3.65 (m, 1H).

$^{19}$F NMR (376 MHz, CDCl$_3$) −165.8-−165.9, −203.8-−204.5.

Step 9: Preparation of Compound 6-9

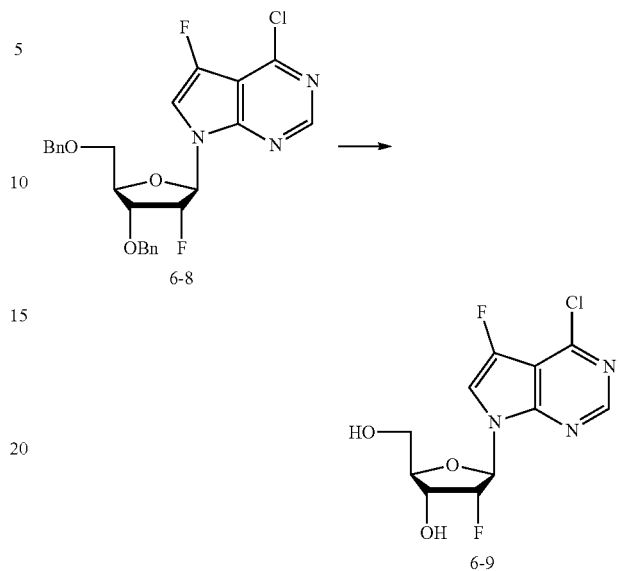

At −70° C., under nitrogen atmosphere, compound 6-8 (0.1 g, 179.1 μmol) was dissolved in dichloromethane (5 mL), followed by dropwise addition of boron trichloride (1 M n-heptane solution, 0.9 mL), and the reaction mixture was stirred for 1 hour at this temperature. The reaction mixture was then quenched with methanol (15 mL), then heated to room temperature, and concentrated under reduced pressure to obtain the crude product, which was purified by silica gel column chromatography (dichloromethane/methanol (v/v)=1/0-20/1) to obtain compound 6-9.

$^1$H NMR (400 MHz, DMSO-d$_6$) 8.73 (s, 1H), 8.03 (d, J=1.5 Hz, 1H), 6.52 (d, J=15.4 Hz, 1H), 5.76 (d, J=6.1 Hz, 1H), 5.35-5.16 (m, 2H), 4.44-4.30 (m, 1H), 4.01-3.93 (m, 1H), 3.80-3.55 (m, 2H).

$^{19}$F NMR (376 MHz, DMSO-d$_6$) −169.15, −204.15-−204.64.

Step 10: Preparation of Compound 6-10

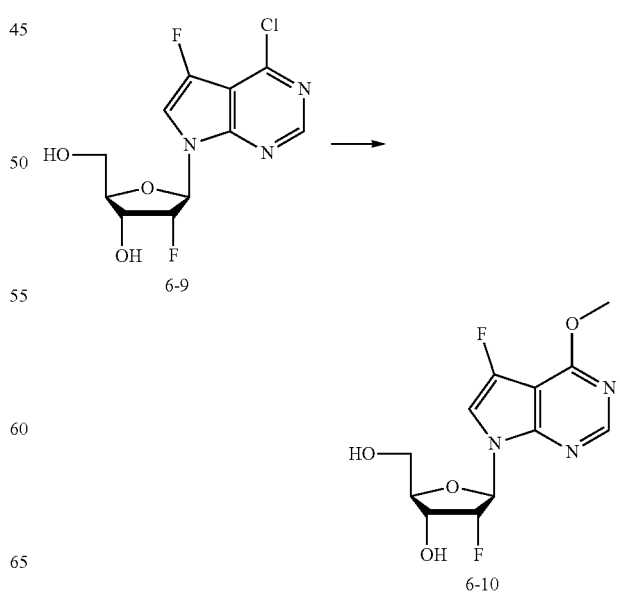

At 10° C., compound 6-9 (0.33 g, 1.1 mmol) was dissolved in the solution of sodium methoxide (0.5 M, 16.5 mL) in methanol. The reaction mixture was performed with stirring at this temperature for 12 hours. The solvent was removed by concentration under reduced pressure, and the crude product was purified by silica gel column chromatography (dichloromethane/methanol (v/v)=1/0-20/1) to obtain compound 6-10.

MS (ESI) m/z (M+H)$^+$=302.0.

$^1$H NMR (400 MHz, DMSO-d$_6$) 8.48 (s, 1H), 7.67 (d, J=2.0 Hz, 1H), 6.50-6.43 (m, 1H), 5.73 (d, J=6.0 Hz, 1H), 5.32-5.28 (m, 0.5H), 5.17 (t, J=5.3 Hz, 1.5H), 4.41-4.30 (m, 1H), 4.10-4.04 (m, 3H), 3.95-3.94 (m, 1H), 3.72-3.70 (m, 1H), 3.60-3.55 (m, 1H).

$^{19}$F NMR (376 MHz, DMSO-d$_6$) −166.9, −204.8.

Step 11: Preparation of Compound 6-11

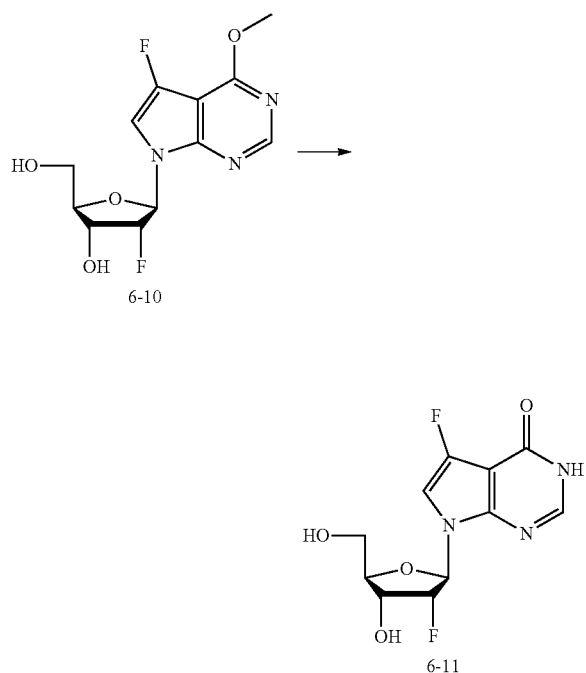

At 20° C., under argon atmosphere, compound 6-10 (0.22 g, 730.3 μmol) was dissolved in acetonitrile (20 mL), followed by successive addition of sodium iodide (547.3 mg, 3.6 mmol) and trimethylchlorosilane (463 μL 3.6 mmol). The reaction was performed with stirring at this temperature for 3 hours. The reaction mixture was then cooled to 0° C., and quenched with methanol (3 mL). After stirring for 5 minutes, the solvent was removed by concentration under reduced pressure, and the crude product was purified by silica gel column chromatography (dichloromethane/methanol (v/v)=1/0-10/1) to obtain compound 6-11.

MS (ESI) m/z (M+H)$^+$=288.0.

$^1$H NMR (400 MHz, DMSO-d$_6$) 12.19 (s, 1H), 7.96 (s, 1H), 7.35 (s, 1H), 6.34-6.31 (m, 1H), 5.70 (br s, 1H), 5.25-5.18 (m, 1H), 5.11-5.05 (m, 1H), 4.34-4.28 (m, 1H), 3.92 (s, 1H), 3.75-3.53 (m, 2H).

$^{19}$F NMR (376 MHz, DMSO-d$_6$) −165.3, −204.8-−205.0.

Step 12: Preparation of Compound 6-12

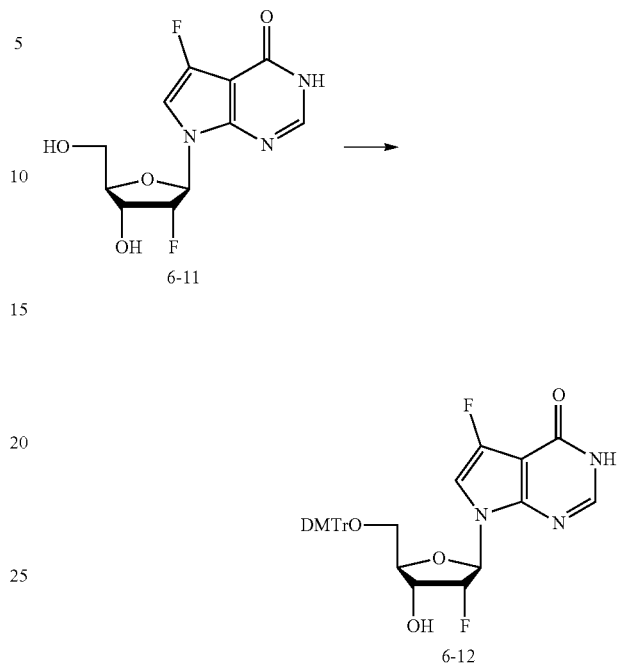

At 20° C., under argon atmosphere, compound 6-11 (0.36 g, 1.25 mmol) was dissolved in pyridine (8 mL), followed by addition of DMTrCl (0.26 g, 767.4 μmol) was added. The reaction was performed with stirring at this temperature for 4 hours. The reaction mixture was quenched with methanol (3 mL). After stirring for 5 minutes, the reaction mixture was concentrated under reduced pressure to remove the solvent, and the crude product was dissolved in ethyl acetate (60 mL). The organic phase was washed with saturated brine (15 mL×3), dried over anhydrous sodium sulfate, filtered, and the filtrate was concentrated under reduced pressure to obtain the crude product, which was purified by silica gel column chromatography (dichloromethane/methanol (v/v)=1/0-20/1) to obtain compound 6-12.

MS (ESI) m/z (M+H)$^+$=592.2.

$^1$H NMR (400 MHz, DMSO-d$_6$) 12.23 (s, 1H), 7.98 (s, 1H), 7.39-7.18 (m, 10H), 6.86-6.83 (m, 4H), 6.37-6.32 (m, 1H), 5.70 (d, J=6.8 Hz, 1H), 5.36-5.17 (m, 1H), 4.52-4.40 (m, 1H), 4.09-4.02 (m, 1H), 3.73 (s, 6H), 3.29-3.19 (m, 2H).

$^{19}$F NMR (376 MHz, DMSO-d$_6$) −165.4, −201.9.

Step 13: Preparation of Compound 6-13

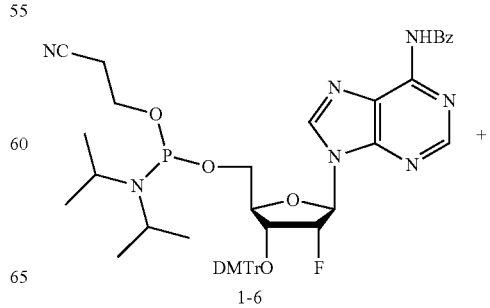

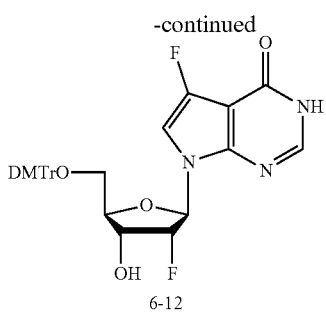

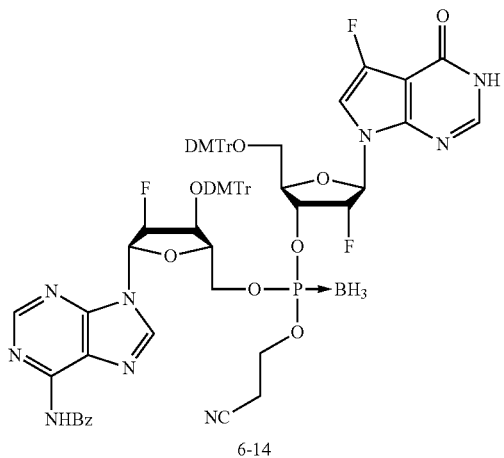

At 20° C., under argon atmosphere, compound 6-12 (0.25 g, 424.0 µmol) was dissolved in acetonitrile (5 mL), followed by successive addition of tetrazole (0.45 M acetonitrile solution, 10 mL) and 4 Å molecular sieve (0.6 g), and stirred for 10 minutes. Compound 1-6 (0.65 g, 742.1 µmol) was then added, and stirred for 50 minutes, the mixture was poured into ethyl acetate (30 mL), followed by filtration. The filtrate was successively washed with saturated sodium bicarbonate solution (10 mL) and saturated brine (10 mL), dried over anhydrous sodium sulfate, followed by filtration. The filtrate was concentrated under reduced pressure to obtain the crude product, which was purified by silica gel column chromatography (dichloromethane/methanol (v/v)=1/0-20/1) to obtain compound 6-13.

Step 14: Preparation of Compound 6-14

Under argon atmosphere, at 25° C., compound 6-13 (0.68 g, 498.4 µmol) was dissolved in dichloromethane (5 mL), followed by addition of 4 Å molecular sieve (0.6 g). After stirring for 30 minutes, borane dimethyl sulfide complex (2 M tetrahydrofuran solution, 747.63 µL) was added dropwise thereto. After completion of the addition, the reaction mixture was stirred at 25° C. for 20 minutes. The reaction mixture was then diluted with dichloromethane (40 mL), followed by filtration. The filtrate was successively washed with water (10 mL) and saturated brine (10 mL), dried over anhydrous sodium sulfate, followed by filtration. The filtrate was concentrated under reduced pressure to obtain crude product 6-14, which was directly used for the next reaction without further purification.

Step 15: Preparation of Compound 6-15

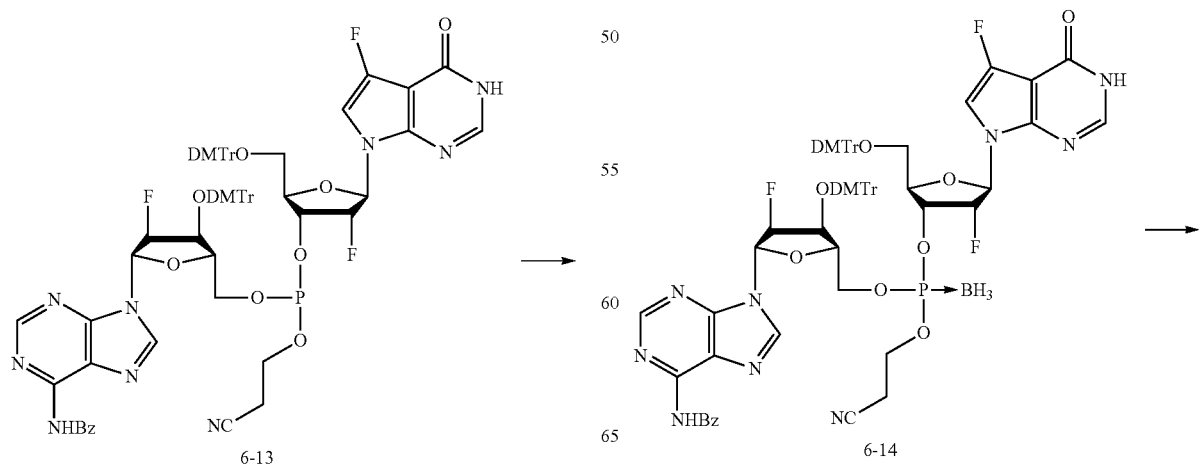

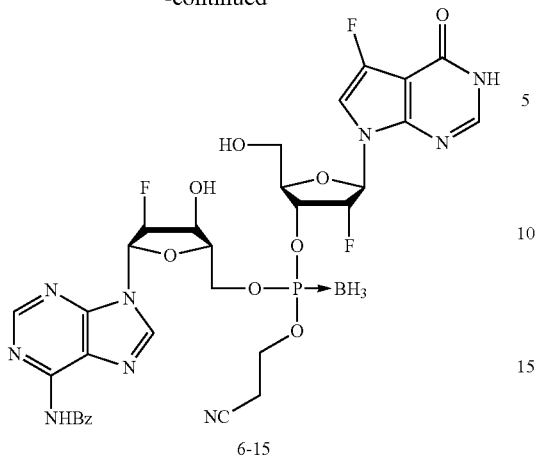

6-15

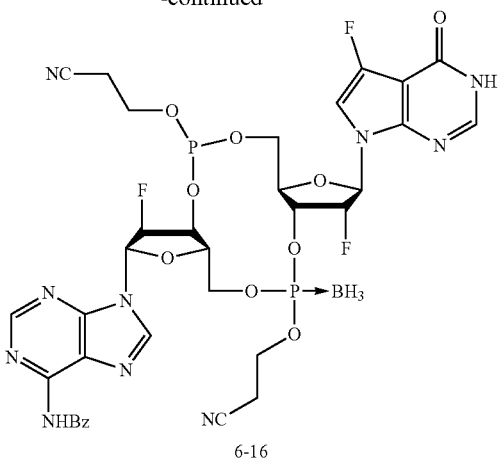

6-16

Compound 6-14 (0.73 g, 529.7 μmol) was dissolved in dichloromethane (5 mL), followed by addition of 2,2-dichloroacetic acid (5 mL, 2.6 mmol, 5% dichloromethane solution). The reaction mixture was stirred at 20° C. for 30 minutes, followed by addition of triethylsilane (5 mL, 31.3 mmol), and stirred for another 30 minutes. The reaction mixture was poured into dichloromethane (60 mL), then successively washed with saturated sodium bicarbonate solution (10 mL×2) and saturated brine (10 mL), dried over anhydrous sodium sulfate, filtered, and the filtrate was concentrated under reduced pressure to obtain the crude product, which was purified by silica gel column chromatography (dichloromethane/methanol (v/v)=1/0-20/1) to obtain compound 6-15.

MS (ESI) m/z (M+H)$^+$=774.3.

$^1$H NMR (400 MHz, DMSO-d$_6$) 12.26 (s, 1H), 11.25 (s, 1H), 8.76 (s, 1H), 8.58-8.57 (m, 1H), 8.03-8.02 (m, 2H), 7.95-7.94 (m, 1H), 7.69-7.62 (m, 1H), 7.59-7.51 (m, 2H), 7.35-7.34 (m, 1H), 6.49-6.31 (m, 2H), 6.01 (d, J=6.5 Hz, 1H), 5.67-5.66 (m, 1H), 5.61-5.52 (m, 1H), 5.45-5.44 (m, 1H), 5.36-5.35 (m, 1H), 5.09-5.08 (m, 1H), 4.85-4.69 (m, 1H), 4.51-4.40 (m, 1H), 4.39-4.31 (m, 1H), 4.27-4.10 (m, 4H), 3.56-3.55 (m, 2H), 2.89-2.88 (m, 2H).

$^{19}$F NMR (376 MHz, DMSO-d$_6$) −164.8, −201.3, −206.9.

$^{31}$P NMR (162 MHz, DMSO-d$_6$) δ 115.0-115.1.

Step 16: Preparation of Compound 6-16

Under argon atmosphere, at 20° C., compound 6-15 (0.22 g, 284.5 μmol), 4 Å molecular sieve (1 g) and tetrazole (0.45 M acetonitrile solution, 10 mL, 4.5 mmol) were dispersed in the mixed solution of acetonitrile (2 mL) and tetrahydrofuran (5 mL), followed by dropwise addition of the solution of 2-cyanoethyl N,N,N',N'-tetraisopropylphosphorodiamidite (120 μL, 377.8 μmol) in acetonitrile (0.5 mL), and then stirred for 1 hour. The reaction mixture was diluted with ethyl acetate (50 mL), followed by filtration. The filtrate was washed with water (20 mL×3), dried over anhydrous sodium sulfate, followed by filtration. The filtrate was concentrated under reduced pressure to obtain the crude product, which was separated and purified by preparative thin layer chromatography (dichloromethane/methanol (v/v)=10/1) to obtain compound 6-16.

Step 17: Preparation of Compound 6-17

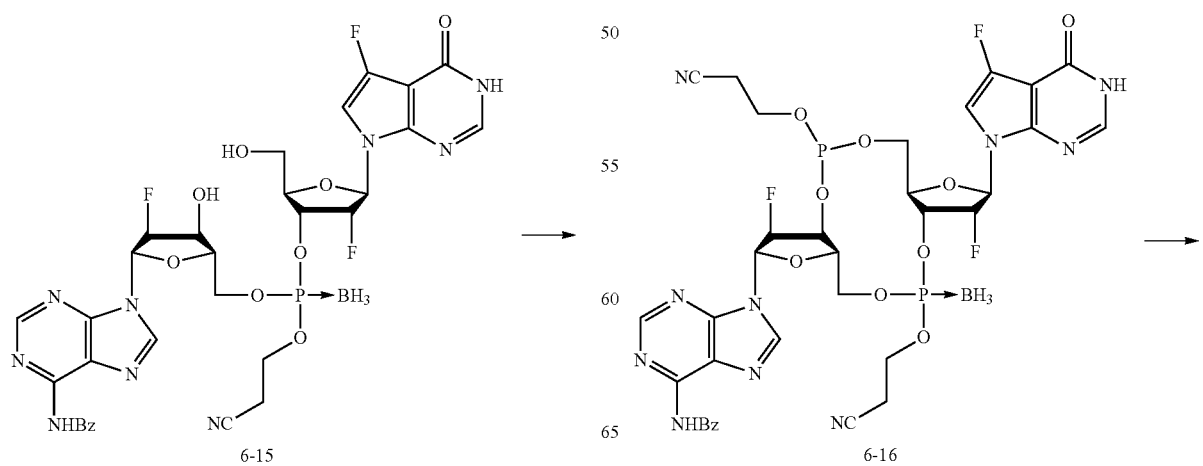

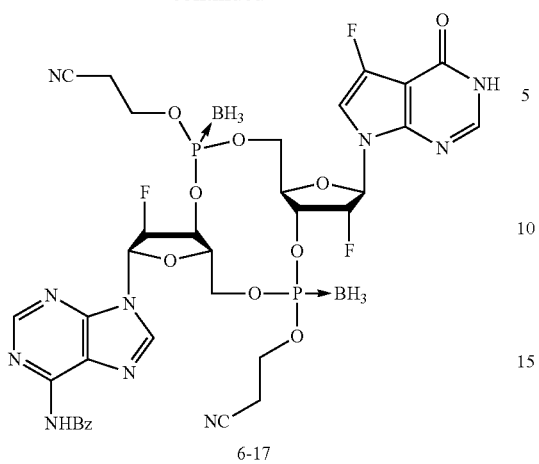

6-17

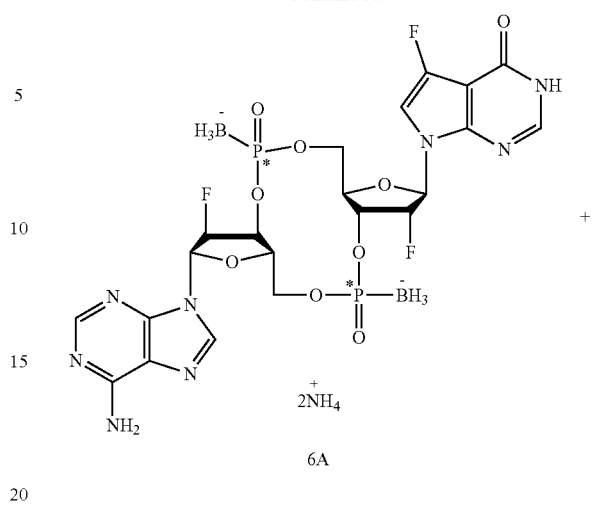

6A

Under argon atmosphere, at 0° C., borane dimethyl sulfide complex (2 M tetrahydrofuran solution, 0.2 mL, 0.4 mmol) was added dropwise to the solution of compound 6-16 (0.1 g, 114.6 μmol) and 4 Å molecular sieve (0.5 g) in tetrahydrofuran (5 mL), and the reaction mixture was stirred at 15° C. for 30 minutes. The reaction mixture was then diluted with ethyl acetate (40 mL), followed by filtration. The filtrate was washed with water (15 mL×3), dried over anhydrous sodium sulfate, followed by filtration. The filtrate was concentrated under reduced pressure to obtain crude product 6-17, which was directly used for the next reaction without further purification.

MS (ESI) m/z (M+H)$^+$=887.2

Step 18: Preparation of Compounds 6A, 6B, 6C and 6D

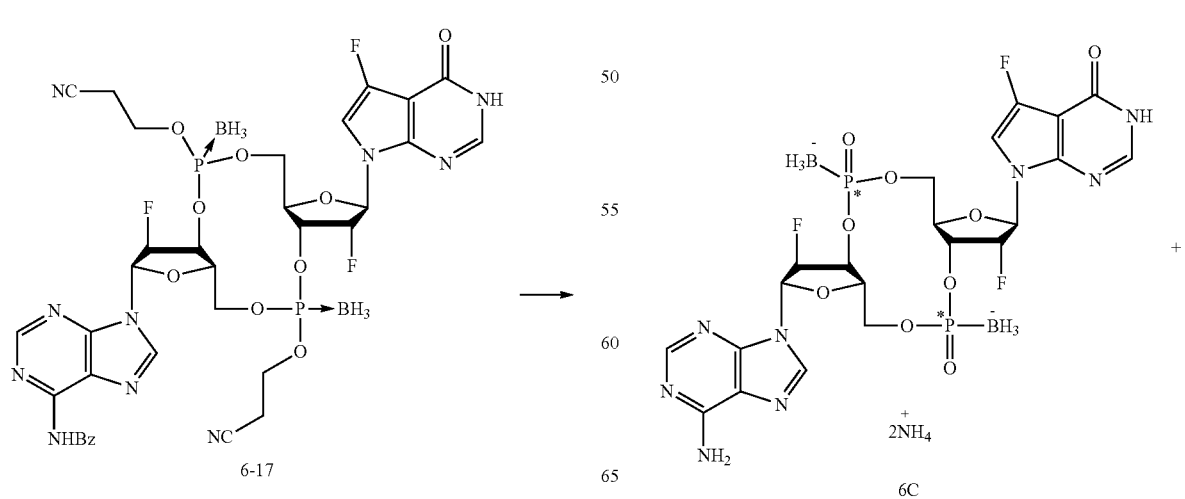

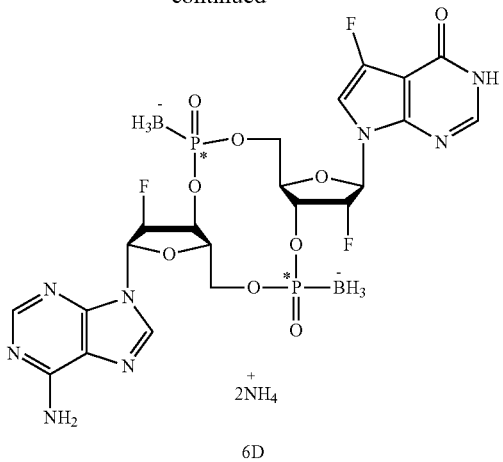

6D

Compound 6-17 (0.11 g, 124.1 mol) was dissolved in 33% methylamine ethanol solution (3 mL). The reaction was performed with stirring at 15° C. for 18 hours. The reaction mixture was concentrated under reduced pressure. The residue was dissolved in water (10 mL), and back-extracted with ethyl acetate (30 mL). The aqueous phase was lyophilized, and the crude product was separated by HPLC (separation conditions: chromatographic column: Xbridge Prep OBD C18 150*40 mm 10 μm; mobile phase: [water (0.05% ammonium hydroxide)-acetonitrile]; acetonitrile %: 0%-30%, flow rate: 25 mL/min, 20 min) to obtain:
Compound 6A (HPLC retention time 6.05 min)
Compound 6B (HPLC retention time 6.47 min)
Compound 6C (HPLC retention time 6.39 min)
Compound 6D (HPLC retention time 7.47 min)
Compound 6A:
MS (ESI) m/z (M–H)⁻=674.7
$^1$H NMR (400 MHz, D$_2$O) δ 8.43 (s, 1H), 8.12 (s, 1H), 7.93 (s, 1H), 7.24 (s, 1H), 6.49-6.38 (m, 2H), 5.87-5.70 (m, 1H), 5.38-5.19 (m, 1H), 5.19-5.03 (m, 1H), 4.86-4.81 (m, 1H), 4.55-4.37 (m, 2H), 4.32-4.18 (m, 2H), 4.07-3.94 (m, 2H), 0.62--0.39 (m, 6H).
$^{19}$F NMR (376 MHz, D$_2$O) –165.05, –201.16--201.51, –203.00--203.35.
$^{31}$P NMR (162 MHz, D$_2$O) δ 95.50-90.45.
Compound 6B:
MS (ESI) m/z (M–H)⁻=674.8
$^1$H NMR (400 MHz, D$_2$O) δ 8.50 (s, 1H), 8.18 (s, 1H), 7.95 (s, 1H), 7.20 (s, 1H), 6.56-6.37 (m, 2H), 5.63-5.40 (m, 1H), 5.39-5.14 (m, 2H), 4.53-4.35 (m, 3H), 4.35-4.23 (m, 2H), 4.10-3.91 (m, 2H), 0.28 (br s, 6H).
$^{19}$F NMR (376 MHz, D$_2$O) –164.19, –199.92--200.68, –201.18--202.10.
$^{31}$P NMR (162 MHz, D$_2$O) δ 95.93-91.70.
Compound 6C:
MS (ESI) m/z (M–H)⁻=674.7
$^1$H NMR (400 MHz, D$_2$O) δ 8.39 (s, 1H), 8.15 (s, 1H), 7.93-7.83 (m, 1H), 7.20 (s, 1H), 6.53-6.35 (m, 2H), 5.71-5.49 (m, 1H), 5.37-5.16 (m, 1H), 5.13-4.90 (m, 2H), 4.55-4.36 (m, 3H), 4.31-4.18 (m, 1H), 4.10-3.96 (m, 2H), 0.36 (br s., 6H).
$^{19}$F NMR (376 MHz, D$_2$O) –165.35, –199.73--200.19, –202.31--202.91.
$^{31}$P NMR (162 MHz, D$_2$O) δ 96.82-90.33.
Compound 6D:
MS (ESI) m/z (M–H)⁻=674.7
$^1$H NMR (400 MHz, D$_2$O) δ 8.25 (s, 1H), 8.06 (s, 1H), 7.66 (s, 1H), 7.05 (s, 1H), 6.29-6.15 (m, 2H), 5.75-5.56 (m, 1H), 5.42-5.23 (m, 1H), 5.23-5.01 (m, 2H), 4.52-4.35 (m, 4H), 4.04-3.93 (m, 2H), 0.34 (br s, 6H).
$^{19}$F NMR (376 MHz, D$_2$O) –164.82, –200.86, –202.28.
$^{31}$P NMR (162 MHz, D$_2$O) δ 96.94-91.91.

Biological Activity Test Experiment

Example 1: STING In Vitro Binding Test

Fluorescence polarization assay (FP assay) was used to detect the affinity of compounds for human STING proteins. There were a certain amount of fluorescein-labeled c-di-GMP and different concentrations of test compounds in the reaction system. When the C-terminal protein of recombinant human STING was added, two small molecules competitively combined with the protein. The rotation of the fluorescein-labeled c-di-GMP in the bound phase is relatively slow in the liquid phase, and the degree of fluorescence polarization detected is relatively high. The degree of fluorescence polarization is inversely proportional to the concentration and affinity of the compound to be tested. By detecting the size of the polarized light in the reaction system, we can accurately know the affinity of the compound to be tested for human STING.

The soluble human STING protein sequence used in the experiment was truncated from the C-terminal part of human wild-type endoplasmic reticulum binding protein STING, from 140 amino acids to 379 amino acids. There are multiple alleles with sequence differences in human STING protein, and different alleles have different affinity for CDN (Yi, et al., "Single Nucleotide Polymorphisms of Human STING can affect innate immune response to cyclic di-nucleotides" PLOS ONE. 2013, 8(10), e77846). Wild-type STING sequences (G230, R232, R293) accounted for approximately 57.9% of the total. The N-terminal of the recombinant STING protein was a 6His-SUMO sequence, which facilitated the correct folding and purification of the protein, after protease removal, the C-terminal STING was used for the FP test.

FP test was conducted in a 384-well plate, wherein the fluorescein-labeled c-di-GMP with a final concentration of 30 nM, 10 μM human STING protein and different concentrations of reference or the tested compound were added in 10 μL of reaction system per well, centrifuged at 1000 g for 1 minute, and incubated at room temperature in the dark for 30 minutes. The plate was read using Envision.

The results of the in vitro binding assay of STING as described above are shown in table 1.

TABLE 1

| Compound No. | FP affinity test IC$_{50}$ (μM) |
| --- | --- |
| 2',3'-cGAMP | 6.66 |
| 1A | 13.96 |
| 1B | 3.21 |
| 1C | 3.73 |
| 1D | 5.61 |
| 2A | 3.58 |
| 2B | 2.00 |
| 3A | 5.91 |
| 3B | 4.35 |
| 3C | 2.93 |
| 3D | 2.70 |
| 4A | 2.76 |
| 4B | 2.26 |
| 4C | 1.44 |
| 4D | 2.86 |

TABLE 1-continued

| Compound No. | FP affinity test IC$_{50}$ (μM) |
|---|---|
| 5A | 2.81 |
| 5B | 5.47 |
| 5C | 4.97 |
| 5D | 5.14 |
| 6A | 2.39 |
| 6B | 1.76 |
| 6C | 2.40 |
| 6D | 2.53 |

Conclusion: in FP affinity test, the compounds of the present disclosure show higher affinity for human wild-type STING protein than that of endogenous 2' 3'-cAMP.

Example 2: THP1-Dual Reporter Gene Activity Assay

THP1-Dual™ cells (InvivoGen catalog code: thpd-nfis) used in the test were constructed by stably integrating two inducible reporter genes into the human monocyte cell line THP1. The promoter sequence composition of the secretory embryonic alkaline phosphatase (SEAP) reporter gene consists of an IFN-β primary promoter and five copies of the upstream NF-κB co-expression transcriptional response element and three copies of the c-Rel binding site. The secretory luciferase (Lucia) reporter gene is driven by five interferon (IFN)-stimulated response elements and a basic promoter of ISG54. This made it possible to study simultaneously the two major downstream signaling pathways of STING: the NF κB pathway by detecting SEAP activity: and the IRF pathway by evaluating the activity of Lucia luciferase.

The compounds were diluted with PB buffer (50 mM HEPES, 100 mM KCl, 3 mM MgCl2, 0.1 mM DTT, 85 mM Sucrose, 1 mM ATP, 0.1 mM GTP, 0.20% BSA). 20 μL of the reference or tested compound was added to each well in a 96-well plate, followed by 180 μL of THP1-Dual cells (approximately 100,000 cells/well) suspended in PB buffer. The plate was incubated for 30 minutes at 37° C. under 50% CO$_2$, and centrifuged at 1000 rpm for 10 minutes. The supernatant was discarded. The plate was washed twice with 200 μL/well RPMI-1640, followed by addition of 200 μL/well RPMI-1640, and incubated for 18 hours. The supernatants were collected and QUANTI-Luc™ was used to quantify the activation of the IRF3 pathway according to the manufacturer's instructions.

The results of the in vitro THP1-dual binding assay as described above are shown in table 2.

TABLE 2

| Compound No. | EC$_{50}$(μM) |
|---|---|
| 2',3'-cGAMP | 20.19 |
| ADU-S100 | 23.39 |
| 1A | 74.69 |
| 1B | 7.38 |
| 1C | 16.76 |
| 1D | 7.48 |
| 2A | 1.75 |
| 2B | 3.39 |
| 3B | 42.21 |
| 3C | 47.17 |
| 3D | 26.13 |
| 4A | 3.06 |
| 4B | 3.68 |
| 4C | 10.18 |
| 4D | 48.20 |

TABLE 2-continued

| Compound No. | EC$_{50}$(μM) |
|---|---|
| 5A | 6.20 |
| 5B | 11.42 |
| 5C | 5.13 |
| 5D | 12.6 |
| 6A | 1.36 |
| 6B | 9.31 |
| 6C | 2.31 |
| 6D | 12.30 |

Conclusion: in human mononuclear cell line THP-1, the compounds of the present disclosure have strong capability to promote the activation of R interferon.

Example 3: Raw-Dual Reporter Gene Activity Assay

The RAW-Dual™ cells used in the test (InvivoGen catalog code: rawd-ismip) were constructed by stably integrating two inducible reporter genes in mouse macrophage cell line RAW264.7. The NF-KB pathway was studied by detecting SEAP activity and the IRF3 pathway was studied by evaluating the activity of luciferase. 200 μL/well of cell suspension (50,000 cells per well) was added to a 96-well plate (Corning 3599 flat plate) and incubated at 37° C. for 18-24 hours. On the second day, the culture medium was discarded, and 200 μL of compound solution prepared in advance with the culture medium was added into each well followed by incubation at room temperature for 30 minutes. After the treatment medium was sucked out, it was washed twice with serum-free culture medium, and 200 μL of culture medium was added into each well, followed by incubation in an incubator at 37° C. for 18-24 hours. On the third day, 20 μL of supernatant was collected per well and QUANTI-Luc™ was used to quantify the activation of IRF3 pathway according to the manufacturer's instructions.

The results of the RAW cell activity assay as described above are shown in table 3.

TABLE 3

| Compound No. | Raw, EC$_{50}$(μM) |
|---|---|
| ADU-S100 | 47.08 |
| 1B | 15.8 |
| 1C | 41.4 |
| 1D | 24.4 |
| 2A | 23.4 |
| 2B | 2.1 |
| 3C | 9.4 |
| 3D | 10.0 |
| 4B | 2.6 |
| 4C | 6.3 |
| 4D | 21.0 |
| 5B | 54.8 |
| 5C | 28.2 |
| 5D | 31.6 |
| 6B | 5.4 |
| 6C | 1.1 |
| 6D | 9.5 |

Conclusion: it is found in test that in the mouse macrophage system RAW report gene assay, the compounds of the present disclosure have strong STING-activating ability.

Example 4: In Vivo Pharmacodynamic Assay 1

In this assay, the efficacy of the compounds was evaluated through 4T1 breast cancer mouse model. 1E5 4T1 breast cancer cells (Institute of Cytology, Shanghai Academy of Sciences) were inoculated subcutaneously in Balb/C mice (Charles River) aged 6-8 weeks, and then randomized into groups of eight after the tumor volume reached 100 mm$^3$. Intratumoral administration was performed sequentially on Day 1, Day 4, and Day 8 after grouping. Single intratumoral administration (IT) was on Day 1 after grouping. The dose of ADU-S100 in each groups were 100 ug per mouse (once) and 30 ug per mouse (three times). The dose of compound 2B in each groups were 30 ug per mouse (once), 100 ug per mouse (once) and 30 ug per mouse (three times). Tumor volumes were measured twice a week after administration. The calculation formula of tumor volume was as follows: $V=0.5a \times b^2$, a and b indicated the long diameters and short diameters of the tumor, respectively. Each point was the mean and standard error (SEM) of the tumor volume. Inter-group differences were statistically analyzed by using two-way ANOVA (statistical differences on Day 25 are presented in the figure, Prism7, **$p<0.0001$). The tumor volume of the administration group is significantly smaller than that of the control group. The tumors disappears completely in the compound 2B 100 ug (once) and 30 ug (three times) groups, and tumor inhibition is superior to that of the same dose of ADU-S100. The results are shown in FIG. 1**.

Example 5: In Vivo Pharmacodynamic Assay 2

In this assay, the efficacy of the compounds was evaluated through CT-26 colon cancer syngeneic mouse model. 3E5 CT-26 colon cancer cells (ATCC-CRL-2638) were inoculated subcutaneously in Balb/C mice (Shanghai Lingchang Biology) aged 6-8 weeks, and then randomized into groups of eight after the tumor volume reached 100 mm$^3$. Intratumoral administration was performed three times sequentially on Day 1, Day 4, and Day 8 after grouping. The dose of compound 2B in each groups was 1 ug per mouse, 3 ug per mouse, 9 ug per mouse, and 18 μg per mouse. The dose of ADU-S100 was 125 μg per mouse. Tumor volumes were measured three times a week after administration. The calculation formula of tumor volume was as follows: $V=0.5a \times b^2$, a and b indicated the long diameters and short diameters of the tumor, respectively. Each point was the mean and standard error (SEM) of the tumor volume. Inter-group differences between the control group and the administration group were statistically analyzed by using two-way ANOVA (the statistical differences on Day 11 are presented in the figure, Prism7, ****$p<0.0001$).

Figure 2:
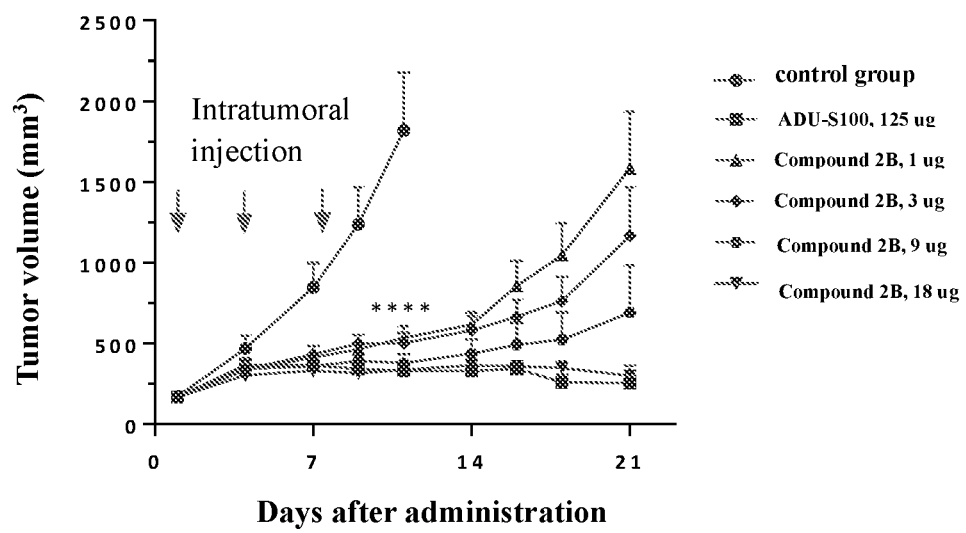
FIG. 2 shows the result of pharmacodynamic test on homologous mouse model of CT-26 colon cancer.

Compared with the control group, the tumor growth rate of mice in the administration group is significantly slower. Compound 2B showed a dose-dependent inhibition on tumor growth in mice. The tumor inhibitory effect of compound 2B (18 μg per mouse) is equivalent to that of compound ADU-S100 (125 μg per mouse). The results are shown in FIG. 2.

Example 6: In Vivo Pharmacodynamic Assay 3

In this assay, the efficacy of the compounds was evaluated through MC38 colon cancer syngeneic mouse model. 3E5 MC38 colon cancer cells (Nanjing Kebai) were inoculated subcutaneously in C57BL/6 mice (Shanghai Bikai) aged 6-8 weeks, and then randomly divided into groups of five to six after the tumor volume reached about 100 mm$^3$. Intratumoral administration was performed sequentially on Day 1, Day 4, and Day 8 after grouping. Single intratumoral administration was on Day 1 after grouping. The dose of ADU-S100 group was 100 ug per mouse (once). The dose of compound 2B in each groups were 100 ug per mouse (once), 30 ug per mouse (three times) and 10 ug per mouse (three times). The dose of compound 6C group was 30 ug per mouse (three times). Tumor volumes were measured twice a week after administration. The calculation formula of tumor volume was as follows: $V=0.5a \times b^2$, a and b indicated the long diameters and short diameters of the tumor, respectively. Each point was the mean and standard error (SEM) of the tumor volume. Inter-group differences between the control group and the administration group were statistically analyzed by using two-way ANOVA (the statistical difference on Day 28 is shown in the figure, Prism7, ****$p<0.0001$).

Figure 3:
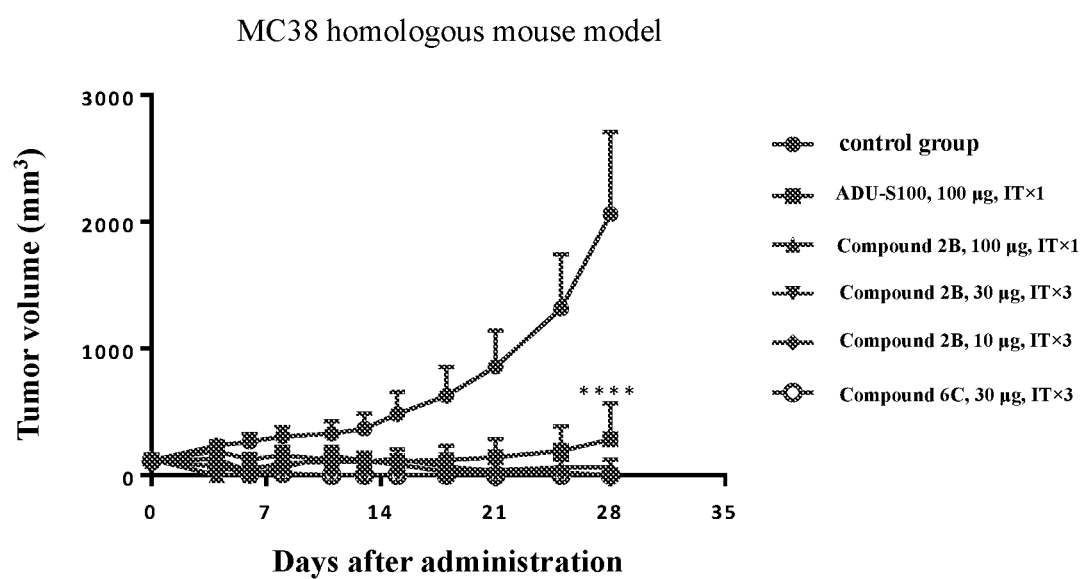
FIG. 3 shows the result of pharmacodynamic test on homologous mouse model of MC38 colon cancer.

Compared with the control group, the tumor growth of mice in the administration group is significantly inhibited. Tumors all disappeared in the compound 2B 30 ug (three times) and 10 ug (three times) groups and in the compound 6C 30 ug (three times) group. The results are shown in FIG. 3.

What is claimed is:

1. A compound of formula (I), an optical isomer thereof or a pharmaceutically acceptable salt thereof,

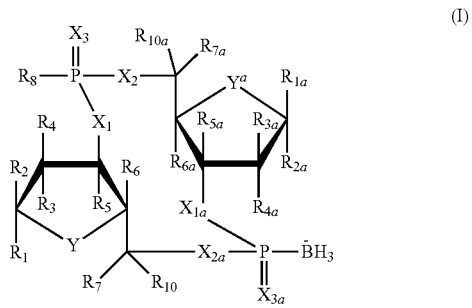

wherein, each of $R_1$ and $R_{1a}$ is independently selected from

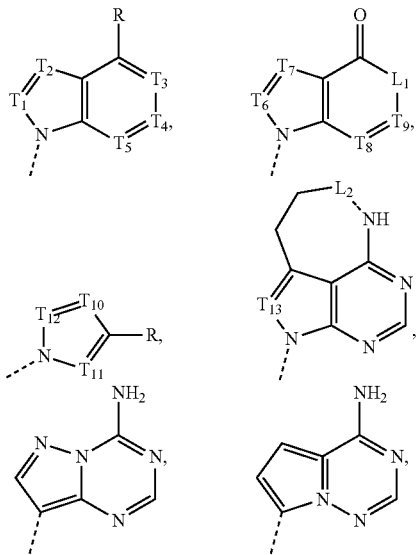

-continued

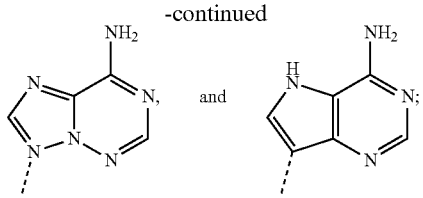
and each of $T_1, T_2, T_3, T_4, T_5, T_6, T_7, T_8, T_9, T_{10}, T_{11}, T_{12}$ and $T_{13}$ is independently selected from —C(R)— and —N—;

each of $L_1$ and $L_2$ is independently selected from —O—, —N(R)—, —C(RR)— and —C(=O)—;

each of R is independently selected from H, halogen, OH, NH$_2$, CN,

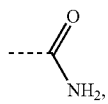

$C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R';

R' is selected from F, Cl, Br, I, OH, NH$_2$ and CH$_3$;

each of $R_2$ and $R_2$, is independently selected from H, halogen, OH, NH$_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_3$ and $R_3$, is independently selected from H, halogen, OH, NH$_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_4$ and $R_4$, is independently selected from H, halogen, OH, NH$_2$, CN, N$_3$, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_5$ and $R_5$, is independently selected from H, halogen, OH, NH$_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

each of $R_6$ and $R_6$, is independently selected from H, halogen, OH, NH$_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol and $C_{1-6}$ alkylamino are optionally substituted by one, two or three of R;

each of $R_7$ and $R_7$, is independently selected from H, halogen, OH, NH$_2$, CN, $C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R;

each of $R_{10}$ and $R_{10a}$ is independently selected from H, halogen, OH, NH$_2$, CN, $C_{1-6}$ alkyl, $C_{1-6}$ alkoxy, $C_{1-6}$ alkylthiol and $C_{1-6}$ alkylamino, wherein the $C_{1-6}$ alkyl, $C_{1-6}$ alkoxy, $C_{1-6}$ alkylthiol and $C_{1-6}$ alkylamino are optionally substituted by one, two or three of R;

alternatively, $R_7$ and Rio are attached together to form a $C_{3-6}$ cycloalkyl, $C_{3-6}$ cycloalkenyl or $C_{3-6}$ cycloalkynyl, wherein the $C_{3-6}$ cycloalkyl, $C_{3-6}$ cycloalkenyl or $C_{3-6}$ cycloalkynyl is optionally substituted by one, two or three of R;

$R_{7a}$ and $R_{10a}$ are attached together to form a $C_{3-6}$ cycloalkyl, $C_{3-6}$ cycloalkenyl or $C_{3-6}$ cycloalkynyl, wherein the $C_{3-6}$ cycloalkyl, $C_{3-6}$ cycloalkenyl or $C_{3-6}$ cycloalkynyl is optionally substituted by one, two or three of R;

$R_8$ is selected from BH$_3^-$ and —S(R$_9$);

$R_9$ is selected from H, CH$_2$OC(=O)R$_{11}$, CH$_2$OC(=O)OR$_{11}$, CH$_2$CH$_2$SC(=O)R$_{11}$ and CH$_2$CH$_2$S SCH$_2$R$_{11}$;

$R_{11}$ is selected from $C_{6-10}$ aryl, 5-10 membered heteroaryl, $C_{1-6}$ heterocycloalkyl and $C_{1-20}$ alkyl, wherein the $C_{1-20}$ alkyl is optionally substituted by one, two, three, four or five of $C_{6-10}$ aryl, $C_{3-6}$ cycloalkyl, OH and F;

alternatively, $R_4$ and $R_6$, or $R_{4a}$ and $R_{6a}$ are attached together to form a 5-6 membered heterocycloalkyl;

each of $X_1$ and $X_{1a}$ is independently selected from —NH—, —O—, —S— and —CH$_2$—;

each of $X_2$ and $X_{2a}$ is independently selected from —NH—, —O—, —S— and —CH$_2$—;

each of $X_3$ and $X_{3a}$ is independently selected from —O— and —S—;

each of Y and $Y_a$ is independently selected from —O—, —S—, —CH$_2$— and —C(=CH$_2$)—;

the 5-6 membered heterocycloalkyl, 5-10 membered heteroaryl or $C_{1-6}$ heterocycloalkyl contains one, two or three of heteroatom or heteroatomic group independently selected from —O—, —NH—, —S—, —C(=O)—, —C(=O)O—, —S(=O)—, —S(=O)$_2$— and N;

and, when $R_1$ or $R_{1a}$ is selected from

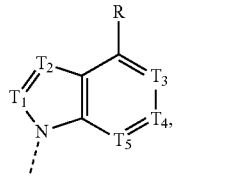 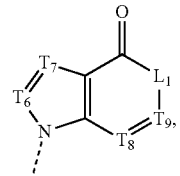

then the compound of formula (I) is not selected from

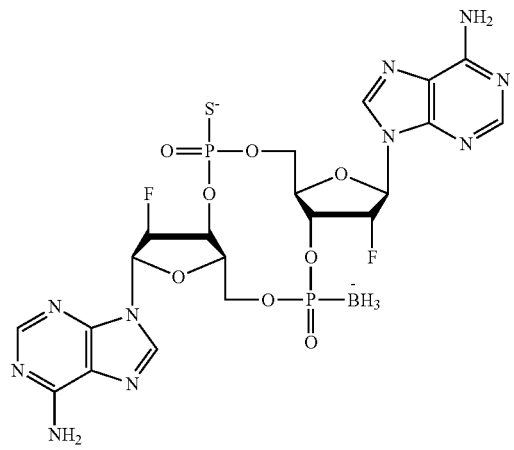

185
-continued
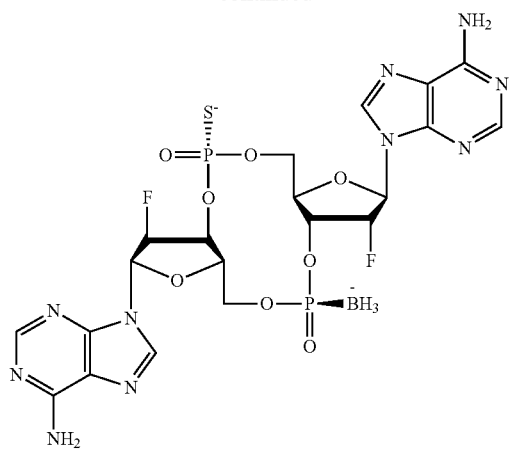
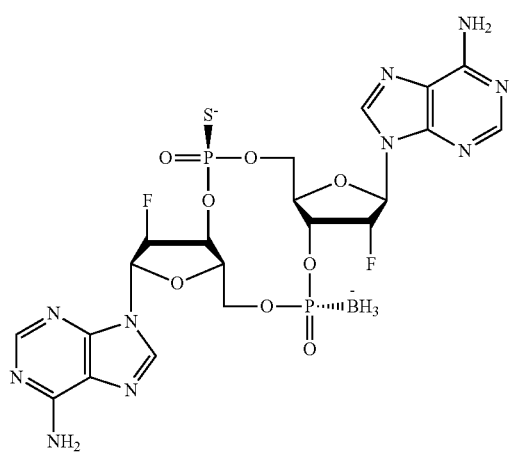
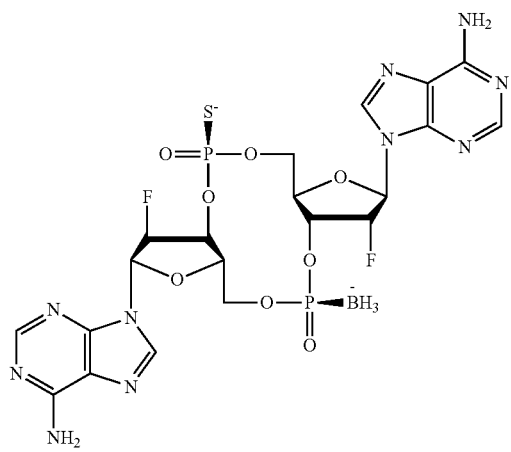
186
-continued
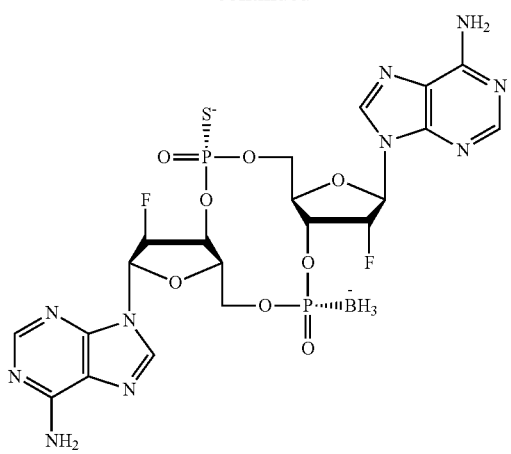
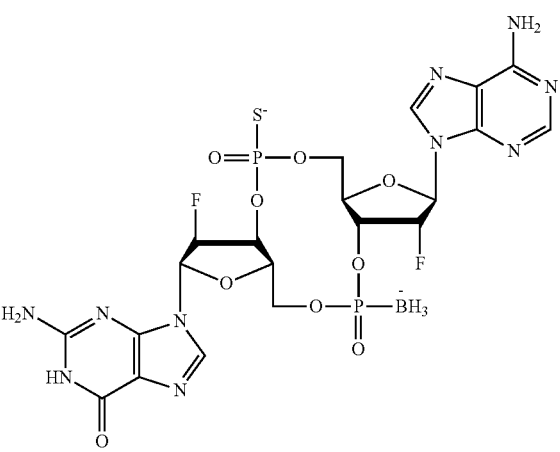
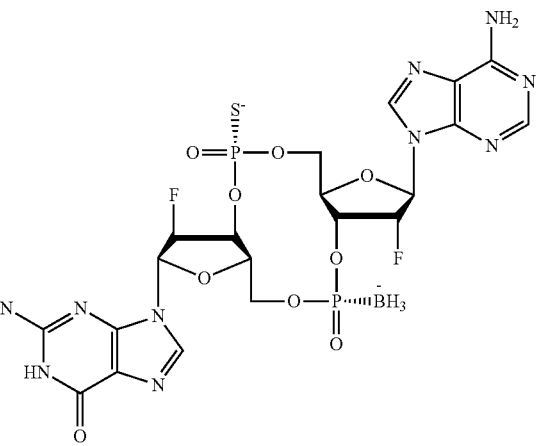

187
-continued
188
-continued
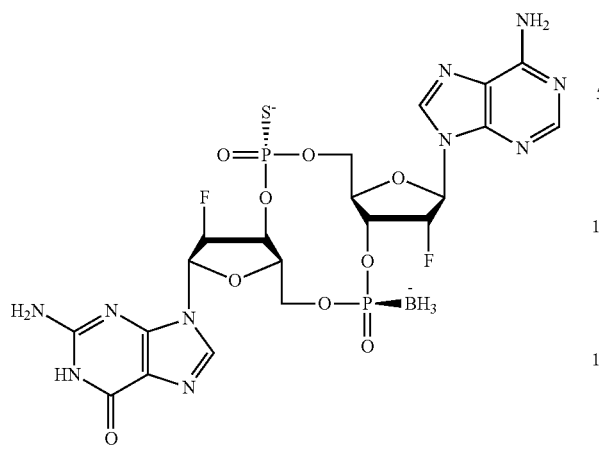
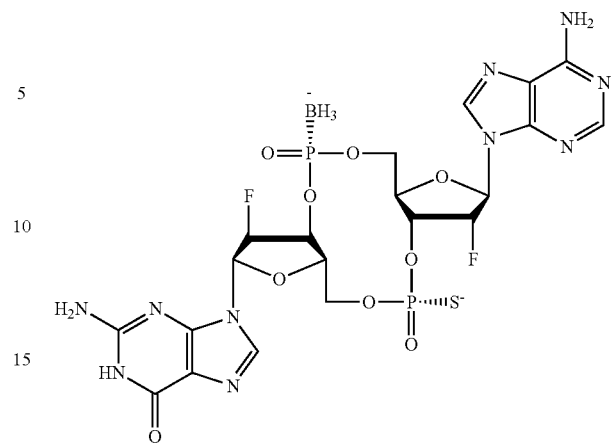
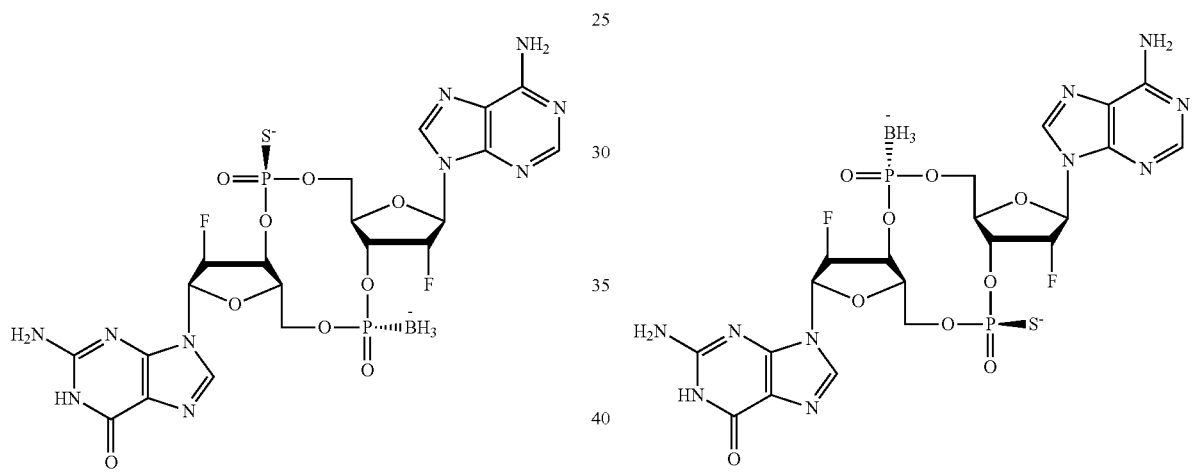
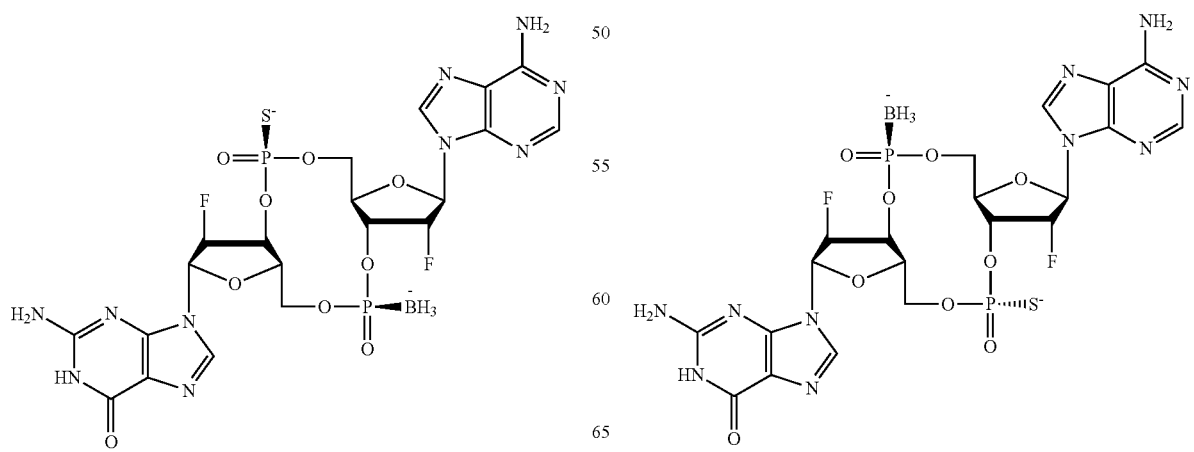

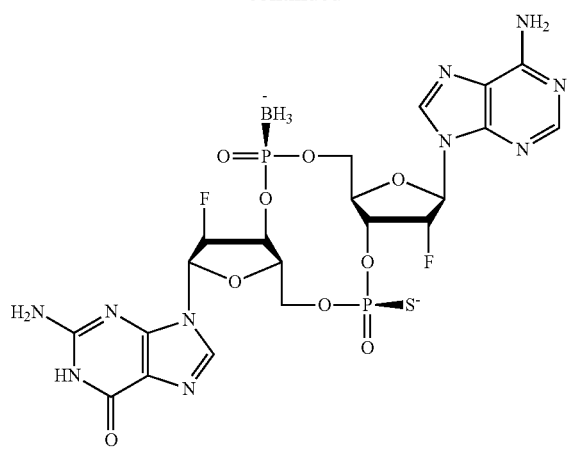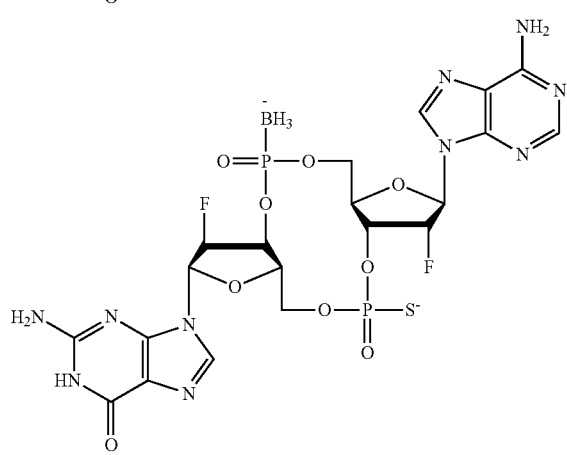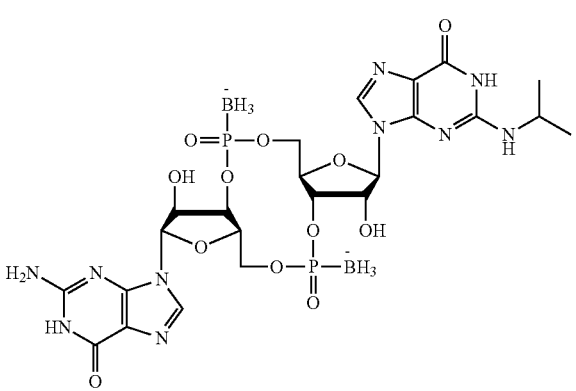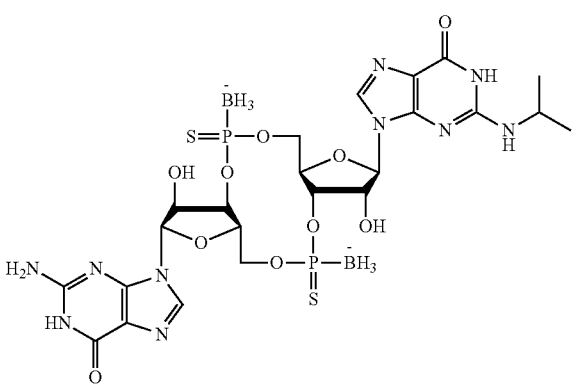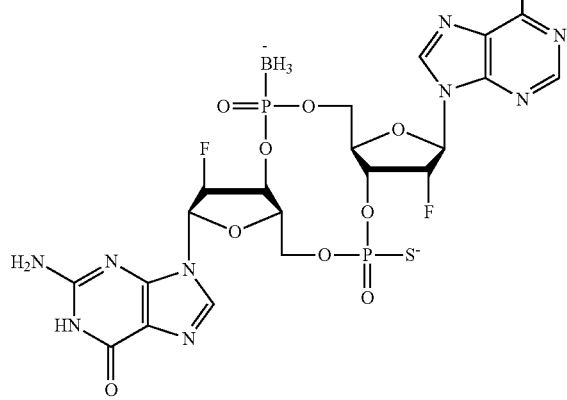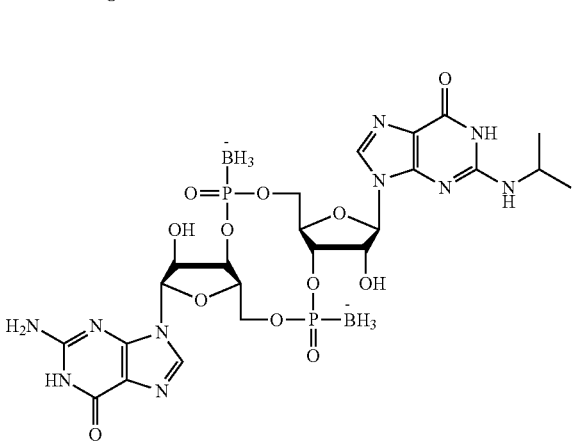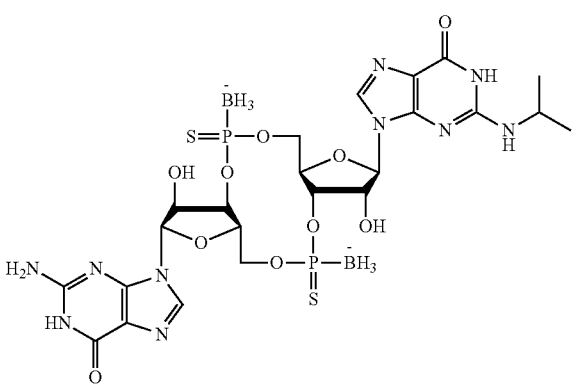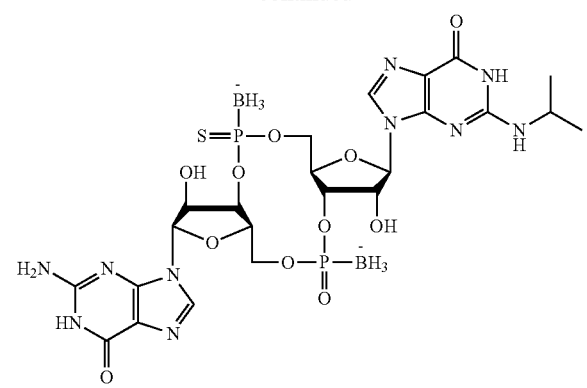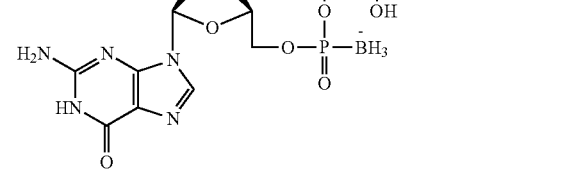

-continued

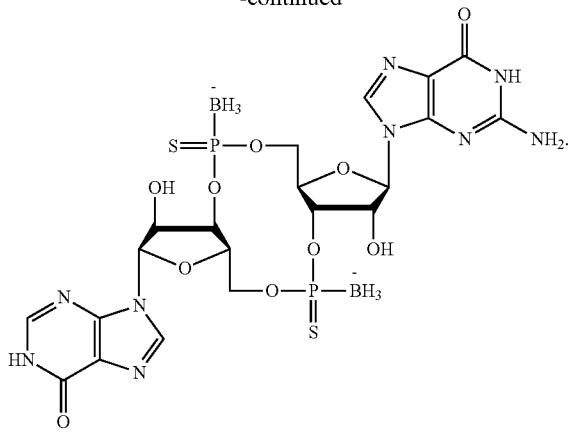

2. The compound, the optical isomer thereof or the pharmaceutically acceptable salt thereof as defined in claim 1, wherein, when $R_8$ is $BH_3^-$, then one of $R_4$ and $R_{4a}$ is selected from F, Cl and Br, and the other one is selected from F, Cl, Br, OH, $OCH_3$ and $N_3$.

3. The compound, the optical isomer thereof or the pharmaceutically acceptable salt thereof as defined in claim 1, wherein each of R is independently selected from H, halogen, OH, $NH_2$, CN,

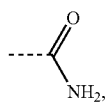

$C_{1-3}$ alkyl, $C_{1-3}$ alkoxy, $C_{1-3}$ alkylthiol and $C_{1-3}$ alkylamino, wherein the $C_{1-3}$ alkyl, $C_{1-3}$ alkoxy, $C_{1-3}$ alkylthiol and $C_{1-3}$ alkylamino are optionally substituted by one, two or three of R'.

4. The compound, the optical isomer thereof or the pharmaceutically acceptable salt thereof as defined in claim 3, wherein each of R is independently selected from H, F, Cl, Br, I, OH, $NH_2$, CN, Me,

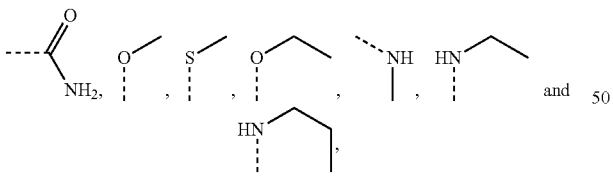

wherein the Me,

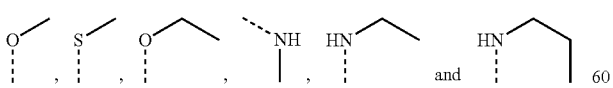

are optionally substituted by one, two or three of R'.

5. The compound, the optical isomer thereof or the pharmaceutically acceptable salt thereof as defined in claim 4, wherein each of R is independently selected from H, F, Cl, Br, I, OH, $NH_2$, CN, Me,

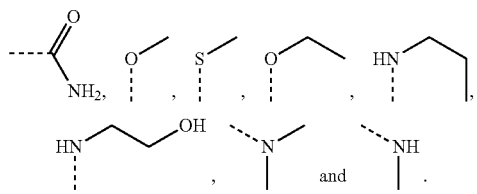

6. The compound, the optical isomer thereof or the pharmaceutically acceptable salt thereof as defined in claim 1, wherein each of $R_1$ and $R_{1a}$ is independently selected from

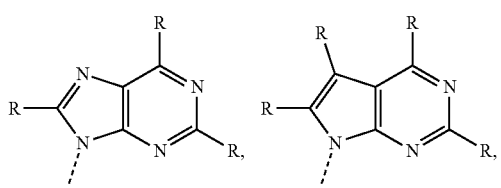

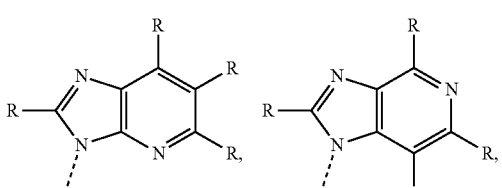

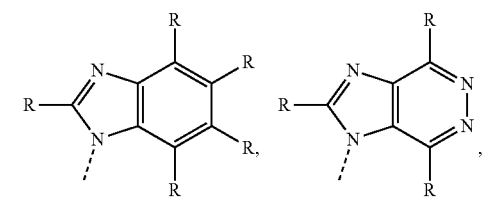

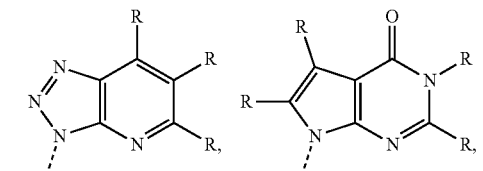

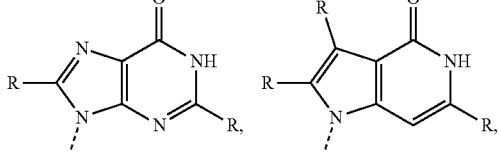

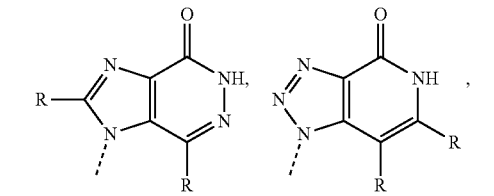

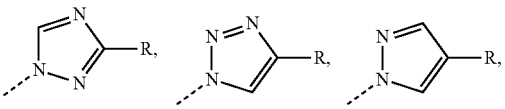

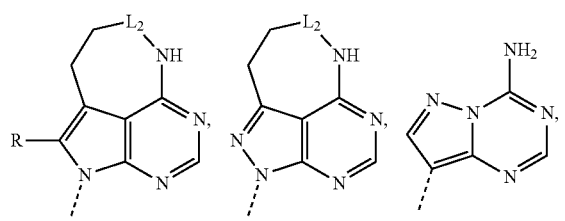
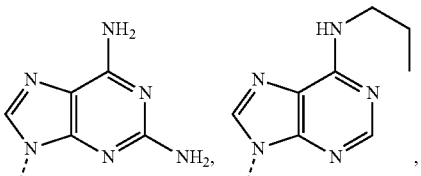
7. The compound, the optical isomer thereof or the pharmaceutically acceptable salt thereof as defined in claim 6, wherein each of $R_1$ and $R_{1a}$ is independently selected from
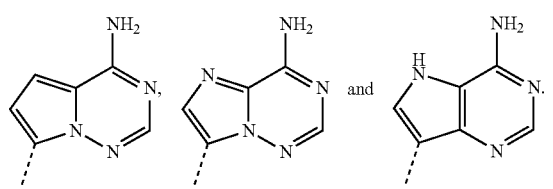
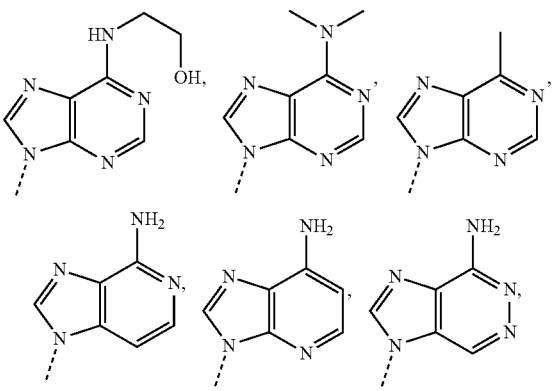
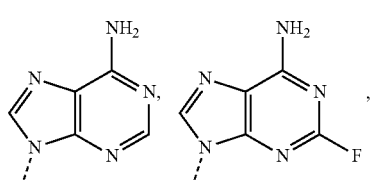
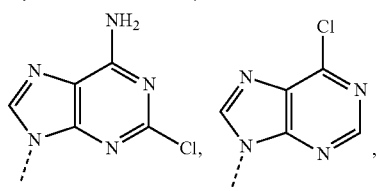
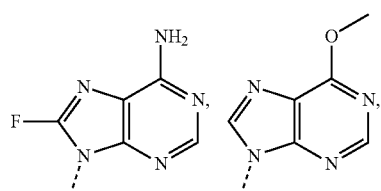
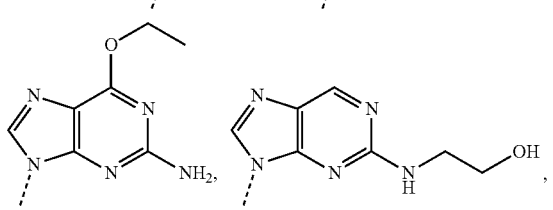
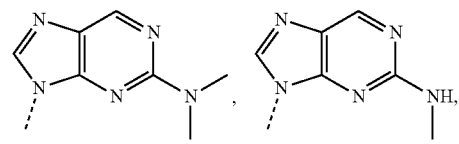
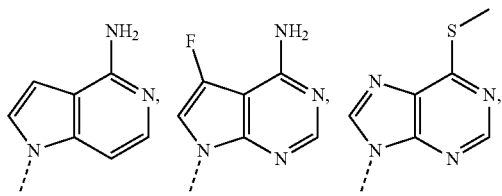
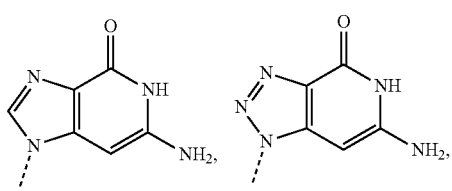

-continued

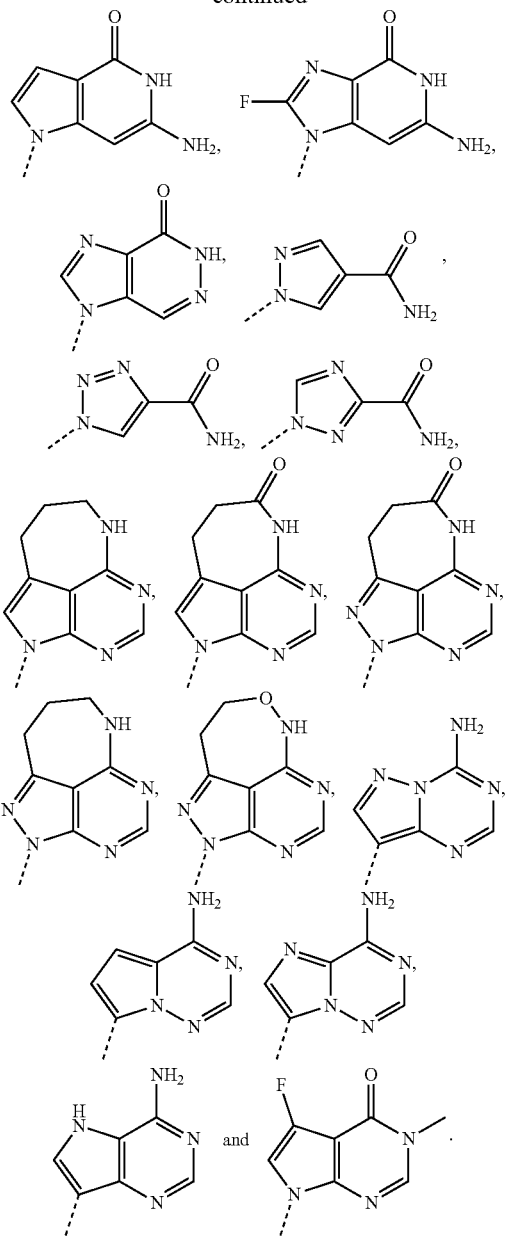

8. The compound, the optical isomer thereof or the pharmaceutically acceptable salt thereof as defined in claim 1, wherein each of $R_2$, $R_{2a}$, $R_3$, $R_{3a}$, $R_5$, $R_{5a}$, $R_6$ and $R_{6a}$ is independently H;

optionally, each of $R_6$ and $R_{6a}$ is independently selected from H and methyl.

9. The compound, the optical isomer thereof or the pharmaceutically acceptable salt thereof as defined in claim 1, wherein each of $R_4$ and $R_{4a}$ is independently selected from F, OH, $NH_2$, $N_3$ and

10. The compound, the optical isomer thereof or the pharmaceutically acceptable salt thereof as defined in claim 1, wherein each of $R_7$ and $R_{7a}$ is independently selected from H and $CH_3$.

11. The compound, the optical isomer thereof or the pharmaceutically acceptable salt thereof as defined in claim 1, wherein $R_4$ and $R_6$ are attached together, and the structure moiety

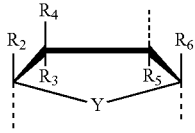

is selected from

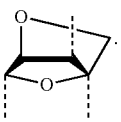

12. The compound, the optical isomer thereof or the pharmaceutically acceptable salt thereof as defined in claim 1, wherein $R_{4a}$ and $R_{6a}$ are attached together, and the structure moiety

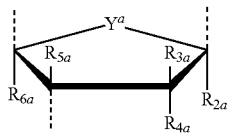

is selected from

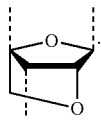

13. The compound, the optical isomer thereof or the pharmaceutically acceptable salt thereof as defined in claim 1, wherein the compound is selected from

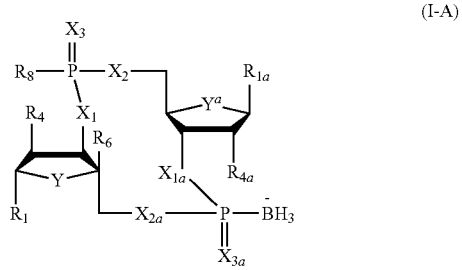

(I-A)

wherein, each of $R_1$ and $R_{1a}$ is independently selected from

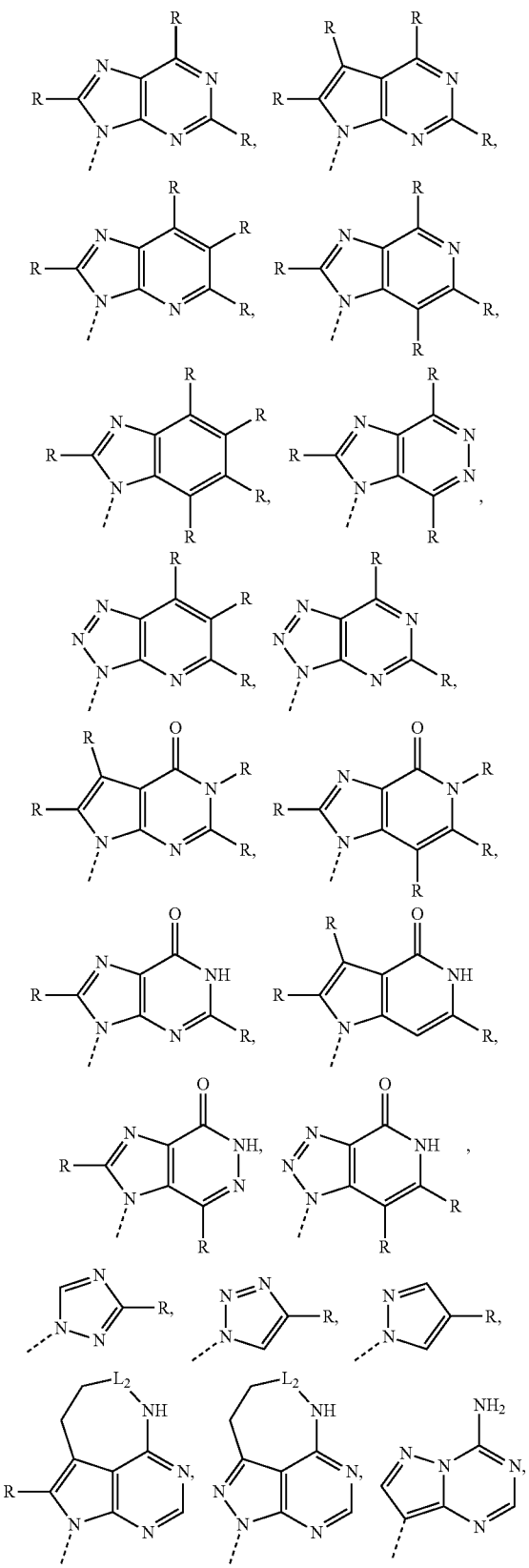

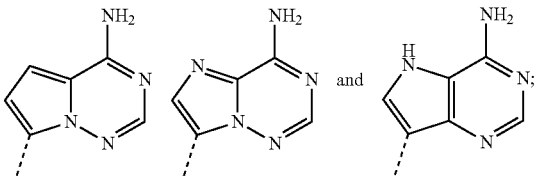

each of $R_4$ and $R_{4a}$ is independently selected from H, halogen, OH, $NH_2$, CN, $N_3$, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol, $C_{1-6}$ alkylamino and $C_{2-6}$ alkynyl are optionally substituted by one, two or three of R;

$R_6$ is selected from H, halogen, OH, $NH_2$, CN, $C_{1-6}$ alkyl, $C_{1-6}$ alkoxy, $C_{1-6}$ alkylthiol, $C_{1-6}$ alkylamino and $C_{2-6}$ alkynyl, wherein the $C_{1-6}$ alkyl, $C_{1-6}$ alkoxy, $C_{1-6}$ alkylthiol and $C_{1-6}$ alkylamino are optionally substituted by one, two or three of R;

alternatively, $R_4$ and $R_6$ are attached together to form a 5-6 membered heterocycloalkyl;

$R_8$ is selected from $BH_3^-$ and —$S(R_9)$;

$R_9$ is selected from H, $CH_2OC(=O)R_{11}$, $CH_2OC(=O)OR_{11}$, $CH_2CH_2SC(=O)R_{11}$ and $CH_2CH_2S\ SCH_2R_{11}$;

$R_{11}$ is selected from $C_{6-10}$ aryl, 5-10 membered heteroaryl, $C_{1-6}$ heterocycloalkyl and $C_{1-20}$ alkyl, wherein the $C_{1-20}$ alkyl is optionally substituted by one, two, three, four or five of $C_{6-10}$ aryl, $C_{3-6}$ cycloalkyl, OH and F;

each of $X_1$ and $X_{1a}$ is independently selected from —NH—, —O—, —S— and —$CH_2$—;

each of $X_2$ and $X_2a$ is independently selected from —NH—, —O—, —S— and —$CH_2$—;

each of $X_3$ and $X_{3a}$ is independently selected from —O— and —S—;

each of Y and $Y_a$ is independently selected from —O—, —S—, —$CH_2$— and —$C(=CH_2)$—;

when $R_8$ is selected from $BH_3^-$, then one of $R_4$ and $R_{4a}$ is selected from F, Cl and Br, and the other one is selected from F, Cl, Br, OH, $OCH_3$ and $N_3$;

when $R_8$ is selected from —$S(R_9)$, then one of $R_4$ and $R_{4a}$ is selected from F, Cl and Br, and the other one is selected from OH, $OCH_3$ and $N_3$;

alternatively, when $R_8$ is selected from —$S(R_9)$, and one of $R_4$ and $R_{4a}$ is selected from F, Cl and Br, and the other one is not selected from OH, $OCH_3$ and $N_3$, then $R_4$ and $R_{4a}$ are not selected from

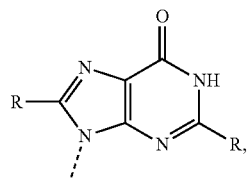

and $R_4$ and $R_{4a}$ are not selected from

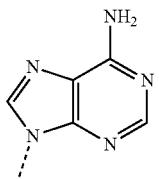

at the same time.

14. The compound, the optical isomer thereof or the pharmaceutically acceptable salt thereof as defined in claim 1, wherein the compound is selected from

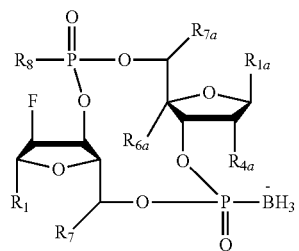
(I-1)

15. The compound, the optical isomer thereof or the pharmaceutically acceptable salt thereof as defined in claim 14, wherein the compound is selected from

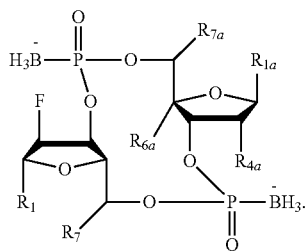
(I-2)

16. The compound, the optical isomer thereof or the pharmaceutically acceptable salt thereof as defined in claim 1, wherein the compound is selected from

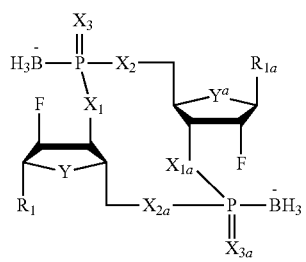
(I-A1)

-continued
and

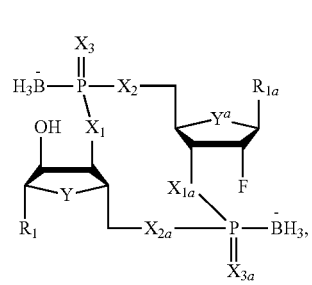
(I-A2)

wherein, each of $R_1$ and $R_{1a}$ is independently selected from

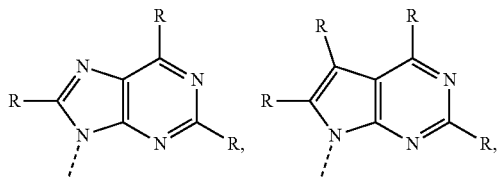

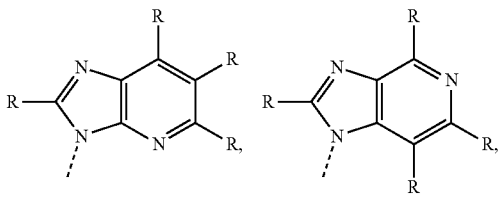

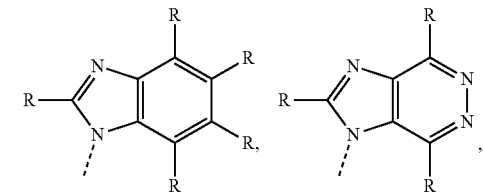

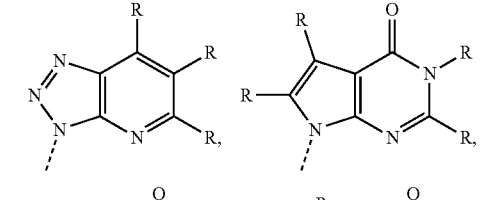

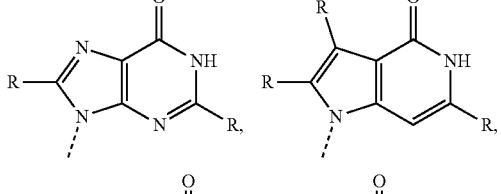

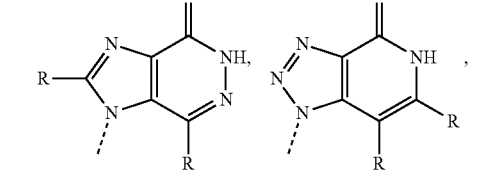

-continued

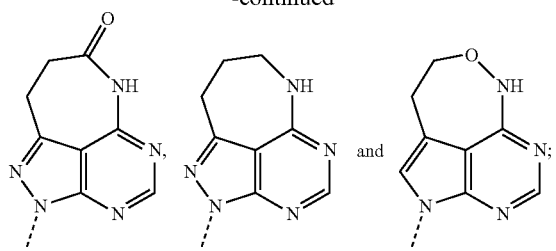

each of $X_1$ and $X_{1a}$ is independently selected from —NH—, —O—, —S— and —CH$_2$—;
each of $X_2$ and $X_{2a}$ is independently selected from —NH—, —O—, —S— and —CH$_2$—;
each of $X_3$ and $X_{3a}$ is independently selected from —O— and —S—;
each of Y and $Y_a$ is independently selected from —O—, —S—, —CH$_2$— and —C(=CH$_2$)—.

17. The compound, the optical isomer thereof or the pharmaceutically acceptable salt thereof as defined in claim 16, wherein the compound is selected from (I-A1a)
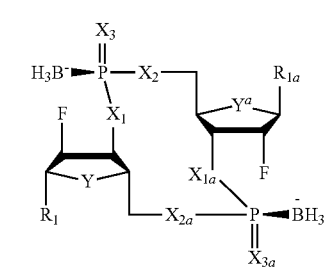

(I-A1b)
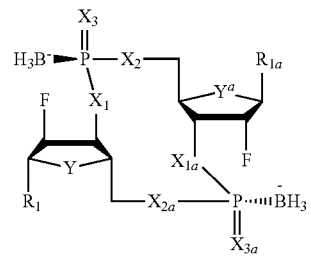

(I-A1c)
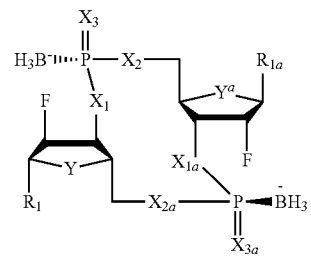

(I-A1d)
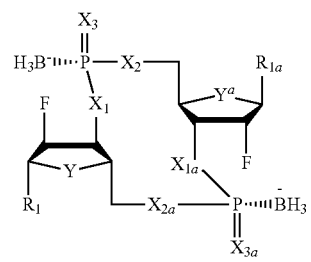

-continued (I-A2a)
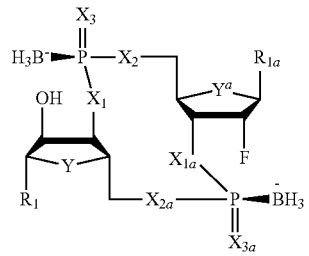

(I-A2b)
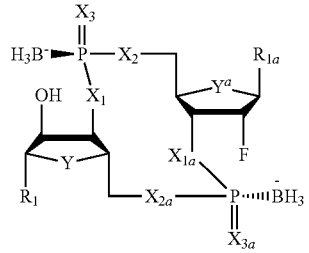

(I-A2c)
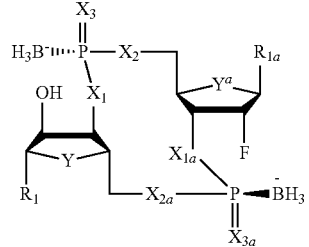

(I-A2d)
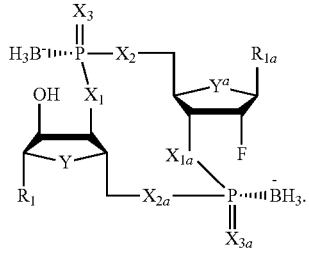

18. The compound, the optical isomer thereof or the pharmaceutically acceptable salt thereof as defined in claim 1, wherein, each of $R_1$ and $R_{1a}$ is independently selected from

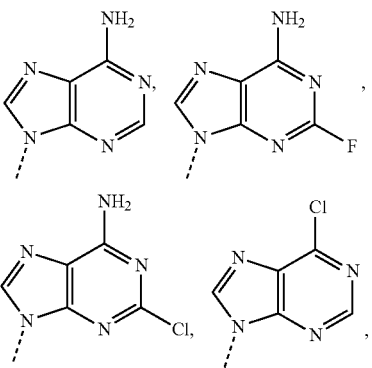

203
-continued
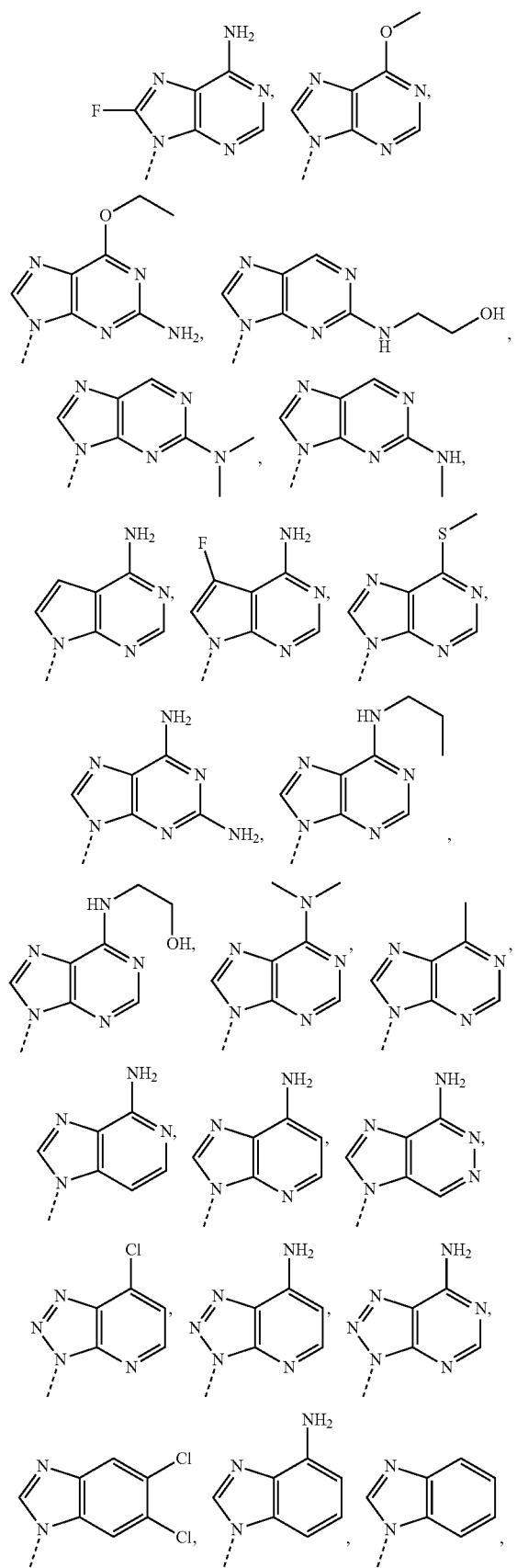
204
-continued
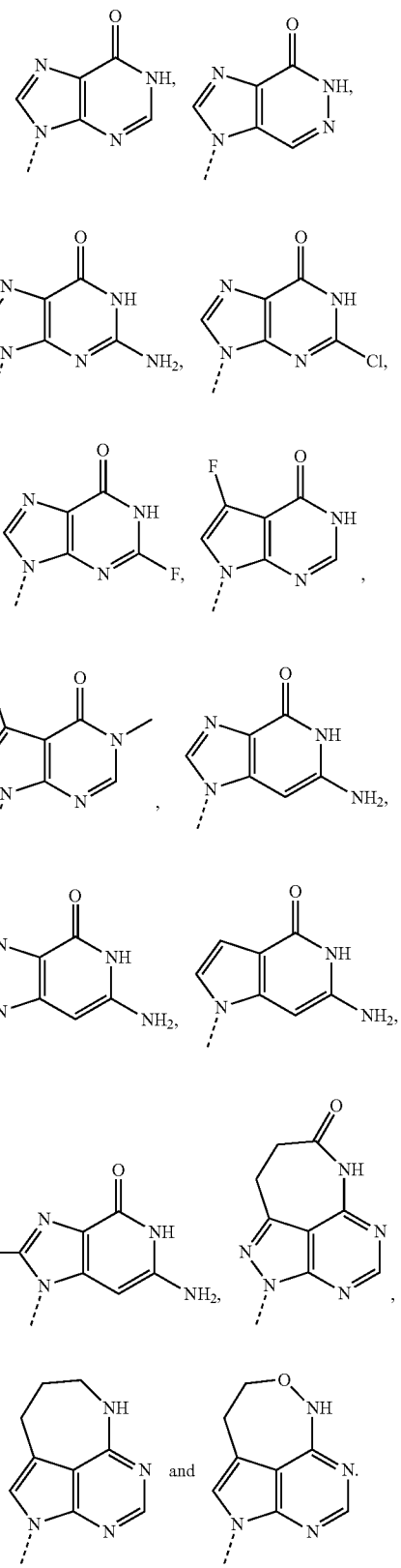
19. A compound, an optical isomer thereof or a pharmaceutically acceptable salt thereof, wherein the compound is selected from 205
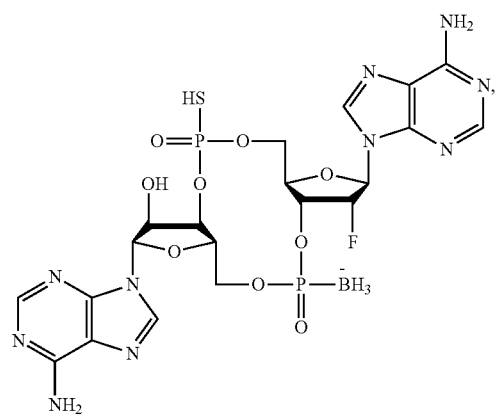
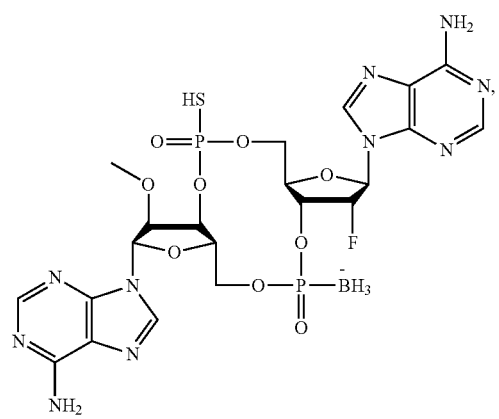
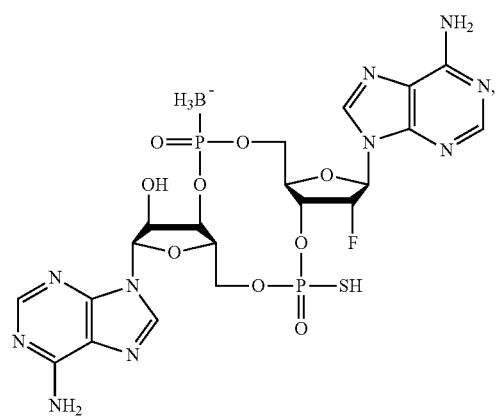
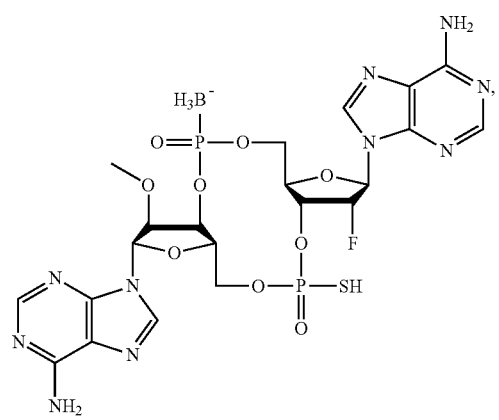
206
-continued
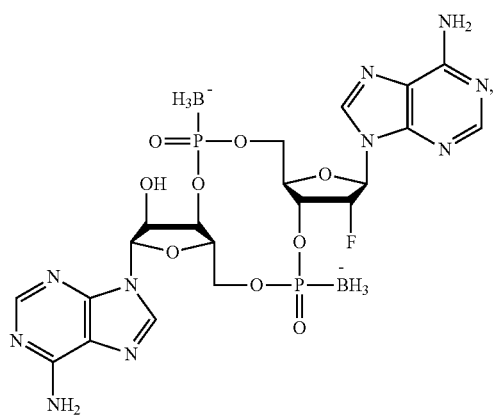
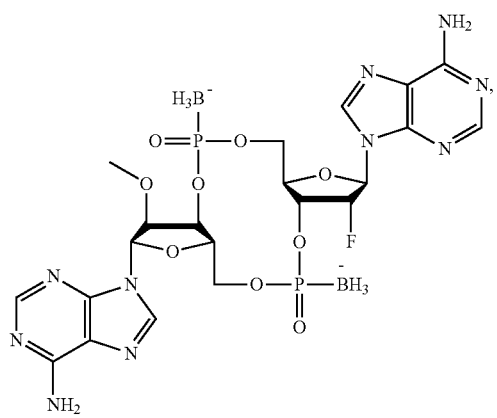
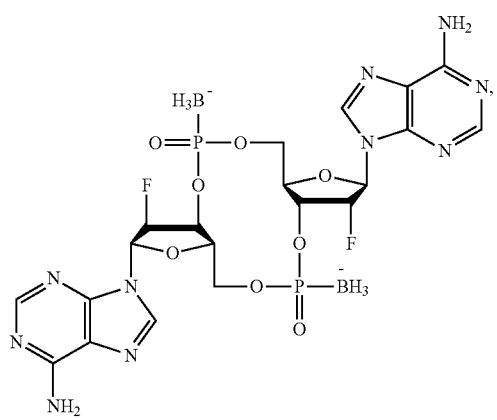
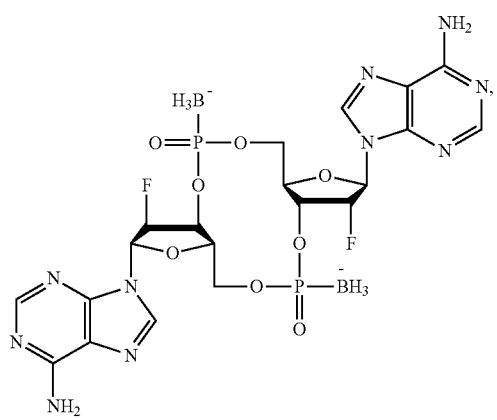

207
-continued
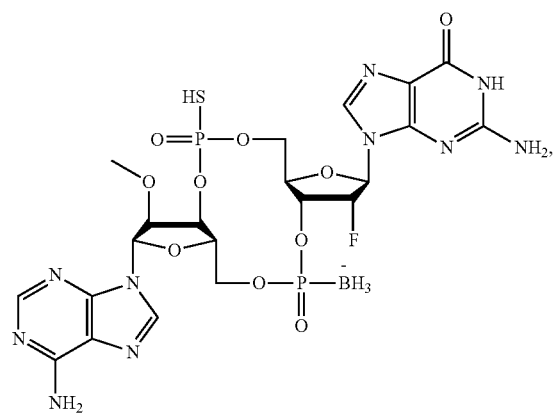
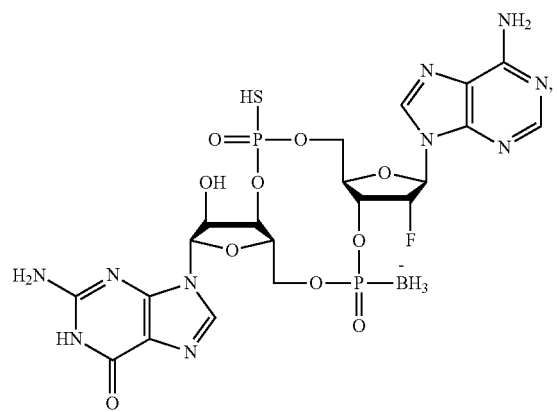
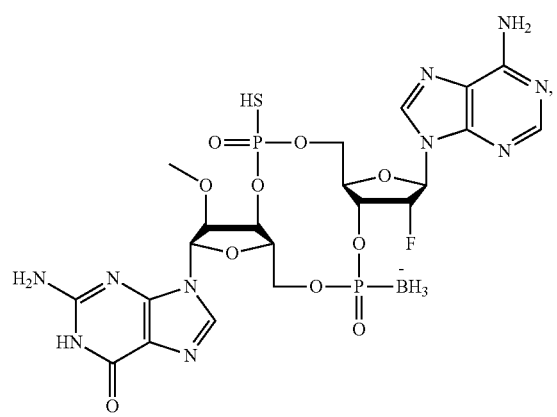
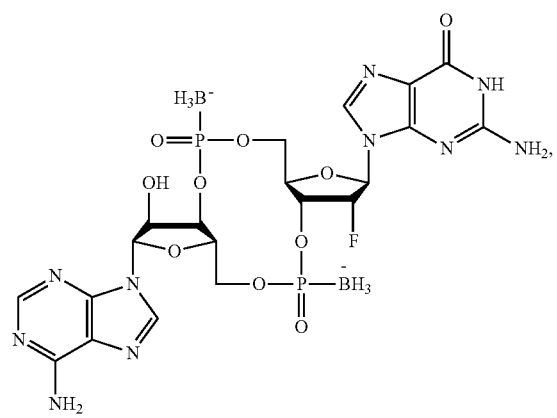
208
-continued
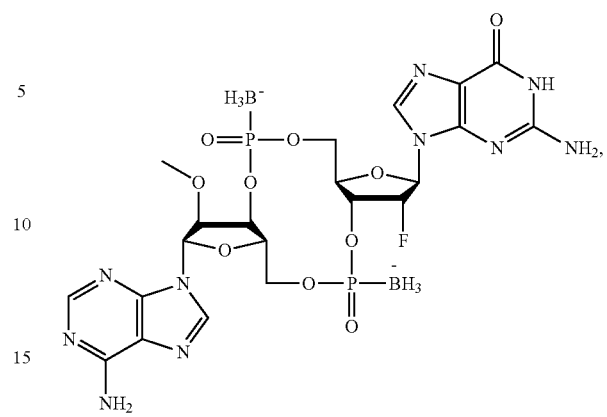
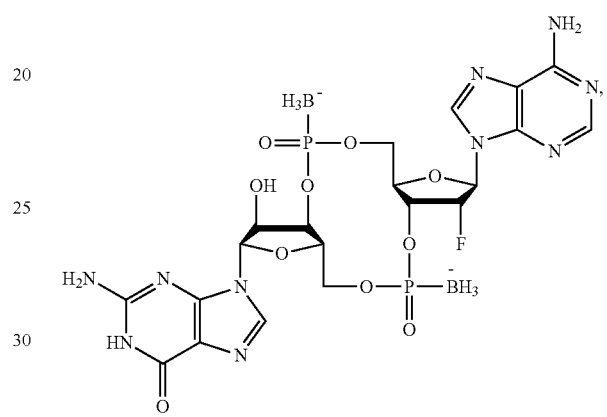
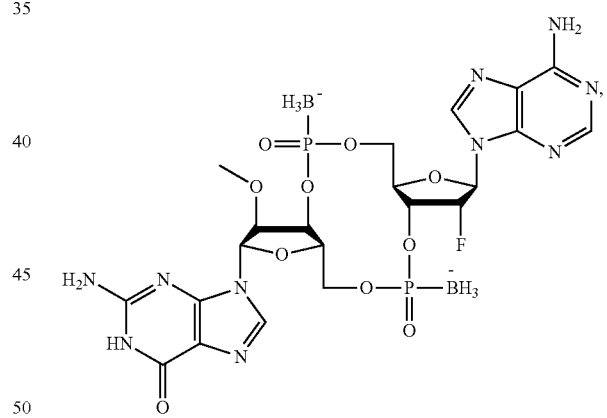
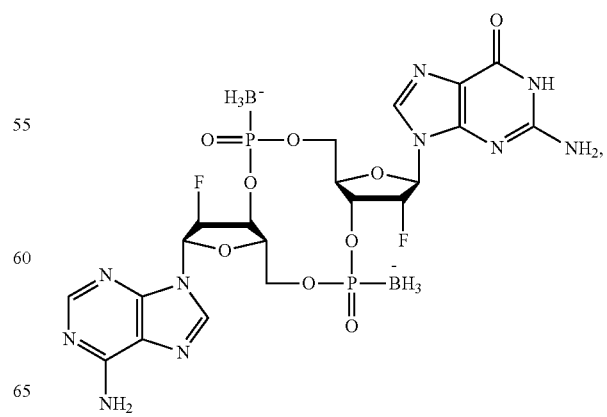

209
-continued
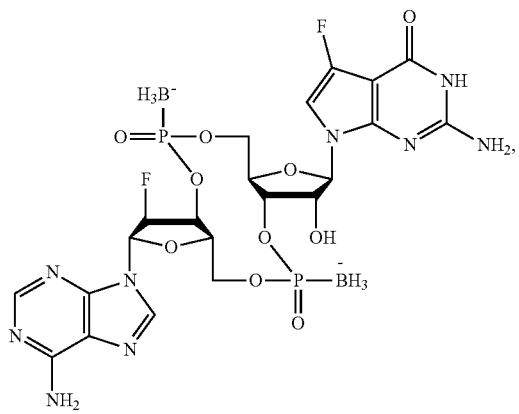
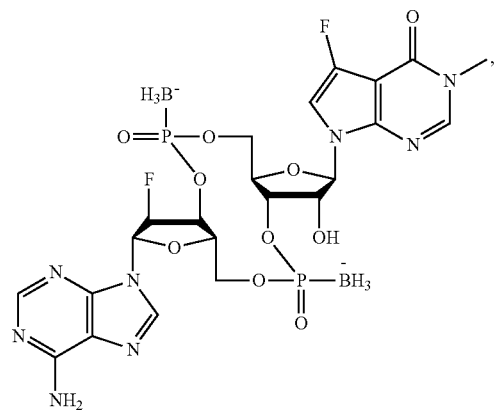
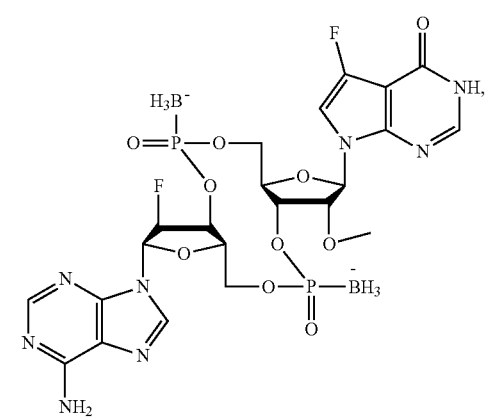
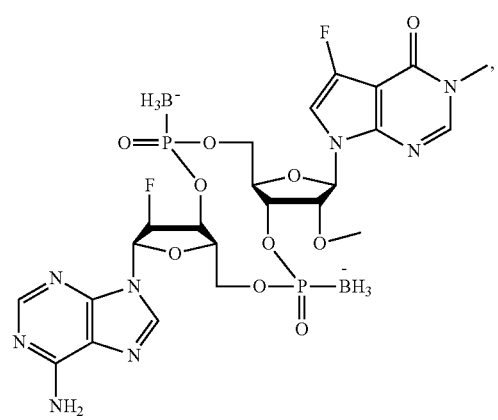
210
-continued
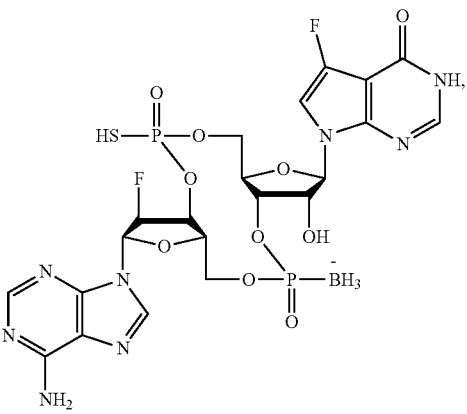
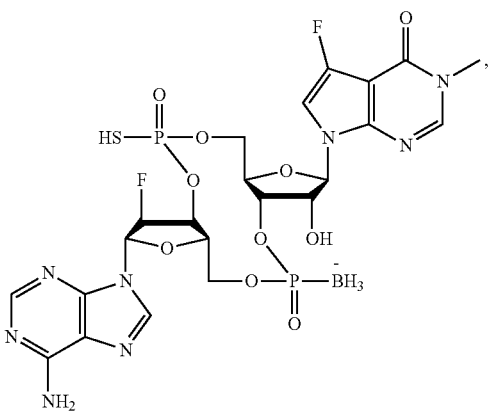
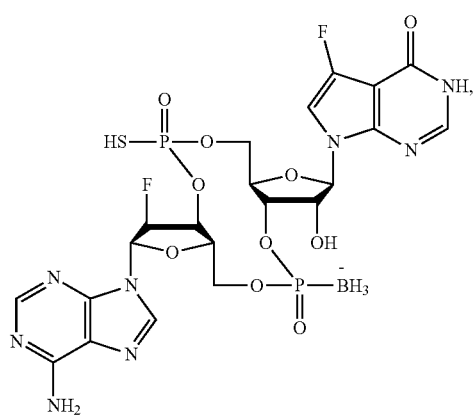
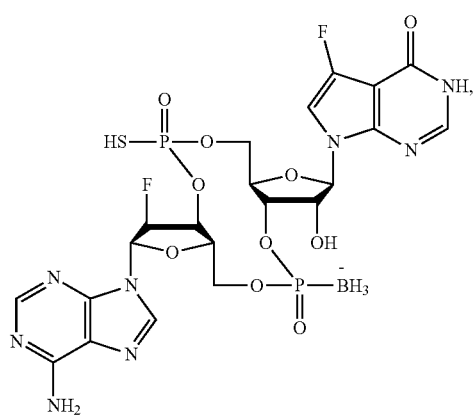

211
-continued
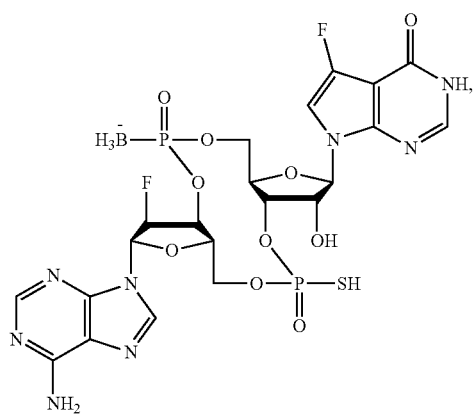
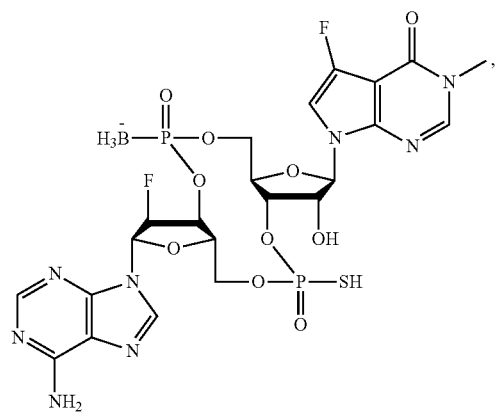
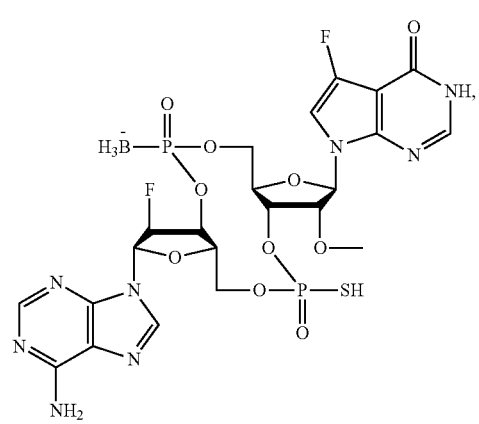
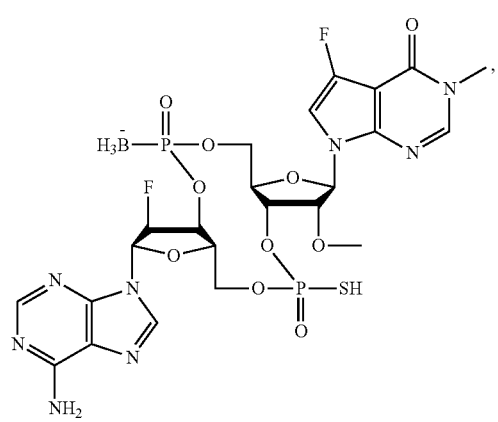
212
-continued
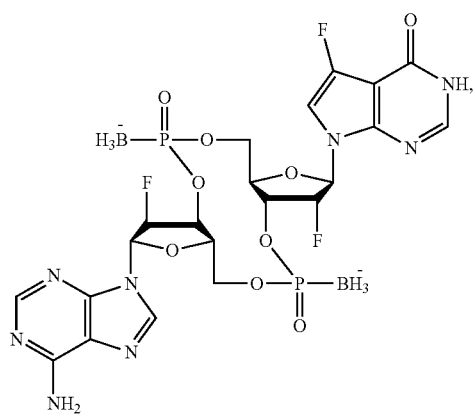
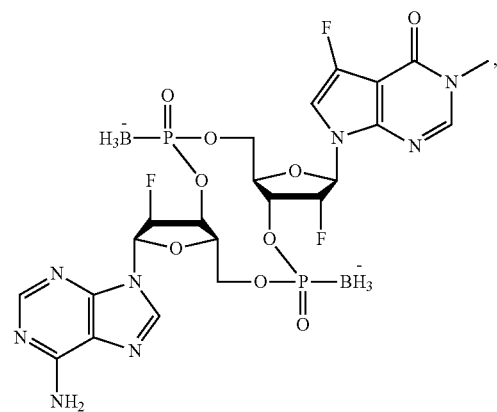
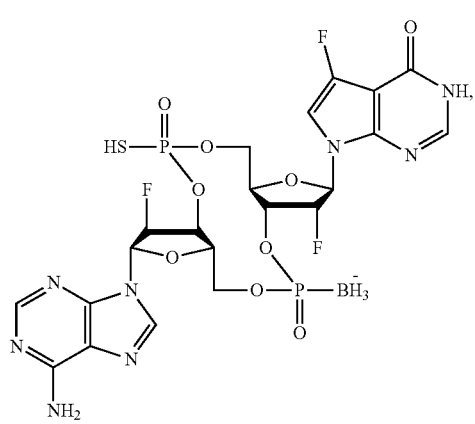
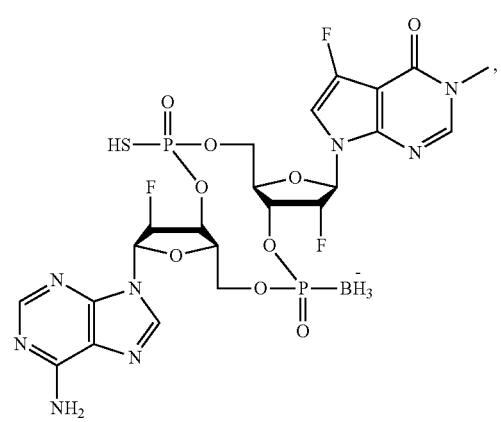

213
-continued
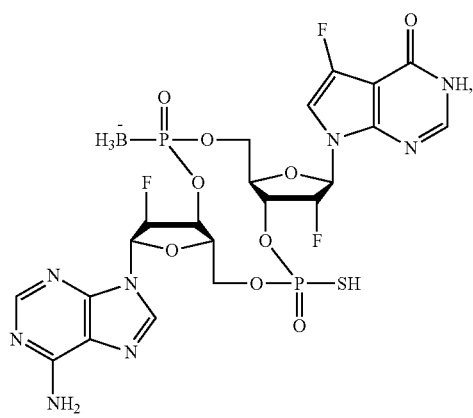
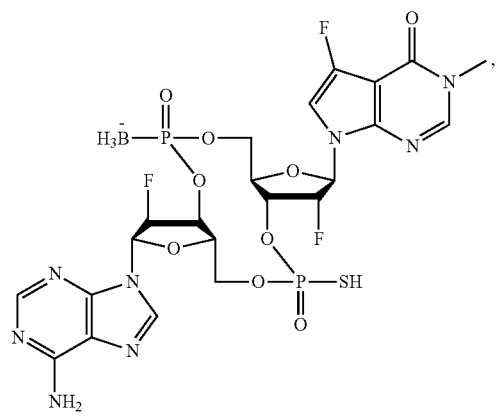
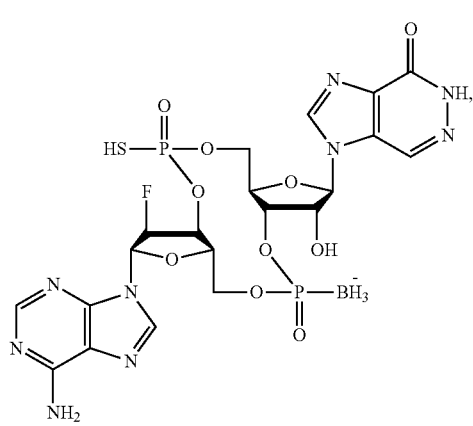
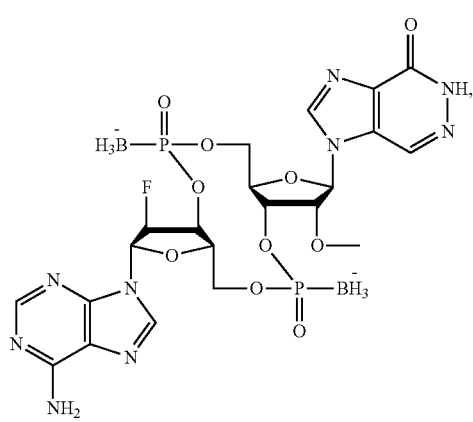
214
-continued
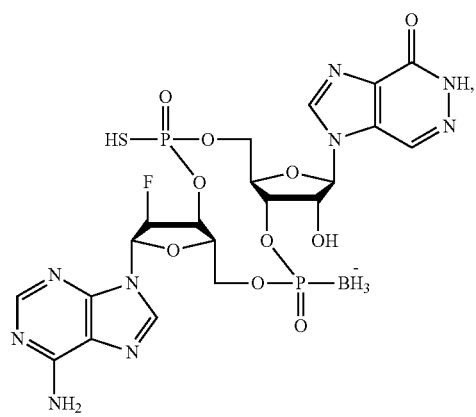
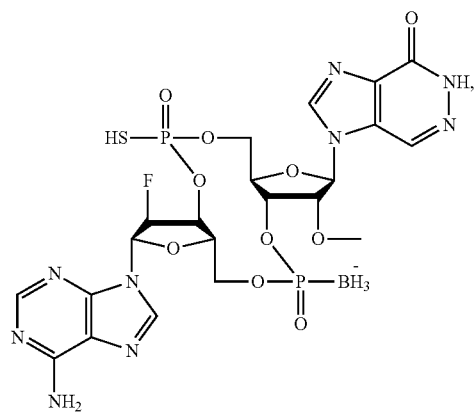
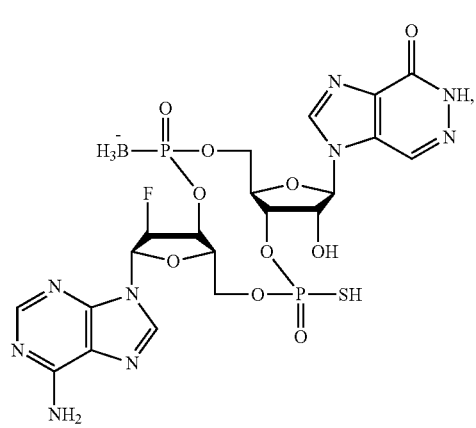
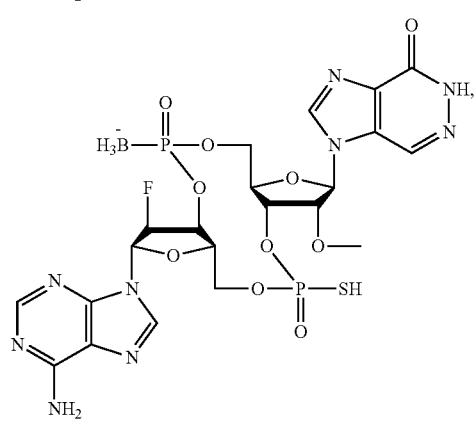

215
-continued
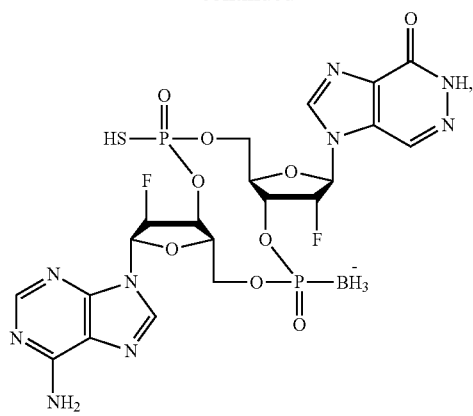
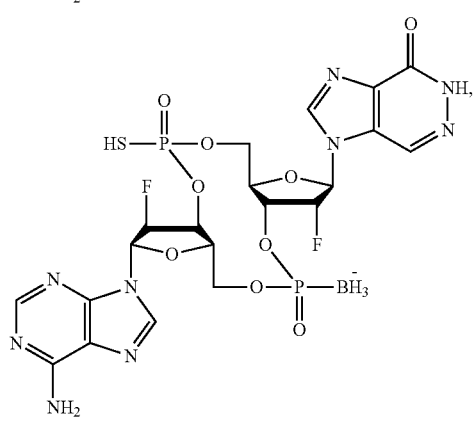
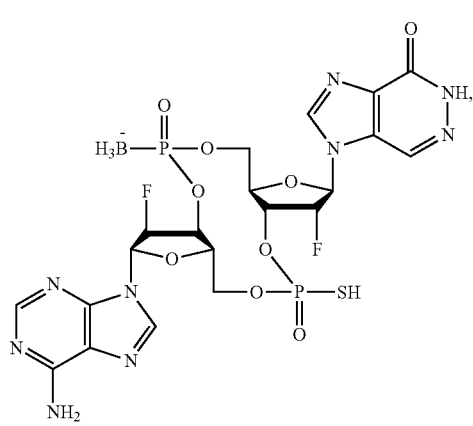
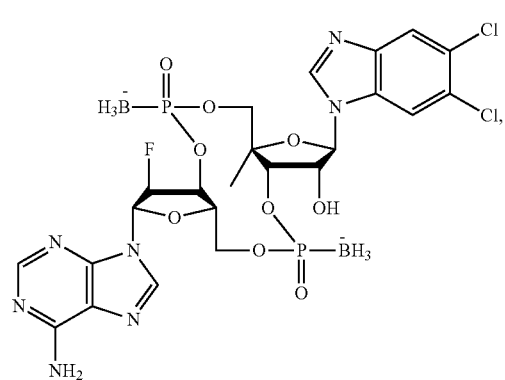
216
-continued
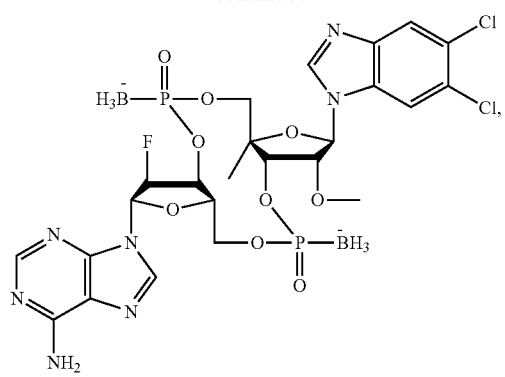
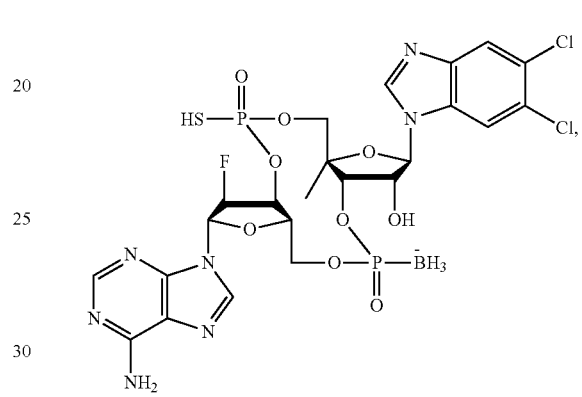
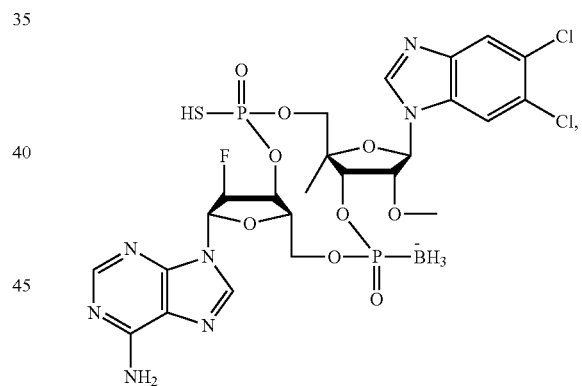
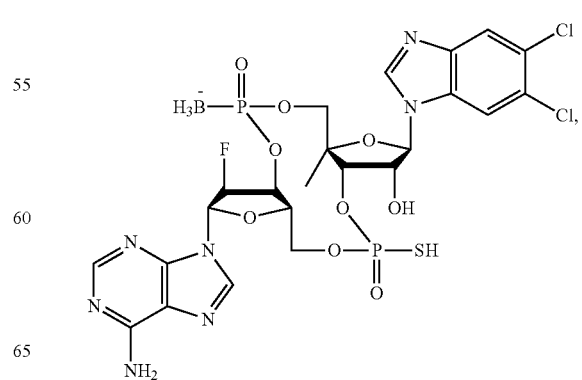

-continued
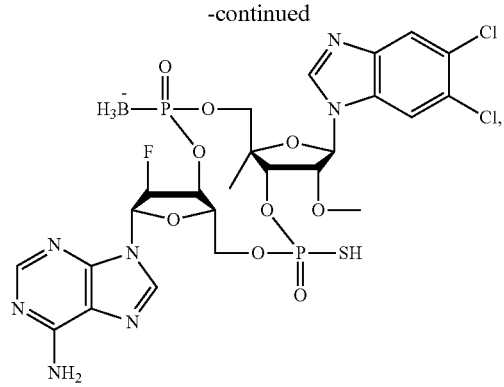
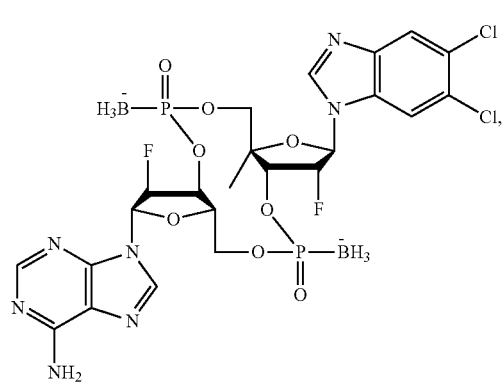
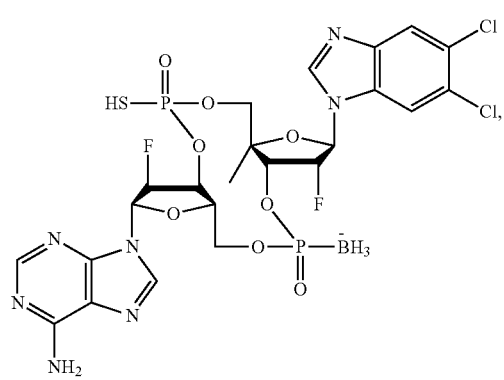
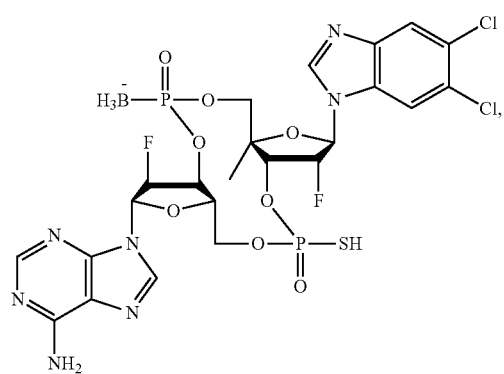
-continued
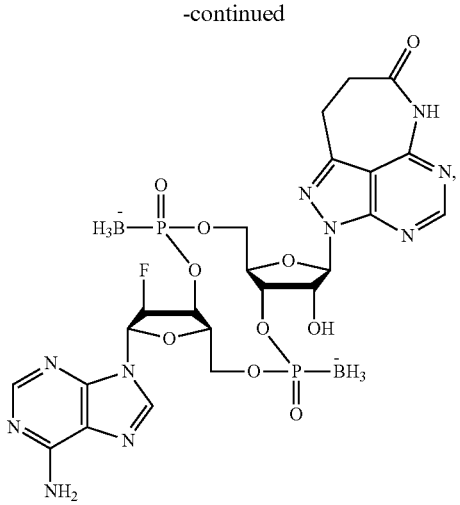
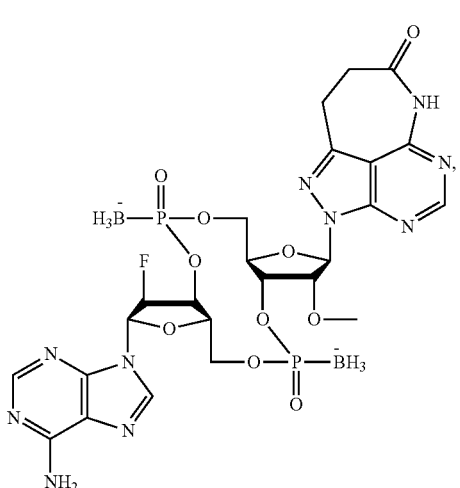
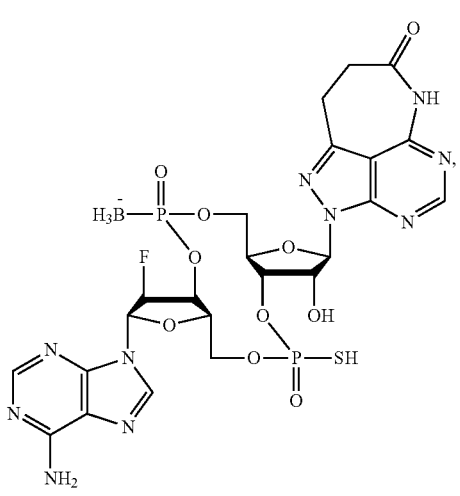

219
-continued
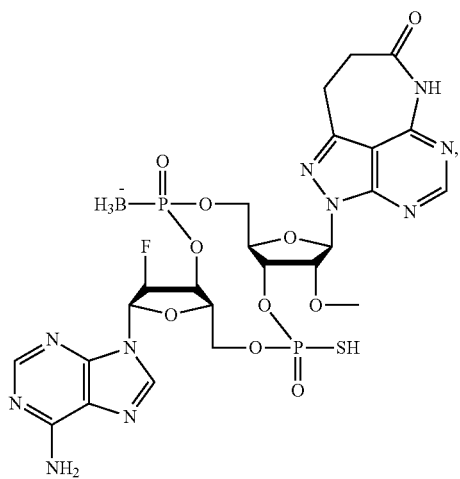
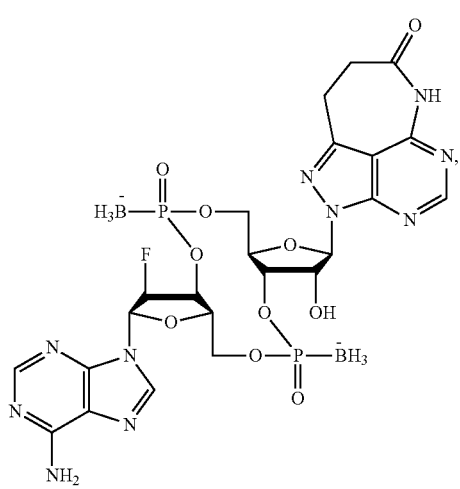
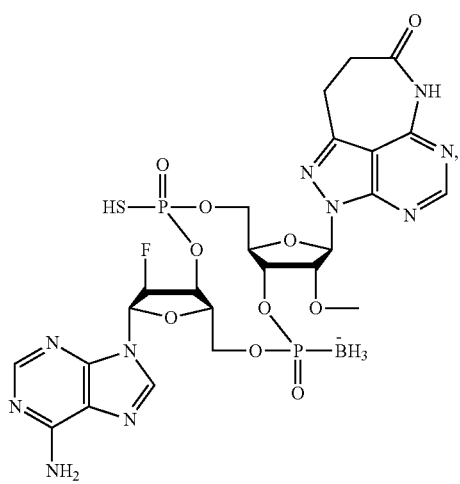
220
-continued
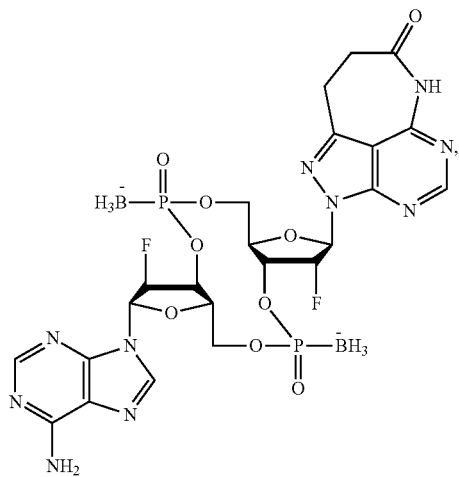
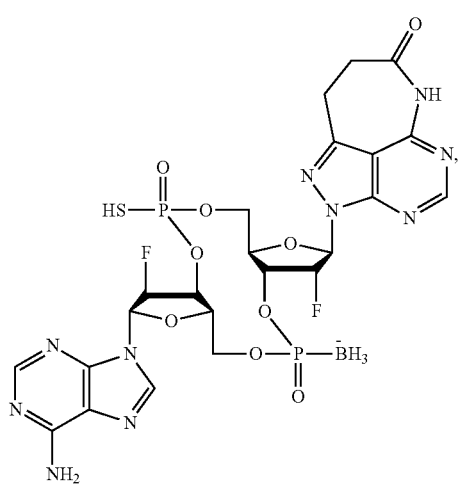
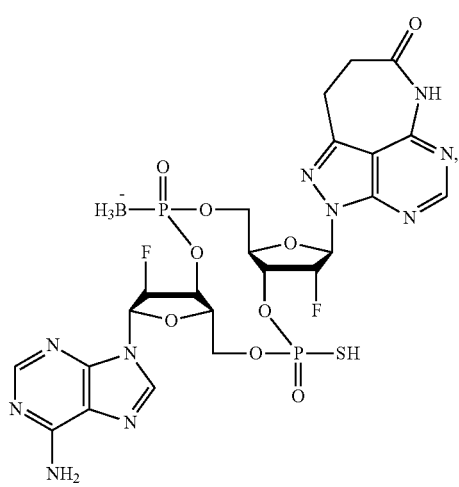

221
-continued
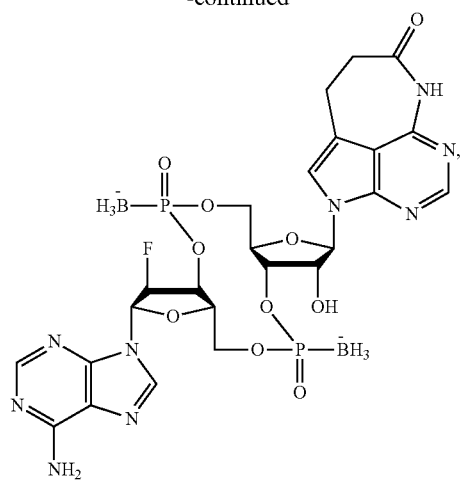
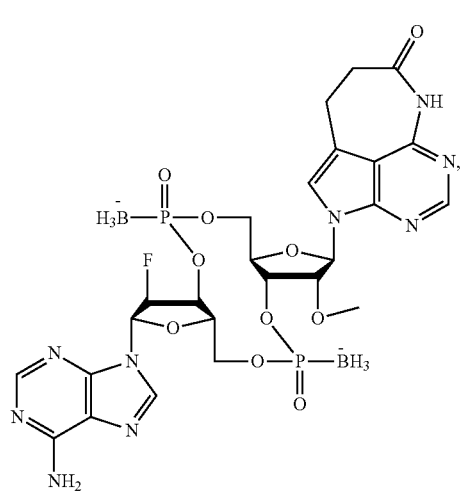
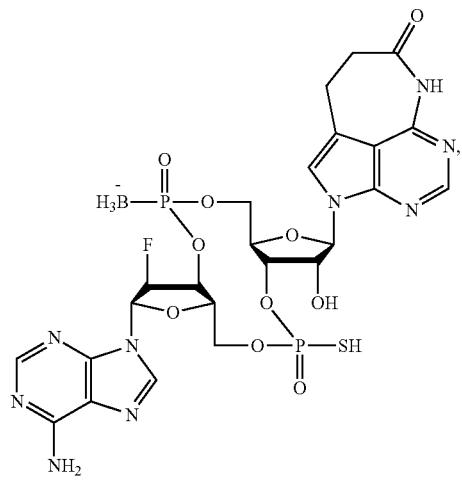
222
-continued
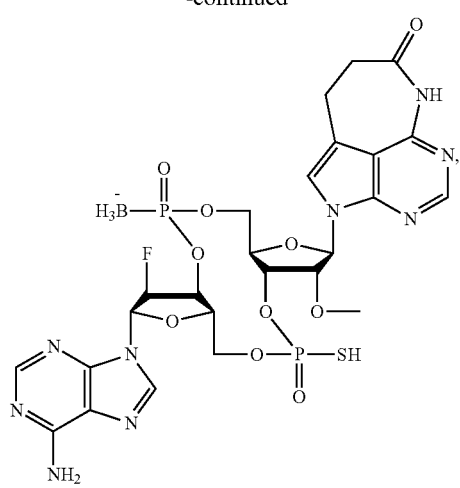
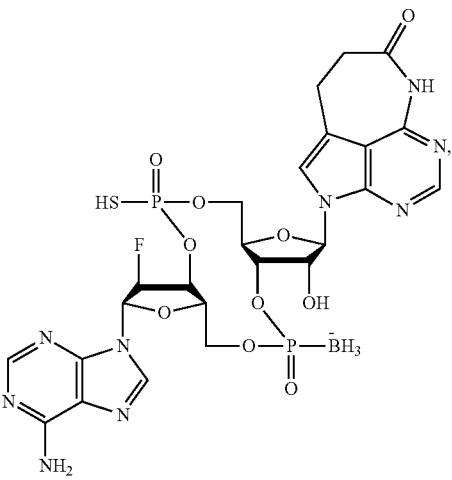
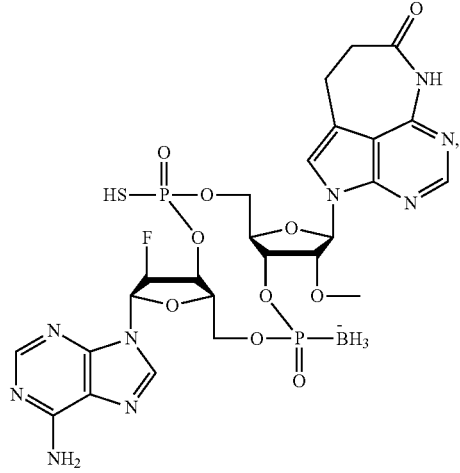

223
-continued
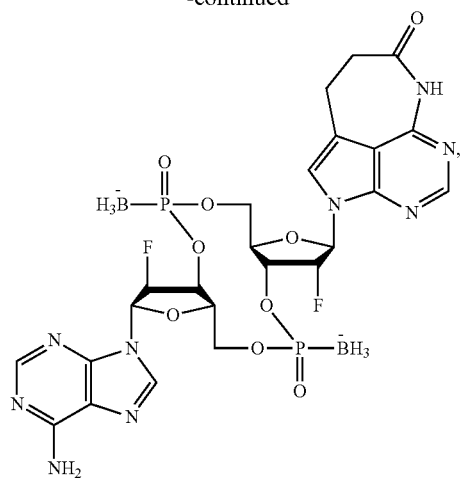
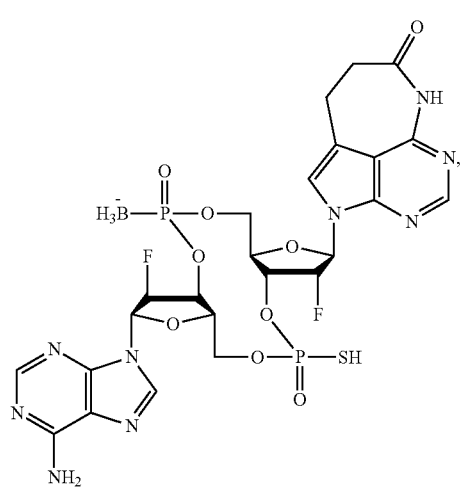
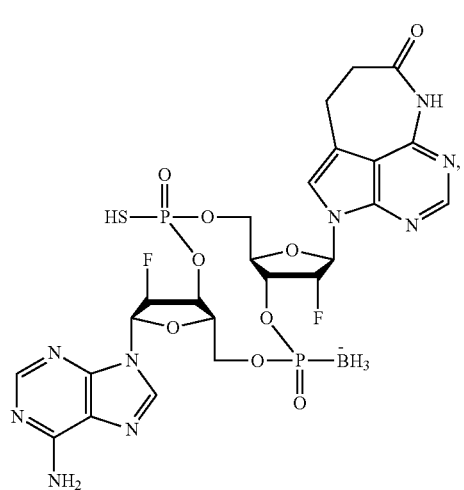
224
-continued
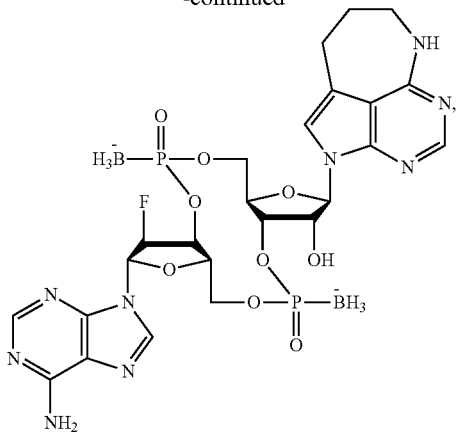
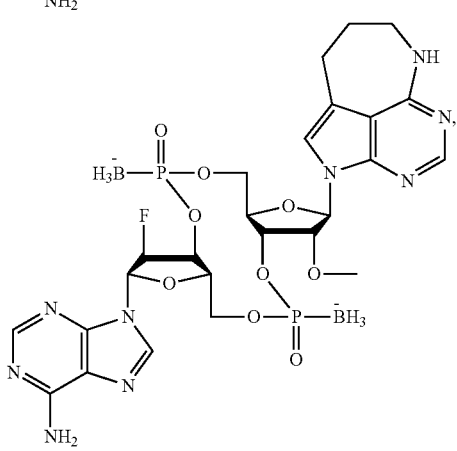
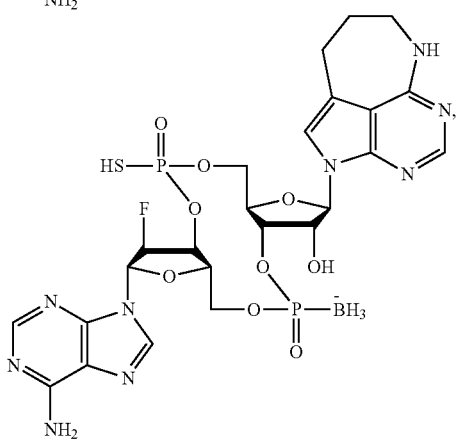
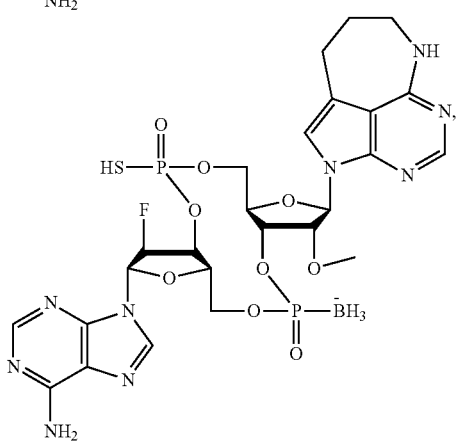

225
-continued
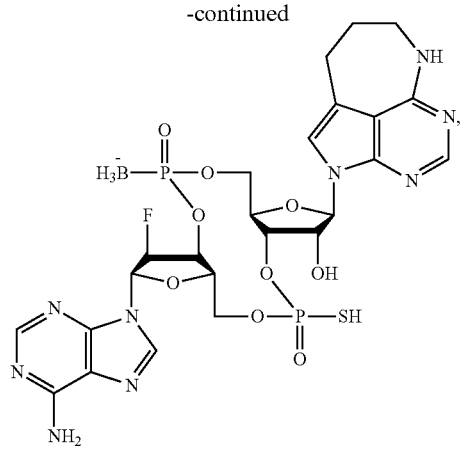
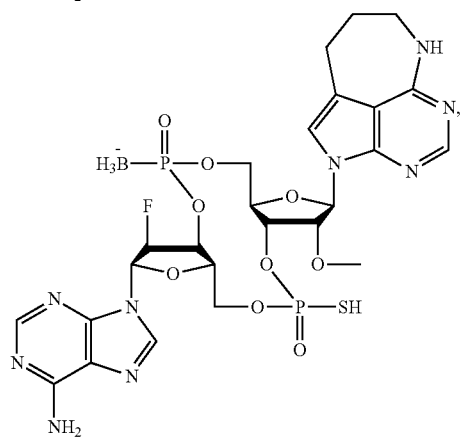
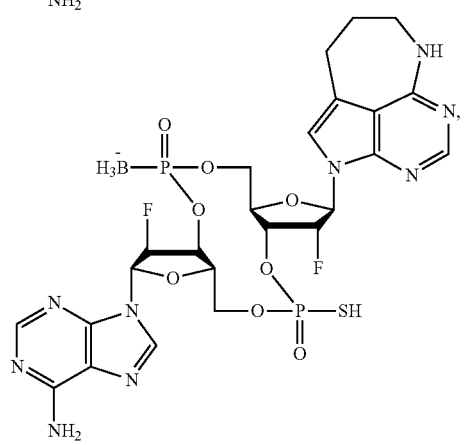
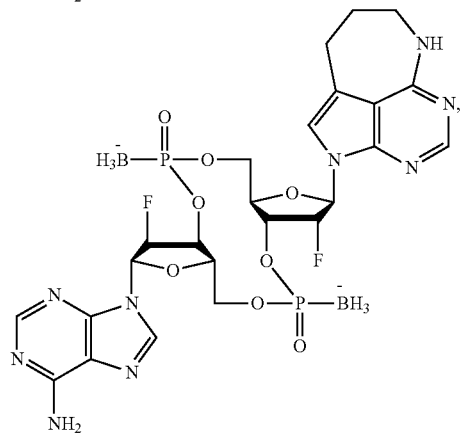
226
-continued
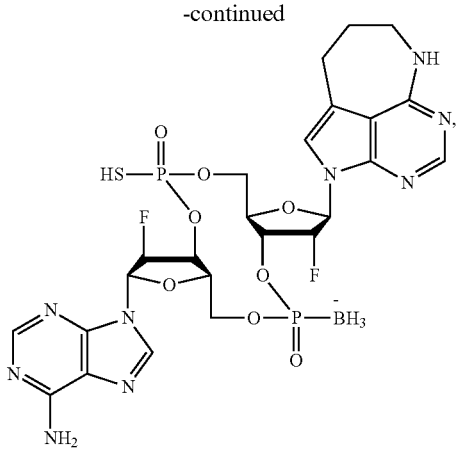
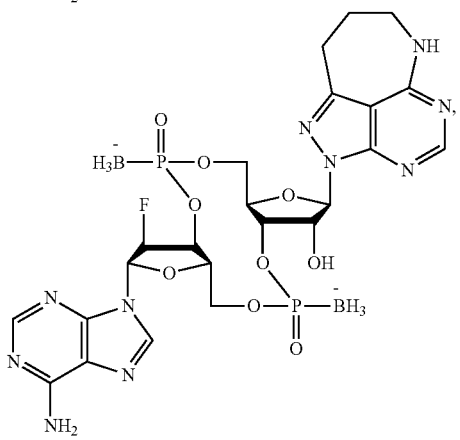
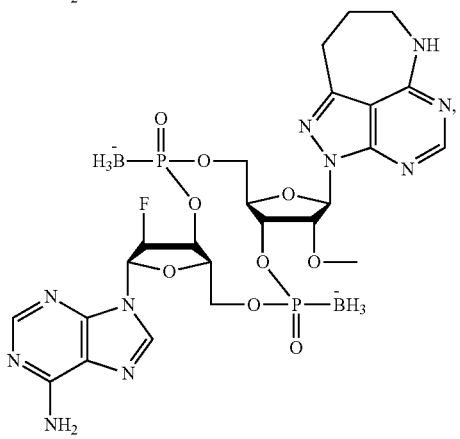
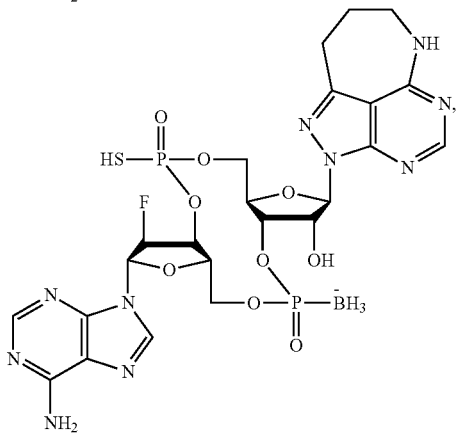

227
-continued
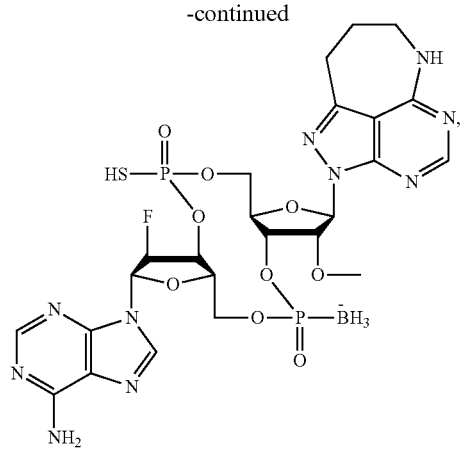
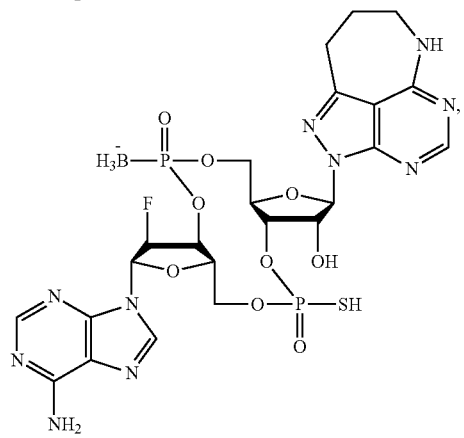
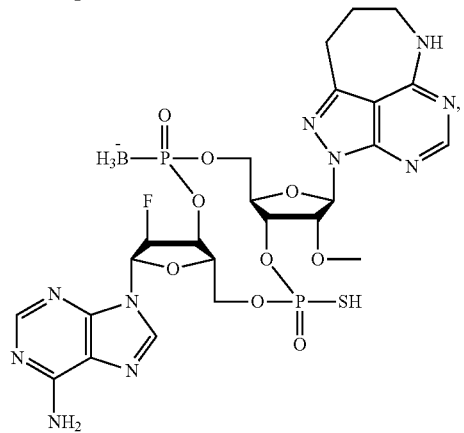
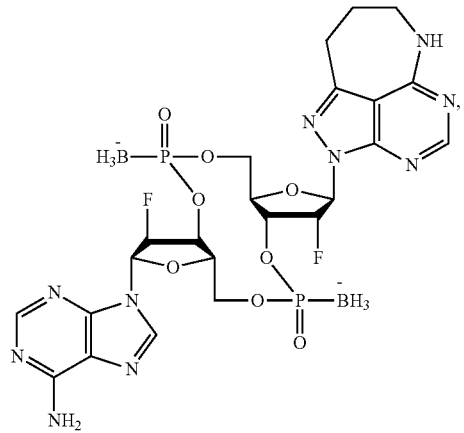
228
-continued
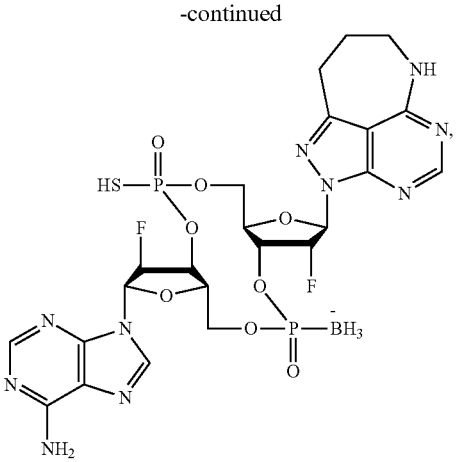
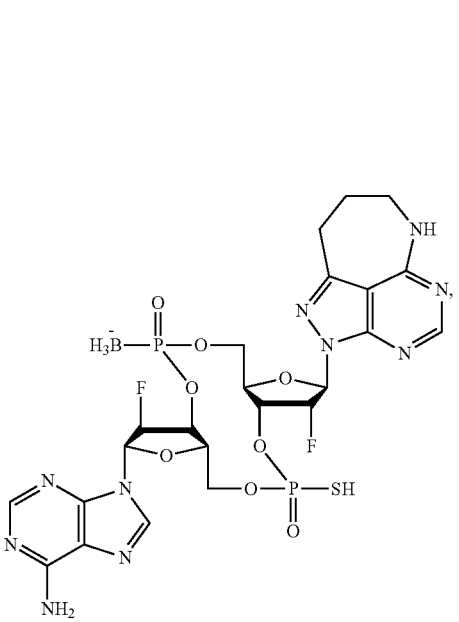
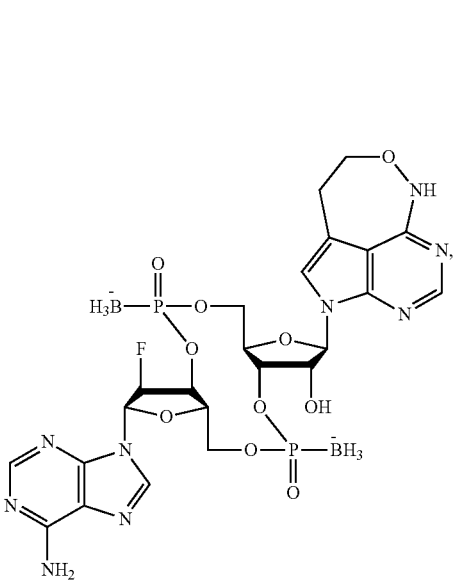

229
-continued
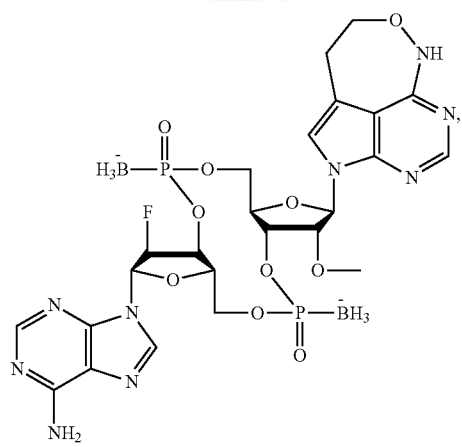
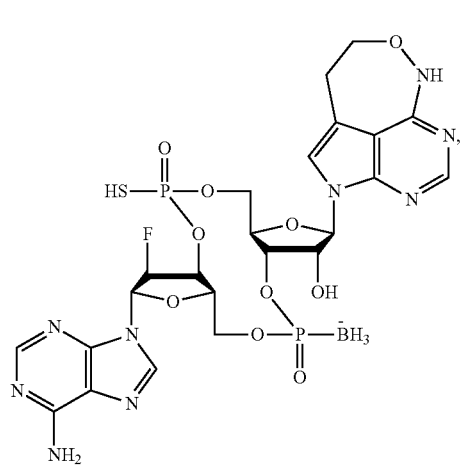
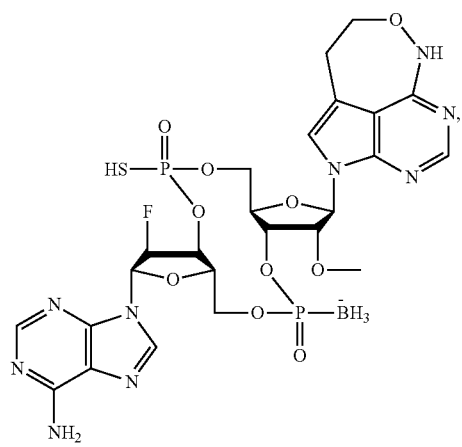
230
-continued
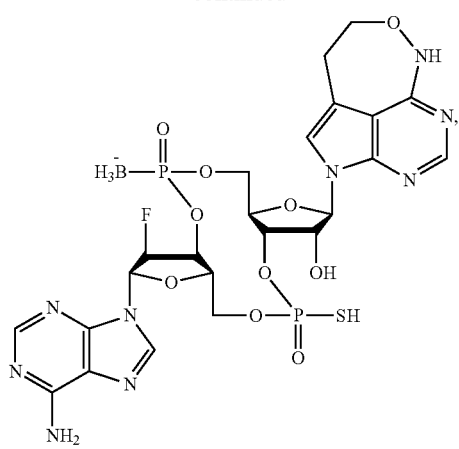
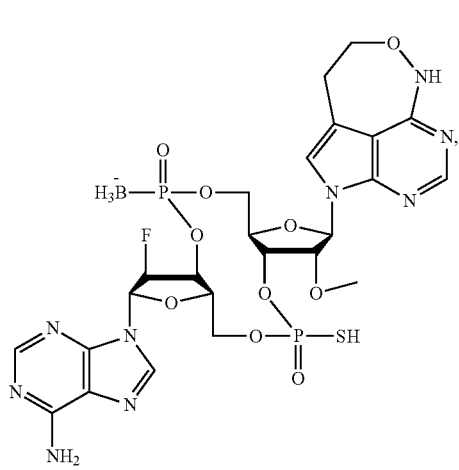
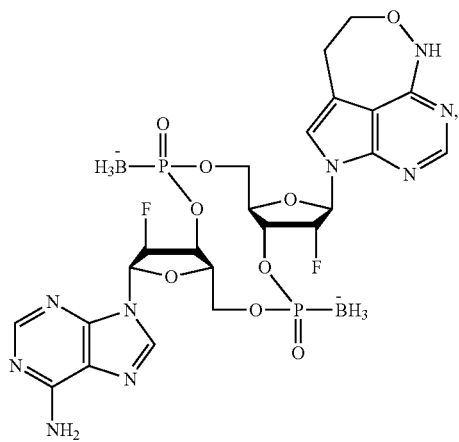

231
-continued
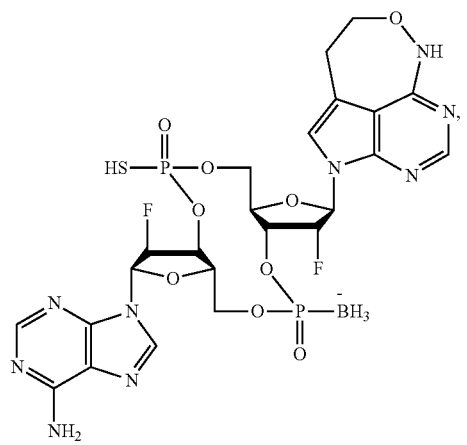
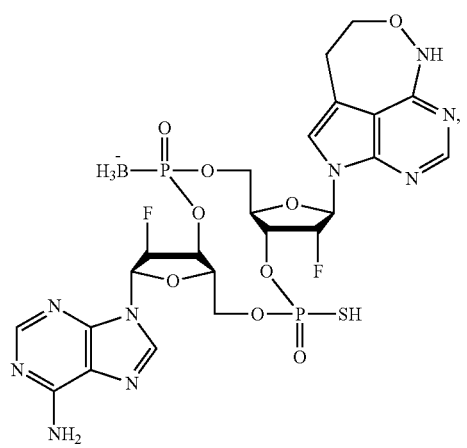
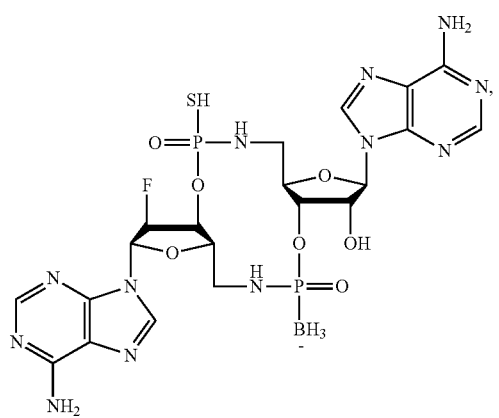
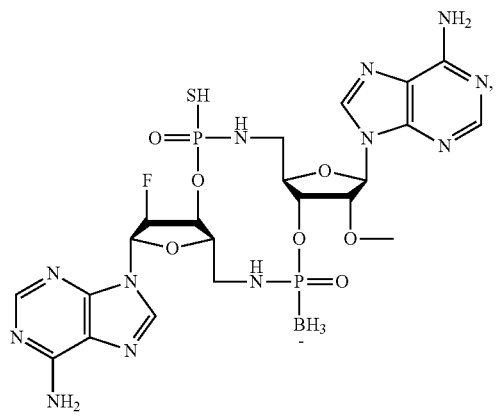
232
-continued
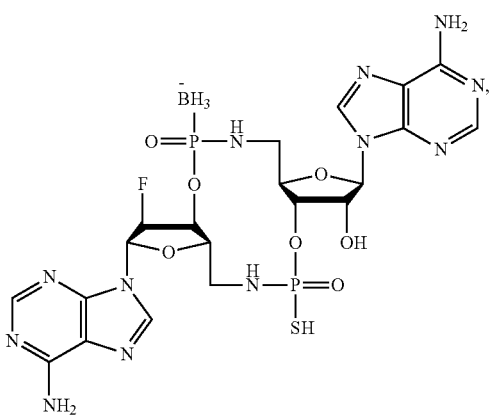
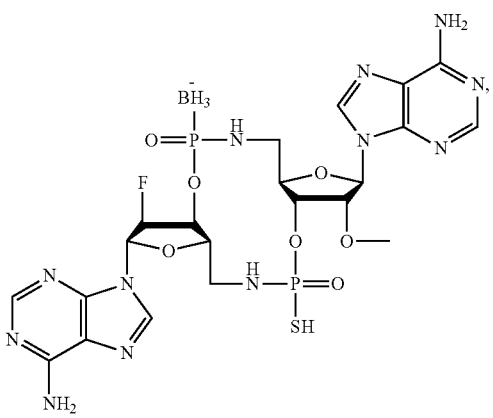
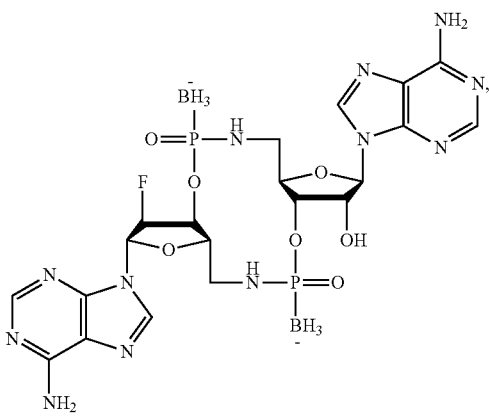
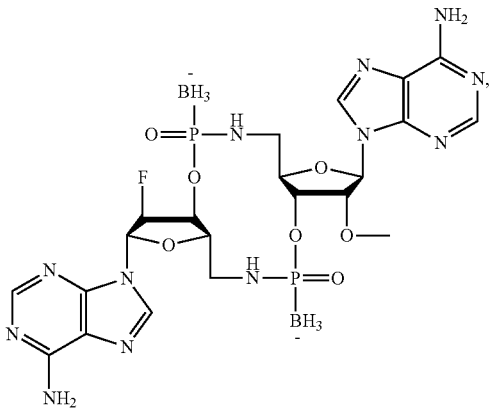

233
-continued
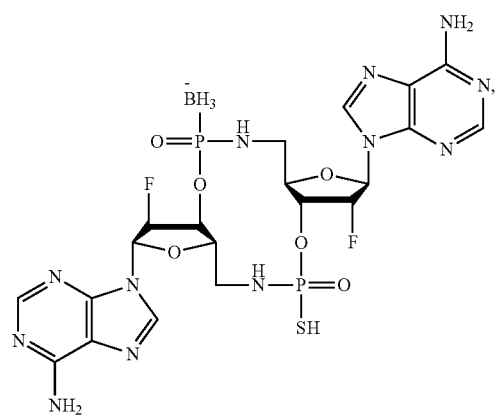
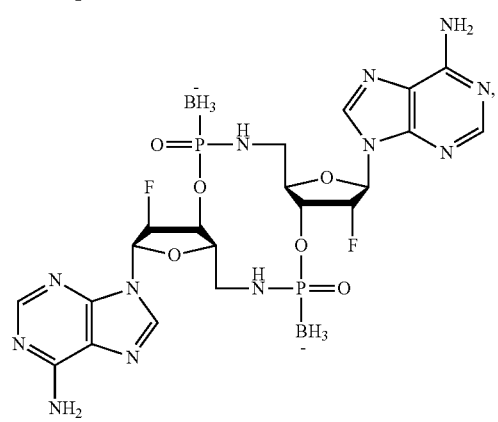
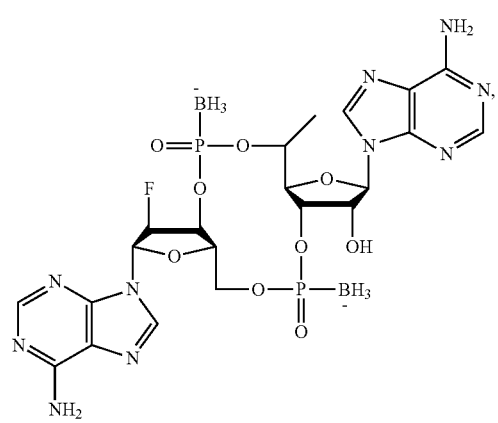
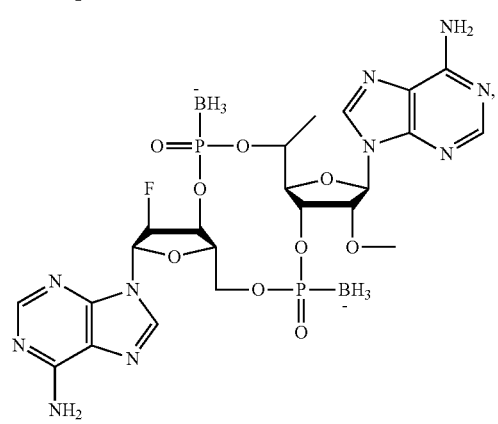
234
-continued
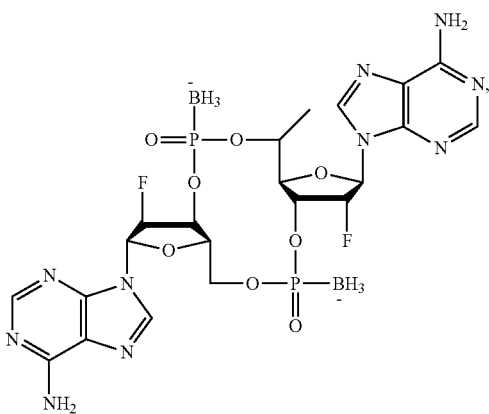
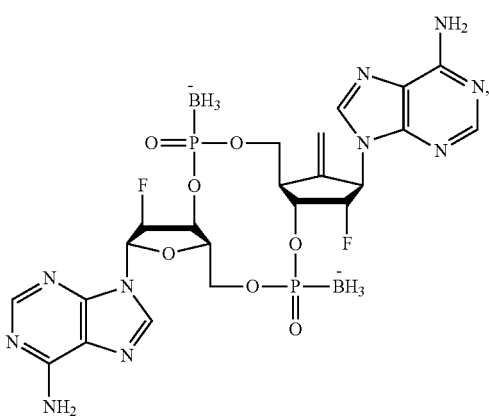
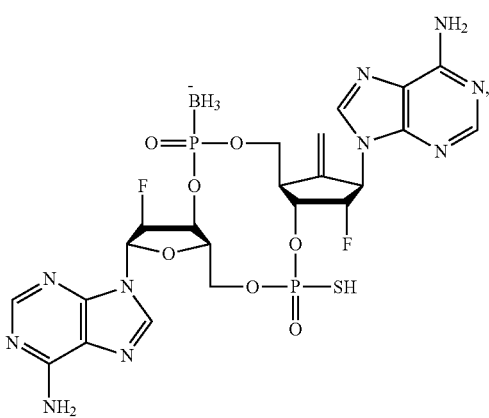
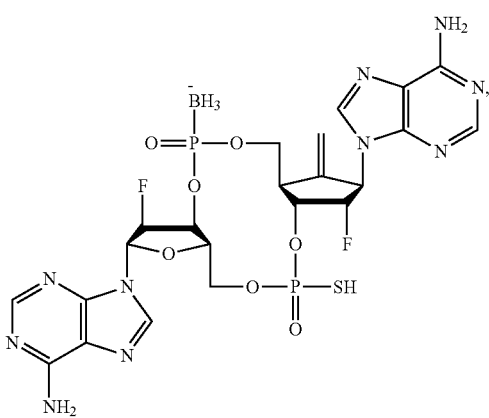

235
-continued
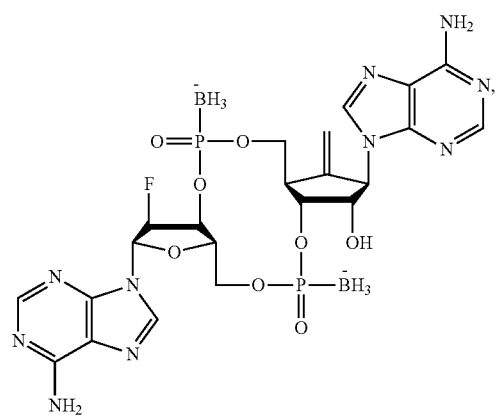
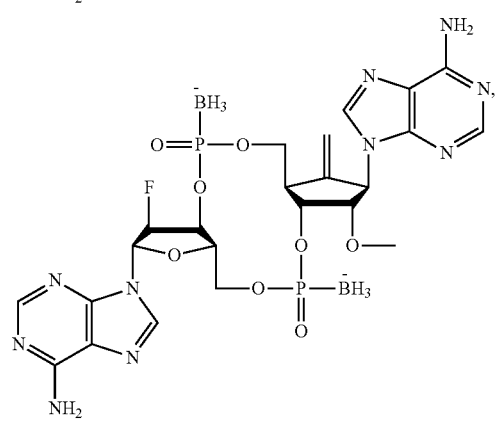
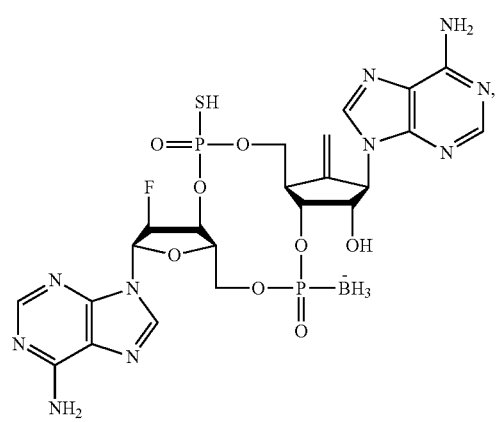
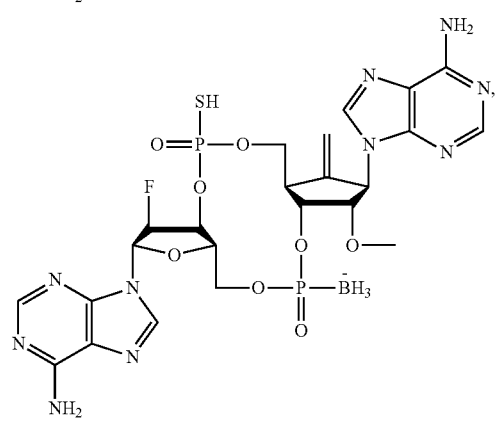
236
-continued
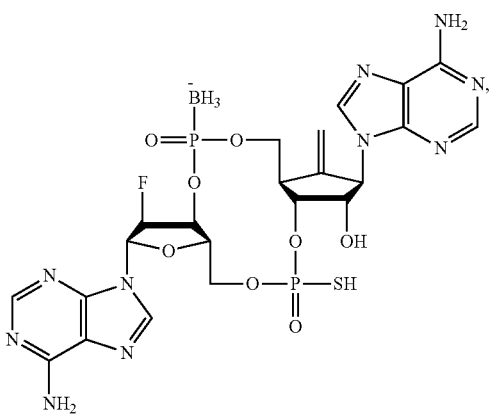
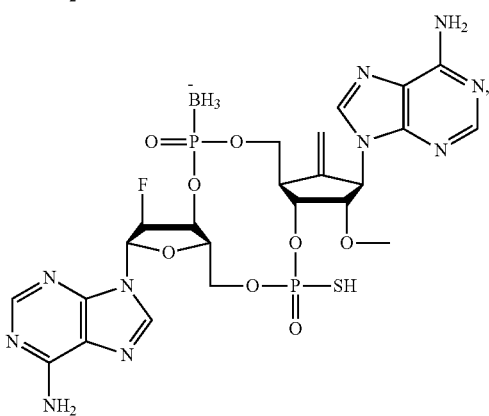
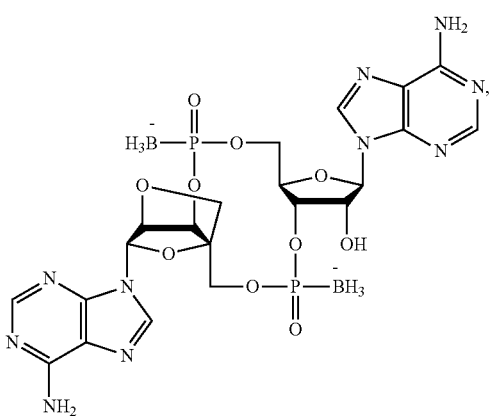
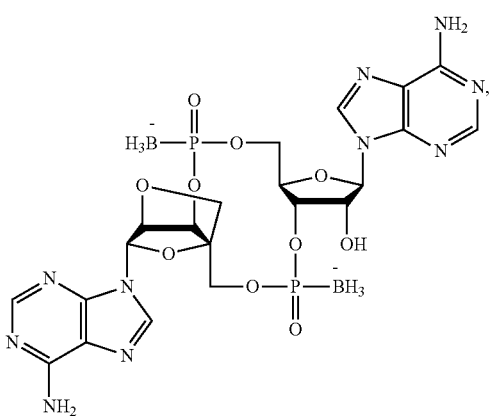

237
-continued
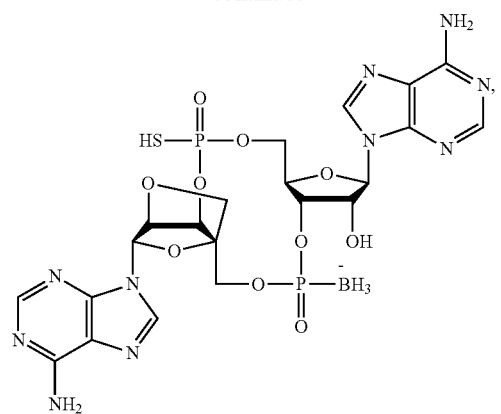
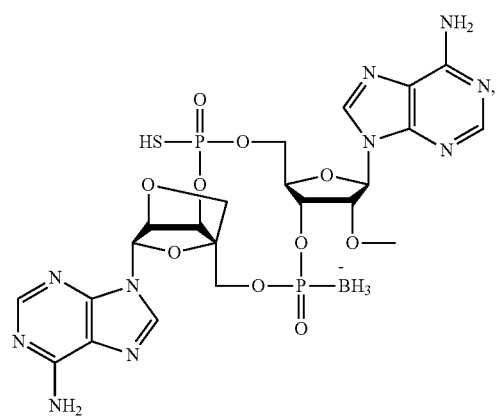
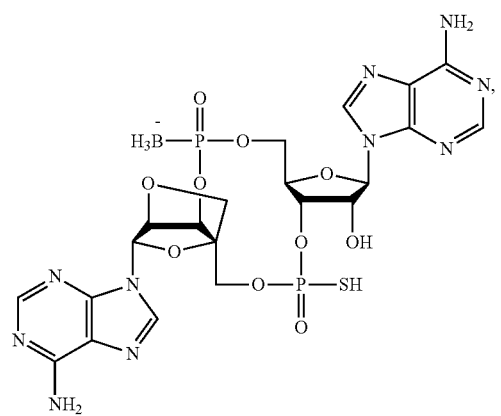
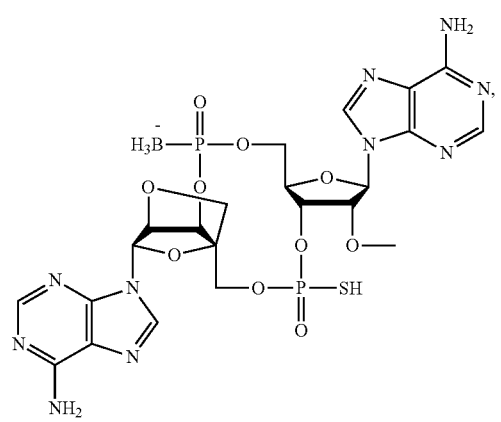
238
-continued
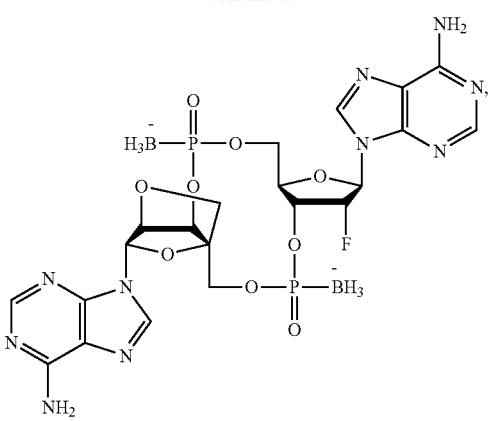
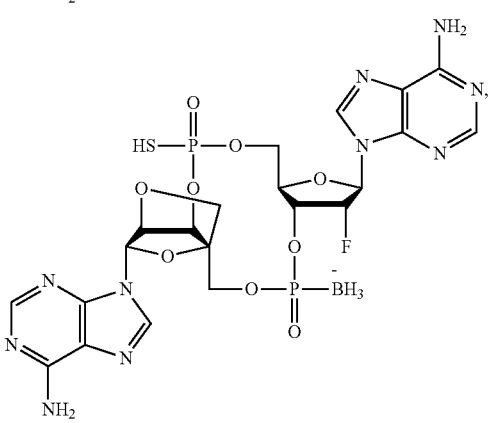
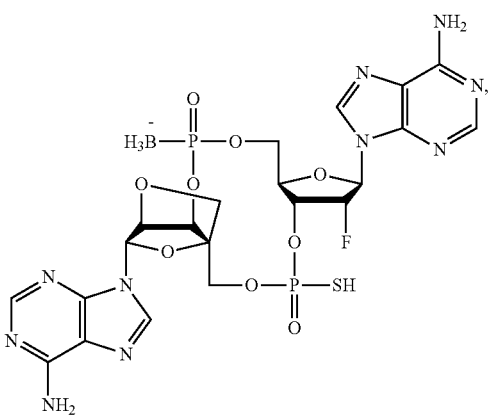
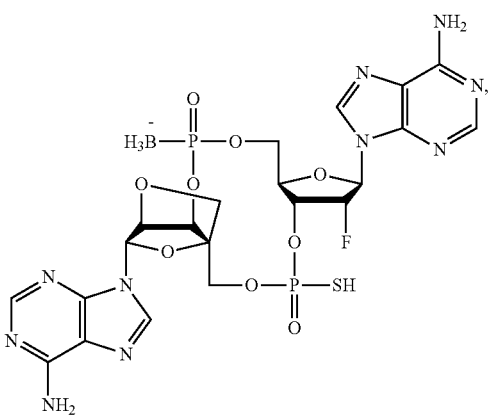

239
-continued
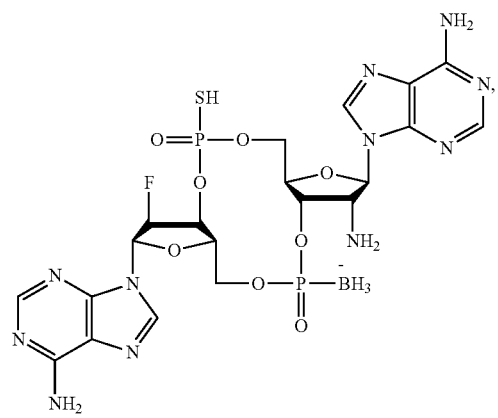
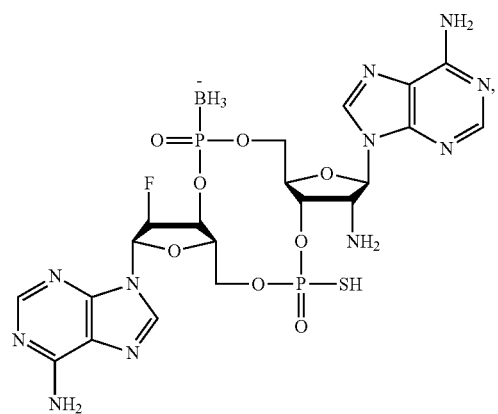
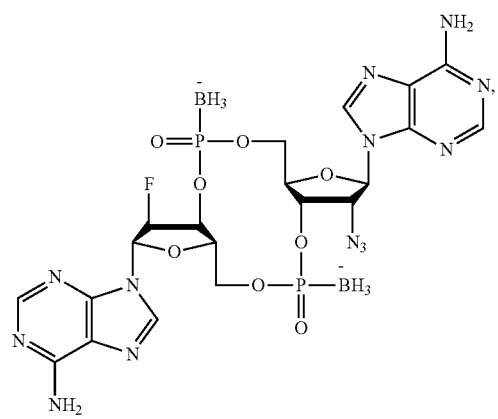
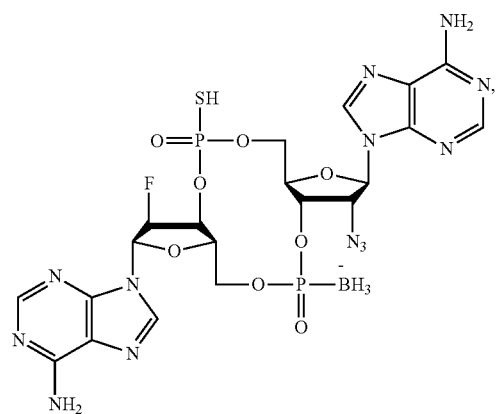
240
-continued
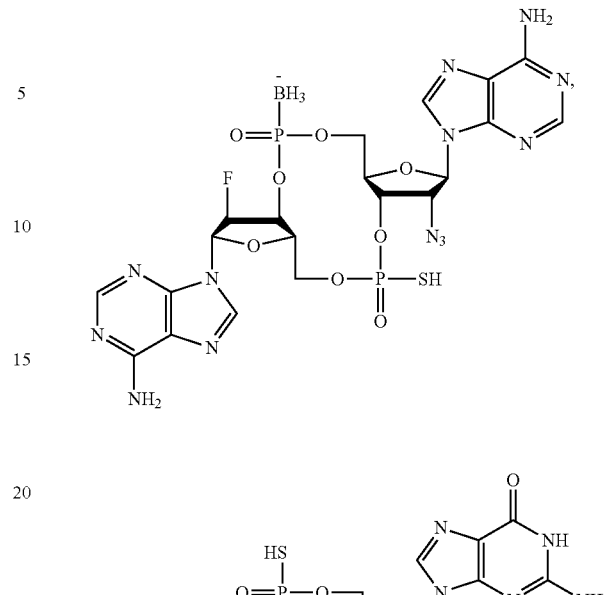
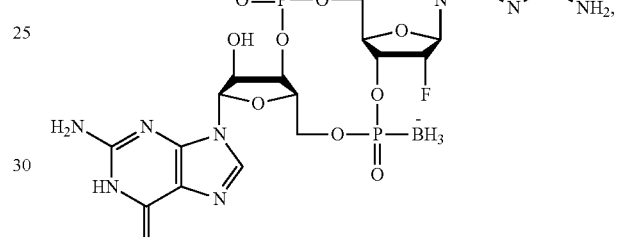
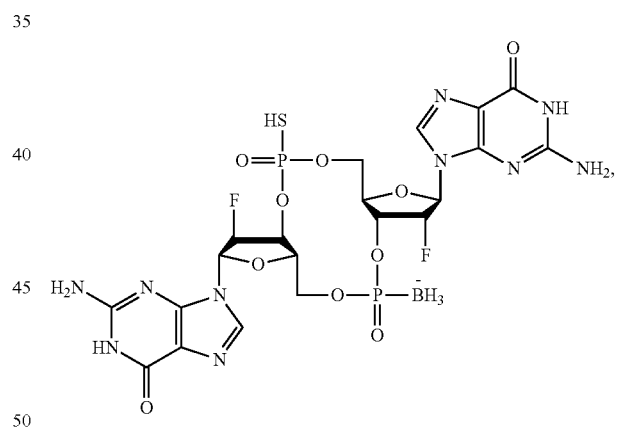
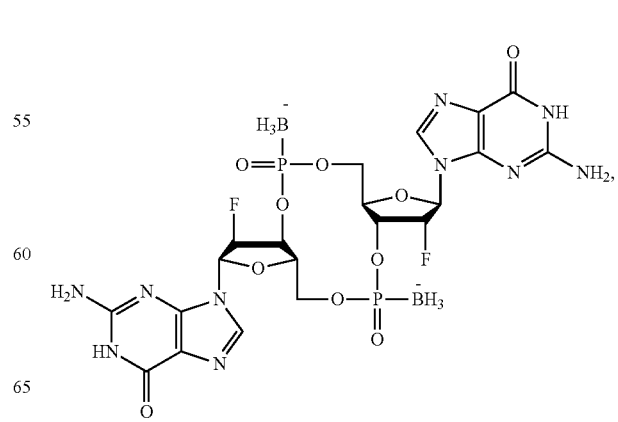

-continued
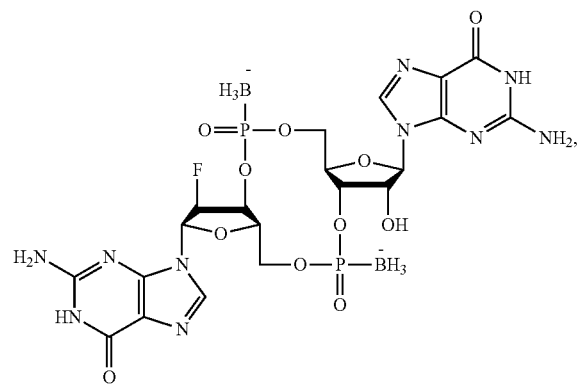
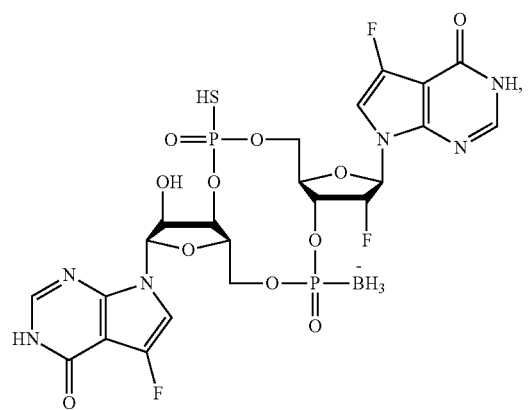
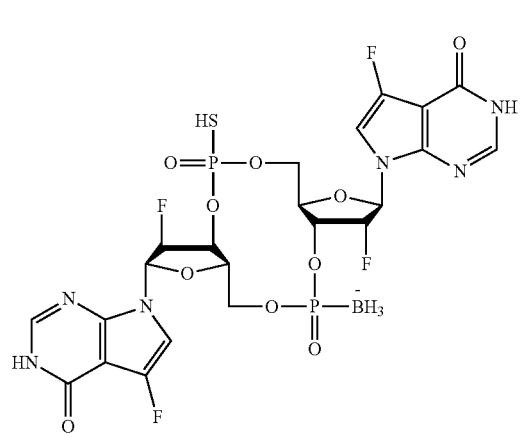
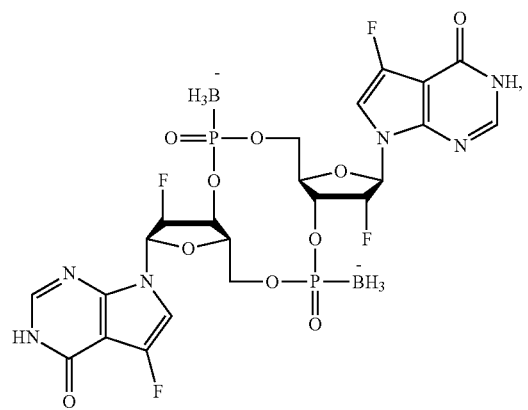
-continued
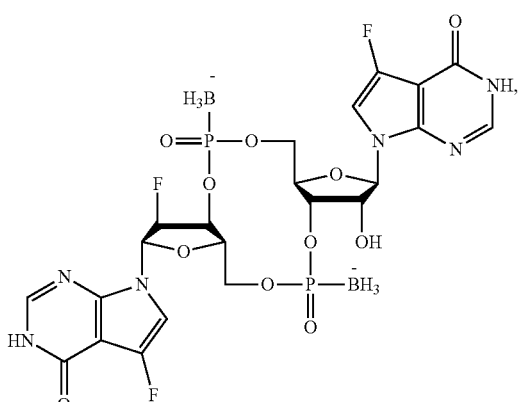
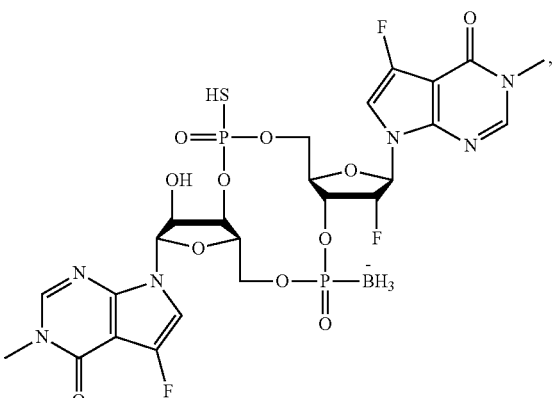
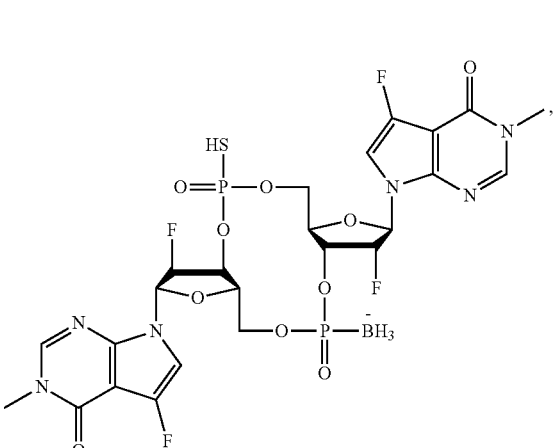
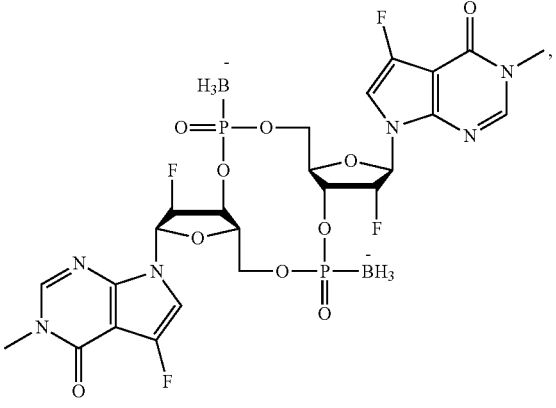

243
-continued
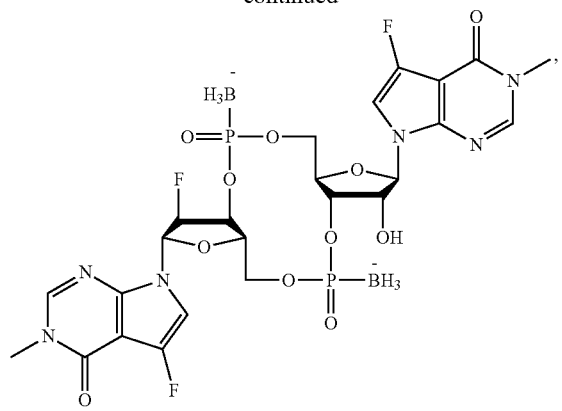
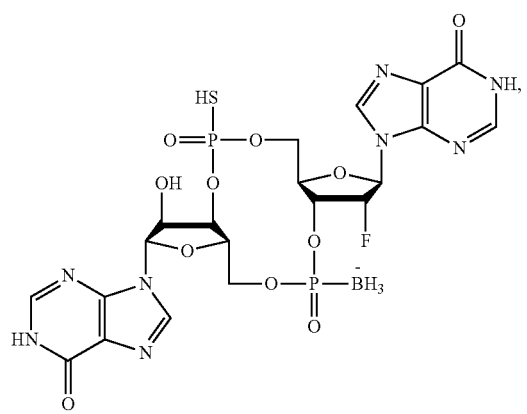
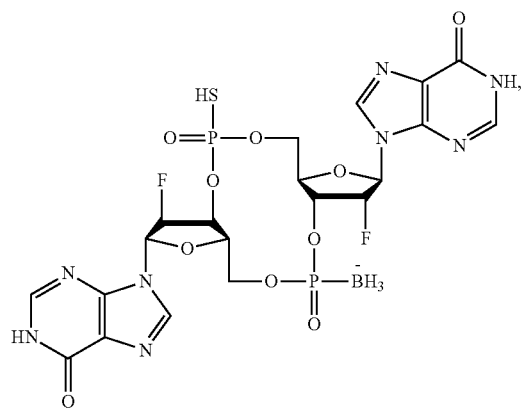
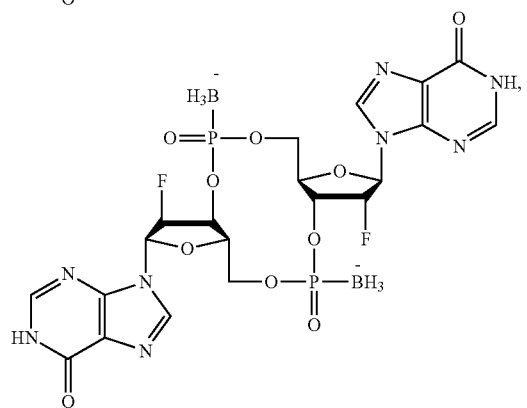
244
-continued
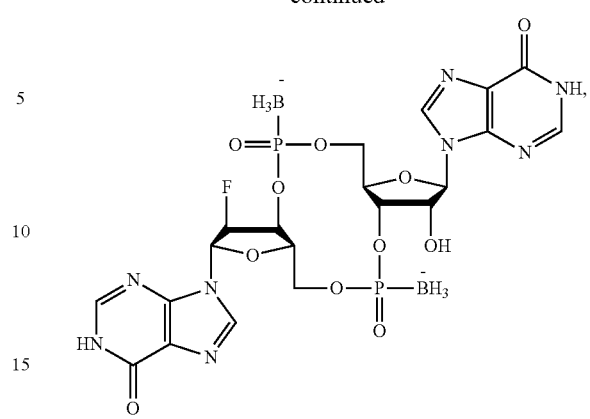
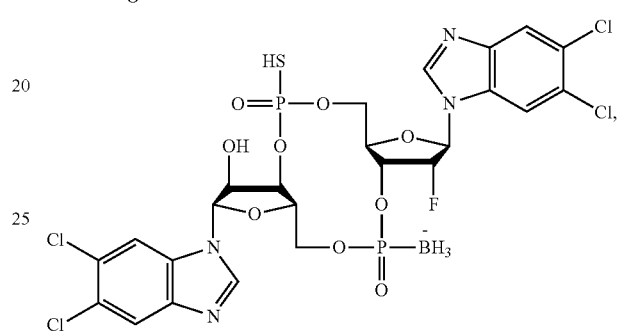
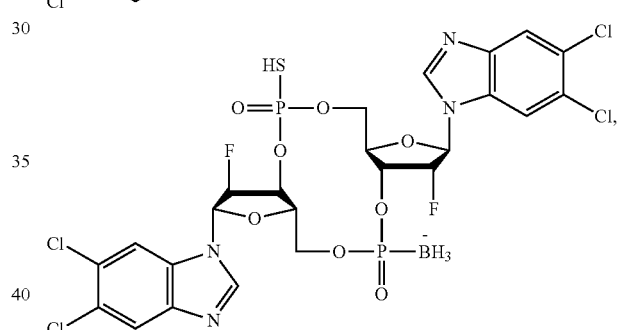
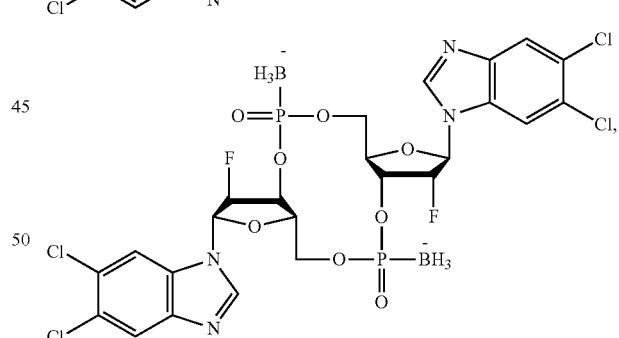
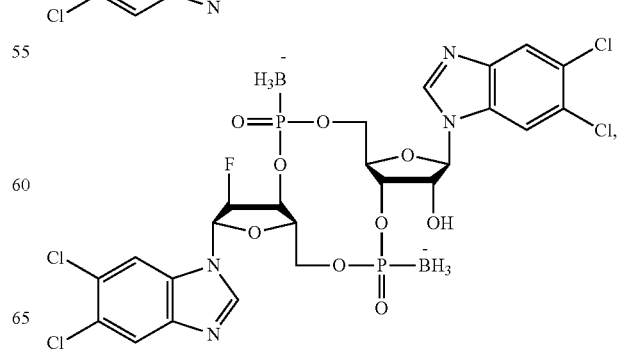

245
-continued
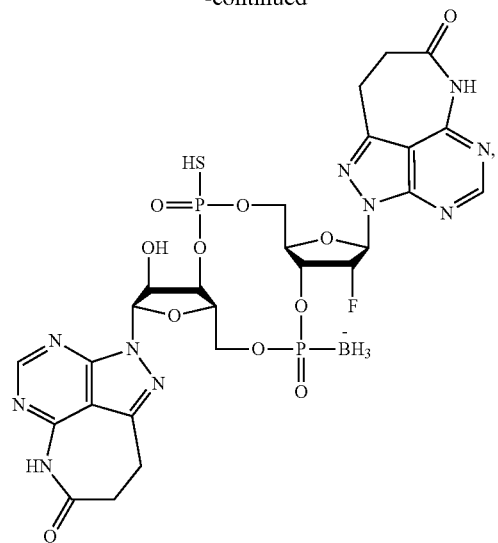
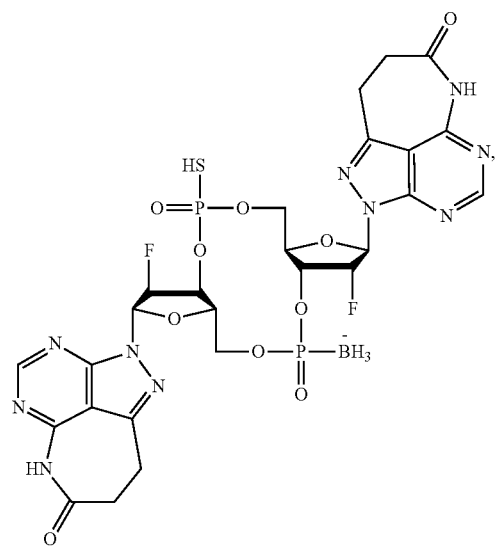
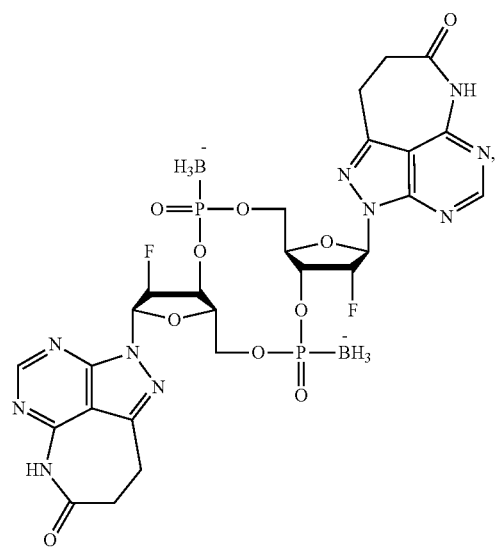
246
-continued
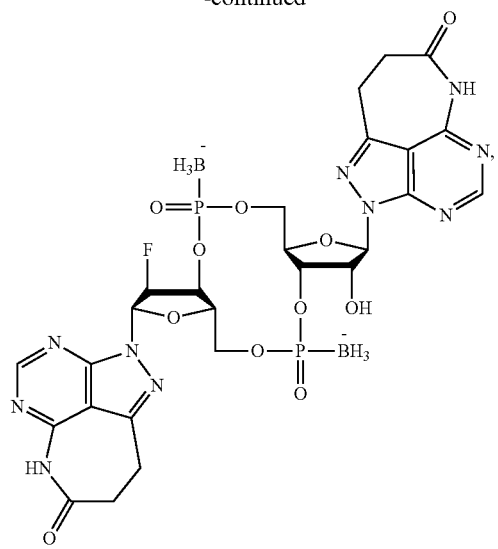
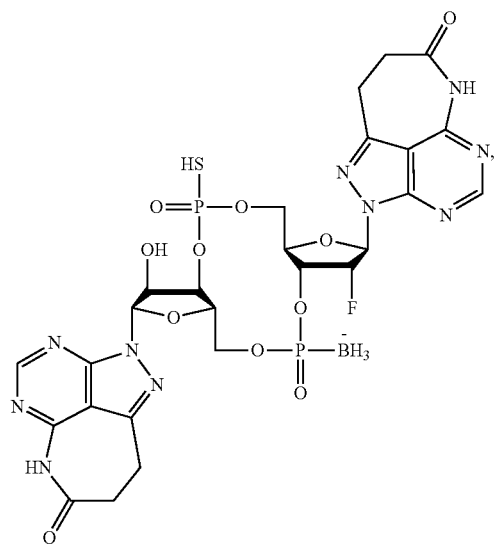
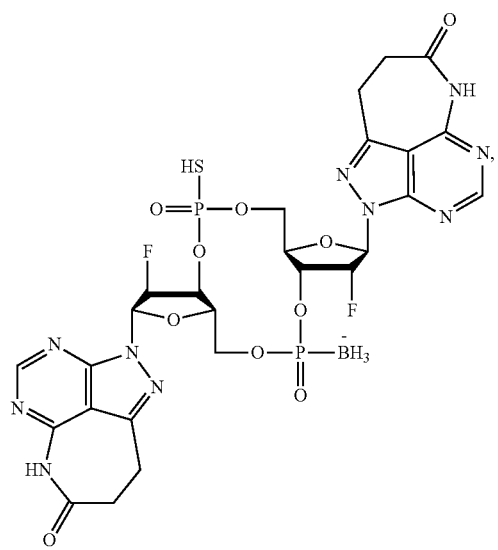

247
-continued
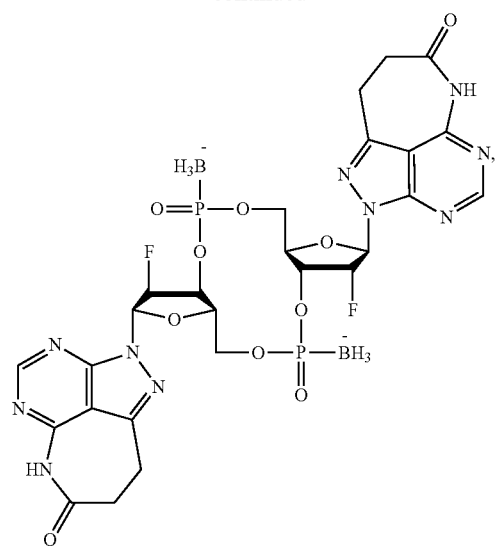
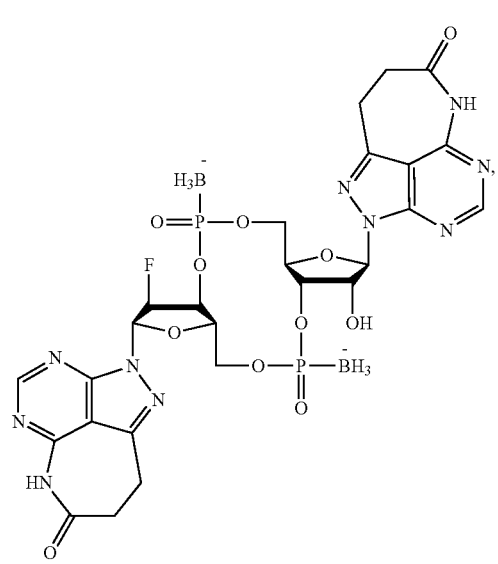
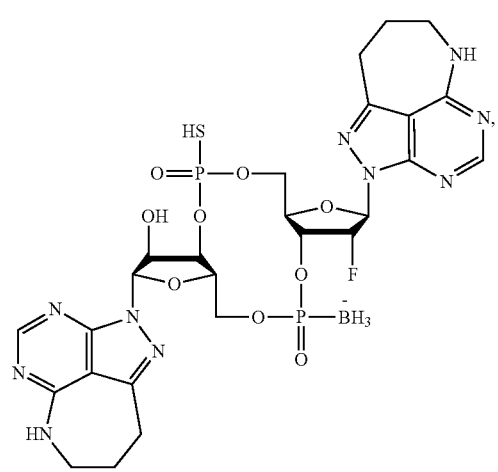
248
-continued
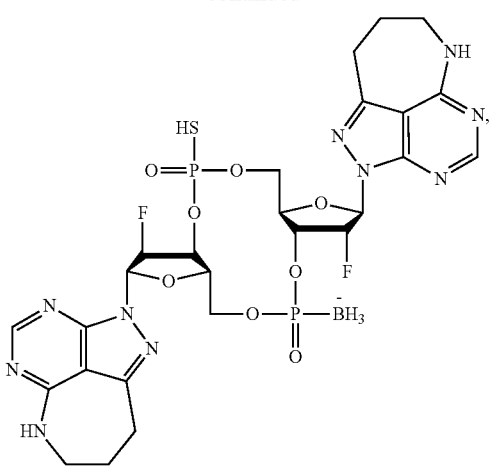
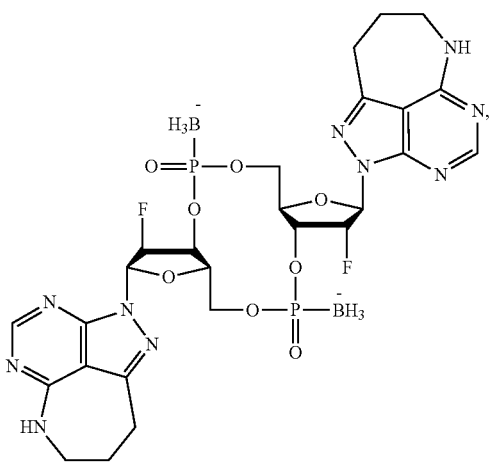
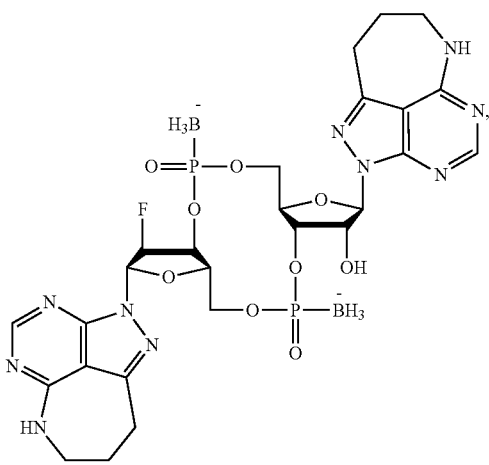

249
-continued
250
-continued
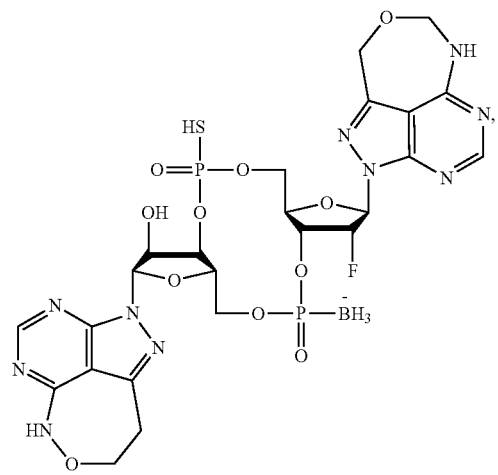
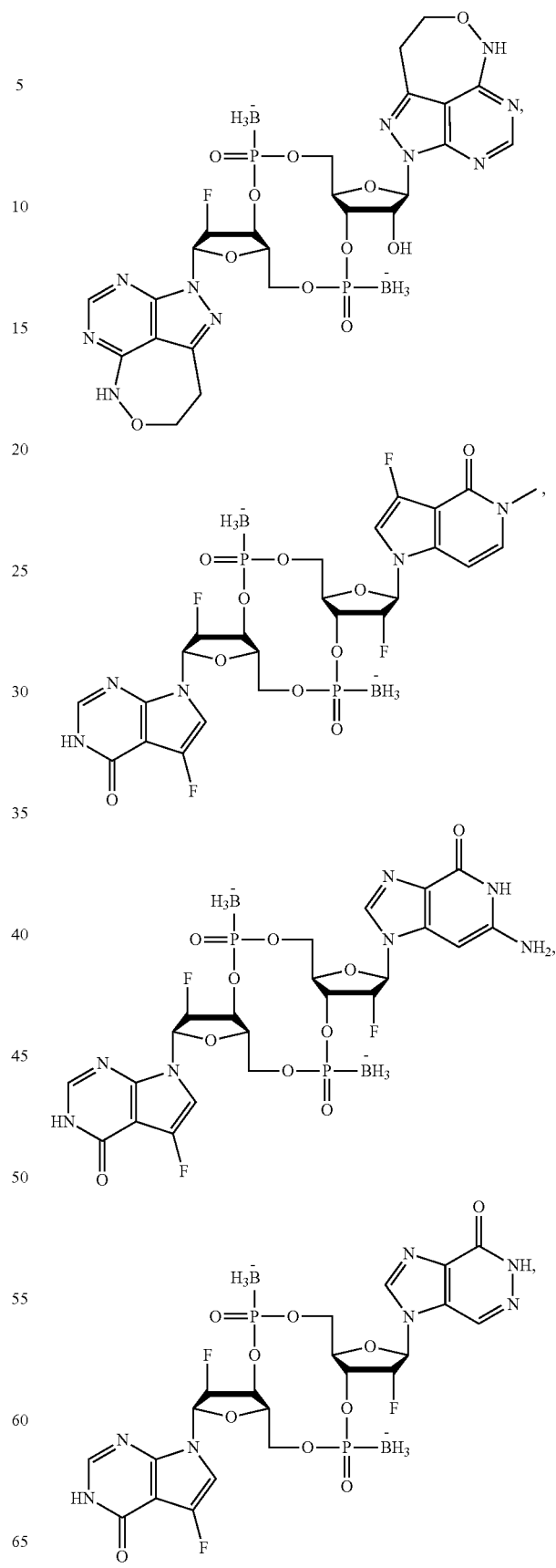

251
-continued
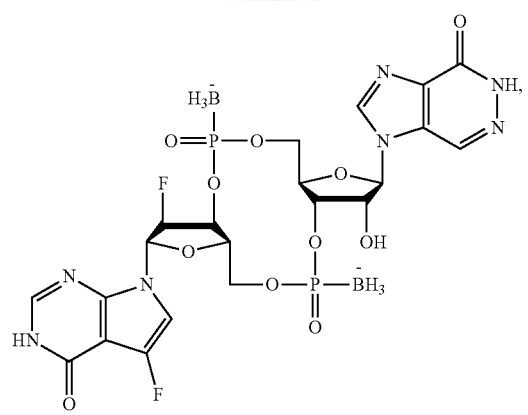
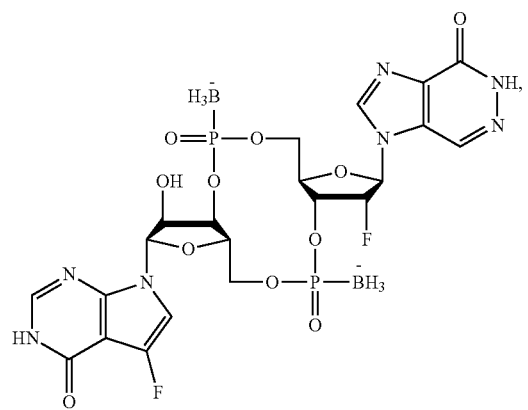
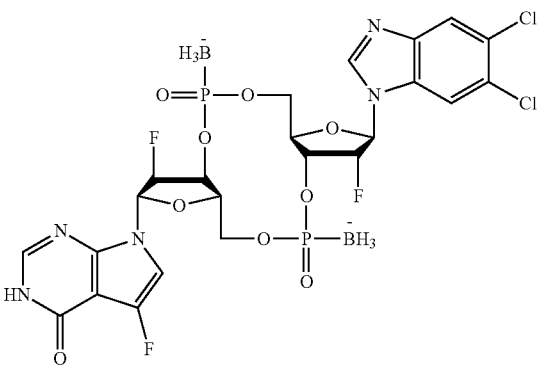
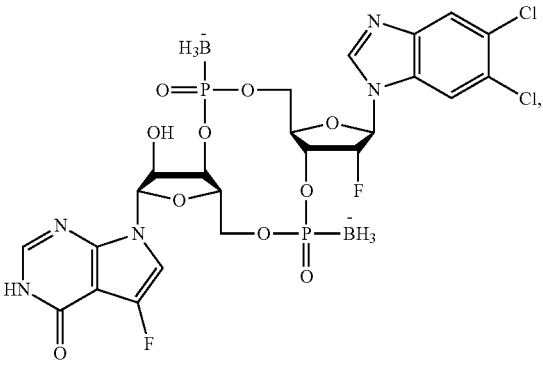
252
-continued
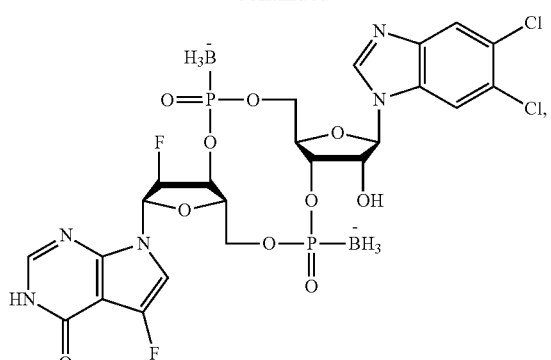
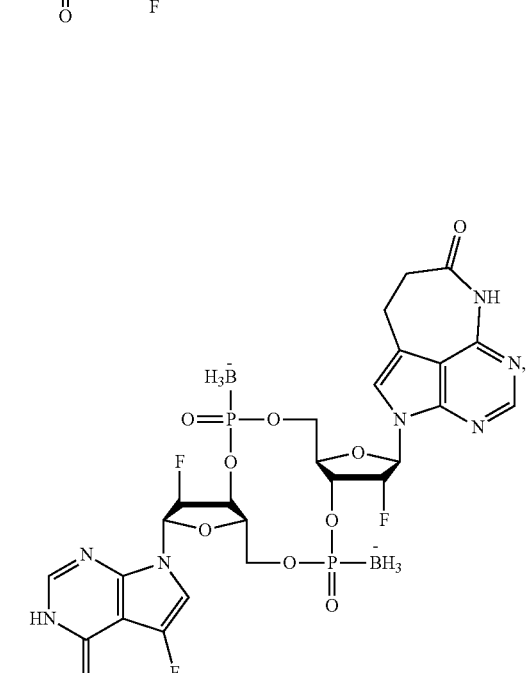
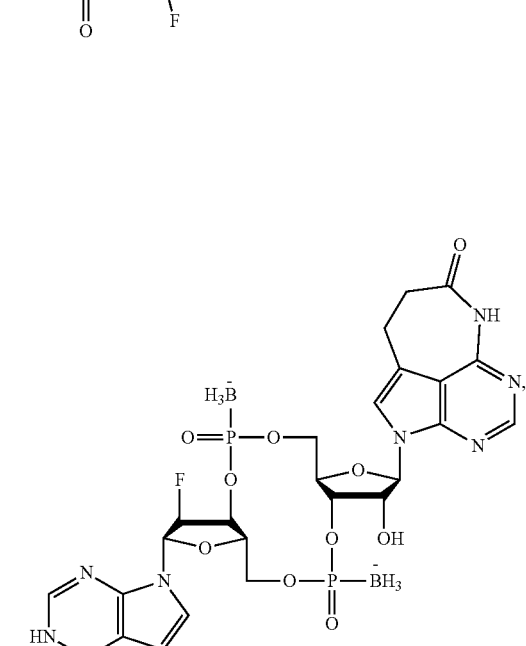

253
-continued
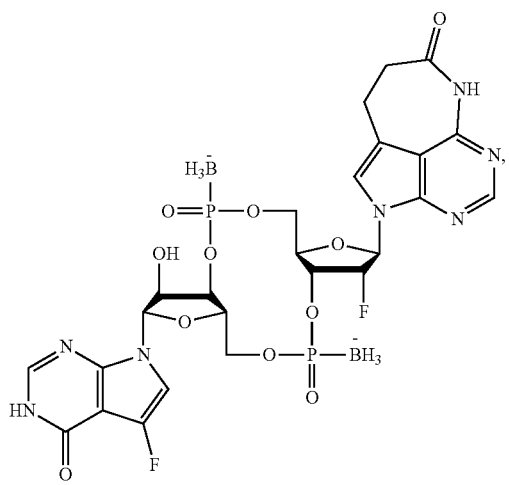
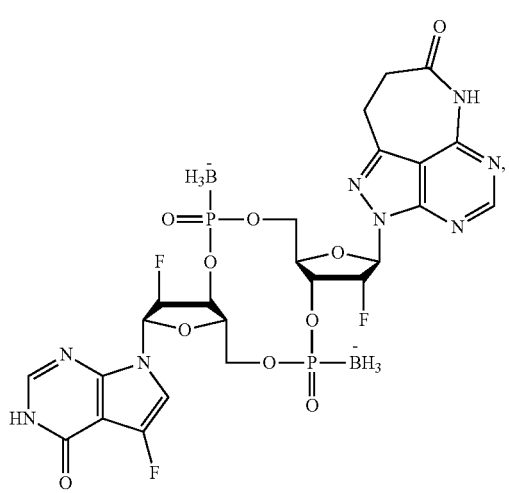
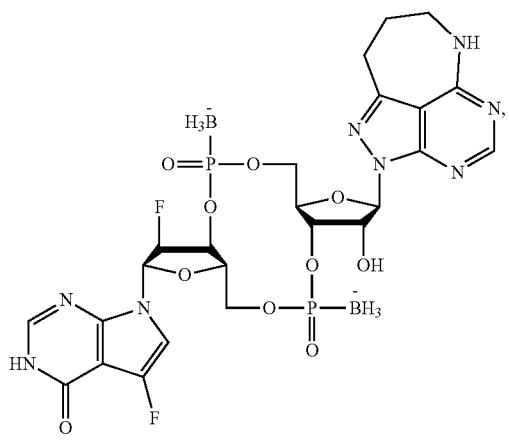
254
-continued
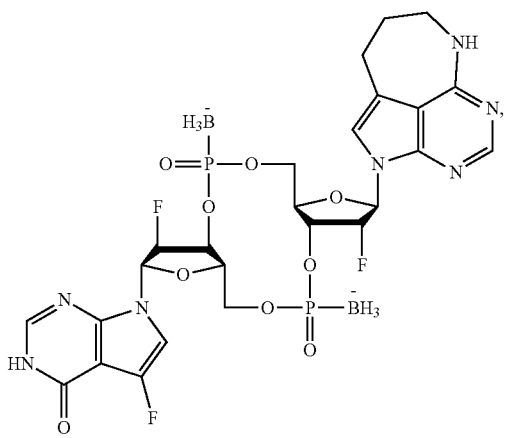
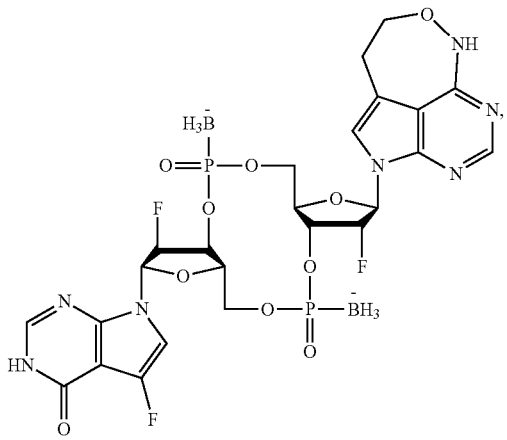
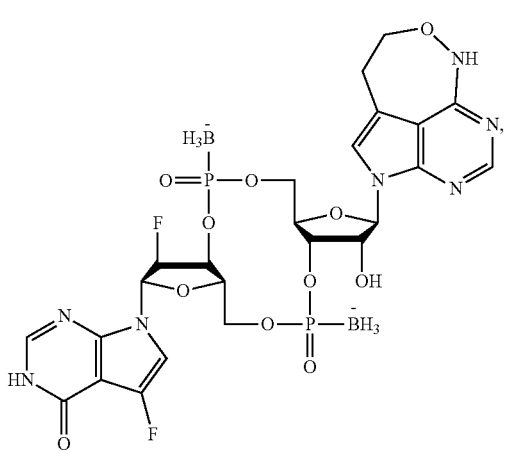

255
-continued
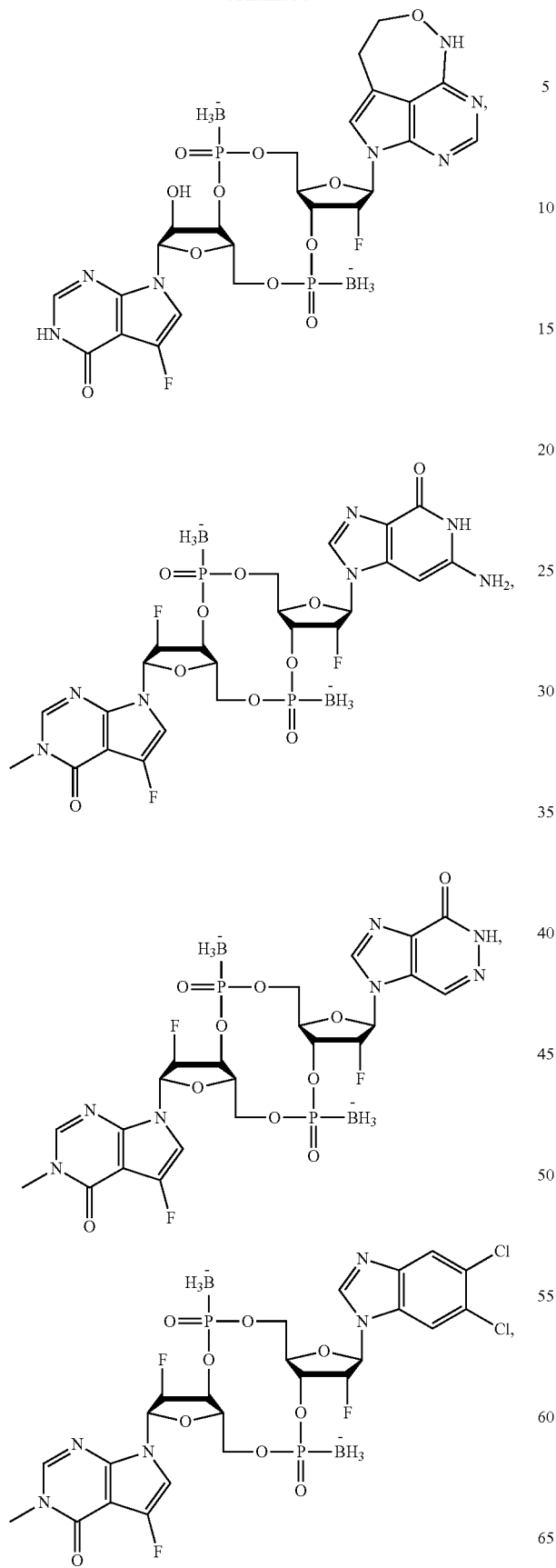
256
-continued
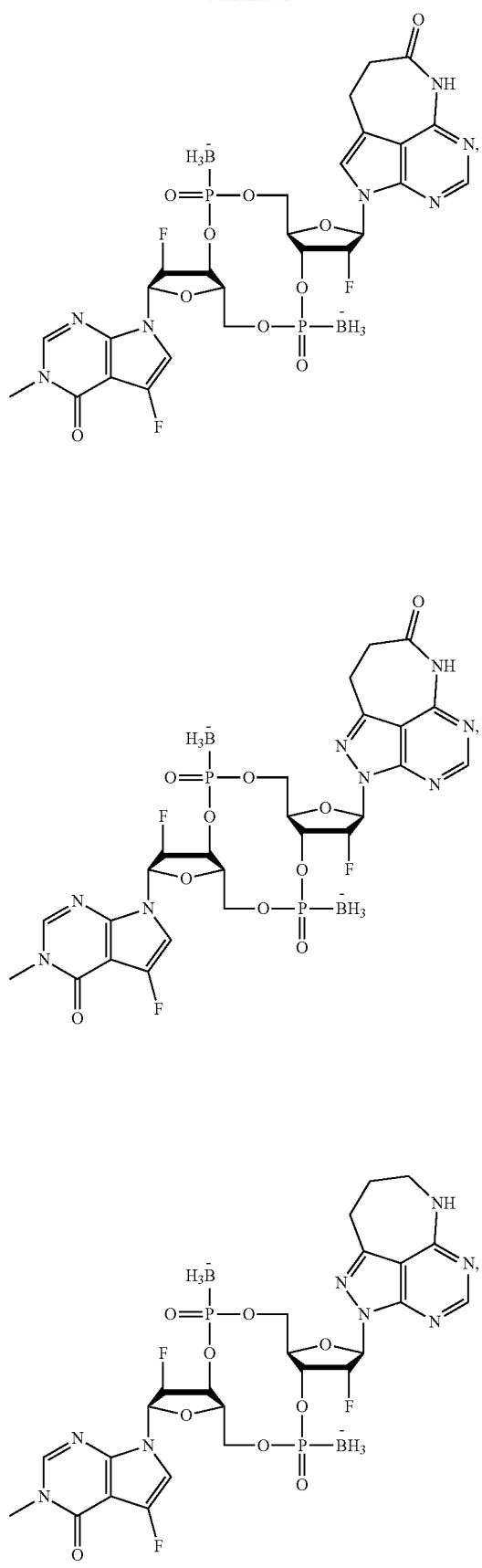

257
-continued
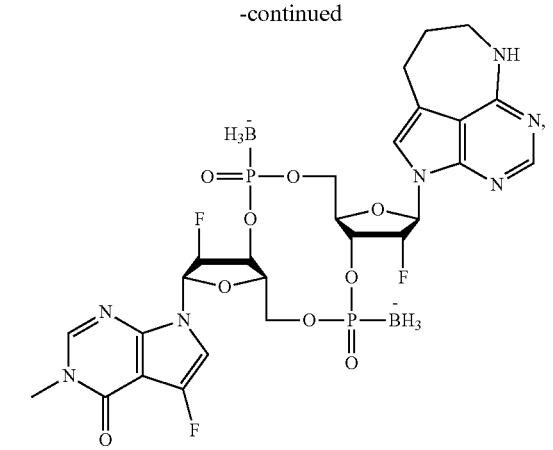
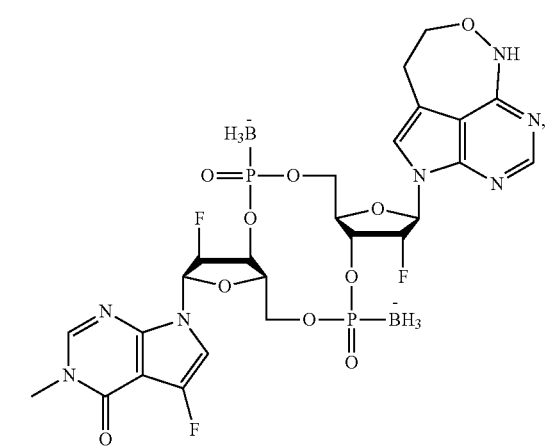
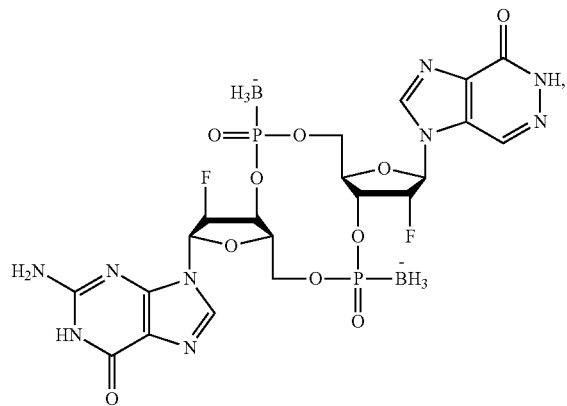
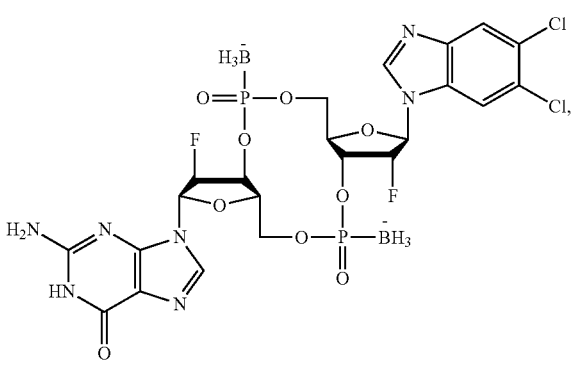
258
-continued
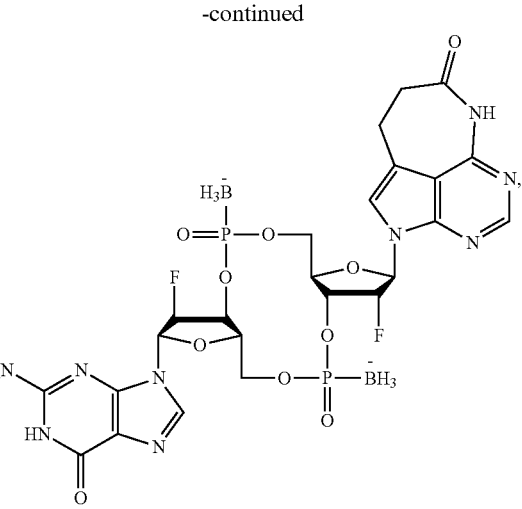

259
-continued
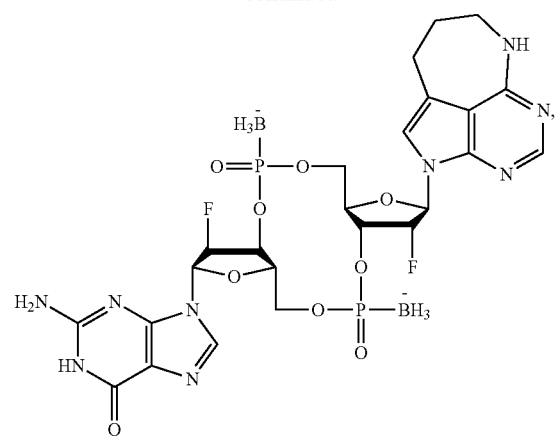
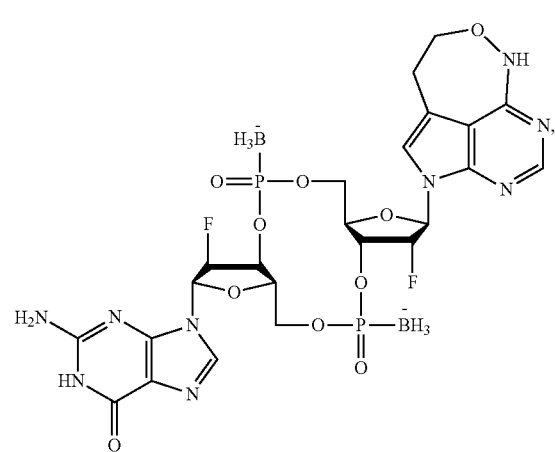
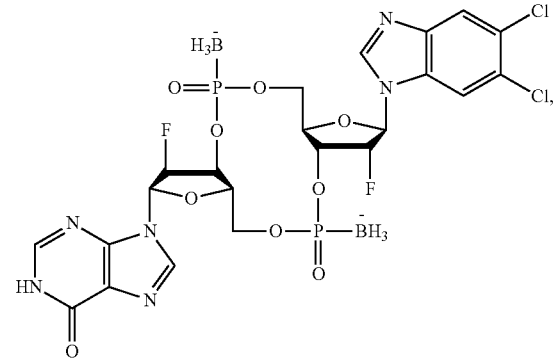
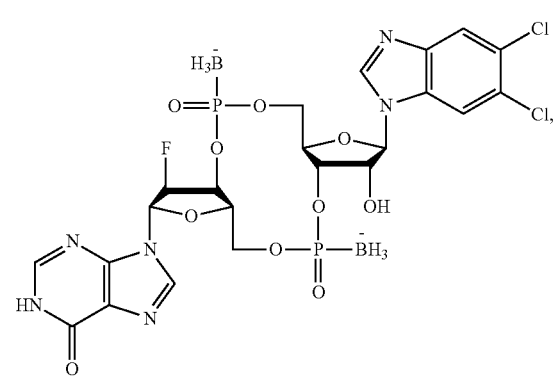
260
-continued
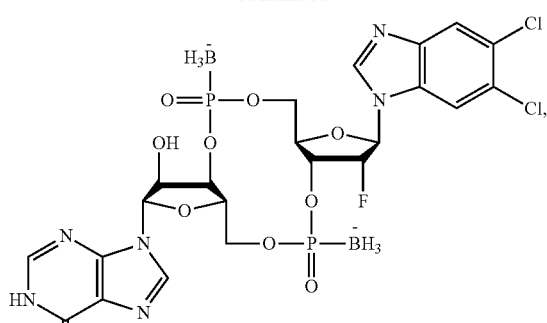
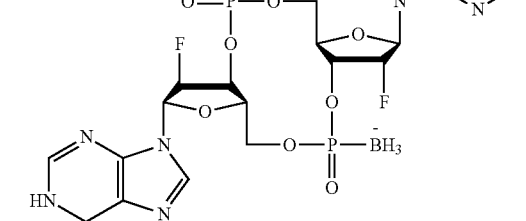

261
-continued
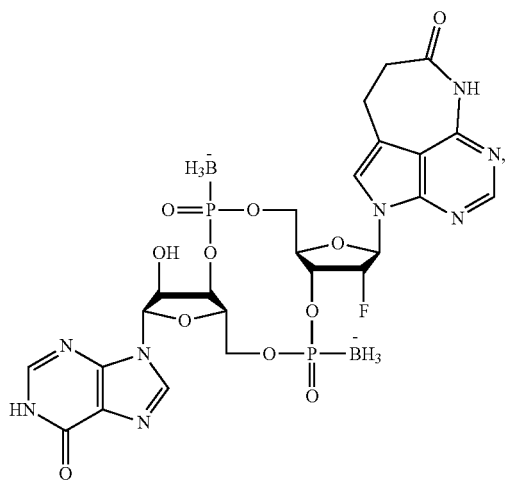
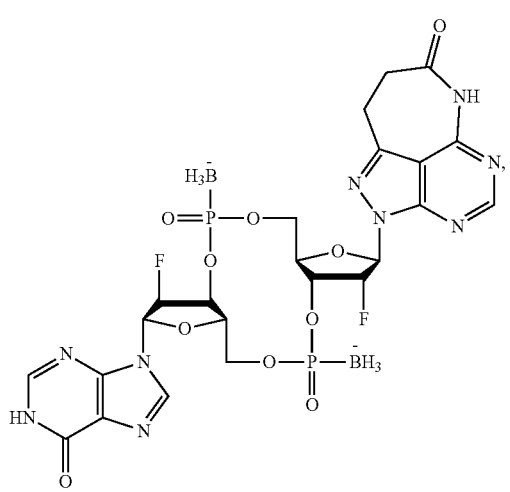
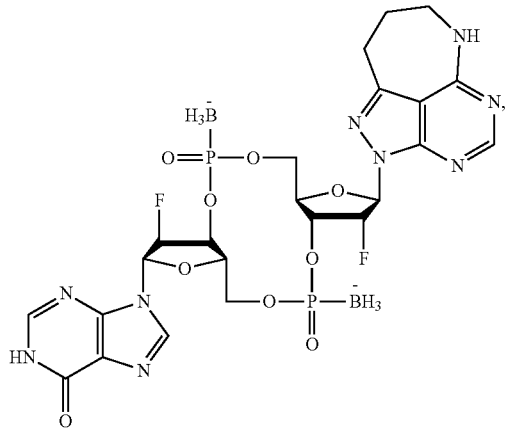
262
-continued
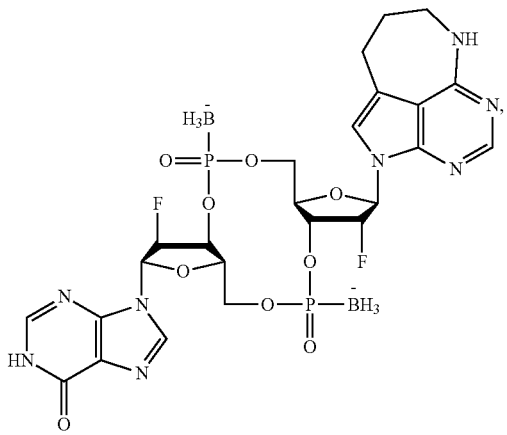
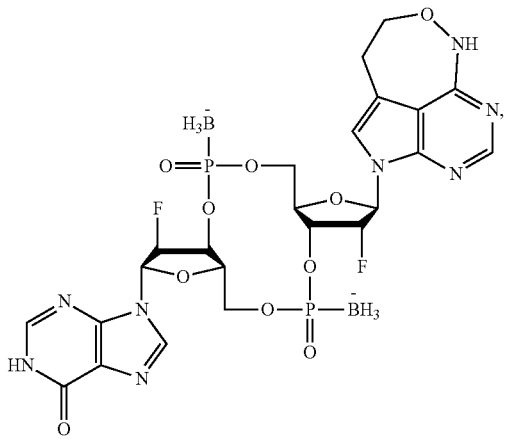
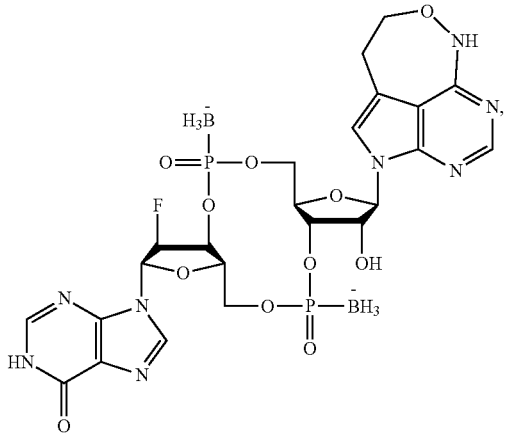

263
-continued
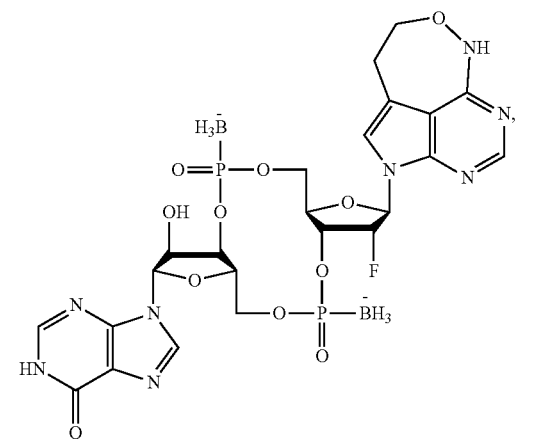
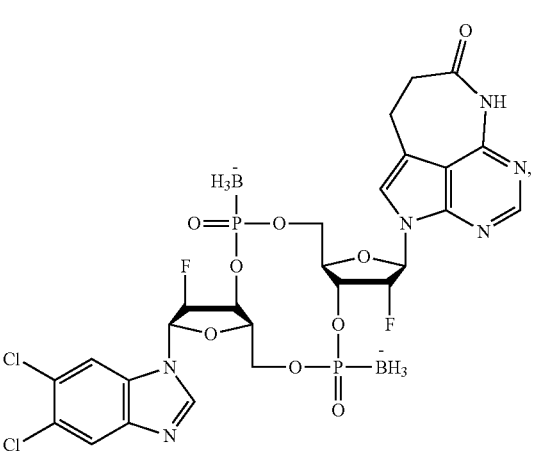
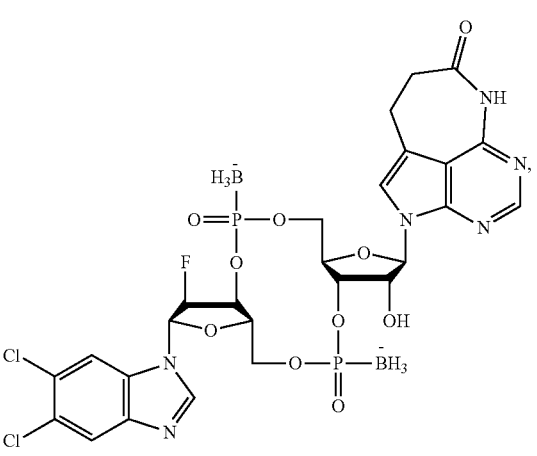
264
-continued
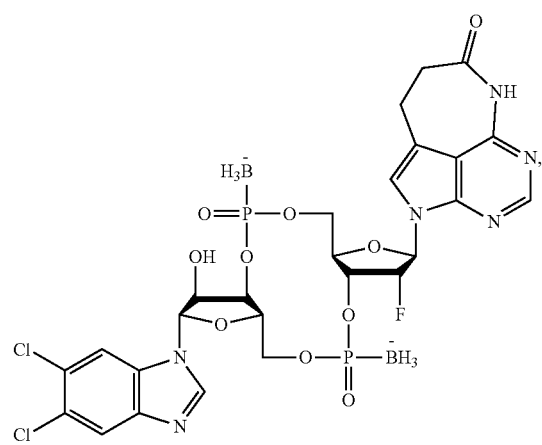
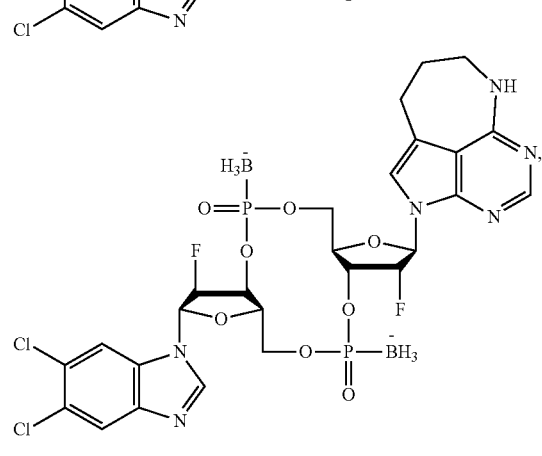
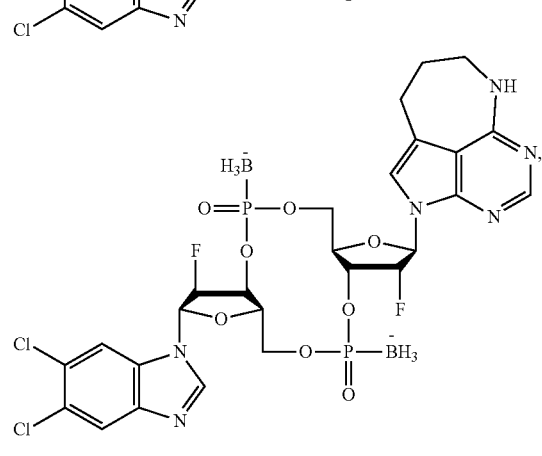
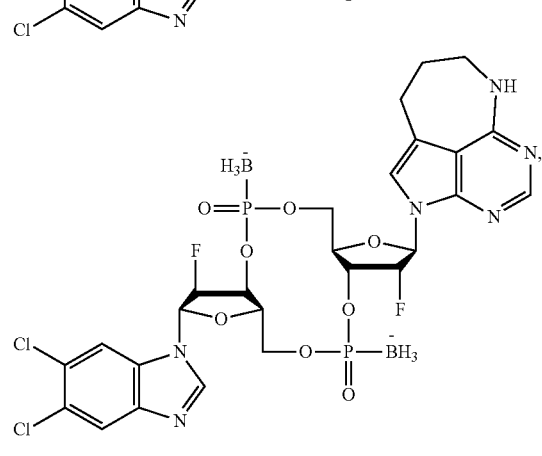

265
-continued
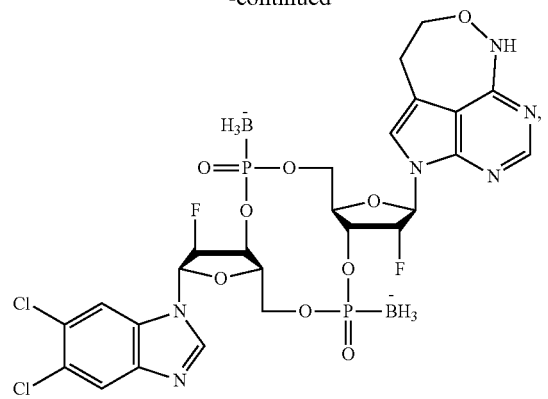
266
-continued
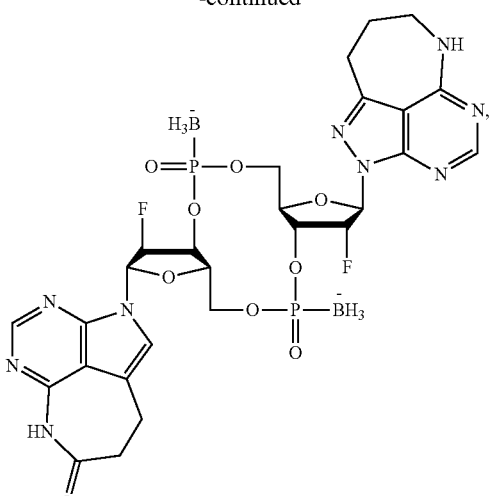
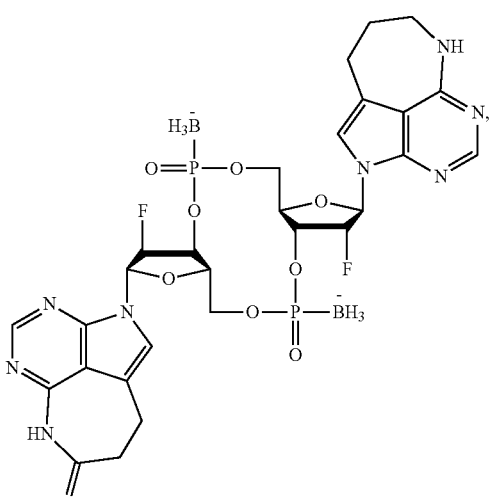
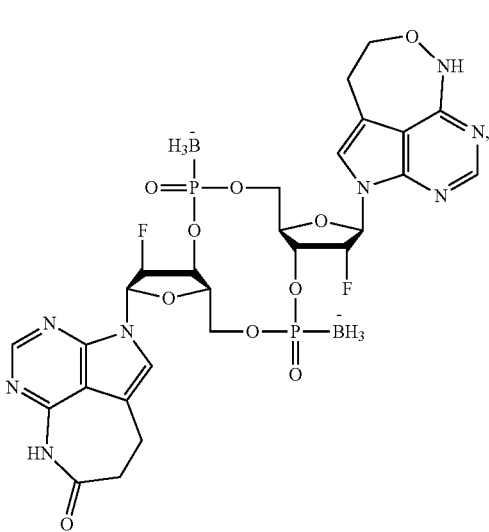

267
-continued
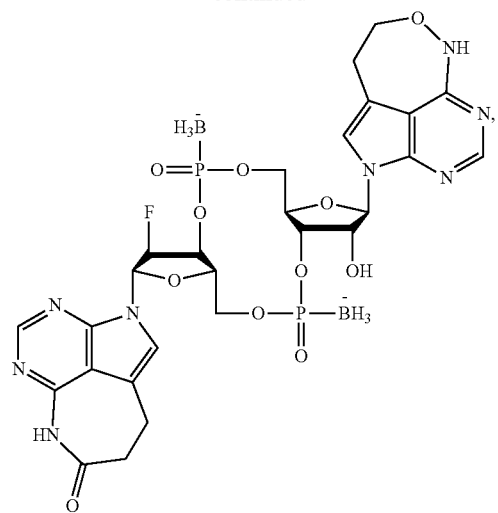
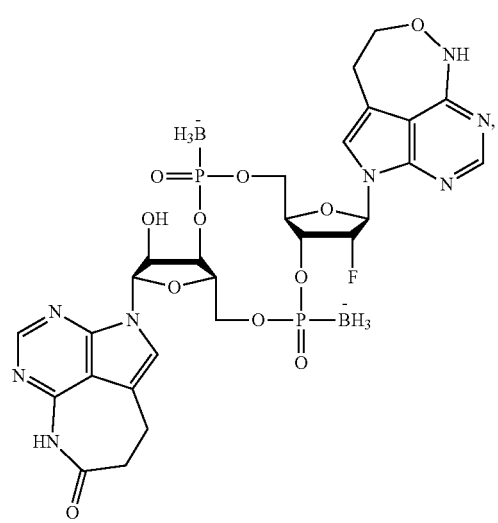
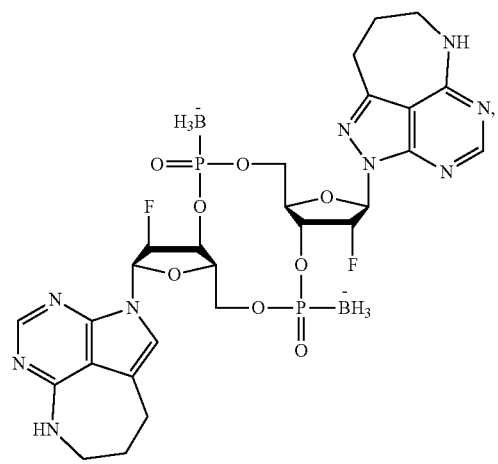
268
-continued
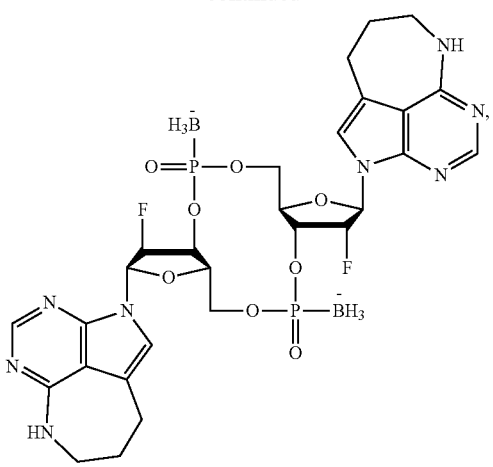
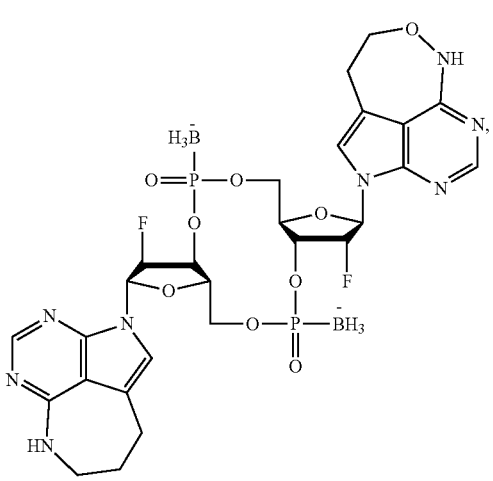
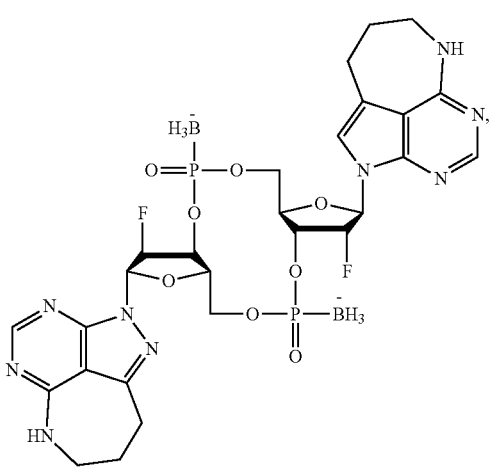

269
-continued
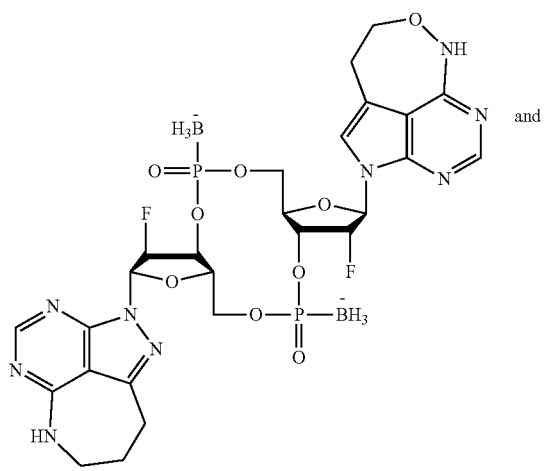
and
270
-continued
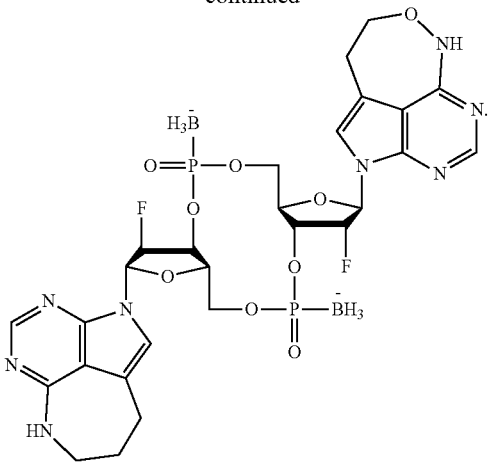
20. A method for treating a STING related disease in a subject in need thereof, wherein the STING related decease is breast cancer or colon cancer, comprising administering a therapeutically effective amount of the compound, the optical isomer thereof or the pharmaceutically acceptable salt thereof as defined in claim 1 to the subject.
* * * * *